United States Patent
Qiu et al.

(10) Patent No.: US 11,472,808 B2
(45) Date of Patent: *Oct. 18, 2022

(54) SUBSTITUTED PYRROLO[1,2-C]PYRIMIDINES AS HEPATITIS B ANTIVIRAL AGENTS

(71) Applicant: Enanta Pharmaceuticals, Inc., Watertown, MA (US)

(72) Inventors: Yao-Ling Qiu, Andover, MA (US); Xiaowen Peng, Sudbury, MA (US); Wei Li, Lexington, MA (US); Xuri Gao, Newtonville, MA (US); Jorden Kass, Arlington, MA (US); Byung-Chul Suh, Lexington, MA (US); Hui Cao, Belmont, MA (US); Jiajun Zhang, Cambridge, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/892,464

(22) Filed: Jun. 4, 2020

(65) Prior Publication Data

US 2020/0385391 A1 Dec. 10, 2020

Related U.S. Application Data

(60) Provisional application No. 62/856,978, filed on Jun. 4, 2019.

(51) Int. Cl.
| | | |
|---|---|---|
| *A61K 31/519* | (2006.01) | |
| *C07D 487/04* | (2006.01) | |
| *C07D 519/00* | (2006.01) | |
| *A61K 45/06* | (2006.01) | |

(52) U.S. Cl.
CPC ......... *C07D 487/04* (2013.01); *C07D 519/00* (2013.01); *A61K 45/06* (2013.01)

(58) Field of Classification Search
CPC .......................... A61K 31/519; C07D 487/04
USPC ...................................... 514/259.1; 544/282
See application file for complete search history.

(56) References Cited

U.S. PATENT DOCUMENTS

| | | | |
|---|---|---|---|
| 3,385,756 A | 5/1968 | Early et al. | |
| 3,975,532 A | 8/1976 | Miller et al. | |
| 4,285,946 A | 8/1981 | Kampe et al. | |
| 4,507,481 A | 3/1985 | Davidson et al. | |
| 5,510,387 A | 4/1996 | Leonidov et al. | |
| 5,656,644 A | 8/1997 | Adams et al. | |
| 6,498,165 B1 | 12/2002 | Armstrong et al. | |
| 6,503,913 B1 | 1/2003 | Goldmann et al. | |
| 6,525,069 B1 | 2/2003 | Ko et al. | |
| 6,667,342 B1 | 12/2003 | Clarke et al. | |
| 7,232,825 B2 | 6/2007 | Chen et al. | |
| 7,312,214 B2 | 12/2007 | Qiao et al. | |
| 7,411,003 B1 | 8/2008 | Liu et al. | |

(Continued)

FOREIGN PATENT DOCUMENTS

| | | |
|---|---|---|
| CN | 106810548 A | 6/2017 |
| CN | 106928215 A | 7/2017 |

(Continued)

OTHER PUBLICATIONS

"(3 'R,4R)-3-[(E)-But-2-enyl]-3'-(2-chloro-4-fluorophenyl)-4'-[1-(difluoromethyl)pyrazol-3-yl]-1'-(1,3-thiazol-2-yl)spiro[1,3-oxazolidine-4,6'-5, 7-dihydro-3H-pyrrolo[1,2-c] pyrimidine]-2-one", PubChem, CID: 138722908, Retrieved from the Internet <URL:https://pubchem.ncbi.nlm.nih.gov/compound/138722908>, 2019, 1-10.

(Continued)

*Primary Examiner* — Douglas M Willis
(74) *Attorney, Agent, or Firm* — Edgar W. Harlan; Carolyn S. Elmore; Elmore Patent Law Group, P.C.

(57) ABSTRACT

The present invention discloses substituted pyrrolo[1,2-c] pyrimidines, such as the compound

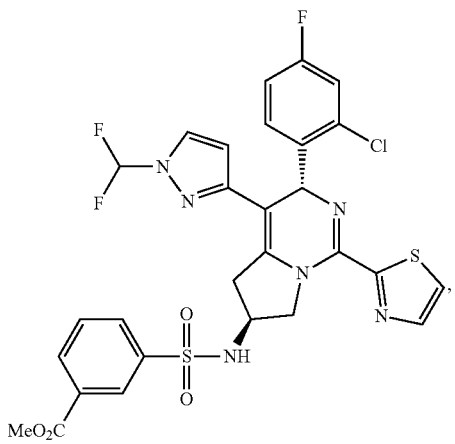

which inhibit the protein(s) encoded by hepatitis B virus (HBV) or interfere with the function of the HBV life cycle of the hepatitis B virus and are also useful as antiviral agents. The present invention further relates to pharmaceutical compositions comprising the aforementioned compounds for administration to a subject suffering from HBV infection. The invention also relates to methods of treating an HBV infection in a subject by administering a pharmaceutical composition comprising the compounds of the present invention.

6 Claims, No Drawings

(56) References Cited

U.S. PATENT DOCUMENTS

| | | |
|---|---|---|
| 7,615,569 B2 | 11/2009 | Fulp et al. |
| 7,741,494 B2 | 6/2010 | Bressi et al. |
| 8,101,643 B2 | 1/2012 | Qiu et al. |
| 8,202,876 B2 | 6/2012 | Albaugh et al. |
| 8,420,823 B2 | 4/2013 | Sato et al. |
| 9,447,086 B2 | 9/2016 | Liu et al. |
| 9,498,479 B2 | 11/2016 | Zhang et al. |
| 9,573,941 B2 | 2/2017 | Liu et al. |
| 9,617,252 B2 | 4/2017 | Liu |
| 9,938,301 B2 | 4/2018 | He et al. |
| 10,179,131 B2 | 1/2019 | Qiu et al. |
| 10,179,792 B2 | 1/2019 | Qiu et al. |
| 10,189,846 B2 | 1/2019 | Qiu et al. |
| 10,253,030 B2 | 4/2019 | He et al. |
| 10,428,070 B2 | 10/2019 | Qiu et al. |
| 10,538,532 B2 | 1/2020 | Qiu et al. |
| 10,640,511 B2 | 5/2020 | Qiu et al. |
| 10,723,733 B2 | 7/2020 | Qiu et al. |
| 2002/0068838 A1 | 6/2002 | Demassey et al. |
| 2003/0232842 A1 | 12/2003 | Goldmann et al. |
| 2004/0209930 A1 | 10/2004 | Carboni et al. |
| 2005/0113450 A1 | 5/2005 | Thorarensen et al. |
| 2005/0203119 A1 | 9/2005 | Ono et al. |
| 2006/0100233 A1 | 5/2006 | Villa et al. |
| 2007/0219239 A1 | 9/2007 | Mjalli et al. |
| 2007/0225373 A1 | 9/2007 | Chen et al. |
| 2009/0023740 A1 | 1/2009 | Fulp et al. |
| 2011/0009622 A1 | 1/2011 | Jitsuoka et al. |
| 2011/0165118 A1 | 7/2011 | Chan et al. |
| 2011/0281950 A1 | 11/2011 | Baiocchi et al. |
| 2012/0009142 A1 | 1/2012 | Karp et al. |
| 2013/0251673 A1 | 9/2013 | Hartman et al. |
| 2013/0267517 A1 | 10/2013 | Guo et al. |
| 2014/0206666 A1 | 7/2014 | Guo et al. |
| 2014/0343032 A1 | 11/2014 | Guo et al. |
| 2014/0357858 A1 | 12/2014 | Ushioda et al. |
| 2015/0005295 A1 | 1/2015 | Haché et al. |
| 2015/0038515 A1 | 2/2015 | Cuconati et al. |
| 2015/0119362 A1 | 4/2015 | Gurney et al. |
| 2015/0133428 A1 | 5/2015 | Velaparthi et al. |
| 2015/0152073 A1 | 6/2015 | Hartman et al. |
| 2015/0152096 A1 | 6/2015 | Zhang et al. |
| 2015/0197493 A1 | 7/2015 | Hartman et al. |
| 2015/0210682 A1 | 7/2015 | Han et al. |
| 2015/0252057 A1 | 9/2015 | Zhu et al. |
| 2015/0266890 A1 | 9/2015 | Vandyck et al. |
| 2015/0274653 A1 | 10/2015 | Vandyck et al. |
| 2016/0115149 A1 | 4/2016 | Vandyck et al. |
| 2016/0185777 A1 | 6/2016 | Hartman et al. |
| 2016/0206616 A1 | 7/2016 | Zhang et al. |
| 2016/0237078 A9 | 8/2016 | Guo et al. |
| 2016/0264562 A1 | 9/2016 | Liu et al. |
| 2016/0264563 A1 | 9/2016 | Ren et al. |
| 2016/0289212 A1 | 10/2016 | Gao et al. |
| 2016/0296515 A1 | 10/2016 | Han et al. |
| 2016/0332996 A1 | 11/2016 | Gao et al. |
| 2016/0347746 A1 | 12/2016 | Zhang |
| 2017/0014408 A1 | 1/2017 | Gao et al. |
| 2017/0022150 A1 | 1/2017 | Gao et al. |
| 2017/0197986 A1 | 7/2017 | He et al. |
| 2017/0217974 A1 | 8/2017 | Gao et al. |
| 2017/0253609 A1 | 9/2017 | Gao et al. |
| 2017/0354641 A1 | 12/2017 | Bastian et al. |
| 2017/0355701 A1 | 12/2017 | Qiu et al. |
| 2017/0355712 A1 | 12/2017 | Campbell et al. |
| 2018/0312507 A1 | 11/2018 | Fu et al. |
| 2018/0312512 A1 | 11/2018 | He et al. |
| 2019/0060258 A1 | 2/2019 | Qiu et al. |
| 2019/0084994 A1 | 3/2019 | Qiu et al. |
| 2019/0119288 A1 | 4/2019 | Qiu et al. |
| 2019/0144448 A1 | 5/2019 | Kotschy et al. |
| 2019/0144449 A1 | 5/2019 | Kotschy et al. |
| 2019/0177316 A1 | 6/2019 | Qiu et al. |
| 2019/0177320 A1 | 6/2019 | Qiu et al. |
| 2019/0224188 A1 | 7/2019 | Panarese et al. |
| 2019/0298865 A1 | 10/2019 | Cuthbertson et al. |
| 2019/0321360 A1 | 10/2019 | Qiu et al. |
| 2019/0337903 A1 | 11/2019 | Khan |
| 2020/0165249 A1 | 5/2020 | Panarese et al. |

FOREIGN PATENT DOCUMENTS

| | | | |
|---|---|---|---|
| CN | 106928245 A | 7/2017 | |
| EP | 2280001 A1 | 2/2011 | |
| WO | 8702367 A2 | 4/1987 | |
| WO | 9504046 A1 | 2/1995 | |
| WO | 0168641 A1 | 9/2001 | |
| WO | 0168647 A1 | 9/2001 | |
| WO | 2004018414 A2 | 3/2004 | |
| WO | 2004052852 A1 | 6/2004 | |
| WO | 2006033995 A2 | 3/2006 | |
| WO | 2008120759 A1 | 10/2008 | |
| WO | 2009158473 A1 | 12/2009 | |
| WO | 2011008597 A1 | 1/2011 | |
| WO | 2013006394 A1 | 1/2013 | |
| WO | 2013096744 A1 | 6/2013 | |
| WO | 2013130703 A2 | 9/2013 | |
| WO | 2013144129 A1 | 10/2013 | |
| WO | 2013181584 A2 | 12/2013 | |
| WO | 2014106019 A2 | 7/2014 | |
| WO | 2014184350 A1 | 11/2014 | |
| WO | 2014184365 A1 | 11/2014 | |
| WO | 2015005295 A1 | 1/2015 | |
| WO | 2015074546 A1 | 5/2015 | |
| WO | 2015113990 A1 | 8/2015 | |
| WO | 2015173164 A1 | 11/2015 | |
| WO | 2016016370 A1 | 2/2016 | |
| WO | 2016023877 A1 | 2/2016 | |
| WO | 2016071215 A1 | 5/2016 | |
| WO | 2016107832 A1 | 7/2016 | |
| WO | 2016128335 A1 | 8/2016 | |
| WO | 2016177655 A1 | 11/2016 | |
| WO | 2017013046 A1 | 1/2017 | |
| WO | 2017017042 A1 | 2/2017 | |
| WO | 2017017043 A1 | 2/2017 | |
| WO | 2017061466 A1 | 4/2017 | |
| WO | 2017140821 A1 | 8/2017 | |
| WO | 2017153919 A1 | 9/2017 | |
| WO | 2017205115 A1 | 11/2017 | |
| WO | 2017216391 A1 | 12/2017 | |
| WO | 2017216685 A1 | 12/2017 | |
| WO | 2017216686 A1 | 12/2017 | |
| WO | WO-2017214395 A1 * | 12/2017 | .............. A61P 31/20 |
| WO | 2018001944 A1 | 1/2018 | |
| WO | 2018001952 A1 | 1/2018 | |
| WO | 2018019297 A1 | 2/2018 | |
| WO | 2018022282 A1 | 2/2018 | |
| WO | 2018047109 A1 | 3/2018 | |
| WO | 2018073753 A1 | 4/2018 | |
| WO | 2018083081 A1 | 5/2018 | |
| WO | 2018083106 A1 | 5/2018 | |
| WO | 2018083136 A1 | 5/2018 | |
| WO | 2018085619 A1 | 5/2018 | |
| WO | 2018087345 A1 | 5/2018 | |
| WO | 2018130152 A1 | 7/2018 | |
| WO | 2018144605 A1 | 8/2018 | |
| WO | 2018154466 A1 | 8/2018 | |
| WO | 2018161960 A1 | 9/2018 | |
| WO | 2018181883 A1 | 10/2018 | |
| WO | 2018196805 A1 | 11/2018 | |
| WO | 2018198079 A1 | 11/2018 | |
| WO | 2018219356 A1 | 12/2018 | |
| WO | 2019069293 A1 | 4/2019 | |
| WO | 2019097479 A1 | 5/2019 | |
| WO | 2019110352 A1 | 6/2019 | |
| WO | 2019123285 A1 | 6/2019 | |
| WO | 2019129681 A1 | 7/2019 | |
| WO | 2019166951 A1 | 9/2019 | |

OTHER PUBLICATIONS

Chemical Abstract Service STN CAplus [online database], Accession No. 2003:1014580. (Year: 2003).

(56) References Cited

OTHER PUBLICATIONS

Chemical Abstract Service STN Database Registry No. 1578268-77-5 [online][Entered STN: Apr. 1, 2014].
Chemical Abstracts Registry No. 1026741-09-2, indexed in the Registry file on Jun. 9, 2008.
Chemical Abstracts Registry No. 115280-56-3, indexed in the Registry file on STN CAS Online Jul. 16, 1988.
Chemical Abstracts Registry No. 1269203-67-9, indexed in the Registry file on STN CAS Online Mar. 21, 2011.
Chemical Abstracts Registry No. 1350251-34-1, indexed in the Registry file on STN CAS Online Dec. 7, 2011.
Chemical Abstracts Registry No. 397288-41-1, indexed in the Registry file on Mar. 1, 2002.
Chemical Abstracts Registry No. 792901-47-4, indexed in the Registry file on STN CAS Online Dec. 6, 2004.
Chemical Abstracts Registry No. 92555-24-3, indexed in the Registry file on Dec. 17, 1984.
Chemical Abstracts Registry No. 950067-32-0, indexed in the Registry file on Oct. 10, 2007.
PubChem CID 57036978, National Center for Biotechnology Information. PubChem Compound Database; CID=57036978, https://pubchem.ncbi.nlm.nih.gov/compound/57036978 (accessed May 19, 2017), create date Jun. 13, 2012.
PubChem CID 69095846 {National Center for Biotechnology Information. PubChem Compound Database; CID=69095846, https://pubchem.ncbi.nlm.nih.gov/compound/69095846 (accessed May 23, 2017), create date Nov. 30, 2012.
PubChem CI D 10194182, National Center for Biotechnology Information. PubChem Compound Database; CI 0=10194182, https://pubchem.ncbi.nlm.nih.gov/compound/10194182 (accessed May 19, 2017), create date Oct. 25, 2006.
Pubchem-'428' Create Date: Sep. 11, 2005 (Sep. 11, 2005) Date Accessed: Jun. 17, 2016.
PUBCHEM-CID 23201920, Create Date: Dec. 5, 2007, p. 3.
PUBCHEM-CID 63186259, Create Date: Oct. 22, 2012 (Oct. 22, 2012) p. 3.
PUBCHEM-SID 15224030 Deposit Date: Oct. 25, 2006.
Pubchern-57224610 ('610') Create Date: Jun. 14, 2012 (Jun. 14, 2012) Date Accessed: Jun. 17, 2016.
CAS Abstract and Indexed Compounds WO 01/68647 (2001).
PubChem SID 79456770 CID 10880307, 2009.
"8-Tert-butyl-4-[(1 E)-1-(difluoromethoxy)buta-1, 3-dienyl]-5-ethyl-12-oxo-6, 9-diazatricyclo[7.4.0.02,6]trideca-1(13),2,4, 10-tetraene-11-carboxylic acid", PubChem-CID-134460393, CreateDate: Jun. 23, 2018 (Jun. 23, 2018), p. 2, Fig.
"N-[4-(cyanomethyl)phenyl]-5-(hexyhydro-1-H -azepine-1-yl)sulfonyl]-2-methoxy-benzamid e", Database Registry [Online] Chemical Abstracts Service, Columbus, Ohio, US; May 6, 2011 (May 6, 2011), XP55358935,accession No. RN: 1291044-81-9.
Ballatore, C. et al., "Carboxylic Acid (Bio)Isosteres in Drug Design", ChemMedChem., vol. 8, No. 3, 2013, 385-395.
Chowshury, Chinmay et al., "A rapid and facile method for the general synthesis of 3-aryl substituted 4,5,6,7-tetrahydro[1,2,3]triazolo[1,5-a]pyrazines and their ring fused analogues", Organic & Biomolecular Chemistry, vol. 9, 2011, 5856-5862.
Clark, M. T. et al., "5-(alkylsulfonyl)salicylanilides as Potential Dental Antiplaque Agent", Journal of Medicinal Chemistry, 29(1), 1986, 25-29.
Das, Jagabandhu et al., "Discovery of 2-Amino-heteroaryl-benzothiazole-6-anilides as Potent p56lck Inhibitors", Biorganic & Medicinal Chemistry Letters, 13, 2003, 2587-2590.
El-Hamouly, Wageeh S. et al., "Synthesis and Antimicrobial Activity of New 3, 4-Dihydropyrimidinones", International Journal of Pharmaceutical Sciences and Research, vol. 2, 2011, 1054-1062.
Janetka, J. W. et al., "Discovery of a novel class of 2-ureido thiophene carboxamide checkpoint kinase inhibitors", Bioorganic & Medicinal Chemistry Letters, 18, 2008, 4242-4248.
Li, X. et al., ACS Medicinal Chemistry Letters, 8, 2017, 969-974.
Noguchi, Chiemi et al., "G to A Hypermutation of Hepatitis B Virus", Hepatology, vol. 41, No. 3, 2005, 626-633.
Qiu, Zongxing et al., "Design and Synthesis of Orally Bioavailable 4-Methyl Heteroaryldihydropyrimidine Based Hepatitis B Virus (HBV) Capsid Inhibitors", Journal of Medicinal Chemistry, 2016.
Yang, et al., "Enzyme-mediated hydrolytic activation of prodrugs", Acta Pharmaceutica Sinica B., vol. 1(3), Sep. 9, 2011, 143-159.

* cited by examiner

SUBSTITUTED PYRROLO[1,2-C]PYRIMIDINES AS HEPATITIS B ANTIVIRAL AGENTS

RELATED APPLICATIONS

This application claims the benefit of U.S. Provisional Application No. 62/856,978, filed on Jun. 4, 2019. The entire teachings of the above application are incorporated herein by reference.

TECHNICAL FIELD

The present invention relates generally to novel antiviral agents. Specifically, the present invention relates to compounds which can inhibit the protein(s) encoded by hepatitis B virus (HBV) or interfere with the function of the HBV life cycle, compositions comprising such compounds, methods for inhibiting HBV viral replication, methods for treating or preventing HBV infection, and processes for making the compounds.

BACKGROUND OF THE INVENTION

HBV infection remains a major public health problem, affecting approximately 2 billion people worldwide. Among them, 350 million people worldwide and 1.4 million in the US develop a chronic infection, which can lead to chronic persistent hepatitis, liver cirrhosis, and hepatocellular carcinoma (HCC). Every year 500,000 to 1 million people die from the end stage of liver diseases caused by HBV infection.

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon and nucleoside analogues/inhibitors of the viral polymerase); drug resistance, low efficacy, and tolerability issues limit their impact. The low cure rates of HBV are attributed at least in part to the presence and persistence of covalently closed circular DNA (cccDNA) in the nucleus of infected hepatocytes. However, persistent suppression of HBV DNA slows liver disease progression and helps to prevent HCC. Current therapy goals for HBV-infected patients are directed to reducing serum HBV DNA to low or undetectable levels, and to ultimately reducing or preventing the development of cirrhosis and HCC.

The HBV is an enveloped, partially double-stranded DNA (dsDNA) virus of the hepadnavirus family (Hepadnaviridae). HBV capsid protein (CP) plays essential roles in HBV replication. The predominant biological function of capsid protein is to act as a structural protein to encapsidate pre-genomic RNA and form immature capsid particles, which spontaneously self-assemble from many copies of core dimers in the cytoplasm. Capsid protein also regulates viral DNA synthesis through different phosphorylation status of its C-terminal phosphorylation sites. Also, capsid protein might facilitate the nuclear translocation of viral relaxed circular genome by means of the nuclear localization signals located in the Arginine-rich domain of the C-terminal region of capsid protein. In the nucleus, as a component of viral cccDNA minichromosome, capsid protein could play a structural and regulatory role in the functionality of cccDNA minichromosomes. Capsid protein also interacts with viral large envelope protein in endoplasmic reticulum (ER) and triggers the release of intact viral particles from hepatocytes.

Capsid related anti-HBV inhibitors have been reported. For example, phenylpropen-amide derivatives, including compounds named AT-61 and AT-130 (Feld J. et al. Antiviral Res. 2007, 76, 168), and a class of thiazolidin-4-ones from Valeant (WO2006/033995), have been shown to inhibit pregenomic RNA (pgRNA) packaging. Heteroaryldihydropyrimi-dines or HAPs were discovered in a tissue culture-based screening (Weber et al., Antiviral Res. 2002, 54, 69). These HAP analogs act as synthetic allosteric activators and are able to induce aberrant capsid formation that leads to degradation of the core protein. A subclass of sulphamoyl-arylamides also shows activity against HBV (WO 2013/006394, WO 2013/096744, and WO 2014184365). It was also shown that the small molecule bis-ANS acts as a molecular 'wedge' and interferes with normal capsid-protein geometry and capsid formation (Zlotnick A. et al. J. Virol. 2002, 4848).

There is a need in the art for novel therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, and enhanced seroconversion rates.

SUMMARY OF THE INVENTION

The present invention relates to novel antiviral compounds, pharmaceutical compositions comprising such compounds, as well as methods to treat or prevent viral (particularly HBV) infection in a subject in need of such therapy with said compounds. Compounds of the present invention inhibit the protein(s) encoded by hepatitis B virus (HBV) or interfere with the life cycle of HBV and are also useful as antiviral agents. In addition, the present invention includes the process for the preparation of the said compounds.

In its principal aspect, the present invention provides a compound of Formula (I):

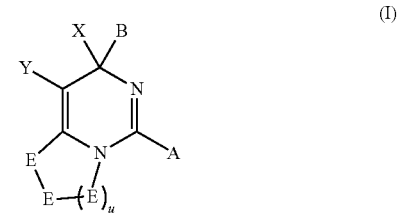

or a pharmaceutically acceptable salt thereof, wherein:

A is optionally substituted aryl or optionally substituted heteroaryl; preferably A is optionally substituted azolyl, optionally substituted pyridyl, or optionally substituted phenyl;

B is selected from the group consisting of hydrogen, halo, CN, optionally substituted —$C_1$-$C_6$ alkyl, and optionally substituted —$C_3$-$C_6$ cycloalkyl; preferably B is hydrogen or optionally substituted methyl;

X is optionally substituted aryl or optionally substituted heteroaryl; preferably X is optionally substituted phenyl;

Alternatively, B and X are taken together with the carbon atom to which they are attached to form an optionally substituted —$C_4$-$C_{12}$ cycloalkenyl or optionally substituted 4- to 12-membered heterocyclic, for example, a —$C_4$-$C_{12}$ cycloalkenyl or 4- to 12-membered heterocyclic which is fused with an aryl or heteroaryl ring wherein each ring is optionally further substituted;

Y is optionally substituted aryl or optionally substituted heteroaryl; preferably Y is optionally substituted azolyl, optionally substituted pyridyl, or optionally substituted phenyl;

E at each occurrence is the same or different and independently selected from —$CR_1R_2$—, —C(O)—, —O—, —$NR_2$—, —S—, and —$S(O)_2$—; u is 0, 1, 2, or 3; $R_1$ is hydrogen, halo, CN, —$NR_{11}R_{12}$, —$N_3$, —$C(O)NR_{11}R_{12}$, —$NR_{11}C(O)R_{12}$, —$NR_{11}C(O)NR_{11}R_{12}$, —$NR_{11}C(O)OR_{12}$, —$OR_{11}$, —$NR_{11}S(O)_2R_{12}$, —$S(O)_2NR_{11}R_{12}$, —$NR_{11}S(O)_2NR_{11}R_{12}$, —$SR_{11}$, —$S(O)_2R_{11}$, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl and optionally substituted heteroaryl; $R_2$ is hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl and optionally substituted heteroaryl;

$R_{11}$ and $R_{12}$ at each occurrence are independently selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl and optionally substituted heteroaryl; $R_{11}$ at each occurrence is the same or different.

Each preferred group stated above can be taken in combination with one, any or all other preferred groups.

DETAILED DESCRIPTION OF THE INVENTION

In one embodiment of the present invention is a compound of Formula (I) as described above, or a pharmaceutically acceptable salt thereof.

Compounds of Formula (I) can have the stereochemistry shown in Formula (Ia) or Formula (Ib),

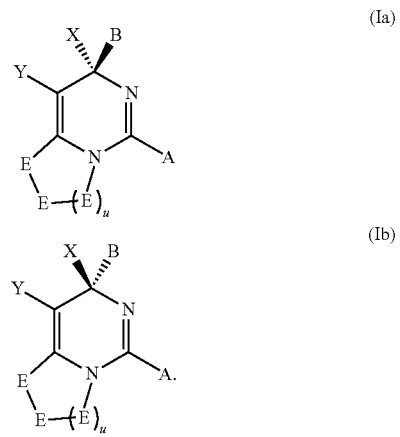

In preferred embodiments, compounds of Formula (I) have the stereochemistry shown in Formula (Ia).

In certain embodiments, the present invention relates to compounds of Formula (I), and pharmaceutically acceptable salts thereof, wherein A is an optionally substituted azolyl, optionally substituted pyridyl, or optionally substituted phenyl.

In certain embodiments, the present invention relates to compounds of Formula (I), and pharmaceutically acceptable salts thereof, wherein B is hydrogen.

In certain embodiments, the present invention relates to compounds of Formula (I), and pharmaceutically acceptable salts thereof, wherein B is halo, preferably fluoro.

In certain embodiments, the present invention relates to compounds of Formula (I), and pharmaceutically acceptable salts thereof, wherein B is methyl, optionally substituted with one or more halo, preferably fluoro. In certain embodiments, B is difluoromethyl or trifluoromethyl.

In certain embodiments, the present invention relates to compounds of Formula (I), and pharmaceutically acceptable salts thereof, wherein X is optionally substituted phenyl. In certain embodiments, the present invention relates to compounds of Formula (I), and pharmaceutically acceptable salts thereof, wherein X is optionally substituted heteroaryl.

In certain embodiments, the present invention relates to compounds of Formula (I) and pharmaceutically acceptable salts thereof, wherein A is optionally substituted thiophenyl, optionally substituted imidazolyl, optionally substituted thiazolyl, optionally substituted oxazolyl, optionally substituted pyridyl.

In certain embodiments, the present invention relates to compounds of Formula (I), and pharmaceutically acceptable salts thereof, wherein Y is optionally substituted phenyl. In certain embodiments, the present invention relates to compounds of Formula (I), and pharmaceutically acceptable salts thereof, wherein Y is optionally substituted heteroaryl. In certain embodiments, the present invention relates to compounds of Formula (I), and pharmaceutically acceptable salts thereof, wherein Y is optionally substituted azolyl or optionally substituted pyridyl.

In certain embodiments, the present invention relates to compounds of Formula (I), and pharmaceutically acceptable salts thereof, wherein X is optionally substituted phenyl; and Y is an optionally substituted heteroaryl. In certain embodiments, the present invention relates to compounds of Formula (I), and pharmaceutically acceptable salts thereof, wherein X is optionally substituted phenyl; and Y is optionally substituted azolyl, optionally substituted pyridyl, or optionally substituted phenyl.

In certain embodiments, the present invention relates to compounds of Formula (I), and pharmaceutically acceptable salts thereof, wherein X is optionally substituted monocyclic heteroaryl; and Y is optionally substituted azolyl, optionally substituted pyridyl, or optionally substituted phenyl.

In another particular embodiment, the present invention relates to compounds of Formula (I), or a pharmaceutically acceptable salt thereof, wherein A and X are each independently an aryl or heteroaryl group derived from one of the following by removal of one hydrogen atom:

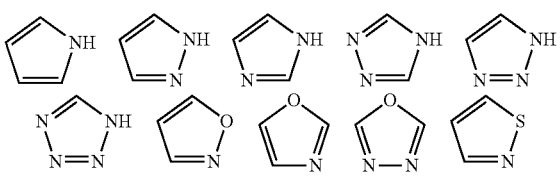

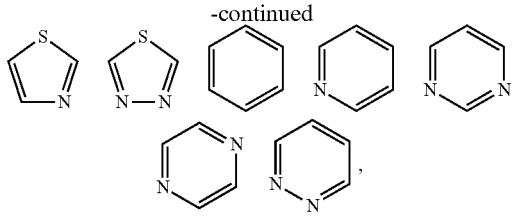

wherein each of the above shown aryl and heteroaryl groups is optionally substituted and is preferably connected to the dihydropyrimidine core through a carbon atom.

In another particular embodiment, the present invention relates to compounds of Formula (I), or a pharmaceutically acceptable salt thereof, wherein at least one of A and X is an aryl or heteroaryl group derived from one of the following by removal of one hydrogen atom:

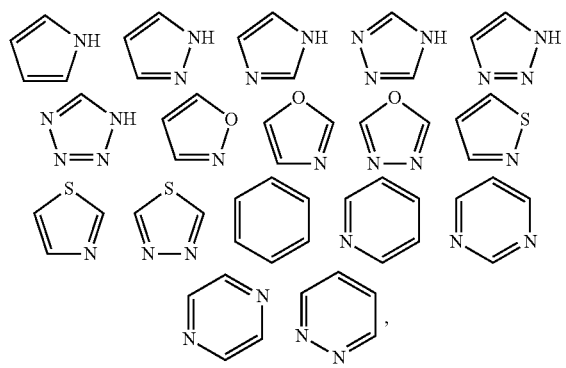

wherein each of the above shown aryl and heteroaryl groups is optionally substituted and is preferably connected to the dihydropyrimidine core through a carbon atom.

In certain embodiments, A and X are each independently selected from the groups set forth below:

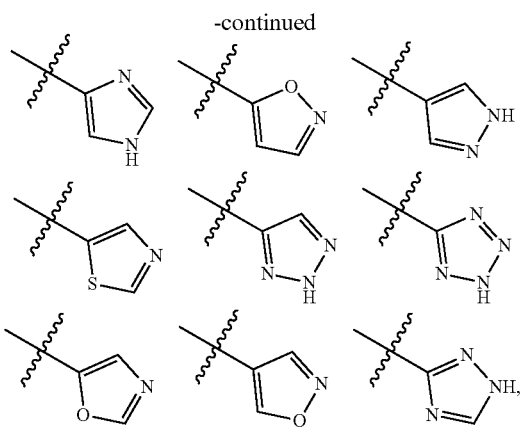

wherein each of the above shown groups is optionally substituted. The preferred substituents are optionally substituted methyl, halo, CN, $OR_{11}$, and $-NR_{11}R_{12}$; wherein $R_{11}$ and $R_{12}$ are as previously defined.

In certain embodiments, at least one of A and X is selected from the groups set forth below:

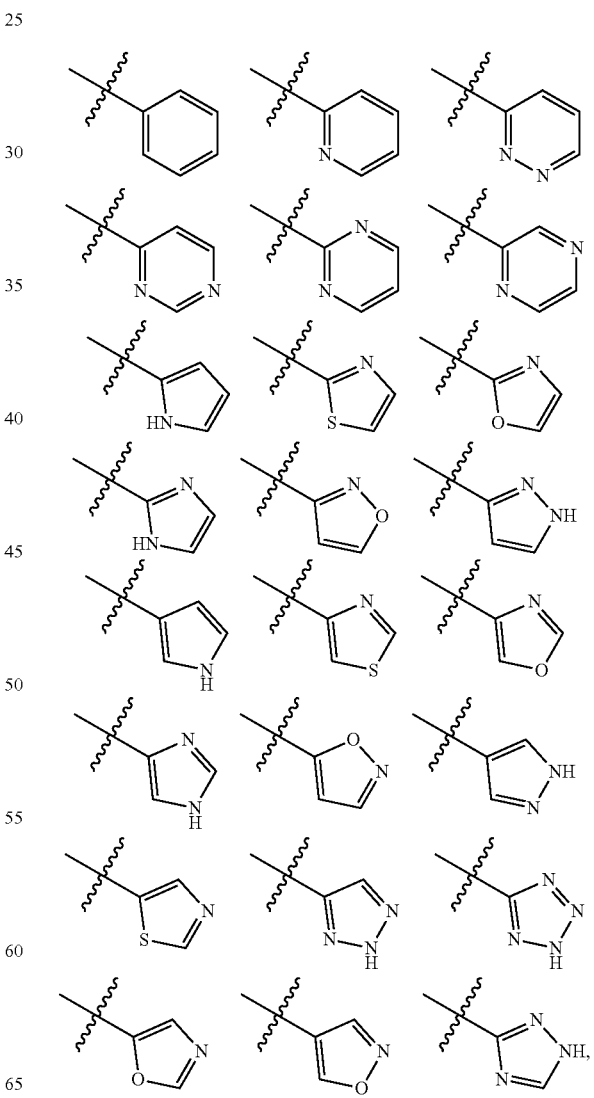

wherein each of the above shown groups is optionally substituted when possible. The preferred substituents are optionally substituted methyl, halo, CN, $OR_{11}$, or $-NR_{11}R_{12}$; wherein $R_{11}$ and $R_{12}$ are as previously defined.

In certain embodiments, the present invention relates to compounds of Formula (I) and pharmaceutically acceptable salts thereof, wherein Y is selected from the groups set forth below:

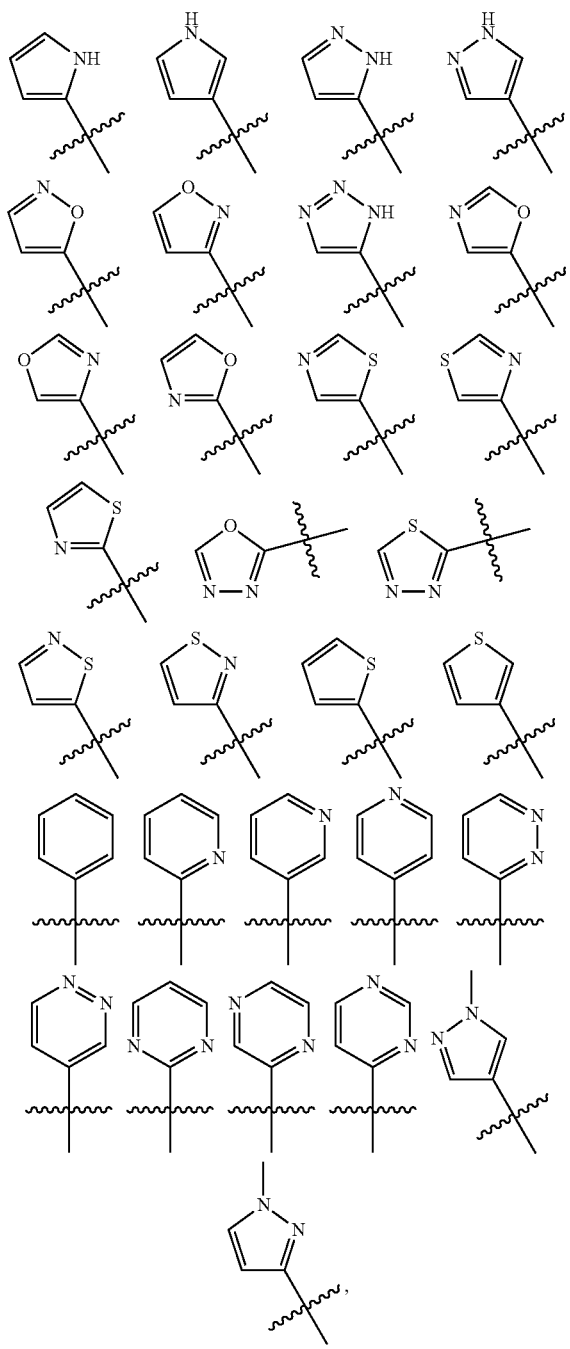

wherein each of the above shown groups is optionally substituted. The preferred substituents include optionally substituted methyl, halo, —CN, $-OR_{11}$, and $-NR_{11}R_{12}$; wherein $R_{11}$ and $R_{12}$ are as previously defined.

In certain embodiments, the present invention relates to compounds of Formula (I) and pharmaceutically acceptable salts thereof, wherein Y is optionally substituted azolyl.

In certain embodiments, the present invention relates to compounds of Formula (I) and pharmaceutically acceptable salts thereof, wherein Y is selected from the groups set forth below:

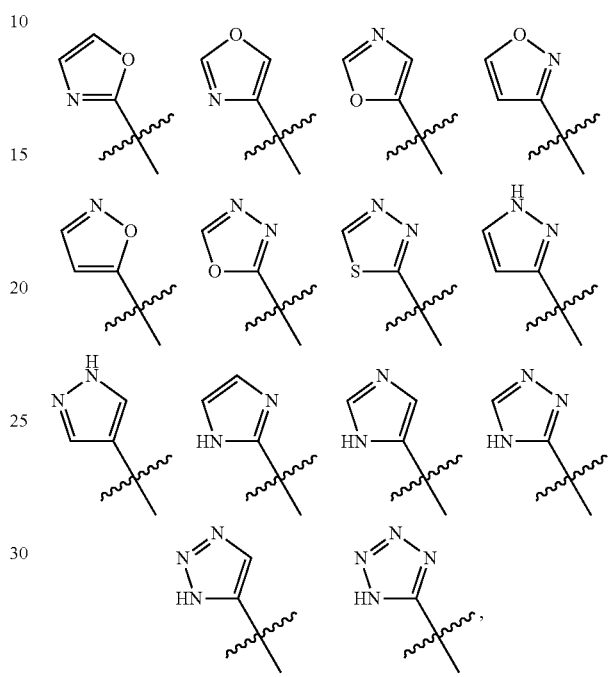

wherein each of the above shown groups is optionally substituted when possible.

In certain embodiments, the present invention relates to compounds of Formula (I) and pharmaceutically acceptable salts thereof, wherein Y is selected from the groups set forth below:

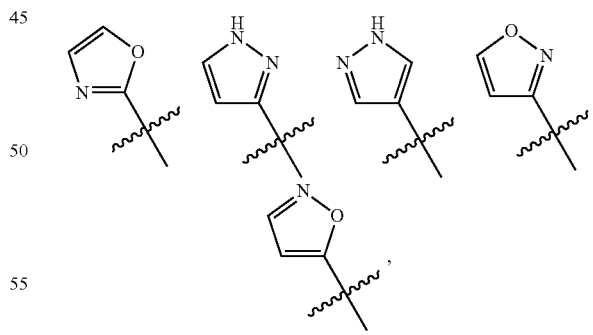

wherein each of the above shown groups is optionally substituted. The preferred substituents include optionally substituted $-C_1$-$C_4$-alkyl, halo, —CN, $-OR_{11}$, and $-NR_{11}R_{12}$; $R_{11}$ and $R_{12}$ are as previously defined.

In certain embodiments, the present invention relates to compounds of Formula (I) and pharmaceutically acceptable salts thereof, wherein Y is selected from the groups set forth below:

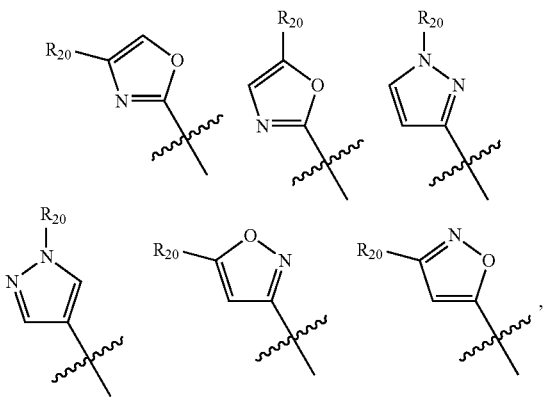

wherein $R_{20}$ is $R_{11}$, $R_{11}$ is as defined above. Preferably, optionally substituted $C_1$-$C_4$-alkyl or $C_3$-$C_6$-cycloalkyl. More preferably, $R_{20}$ is optionally substituted methyl or optionally substituted cyclopropyl. In certain embodiments, $R_{20}$ is difluoromethyl, trifluoromethyl, cyclopropyl or 2,2,2-trifluoroethyl.

In another embodiment, the compound of Formula (I) is represented by Formula (IIa) or (IIb) or a pharmaceutically acceptable salt thereof:

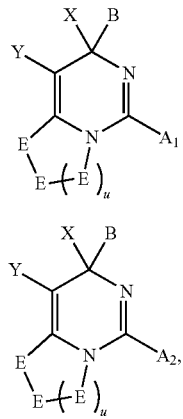

IIa

IIb wherein $A_1$ is a optionally substituted 5-membered heteroaryl group containing 1 to 4 heteroatoms selected from O, N, and S; preferably $A_1$ is an optionally substituted azole group including but not limited to pyrrolyl, pyrazolyl, imidazolyl, thiazolyl, oxazolyl, isooxazolyl, thiadiazolyl, oxadiazolyl; each optionally substituted; $A_2$ is an optionally substituted phenyl, thiophenyl or 6-membered heteroaryl group including but not limited to pyridinyl, pyrazinyl, or pyrimidinyl; each optionally substituted; B, X, Y, E and u are as previously defined.

In certain embodiments, the present invention relates to compounds of Formula (IIa) or (IIb) and pharmaceutically acceptable salts thereof, wherein two vicinal E groups are taken together to form a C=C double-bond, a C=N double-bond or a fused ring.

In certain embodiments, the present invention relates to compounds of Formula (IIa) or (IIb) or pharmaceutically acceptable salts thereof, wherein

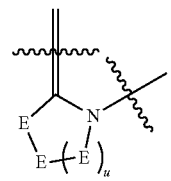

is selected from the groups set forth below:

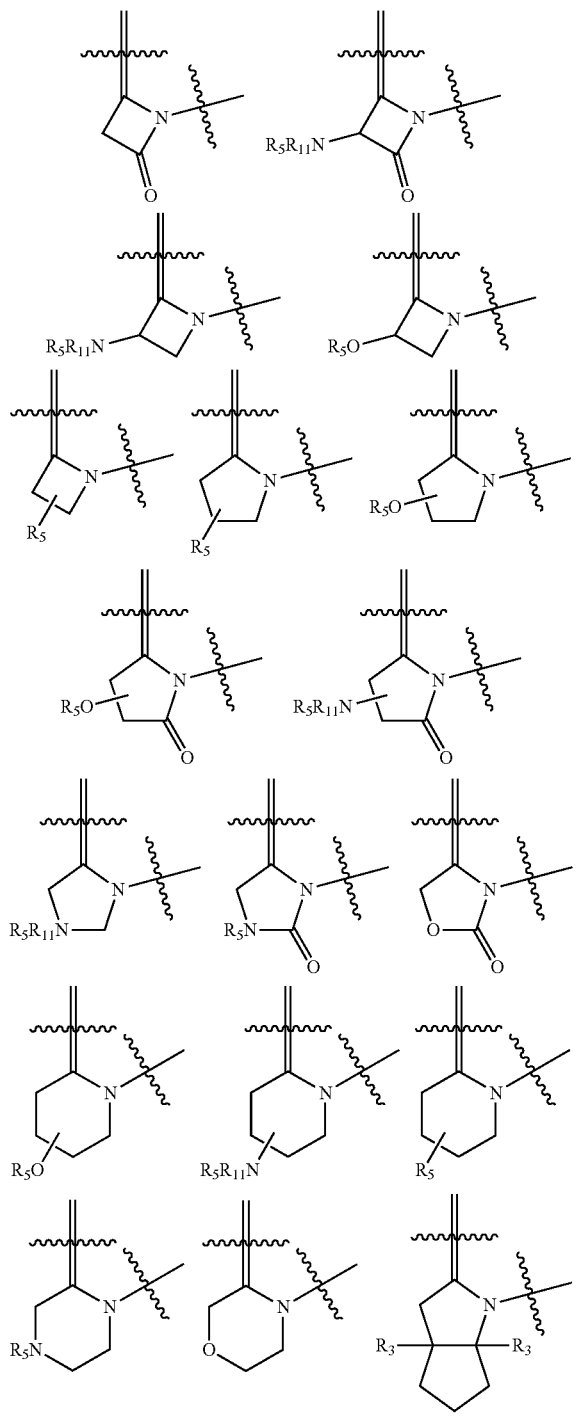

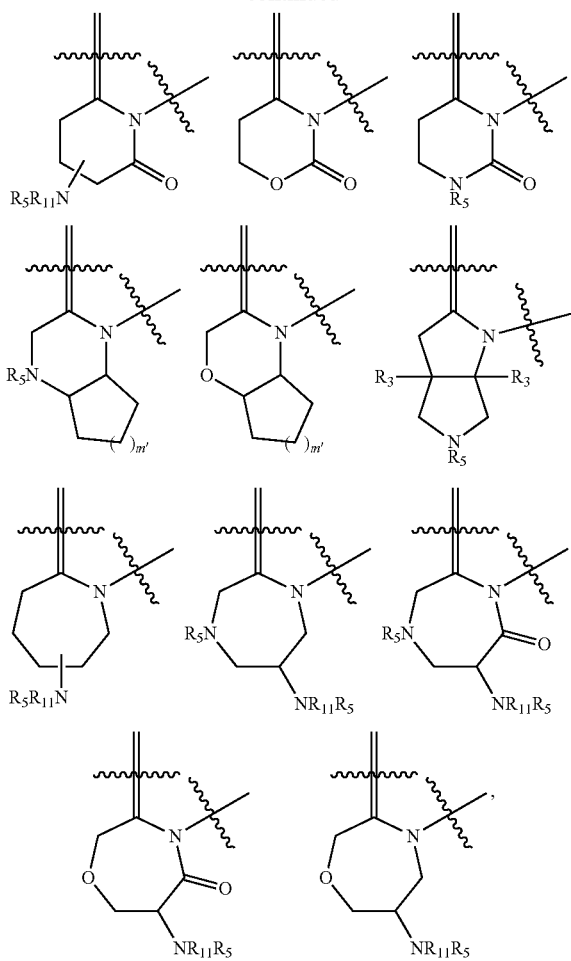

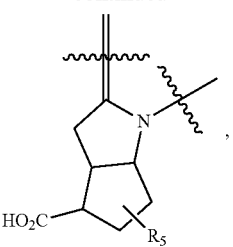

wherein each of the above shown groups is optionally substituted; the preferred substituents include halo, $-OR_{11}$, $-CN$, $-CO_2R_{11}$, $-C(O)NR_{11}R_{12}$, optionally substituted methyl, and optionally substituted phenyl; $R_3$ is selected from the group consisting of hydrogen, optionally substituted $-C_1$-$C_8$ alkyl, optionally substituted $-C_2$-$C_8$ alkenyl, optionally substituted $-C_2$-$C_8$ alkynyl, optionally substituted $-C_3$-$C_8$ cycloalkyl, $-CN$, $-OR_{11}$, and $-NR_{11}R_{12}$; $R_8$ is selected from the group consisting of hydrogen, optionally substituted $-C_1$-$C_8$ alkyl, optionally substituted $-C_2$-$C_8$ alkenyl, optionally substituted $-C_2$-$C_8$ alkynyl, optionally substituted $-C_3$-$C_8$ cycloalkyl, optionally substituted 3- to 8-membered heterocyclic, optionally substituted aryl, optionally substituted heteroaryl, $-C(O)OR_{11}$, $-C(O)NR_{11}R_{12}$, $-S(O)_2R_{11}$, $-S(O)_2NR_{11}R_{12}$, $-C(O)NR_{11}S(O)_2R_{12}$; m' is 1, 2, or 3; $R_{11}$, and $R_{12}$ are as previously defined.

More preferably, $R_5$ is selected from the groups set forth below:

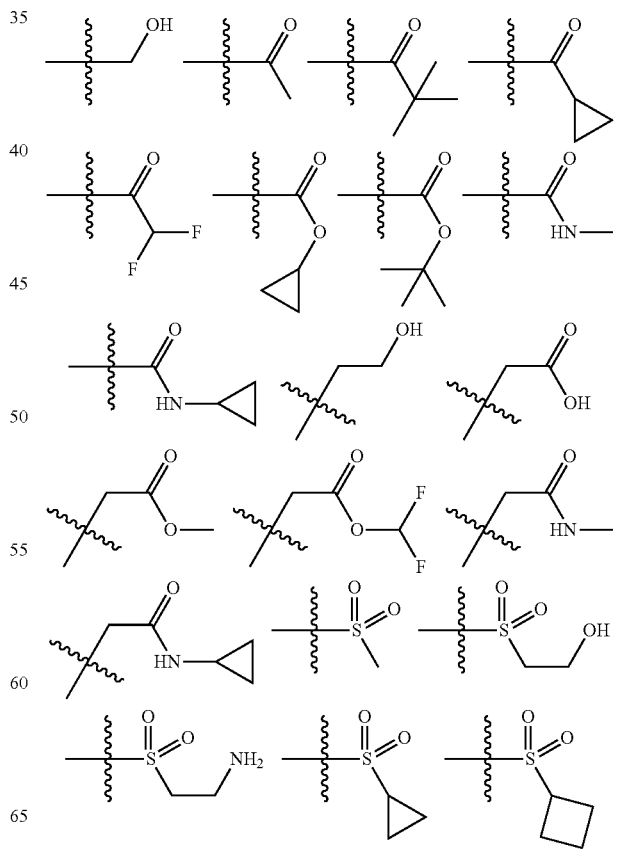

or

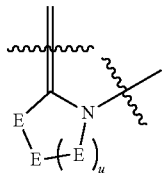

is selected from the groups set forth below:

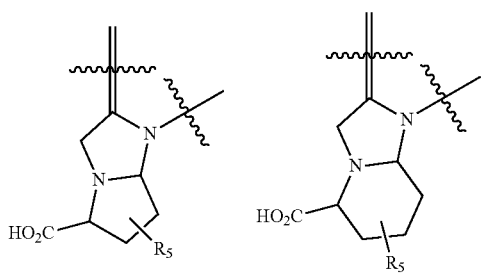

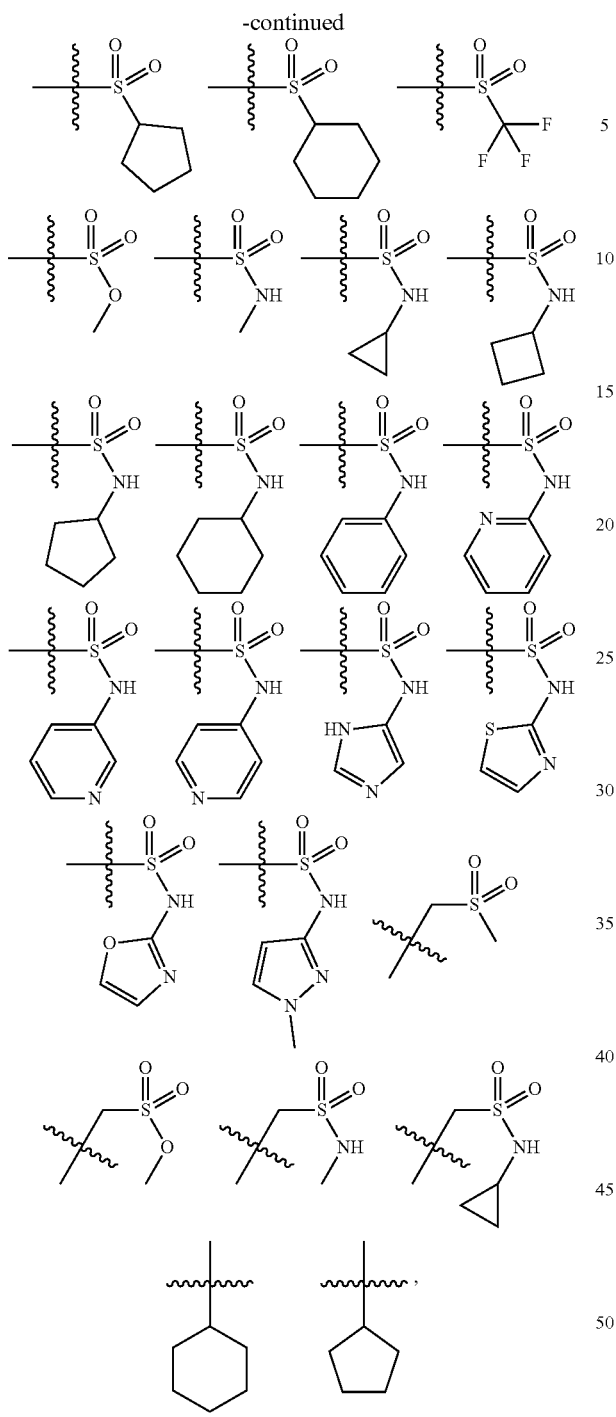

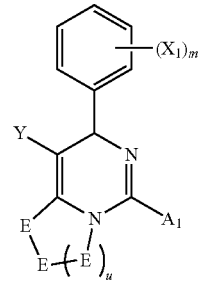

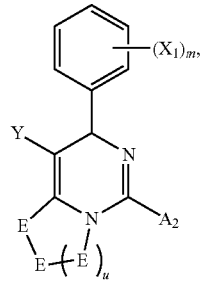

wherein $X_1$ is optionally substituted methyl, halo, CN, $OR_{11}$, or $NR_{11}R_{12}$; m is 0, 1, 2, 3, 4 or 5; $A_1$, $A_2$, Y, E, $R_{11}$, $R_{12}$ and u are as previously defined.

In certain embodiments, the compound of Formula (I) is represented by Formula (IIa-1) or (IIb-1), or a pharmaceutically acceptable salt thereof, wherein m is 0 or m is 1-5 and each $X_1$ is halo. In certain embodiments, the compound of Formula (I) is represented by Formula (IIa-1) or (IIb-1), or a pharmaceutically acceptable salt thereof, wherein Y is optionally substituted azolyl.

In certain embodiment, the compound of Formula (I) is represented by Formula (IIa-2) or (IIb-2), or a pharmaceutically acceptable salt thereof,

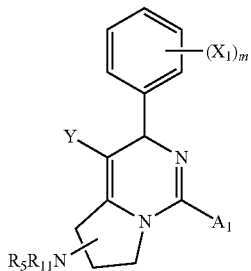

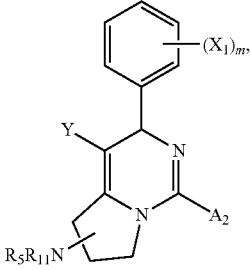

wherein $A_1$, $A_2$, $X_1$, m, Y, $R_5$ and $R_{11}$ are as previously defined.

wherein each of the above shown groups is optionally substituted when possible; the preferred substituents include halo, —$OR_{11}$, —CN, —$CO_2R_{11}$, —C(O)$NR_{11}R_{12}$, optionally substituted methyl, and optionally substituted phenyl. In another embodiment, $R_5$ is —$SO_2NH_2$.

Alternatively, $R_5$ and $R_{11}$ are taken together with the nitrogen atom to which they are attached to form an optionally substituted 3- to 12-membered heterocyclic.

In another embodiment, the compound of Formula (I) is represented by Formula (IIa-1) or (IIb-1), or a pharmaceutically acceptable salt thereof:

In certain embodiments, the compound of Formula (I) is represented by Formula (IIa-2) or (IIb-2), or a pharmaceutically acceptable salt thereof, wherein $A_1$, $A_2$, $X_1$, m, $R_5$ and $R_{11}$ are as previously defined, and Y is optionally substituted azolyl. Preferably Y is optionally substituted pyrazolyl or oxazolyl.

In certain embodiments, the compound of Formula (I) is represented by Formula (IIa-3) or (IIb-3), or a pharmaceutically acceptable salt thereof,

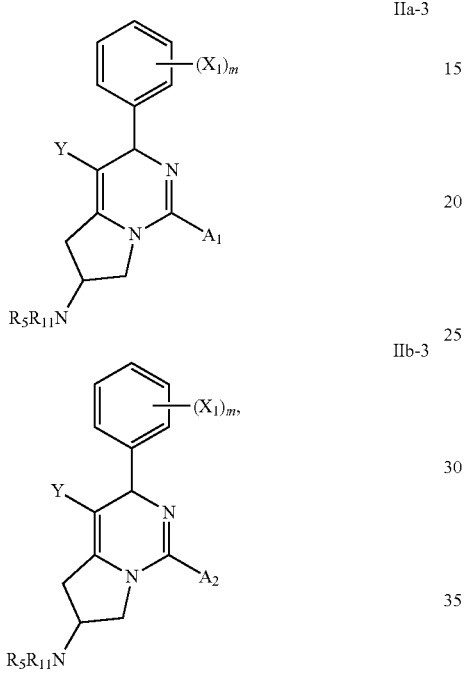

IIa-3

IIb-3 wherein $A_1$, $A_2$, $X_1$, m, Y, $R_5$ and $R_{11}$ are as previously defined.

In certain embodiments, the compound of Formula (I) is represented by Formula (IIa-3) or (IIb-3), or a pharmaceutically acceptable salt thereof, wherein $A_1$, $A_2$, $X_1$, m, $R_5$ and $R_{11}$ are as previously defined, and Y is optionally substituted azolyl. Preferably Y is optionally substituted pyrazolyl or oxazolyl.

In certain embodiments, the compound of Formula (I) is represented by Formula (IIa-4), (IIb-4), (IIa-5), or (IIb-5), or a pharmaceutically acceptable salt thereof,

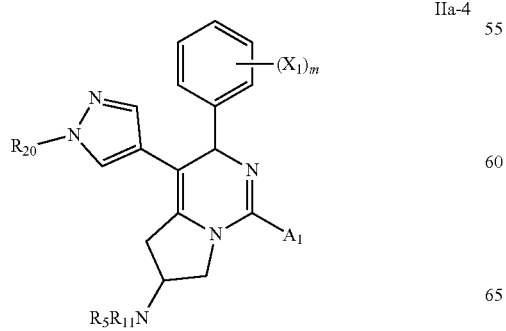

IIa-4

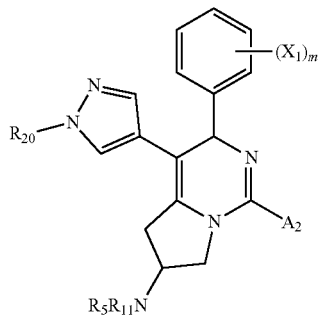

IIb-4

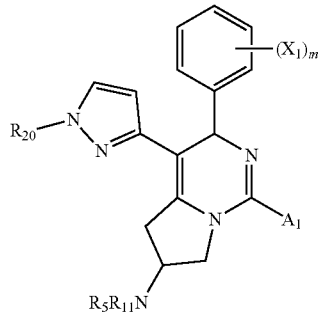

IIa-5

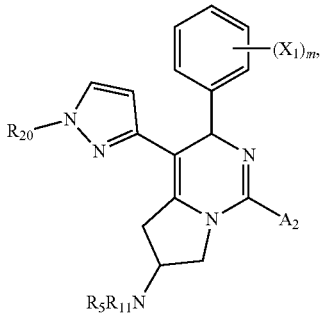

IIb-5 wherein $A_1$, $A_2$, $X_1$, m, $R_5$, $R_{11}$ and $R_{20}$ are as previously defined.

In certain embodiments, the compound of Formula (I) is represented by Formula (III-1) or (III-2), or a pharmaceutically acceptable salt thereof,

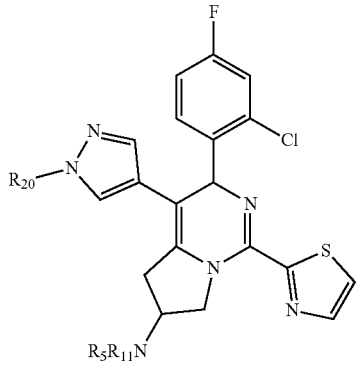

III-1

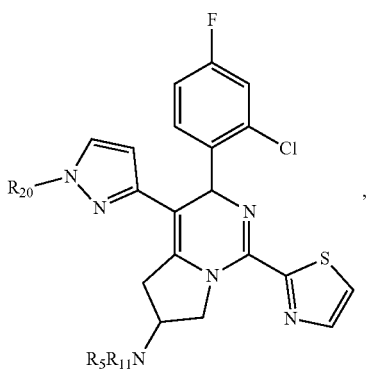

wherein $R_5$, $R_{11}$ and $R_{20}$ are as previously defined.

In certain embodiments of the compounds of Formulae (IIa-5) (IIb-5) and ((III-2), $R_{20}$ is not methyl. In other embodiments of the compounds of Formulae (IIa-5), (IIb-5), and (III-2), $R_{20}$ is not methyl, ethyl or difluoromethyl.

In certain embodiments of the compounds of Formulae (IIa-5), (IIb-5) and (III-2), $R_{20}$ is difluoromethyl, cyclopropyl, isopropyl, trifluoromethyl or 2,2,2-trifluoroethyl. In certain embodiments of the compounds of Formulae (IIa-5), (IIb-5) and (III-2), $R_{20}$ is methyl, ethyl, or difluoromethyl. In certain embodiments of the compounds of Formulae (IIa-5), (IIb-5) and (III-2), $R_{20}$ is difluoromethyl. In one embodiment, the compounds of the invention do not include the compound of Formula (III-2) where $R_{20}$ is methyl, $R_{11}$ is hydrogen and $R_5$ is $-S(O)_2$-cyclopropyl.

In certain embodiments, the compound of Formula (I) is represented by Formula (IV-1), or Formula (IV-2), or a pharmaceutically acceptable salt thereof,

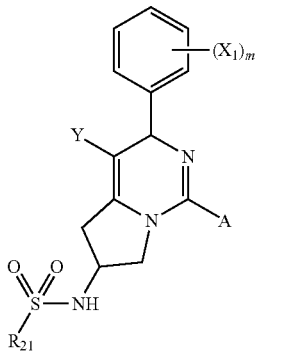

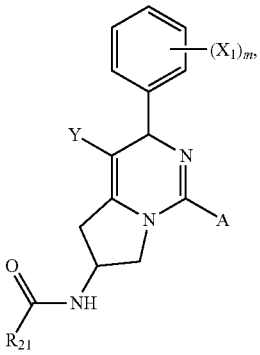

wherein $R_{21}$ is selected from the group consisting of hydrogen, optionally substituted $-C_1$-$C_8$ alkyl, $-OR_{11}$, $-NR_{11}R_{12}$, optionally substituted $-C_3$-$C_{12}$ cycloalkyl, optionally substituted $-C_3$-$C_{12}$ cycloalkenyl, optionally substituted 3- to 12-membered heterocyclic, optionally substituted aryl and optionally substituted heteroaryl; $X_1$, m, Y, A, $R_{11}$ and $R_{12}$ are as previously defined. Alternatively, $R_{11}$ and $R_{12}$ are taken together with the nitrogen atom to which they are attached to an optionally substituted 3- to 12-membered hetercyclic.

In certain embodiments, the compound of Formula (I) is represented by Formula (IV-3), or a pharmaceutically acceptable salt thereof,

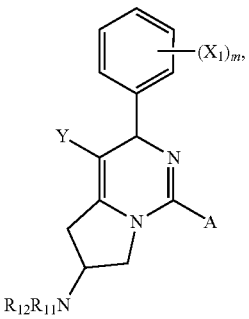

wherein $R_{11}$, $R_{12}$, $X_1$, m, Y, and A are as previously defined.

In certain embodiments, the compound of Formula (I) is represented by Formula (IV-1a), or Formula (IV-1b), or Formula (IV-2a), or Formula (IV-2b), or a pharmaceutically acceptable salt thereof, -continued IV-2a

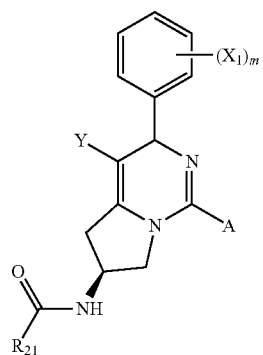

IV-2b

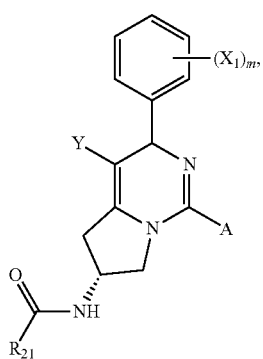

wherein $X_1$, m, Y, A, and $R_{21}$ are as previously defined.

In certain embodiments, the compound of Formula (I) is represented by Formula (IV-3a) or Formula (IV-3b), or a pharmaceutically acceptable salt thereof, IV-3a

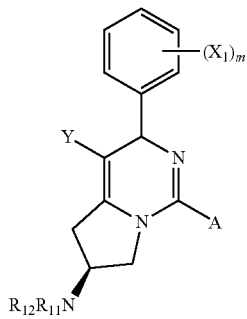

IV-3b

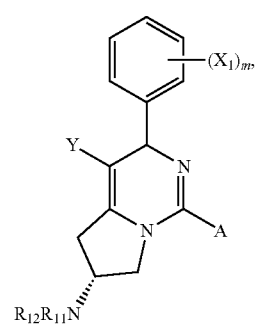

wherein $R_{11}$, $R_{12}$, $X_1$, m, Y, and A are as previously defined.

In preferred embodiments, compounds of Formula (I) have the stereochemistry shown in Formula (IV-1a), Formula (IV-2a), and Formula (IV-3a).

In certain embodiments, the compound of Formula (I) is represented by Formula (V-1a), or Formula (V-1b), or Formula (V-2a), or Formula (V-2b), or a pharmaceutically acceptable salt thereof, V-1a

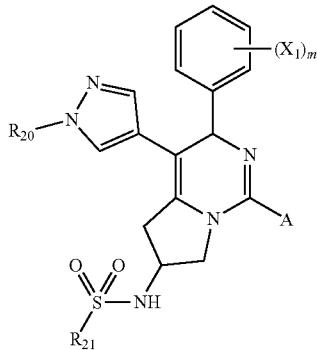

V-1b

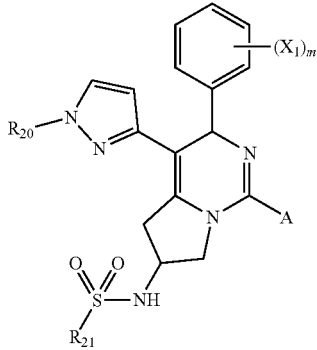

V-2a

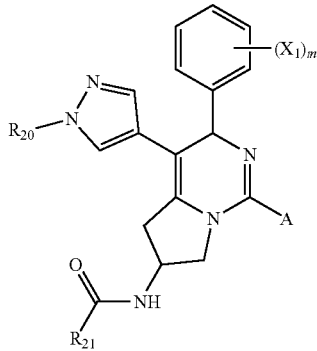

V-2b

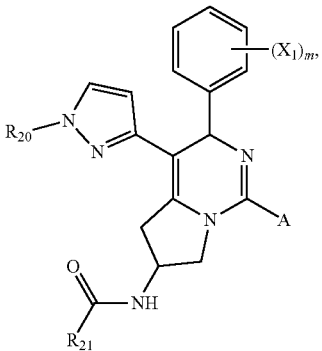

wherein $X_1$, m, A, $R_{20}$ and $R_{21}$ are as previously defined.

In certain embodiments, the compound of Formula (I) is represented by Formula (V-3a) or Formula (V-3b), or a pharmaceutically acceptable salt thereof, V-3a

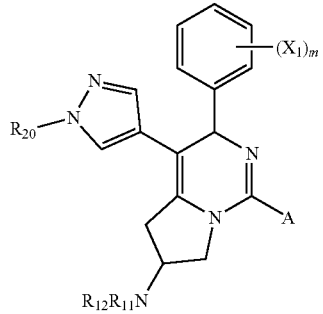

V-3b

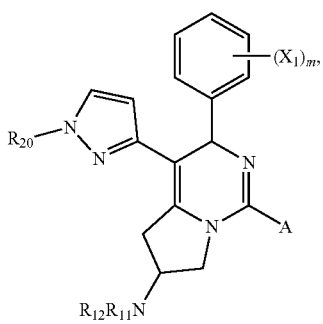

wherein $X_1$, m, A, $R_{10}$ and $R_{12}$ are as previously defined.

In certain embodiments, the compound of Formula (I) is represented by Formula (VI-1a), or Formula (VI-1b), or Formula (VI-2a), or Formula (VI-2b), or a pharmaceutically acceptable salt thereof, VI-1a

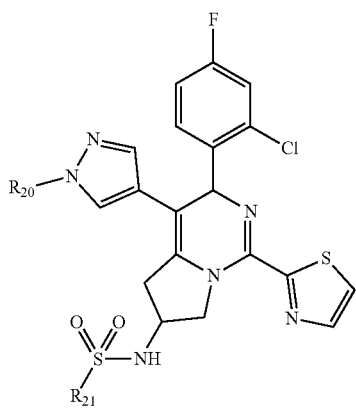

VI-1b

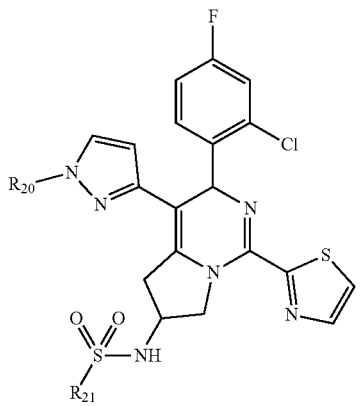

VI-2a

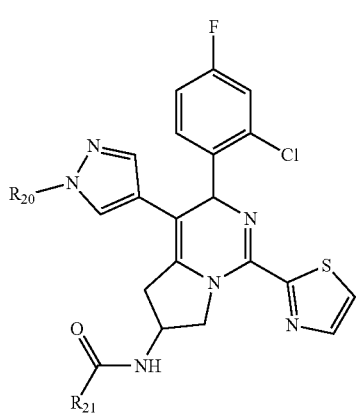

VI-2b

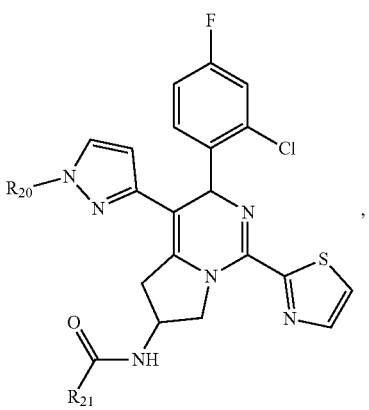

wherein $R_{20}$ and $R_{21}$ are as previously defined.

In certain embodiments, the compound of Formula (I) is represented by Formula (VI-3a), or Formula (VI-3b), or a pharmaceutically acceptable salt thereof, VI-3a

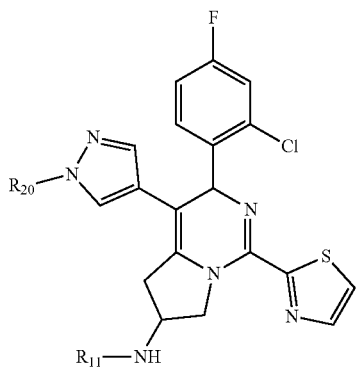

VII-1b

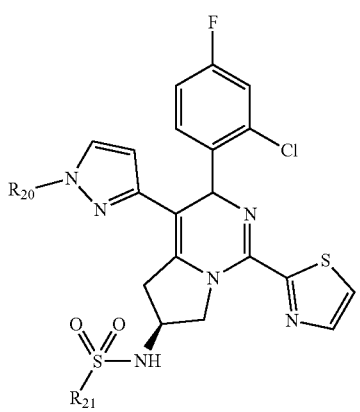

VI-3b

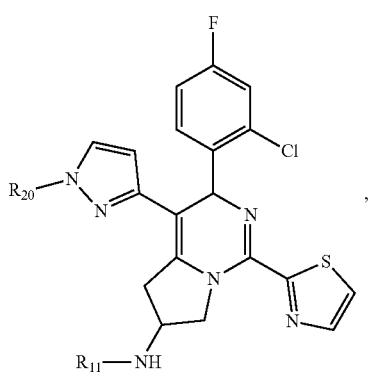

,

VII-2a

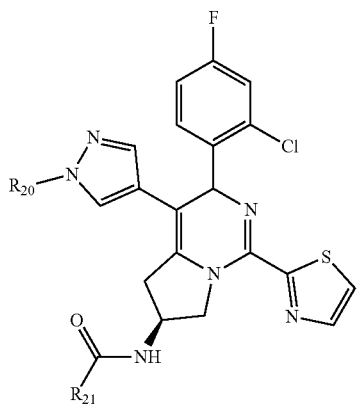

wherein R$_{20}$ and R$_{21}$ are as previously defined.

In certain embodiments, the compound of Formula (I) is represented by Formula (VII-1a), or Formula (VII-1b), or Formula (VII-2a), or Formula (VII-2b), or a pharmaceutically acceptable salt thereof, VII-1a

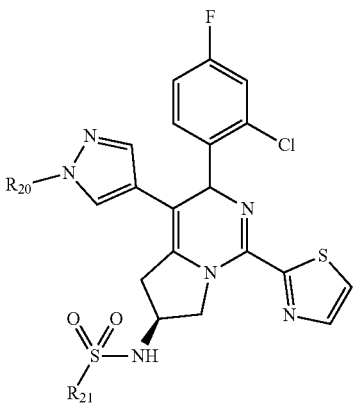

VII-2b

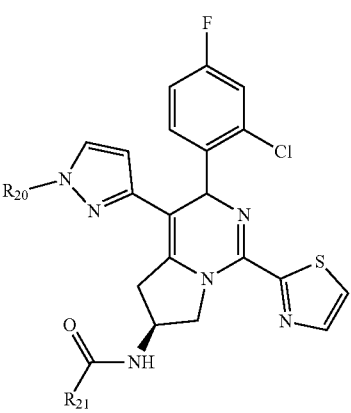

, wherein R$_{20}$ and R$_{21}$ are as previously defined.

In certain embodiments, the compound of Formula (I) is represented by Formula (VII-3a), or Formula (VII-3b), or a pharmaceutically acceptable salt thereof, VII-3a

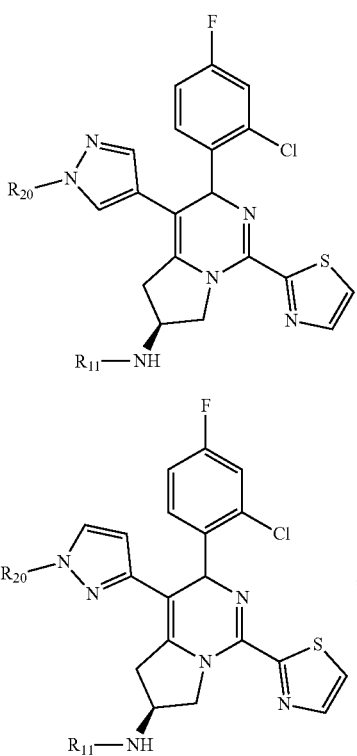

VII-3b wherein $R_{20}$ and $R_{11}$ are as previously defined.

In another embodiment, the compound of Formula (I) is represented by Formula (VIIIa-1) or (VIIIb-1), or a pharmaceutically acceptable salt thereof:

VIIIa-1

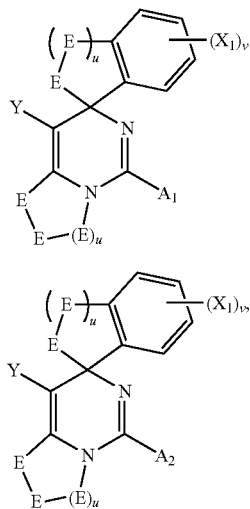

VIIIb-1

Wherein E at each occurrence is the same or different; u at each occurrence is the same or different and independently selected from 0, 1, 2, or 3; v is 0, 1, 2, 3, or 4; $X_1$, $A_1$, $A_2$, Y, and E are as previously defined.

In certain embodiments, the present invention relates to compounds of Formula (VIIIa-1) or (VIIIb-1) and pharmaceutically acceptable salts thereof, wherein two vicinal E groups are taken together to form an optionally substituted C=C double-bond or an optionally substituted fused ring. In certain embodiments, two non-adjacent E groups are taken together to form a bridging group.

In certain embodiments, the compound of Formula (I) is represented by Formula (XIa) or (XIb), or a pharmaceutically acceptable salt thereof, XIa

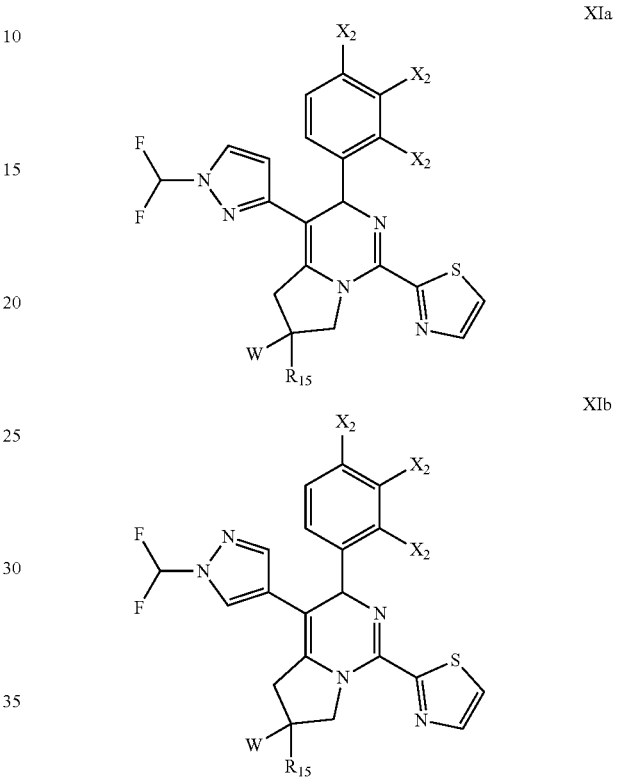

XIb wherein $X_2$ at each occurrence is independently selected from hydrogen or halogen; W is selected from the group consisting of hydrogen, halogen, CN, $-N_3$, $-OR_{11}$, $-NR_{11}R_{12}$, protected hydroxy, protected amino, optionally substituted $-C_1-C_8$ alkyl, optionally substituted $-C_2-C_8$ alkenyl, optionally substituted $-C_2-C_8$ alkynyl, optionally substituted $-C_3-C_8$ cycloalkyl, optionally substituted 3- to 8-membered heterocyclic, optionally substituted aryl, optionally substituted heteroaryl, $-C(O)R_{11}$, $-C(O)OR_{11}$, $-NR_{11}CONR_{11}R_{12}$, $-S(O)_2R_{11}$, $-S(O)_2NR_{11}R_{12}$, $-NR_{11}S(O)_2R_{12}$, $-NR_{11}S(O)_2NR_{11}R_{12}$, $-P(O)(OR_{11})_2$, and $-NR_{11}P(O)(OR_{11})_2$, $R_3$, $R_{15}$, $R_{11}$ and $R_{12}$ are as previously defined.

In an embodiment, the present invention relates to compounds of Formula (XIa) and (XIb), and pharmaceutically acceptable salts thereof, wherein W is selected from the group consisting of hydrogen, halogen, CN, $-N_3$, $-OR_{11}$, $-NR_{11}R_{12}$, protected hydroxy, and protected amino; and $R_{15}$ is optionally substituted $-C_1-C_8$ alkyl. It will be appreciated that the description of the present invention herein should be construed in congruity with the laws and principles of chemical bonding. In some instances, it may be necessary to remove a hydrogen atom in order to accommodate a substituent at any given location.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In one aspect, the compounds of the invention are useful in HBV treatment by disrupting, accelerating, reducing, delaying and/or inhibiting normal viral capsid assembly and/or disassembly of immature or mature particles, thereby inducing aberrant capsid morphology and leading to antiviral effects such as disruption of virion assembly and/or disassembly, virion maturation, and/or virus egress. In one embodiment, a disruptor of capsid assembly interacts with mature or immature viral capsid to perturb the stability of the capsid, thus affecting assembly and/or disassembly. In another embodiment, a disruptor of capsid assembly perturbs protein folding and/or salt bridges required for stability, function and/or normal morphology of the viral capsid, thereby disrupting and/or accelerating capsid assembly and/or disassembly. In yet another embodiment, the compounds of the invention bind capsid and alter metabolism of cellular polyproteins and precursors, leading to abnormal accumulation of protein monomers and/or oligomers and/or abnormal particles, which causes cellular toxicity and death of infected cells. In another embodiment, the compounds of the invention cause failure of the formation of capsid of optimal stability, affecting efficient uncoating and/or disassembly of viruses (e.g., during infectivity).

In one embodiment, the compounds of the invention disrupt and/or accelerate capsid assembly and/or disassembly when the capsid protein is immature. In another embodiment, the compounds of the invention disrupt and/or accelerate capsid assembly and/or disassembly when the capsid protein is mature. In yet another embodiment, the compounds of the invention disrupt and/or accelerate capsid assembly and/or disassembly during vial infectivity. In yet another embodiment, the disruption and/or acceleration of capsid assembly and/or disassembly attenuates HBV viral infectivity and/or reduces viral load. In yet another embodiment, disruption, acceleration, inhibition, delay and/or reduction of capsid assembly and/or disassembly eradicates the virus from the host organism. In yet another embodiment, eradication of the HBV from a host advantageously obviates the need for chronic long-term therapy and/or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibit, disrupt or accelerate) the activity of HBV cccDNA. In yet another embodiment, the compounds of the invention can be used in methods of diminishing or preventing the formation of HBV cccDNA. In another embodiment, the additional therapeutic agent is selected from core inhibitor, which includes GLS4, GLS4JHS, JNJ-379, ABI-H0731, ABI-H2158, AB-423, AB-506, WX-066, and QL-0A6A; immune modulator or immune stimulator therapies, which includes T-cell response activator AIC649 and biological agents belonging to the interferon class, such as interferon alpha 2a or 2b or modified interferons such as pegylated interferon, alpha 2a, alpha 2b, lamda; or STING (stimulator of interferon genes) modulator; or TLR modulators such as TLR-7 agonists, TLR-8 agonists or TLR-9 agonists; or therapeutic vaccines to stimulate an HBV-specific immune response such as virus-like particles composed of HBcAg and HBsAg, immune complexes of HBsAg and HBsAb, or recombinant proteins comprising HBx, HBsAg and HBcAg in the context of a yeast vector; or immunity activator such as SB-9200 of certain cellular viral RNA sensors such as RIG-I, NOD2, and MDA5 protein, or RNA interence (RNAi) or small interfering RNA (siRNA) such as ARC-520, ARC-521, ARO-HBV, ARB-1467, and ALN-HBV RNAi, or antiviral agents that block viral entry or maturation or target the HBV polymerase such as nucleoside or nucleotide or non-nucleos(t)ide polymerase inhibitors, and agents of distinct or unknown mechanism including agents that disrupt the function of other essential viral protein(s) or host proteins required for HBV replication or persistence such as REP 2139, RG7834, and AB-452. In an embodiment of the combination therapy, the reverse transcriptase inhibitor is at least one of Zidovudine, Didanosine, Zalcitabine, ddA, Stavudine, Lamivudine, Aba-cavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another embodiment of the combination therapy, the TLR-7 agonist is selected from the group consisting of SM360320 (9-benzyl-8-hydroxy-2-(2-methoxy-ethoxy)adenine), AZD 8848 (methyl [3-({[3-(6-amino-2-butoxy-8-oxo-7,8-dihydro-9H-purin-9-yl)propyl][3-(4-morpholinyl) propyl] amino ]methyl)phenyl] acetate), GS-9620 (4-Amino-2-butoxy-8-[3-(1-pyrrolidinylmethyl)benzyl]-7, 8-dihydro-6(5H)-pteridinone), AL-034 (TQ-A3334), and RO6864018.

In another embodiment of the combination therapy, the TLR-8 agonist is GS-9688.

In an embodiment of these combination therapies, the compound and the additional therapeutic agent are co-formulated. In another embodiment, the compound and the additional therapeutic agent are co-administered.

In another embodiment of the combination therapy, administering the compound of the invention allows for administering of the additional therapeutic agent at a lower dose or frequency as compared to the administering of the at least one additional therapeutic agent alone that is required to achieve similar results in prophylactically treating an HBV infection in an individual in need thereof.

In another embodiment of the combination therapy, before administering the therapeutically effective amount of the compound of the invention, the individual is known to be refractory to a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In still another embodiment of the method, administering the compound of the invention reduces viral load in the individual to a greater extent compared to the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In another embodiment, administering of the compound of the invention causes a lower incidence of viral mutation and/or viral resistance than the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

It should be understood that the compounds encompassed by the present invention are those that are suitably stable for use as pharmaceutical agent.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "azole group," as used herein, refers to 5-membered heteroaromatic ring containing at least one nitrogen atom. Preferred azole groups contain a nitrogen atom and at least one additional heteroatom, preferably a nitrogen, oxygen or sulfur atom. Azole groups include, but are not limited to pyrazolyl, imidazolyl, thiazolyl, oxazolyl, isoxazolyl, 1,2,3-triazolyl, 1,2,4-triazolyl, tetrazolyl. An azole group is termed "ortho" substituted in reference to two substituents which are on adjacent ring atoms. An azole group is termed "meta" substituted in reference to two substituents which are not on adjacent ring positions.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon double bond by the removal of a single hydrogen atom. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), S(O)$_2$, C(O)O, C(O)NH, OC(O)O, OC(O)NH, OC(O)$NH_2$, S(O)$_2$NH, S(O)$_2NH_2$, NHC(O)$NH_2$, NHC(O)C(O)NH, NHS(O)$_2$NH, NHS(O)$_2NH_2$, C(O)NHS(O)$_2$, C(O)NHS(O)$_2$NH or C(O)NHS(O)$_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —C$_1$, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —NO$_2$, —N$_3$, —CN, —NH$_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH— heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_8$-alkenyl, —OCO$_2$—$C_2$-$C_8$-alkynyl, —OCO$_2$—$C_3$-$C_{12}$-cycloalkyl, —OCO$_2$-aryl, —OCO$_2$-heteroaryl, —OCO$_2$-heterocycloalkyl, —CO$_2$—$C_1$-$C_{12}$ alkyl, —CO$_2$—$C_2$-$C_8$ alkenyl, —CO$_2$—$C_2$-$C_8$ alkynyl, CO$_2$—$C_3$-$C_{12}$-cycloalkyl, —CO$_2$— aryl, CO$_2$-heteroaryl, CO$_2$-heterocyloalkyl, —OCONH$_2$, —OCONH-$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —NHCO$_2$—$C_1$-$C_{12}$-alkyl, —NHCO$_2$—$C_2$-$C_8$-alkenyl, —NHCO$_2$—$C_2$-$C_8$-alkynyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —SO$_2$NH$_2$, —SO$_2$NH—$C_1$-$C_{12}$-alkyl, —SO$_2$NH—$C_2$-$C_8$-alkenyl, —SO$_2$NH—$C_2$-$C_8$-alkynyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_8$-alkenyl, —NHSO$_2$—$C_2$-$C_8$-alkynyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. In certain embodiments, the substituents are independently selected from halo, preferably Cl and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$-alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy, —CN; —OH; NH$_2$; $C_1$-$C_4$-alkylamino; di($C_1$-$C_4$-alkyl)amino; and NO$_2$. It is understood that the aryls, heteroaryls, alkyls, and the like can be further substituted. In some cases, each substituent in a substituted moiety is additionally optionally substituted with one or more groups, each group being independently selected from $C_1$-$C_4$-alkyl; —CF$_3$, —OCH$_3$, —OCF$_3$, —F, —Cl, —Br, —I, —OH, —NO$_2$, —CN, and —NH$_2$. Preferably, a substituted alkyl group, such as a substituted methyl group, is substituted with one or more halogen atoms, more preferably one or more fluorine or chlorine atoms.

The term "halo" or "halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis,* John Wiley and Sons (1994); and L. Paquette, ed., *Encyclo-* pedia of Reagents for Organic Synthesis, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semisolid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.

Combination and Alternation Therapy

It has been recognized that drug-resistant variants of HIV, HBV and HCV can emerge after prolonged treatment with an antiviral agent. Drug resistance most typically occurs by mutation of a gene that encodes for a protein such as an enzyme used in viral replication, and most typically in the case of HIV, reverse transcriptase, protease, or DNA polymerase, and in the case of HBV, DNA polymerase, or in the case of HCV, RNA polymerase, protease, or helicase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. The compounds can be used for combination are selected from the group consisting of a HBV polymerase inhibitor, interferon, TLR modulators such as TLR-7 agonists or TLR-8 agonists, therapeutic vaccines, immune activator of certain cellular viral RNA sensors, viral entry inhibitor, viral maturation inhibitor, distinct capsid assembly modulator, antiviral compounds of distinct or unknown mechanism, and combination thereof. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

Preferred compounds for combination or alternation therapy for the treatment of HBV include 3TC, FTC, L-FMAU, interferon, siRNA, adefovir dipivoxil, entecavir, telbivudine (L-dT), valtorcitabine (3'-valinyl L-dC), β-D-dioxolanyl-guanine (DXG), β-D-dioxolanyl-2,6-diaminopurine (DAPD), and β-D-dioxolanyl-6-chloropurine (ACP), famciclovir, penciclovir, lobucavir, ganciclovir, and ribavirin.

Although the invention has been described with respect to various preferred embodiments, it is not intended to be limited thereto, but rather those skilled in the art will recognize that variations and modifications may be made therein which are within the spirit of the invention and the scope of the appended claims.

ABBREVIATIONS

Abbreviations which may be used in the descriptions of the scheme and the examples that follow are: Ac for acetyl; AcOH for acetic acid; AIBN for azobisisobutyronitrile; BINAP for 2,2'-bis(diphenylphosphino)-1,1'-binaphthyl; Boc$_2$O for di-tert-butyl-dicarbonate; Boc for t-butoxycarbonyl; Bpoc for 1-methyl-1-(4-biphenylyl)ethyl carbonyl; Bz for benzoyl; Bn for benzyl; BocNHOH for tert-butyl N-hydroxycarbamate; t-BuOK for potassium tert-butoxide; Bu$_3$SnH for tributyltin hydride; BOP for (benzotriazol-1-yloxy)tris(dimethylamino)phosphonium Hexafluorophosphate; Brine for sodium chloride solution in water; BSA for N,O-bis(trimethylsilyl)acetamide; CDI for carbonyldiimidazole; DCM or CH$_2$Cl$_2$ for dichloromethane; CH$_3$ for methyl; CH$_3$CN for acetonitrile; Cs$_2$CO$_3$ for cesium carbonate; CuCl for copper (I) chloride; CuI for copper (I) iodide; dba for dibenzylidene acetone; dppb for diphenylphos-phinobutane; DBU for 1,8-diazabicyclo[5.4.0]-undec-7-ene; DCC for N,N'-dicyclohexyl-carbodiimide; DEAD for diethylazodicarboxylate; DIAD for diisopropyl azodicarboxylate; DIPEA or (i-Pr)$_2$EtN for N,N,-diisopropylethyl amine; Dess-Martin periodinane for 1,1,1-tris(acetyloxy)-1,1-dihydro-1,2-benziodoxol-3-(1H)-one; DMAP for 4-dimethylamino-pyridine; DME for 1,2-dimethoxyethane; DMF for N,N-dimethylformamide; DMSO for dimethyl sulfoxide; DMT for di(p-methoxyphenyl)-phenylmethyl or dimethoxytrityl; DPPA for diphenylphosphoryl azide; EDC for N-(3-dimethylaminopropyl)-N'-ethylcarbodiimide; EDC HCl for N-(3-dimethylaminopropyl)-N'-ethylcarbodiimide hydrochloride; EtOAc for ethyl acetate; EtOH for ethanol; Et$_2$O for diethyl ether; HATU for O-(7-azabenzotriazol-1-yl)-N,N,N',N',-tetramethyluronium Hexafluoro-phosphate; HCl for hydrogen chloride; HOBT for 1-hydroxybenzotriazole; K$_2$CO$_3$ for potassium carbonate; n-BuLi for n-butyl lithium; i-BuLi for i-butyl lithium; t-BuLi for t-butyl lithium; PhLi for phenyl lithium; LDA for lithium diisopropylamide; LiTMP for lithium 2,2,6,6-tetramethyl-piperidinate; MeOH for methanol; Mg for magnesium; MOM for methoxymethyl; Ms for mesyl or —SO$_2$—CH$_3$; Ms$_2$O for methanesulfonic anhydride or mesyl-anhydride; MTBE for t-butyl methyl ether; NaN(TMS)$_2$ for sodium bis(trimethylsilyl) amide; NaCl for sodium chloride; NaH for sodium hydride; NaHCO$_3$ for sodium bicarbonate or sodium hydrogen carbonate; Na$_2$CO$_3$ sodium carbonate; NaOH for sodium hydroxide; Na$_2$SO$_4$ for sodium sulfate; NaHSO$_3$ for sodium bisulfite or sodium hydrogen sulfite; Na$_2$S$_2$O$_3$ for sodium thiosulfate; NH$_2$NH$_2$ for hydrazine; NH$_4$HCO$_3$ for ammonium bicarbonate; NH$_4$Cl for ammonium chloride; NMO for N-methylmorpholine N-oxide; NaIO$_4$ for sodium periodate; Ni for nickel; OH for hydroxyl; OsO$_4$ for osmium tetroxide; PPA for polyphophoric acid; PTSA for p-toluenesulfonic acid; PPTS for pyridinium p-toluenesulfonate; PhI(OPiv)$_2$ for Bis(tert-butylcarbonyloxy)iodobenzene; Rh$_2$(Esp)$_2$ for Bis[rhodium(α,α,α',α'-tetramethyl-1,3-benzenedipropionic acid)]; TBAF for tetrabutylammonium fluoride; TEA or Et$_3$N for triethylamine; TES for triethylsilyl; TESCl for triethylsilyl chloride; TESOTf for triethylsilyl trifluoromethanesulfonate; TFA for trifluoroacetic acid; THF for tetrahydrofuran; TMEDA for N,N,N',N'-tetramethylethylene-diamine; TPP or PPh$_3$ for triphenyl-phosphine; Troc for 2,2,2-trichloroethyl carbonyl; Ts for tosyl or —SO$_2$—C$_6$H$_4$CH$_3$; Ts$_2$O for tolylsulfonic anhydride or tosyl-anhydride; TsOH for p-tolylsulfonic acid; Pd for palladium; Ph for phenyl; POPd for dihydrogen dichlorobis(di-tert-butylphosphinito-KP)palladate(II); Pd$_2$(dba)$_3$ for tris(dibenzylideneacetone) dipalladium (O); Pd(PPh$_3$)$_4$ for tetrakis (triphenylphosphine)-palladium (O); PdCl$_2$(PPh$_3$)$_2$ for trans-dichlorobis-(triphenylphosphine)palladium (II); Pt for platinum; Rh for rhodium; rt for room temperature; Ru for ruthenium; TBS for tert-butyl dimethylsilyl; TMS for trimethylsilyl; or TMSCl for trimethylsilyl chloride.

Synthetic Methods

The compounds and processes of the present invention will be better understood in connection with the following synthetic schemes that illustrate the methods by which the compounds of the invention may be prepared. These schemes are of illustrative purpose, and are not meant to limit the scope of the invention. Equivalent, similar, or suitable solvents, reagents or reaction conditions may be substituted for those particular solvents, reagents, or reaction conditions described herein without departing from the general scope of the method of synthesis.

The nature of the group B in Formula I will have a significant effect on the choice of the synthesis methods, as demonstrated below:

Scheme 1

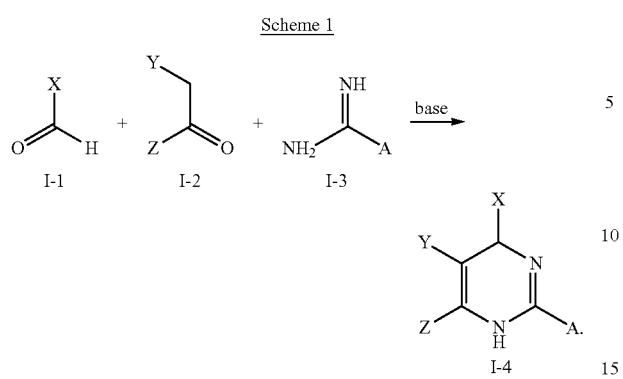

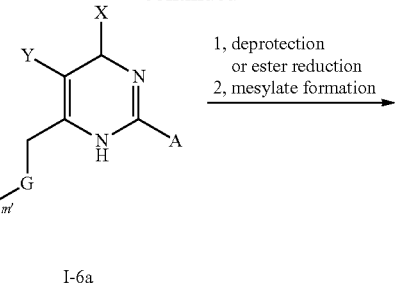

When B in Formula I is a hydrogen, an illustrative method is shown in Schemes 1 and Scheme 1a, the X, A and Y are as defined previously for formula I, Z is selected from the group consisting of hydrogen, optionally substituted —$C_1$-$C_{12}$ alkyl, optionally substituted —$C_2$-$C_{12}$ alkenyl, optionally substituted —$C_2$-$C_{12}$ alkynyl, optionally substituted —$C_3$-$C_8$ cycloalkyl, optionally substituted 3- to 8-membered heterocyclic, optionally substituted aryl, optionally substituted heteroaryl, —$C(O)NR_{11}R_{12}$, and —$C(O)OR_{11}$. The starting material aldehyde I-1, a ketone I-2 wherein Y is an electron withdrawing group, such as an ester, or an aromatic group (the desired aryl or heteroaryl) and an amidine I-3 are all either commercially available or can be easily prepared by those familiar with the skill of the arts. The dihydropyrimidine core I-4 can be prepared in one pot process from an aldehyde I-1, a ketone I-2 and an amidine I-3 (or its salt) in the presence of a suitable base as such potassium acetate or potassium bicarbonate in a solvent like methanol, or trifluoroethanol. Most frequently, elevated temperature is required for this transformation. Starting from this core I-4, A, X, Y, Z could be individually manipulated and converted to varieties of functional groups.

For instance, when Z in I-4 is a methyl, this methyl can be further functionalized easily. One specific example is shown in scheme 1a, when I-4a is treated with NBS, the methyl bromide I-5 will be obtained. The bromide can be displaced with nucleophiles. Therefore, when I-5a is reacted with various bi-functional molecules Z'($CH_2$)$_m$GH, in which GH is a nucleophile, such as an amine, an alcohol or a malonate; Z' is precursor of a leaving group, such as a protected hydroxyl or a ester, in the presence of a suitable base such as TEA or pyridine, will provide a more complicated structure I-6a. Next the Z' is converted to a desired leaving group by either de-protection or reduction to free the alcohol, followed by mesylate formation to afford the I-7a. Alternatively, bromide or tosylate may be used. When I-7a is treated with a base, like TEA or $K_2CO_3$, in a proper solvent such as THF, acetonitrile or DMF will give the cyclized product I-8a.

Scheme 1a

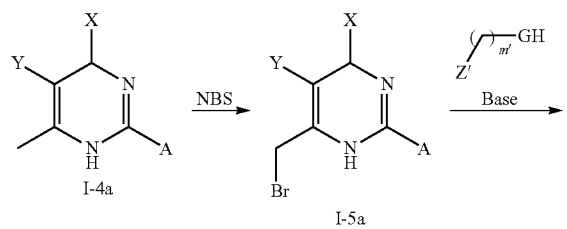

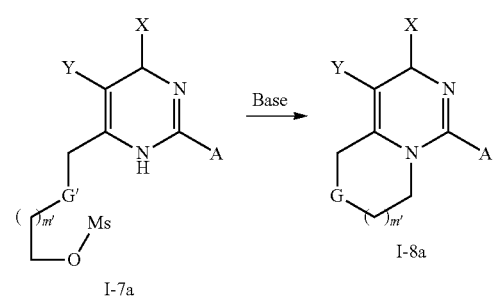

Next, Y in the formula I-8a can be further manipulated. For instance, as shown in Scheme 1b, wherein Y is an ester, $R_3$ is as defined as previously. In the case while $R_3$ is t-Butyl or allyl, then ester I-8b can be converted to an advanced carboxyl acid intermediate I-9b when treated with strong acid (HCl or TFA) or Pd(PPh$_3$)$_4$/Morpholine, respectively. By taking advantage of this carboxyl acid as a key intermediate, various functional groups can be generated from it. One specific example is shown in the same scheme, this carboxyl acid is converted to the acyl chloride followed by treating with amines to give the amide I-10b. Alternatively this transformation also can be completed in the presence of a dehydration reagent such as EDC or DCC as well as a base like TEA, DIPEA. When $R_1$ and $R_2$ are hydrogen, this amide when treated with a dehydration reagent such as TFAA will afford a nitrile. This nitrile can serve as advanced intermediate for azoles. When $R_1$ is methyl, $R_2$ is methoxyl, a Weinreb amide is obtained. In the next step, this Weinreb amide is reduced to an aldehyde or reacted with all sorts of Grignard reagent will offer various ketone, which could serve as later stage intermediate for further functional group manipulation for more complicated heteroaryl including azoles. One example is shown in the same scheme, the Weinreb amide I-10b can be reduced to afford the aldehyde I-11b, which when reacted with acetone in the presence of a base such as LDA will offer the α,β-unsaturated ketone I-12b. I-12b is treated with hydroxyl amine followed by an iodine induced cyclization to afford the isoxazole I-13c. More related arts can be found in the various publications (for example, J. A Joule and K. Mills, Heterocyclic Chemistry, 5$^{th}$ edition, 557 and reference therein). G, m' and $R_3$ are as previously defined.

Scheme 1b

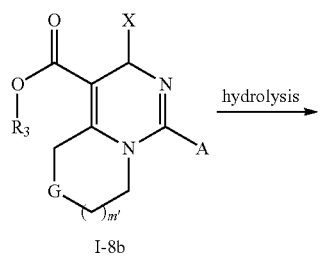

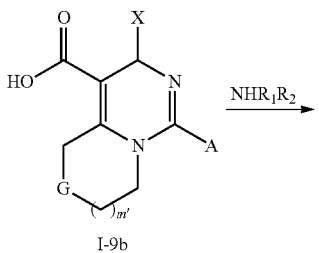

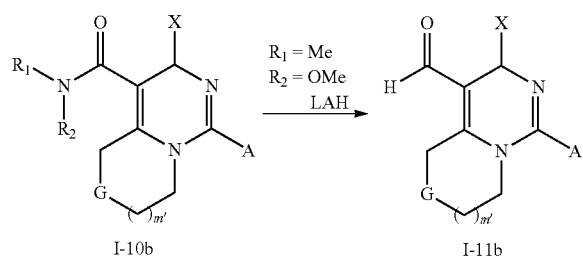

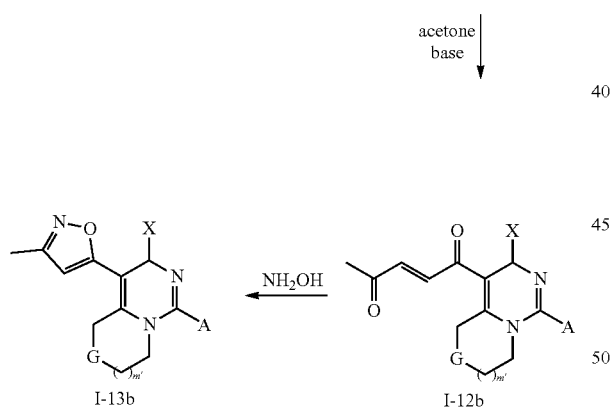

Scheme 1c

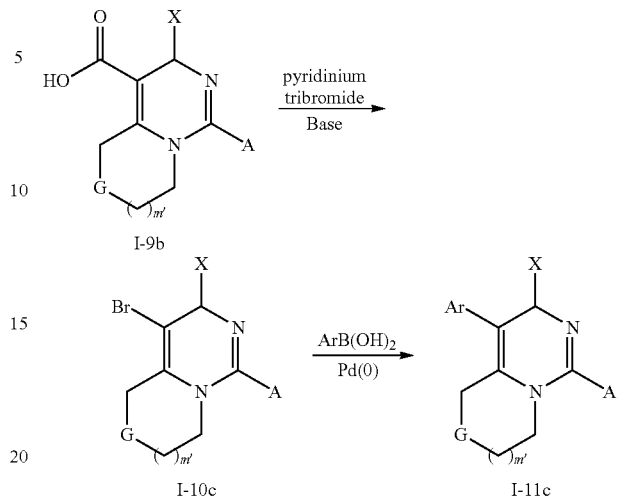

In yet another specific example as shown Scheme 1d, the compound I-4d can be protected with a proper protecting group such as Boc, or Cbz to give I-5d. Hydrolysis the ester of I-5d following similar procedure as described in Scheme 1b will afford the acid I-6d. When the carboxyl acid I-6d is treated with at least two equivalents of NBS, the di-bromo compound I-7d will be obtained. Starting from this di-bromo I-7d, following similar chemical procedure described in Scheme 1a for converting I-5a to I-8a, the 5-bromo compound I-10c will be generated. From it, target I-11c will be obtained as discussed in Scheme 1c.

Scheme 1d

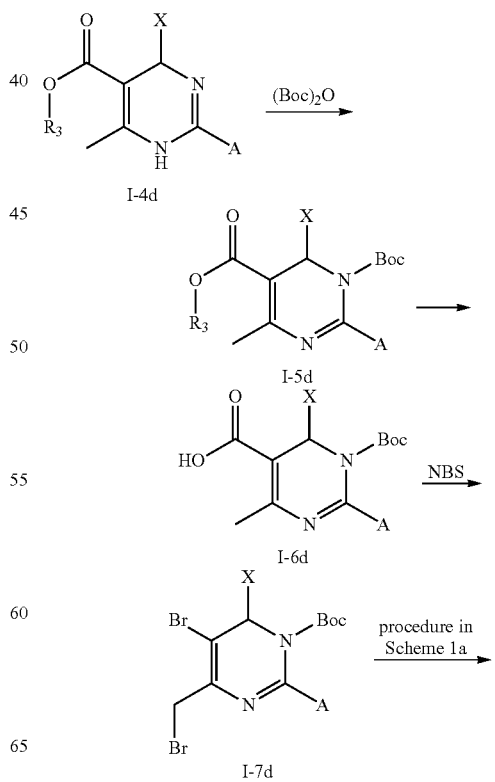

In yet another specific example as shown in Scheme 1c, when the carboxyl acid I-9b is treated with pyridinium tribromide in the presence a base such as pyridine, a bromide I-10c will be produced. The bromide reacts with various aryl or heteroaryl boronic ester/acid or tin reagent, which can be commercial available or easily prepared by those familiar with the skill of the arts, under the Pd(0) catalyzed coupling conditions to give the target molecule I-11c. (see reviews: A. Suzuki, *Pure Applied Chem.*, 1991, 63, 419; A. Suzuki, *Handbook of Organopalladium Chemistry for Organic Synthesis*, 2002, 1, 249; A. Anastasia, et al, *Handbook of Organopalladium Chemistry for Organic Synthesis*, 2002, 1, 311).

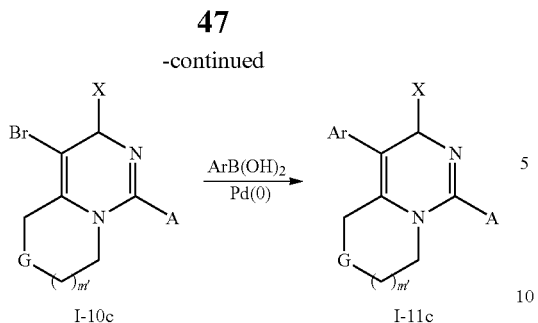

In yet another specific example as shown Scheme 1e, if the amidine I-3 shown in Scheme 1 is replaced with a urea, a dihydropyrimidine-2-one I-4a analogue to I-4 is generated. It is well known in literature (A. Karnail, et al, Journal of Organic Chemistry, 1989, 54, 5898) that when this family molecules are treated with (Boc)$_2$O in the present of a base such as TEA, or DIPEA, a N-3 Boc protected product I-5e will be obtained. Alkylation of this intermediate I-5e with an alkylation reagent, like RBr with the desired R group in the presence of a proper base such as NaH will afford the N-1 alkylated intermediate I-6e. When I-6e is treated with an acid, like HCl or TFA, the N-3 Boc protecting group will be removed, which is followed by heating this material in POCl$_3$ to lead to the 2-chloro dihydropyrimidine I-7e. This chloride reacts with various aryl or heteroaryl boronic ester/acid or tin reagent, which can be commercial available or easily prepared by those familiar with the skill of the arts, under the Pd(0) catalyzed coupling conditions to give the target molecule I-8e contains the desired A group. When I-8e is reacted with 1 equivalent NBS, the 6-methyl will be brominated to offer advanced intermediated I-9e. The bromide in I-9e can be displaced with the desired M group with MH in the presence of proper base to afford I-10e. In molecule I-10e, if the Y is desired aryl or heteroaryl group, then I-10e is a desired target; if Y is an ester, then all the chemistry described in Scheme 1b and Scheme 1c can be applied to afford the desired product. R and M are as previously defined.

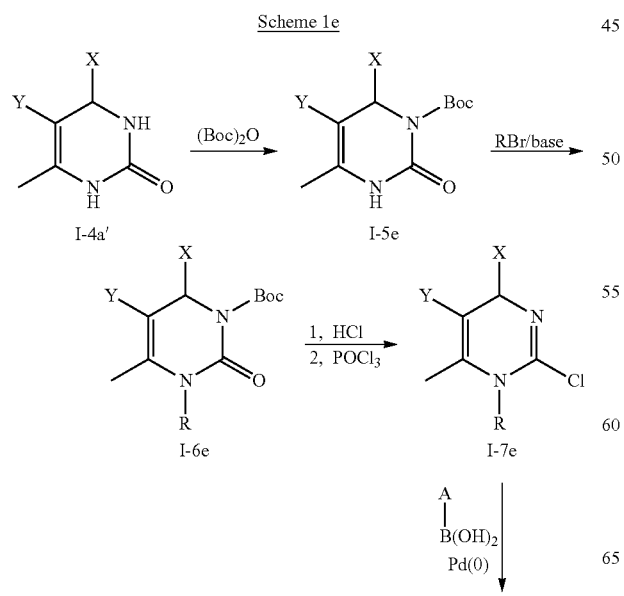

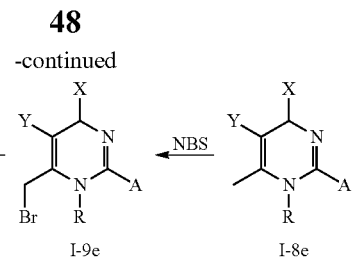

On the other hand, if the R in I-9e contains a nucleophile such as I-9e' as shown in Scheme 1f, when treated with a base, TEA, or NaH will afford the intermediate I-8a.

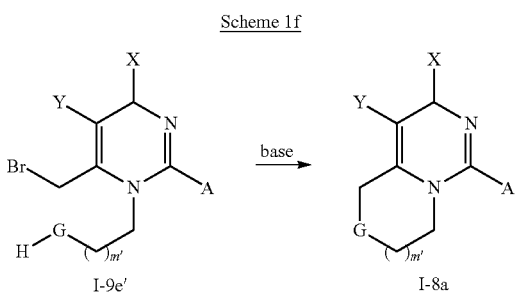

In yet another specific example as shown in Scheme 1g, the ketone I-2g can be commercially available or easily prepared by those familiar with the skill of the arts, wherein Z is a methyl group with a bi-functional group Z'(CH$_2$)$_m$G attached, in which G-H is a nucleophile, such as an amine, an alcohol or a malonate; The one-pot ring formation process involving a aldehyde I-1, a ketone I-2g and an amidine I-3 (or its salt) similar as described in Scheme 1 will provide a more complicated dihydropyrimidine I-6a. Z' is precursor of a leaving group, such as a protected hydroxyl or a ester. Following a similar reaction sequence as in Scheme 1a, dihydropyrimidine I-6a can be converted to cyclized product I-8a. In the case where Y is a t-butyl or allyl ester or other activated ester, Y can be transformed into an aryl group following the reaction sequence as describe in Scheme 1b and Scheme 1c. Alternatively, Y in dihydropyrimidine I-6a can be converted to an ary group first, followed by transformation of Z' and the ensuing cyclization to afford I-11c.

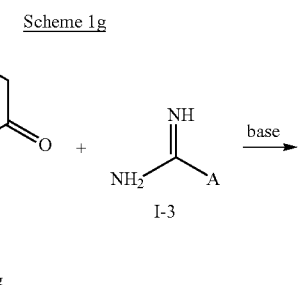

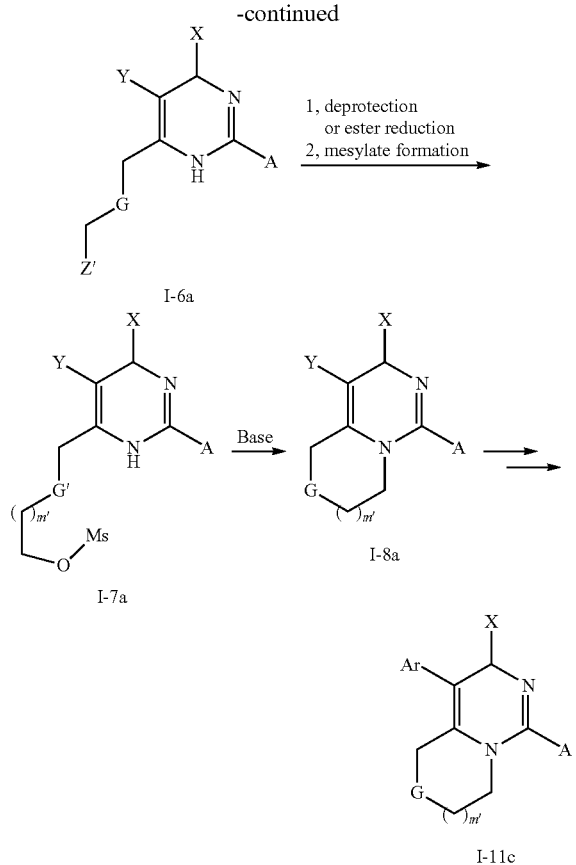

On the other hand when B is CN or an alkyl group, a step wise route is required for the preparation of the final targets. As illustrated in Scheme 2, aldehyde I-1 and I-2 are reacted with each other in the presence of a catalyst system, such as piperidine/acetic acid to afford the α,β-unsaturated ketone II-1. This α,β-unsaturated ketone II-1 reacts with a copper reagent CuB, which can be commercially available or can be easily generated in situ from CuI and BMgX (or BLi). The newly formed α,β-unsaturated ketone 11-2 then reacts with I-3 in a similar process described above as in the one-pot process to afford the desired target I.

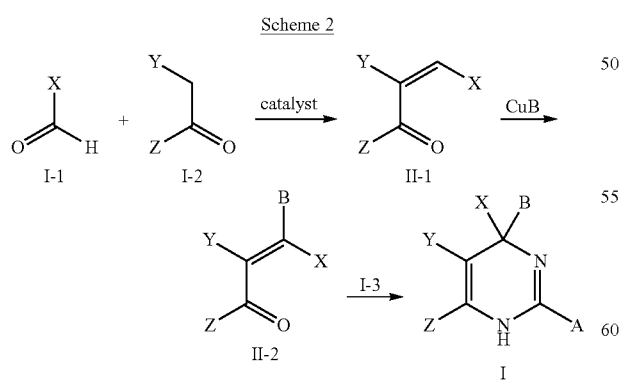

In a specific example, while B is a methyl, X is a aryl or heteroaryl, I in Scheme 2 can be introduced with a chemistry described in Scheme 2a following similar published precedents (For example, WO 2013/102655). A distal acetylene I-1a served as a methyl ketone equivalent reacts with ketone I-2 in the presence of InCl₃ will provide the α,β-unsaturated ketone II-1a, which in turn when reacts with amidine I-3 will provide Ia, the 4-methyl analogue of I.

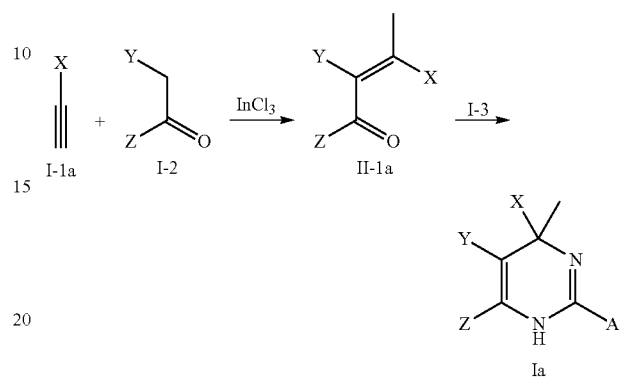

With I in hand, all the chemistry described in Scheme 1a to Scheme 1f can be applied here to give the desired targets.

Alternatively, in certain cases, even when B is hydrogen, a step wise procedure similar as in Scheme 2 is required to achieve the targets.

It will be appreciated that, with appropriate manipulation and protection of any chemical functionality, synthesis of compounds of Formula (I) is accomplished by methods analogous to those above and to those described in the Experimental section. Suitable protecting groups can be found, but are not restricted to, those found in T W Greene and P G M Wuts "Protective Groups in Organic Synthesis", 3rd Ed (1999), J Wiley and Sons.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

EXAMPLES

The compounds and processes of the present invention will be better understood in connection with the following examples, which are intended as an illustration only and not limiting of the scope of the invention.

Intermediate 1

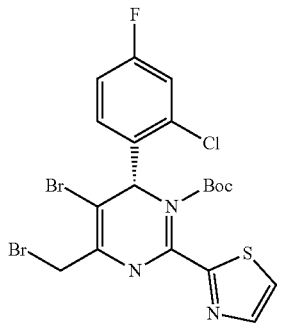

Step 1-1a. A solution of ethyl (R)-2-hydroxypropanoate (5 g, 42.3 mmol) and 2,2,6-trimethyl-4H-1,3-dioxin-4-one (6 g, 42.3 mmol) was stirred for 4 hours at 120° C. The mixture was concentrated under vacuum to give desired product (9 g, crude) as yellow oil, which was used in the next step without further purification. ESI MS m/z=203.25 [M+H]+.

Step 1-1b. A solution of the compound from step 1-1a (5 g, 24.5 mmol), 2-chloro-4-fluorobenzaldehyde (4.3 g, 27.3 mmol), TsOH (cat) and HOAc (cat) in toluene (60 mL) was stirred at 110° C. overnight. The mixture was concentrated. The residue was chromatographed (silica, ethyl acetate/petroleum ether) to give the desired product (5.93 g, 70.0%) as yellow solid. ESI MS m/z=343.00 [M+H]+.

Step 1-1c. A solution of the compound from step 1-1b (5 g, 14.6 mmol), thiazole-2-carboximidamide HCl salt (2.38 g, 14.6 mmol) and K₂CO₃ (2.01 g, 14.6 mmol) in DMF (20 mL) was stirred for 2 hours at 80° C. It was diluted with EtOAc and washed with brine, filtered and concentrated. After the residue was purified by silica gel column (ethyl acetate/petroleum ether), the mixture was recrystallized from EtOH at 0° C. to give the desired product as yellow solid (1.25 g, 25.0%). ESI MS m/z=452.05 [M+H]+.

Step 1-1d. A solution of the compound from step 1-1c (950 mg, 2.10 mmol), (Boc)₂O (915.6 mg, 4.20 mmol) and DMAP (307 mg, 2.51 mmol) in DCM (30 mL) was stirred for 1 hour at rt. The reaction mixture was concentrated. The residue was chromatographed (silica, ethyl acetate/petroleum ether) to give the desired compound as a yellow solid (1.07 g, 92%). ESI MS m/z=552.30 [M+H]+.

Step 1-1e. A solution of the compound from step 1-1d (965 mg, 1.75 mmol) in a solution of NaOH [40 mL, 2 M in H₂O/MeOH (1:5)] was stirred for 18 hours at rt. After being acidified with aq HCl (4N) to pH 5, the mixture was extracted with DCM. The organic layer was washed with aq. NH₄Cl and H₂O, dried (Na₂SO₄) and concentrated. The residue was chromatographed (silica, ethyl acetate/petroleum ether) to give the desired compound as yellow solid (620 mg, 78%). ESI MS m/z=452.15 [M+H]+.

Step 1-1f. A solution of the compound from step 1-1e (250 mg, 0.55 mmol) in DCM (10 mL) was treated with NBS (295 mg, 1.66 mmol) for 6 hours at rt. The reaction was quenched by the addition of water (2 mL) and extracted with DCM. The organic layer was dried (Na₂SO₄), concentrated. The residue was chromatographed (C₁₈ column, MeCN/H₂O) to give the title compound as yellow solid (103.5 mg, 33%). ESI MS m/z=566.10, 568.10 [M+H]+. ¹H NMR (400 MHz, DMSO-d₆) δ 8.04 (m, 2H), 7.98 (d, 1H), 7.57 (m, 1H), 7.23 (m, 1H), 6.35 (s, 1H), 4.45 (m, 2H), 1.15 (s, 9H).

Example 1

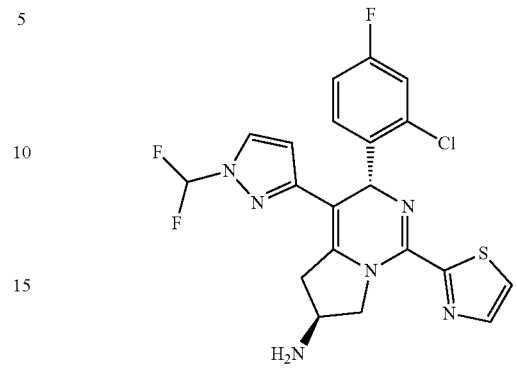

Step 1a. To a suspension of Intermediate 1 (15.00 g, 25.60 mmol) and ethyl 2-((diphenylmethylene)amino)acetate (14.18 g, 53.0 mmol) in toluene (270 ml) cooled at 0° C. was added O-Allyl-N-(9-anthracenylmethyl)cinchonidinium bromide (1.606 g, 2.650 mmol), followed by 50% KOH aq (88.0 ml, 1.326 mol) dropwise. The mixture was vigorously stirred at 0° C. for 2 h before being diluted with saturated NaHCO₃aq and MTBE. The organic layer was washed with saturated NaHCO₃aq (*1), brine (*1), dried over Na₂SO₄ (s), filtered and concentrated. The residue was dried under vacuum to afford the desired compound as red oil, which was used directly for next step. ESI MS m/z=751.14, 753.14 [M+H]+.

Step 1b. A clear orange solution of the compound from step 1a (25.60 mmol) in THF (100 ml), Water (100.00 ml) and AcOH (66.67 ml) was stirred at rt for 4 h before being concentrated. The residue was carefully diluted with DCM and saturated NaHCO₃aq. The organic layer was dried over Na₂SO₄ (s), filtered and concentrated. The residue was dried under vacuum to afford the desired compound as a red oil, which was used directly for next step. ESI MS m/z=587.06, 589.06 [M+H]+.

Step 1c. To a solution of step 1b (26.0 g, 44.2 mmol) in THF (200 ml) at rt was added a solution of Boc-anhydride (11.29 ml, 48.6 mmol) in THF (15 ml) slowly. The resulting solution was stirred at rt for 2 h before being concentrated. The residue was purified by flash column chromatography (silica, hexanes/EtOAc) to afford the desired compound as yellow solid (30.00 g, 99%). ESI MS m/z=687.12, 689.12 [M+H]+.

Step 1d. To a mixture of the compound from step 1c (5.200 g, 7.56 mmol), potassium phosphate tribasic (3.21 g, 15.12 mmol), palladium(II) acetate (0.170 g, 0.756 mmol), 1-(difluoromethyl)-3-(4,4,5,5-tetramethyl-1,3,2-dioxaborolan-2-yl)-1H-pyrazole (2.77 g, 11.34 mmol) and SPhos (0.621 g, 1.512 mmol) in THF (20 ml) at rt was added water (1.000 ml) dropwise. The mixture was flushed with N₂ and vigorously stirred at rt overnight before being diluted with EtOAc, half brine and 10% citric acid solution to pH~4. The organic layer was dried over Na₂SO₄ (s), filtered and concentrated. The residue was purified by flash column chromatography (silica, hexanes/EtOAc) to afford the desired compound as yellow foam (5.200 g, 95%). ESI MS m/z=725.48, 727.47 [M+H]+.

Step 1e. To a solution of the compound from step 1d (5.800 g, 8.00 mmol) in THF (120 ml) at rt was added one third of a solution of LiBH₄ (2.0 M in THF, 13.20 ml, 26.4 mmol) every one hour. After addition, the resulting clear solution was stirred at rt for 3 h. The mixture was poured portionwise slowly into a mixture of 10% citric acid solution and DCM. The mixture was diluted with EtOAc (*1). The organic layere was washed with saturated NaHCO₃ solution (*1), brine (*1), dried over Na₂SO₄ (s), filtered and concentrated. The residue was purified by flash column chromatography (silica, hexanes/EtOAc) to afford the desired compound as yellow foam (2.700 g, 49%). ESI MS m/z=683.19, 685.19 [M+H]⁺.

Step 1f. To a solution of the compound from step 1e (14.100 g, 20.64 mmol) in 1,4-dioxane (120 ml) and water (40.0 ml) at rt was added sodium bicarbonate (8.67 g, 103 mmol). The mixture was stirred at 120° C. in a sealed thick-wall flask overnight (22 h) before being allowed to cool down to rt and diluted with water and EtOAc. The aqueous layer was extracted with EtOAc (*1). The combined organic layers were washed with brine (*1), dried over Na₂SO₄ (s), filtered and concentrated. The residue was purified by flash column chromatography (silica, hexanes/EtOAc) to afford the desired compound as yellow foam (10.000 g, 83%). ESI MS m/z=583.15, 585.15 [M+H]⁺.

Step 1g. To a solution of the compound from step 1f (10.000 g, 17.15 mmol) in DCM (200 ml) at 0° C. was added DMAP (6.29 g, 51.5 mmol), followed by a solution of methanesulfonyl chloride (2.65 ml, 34.3 mmol) in DCM (15 ml) dropwise. The mixture was stirred at 0° C. for 0.5 h and then heated at 35° C. for 2.5 h before being allowed to cool down to rt and concentrated. The residue was taken up in DCM and filtered. The filtrate was directly purified by flash column chromatography (silica, hexanes/EtOAc) to afford the desired compound as yellow foam (7.800 g, 80%). ESI MS m/z=565.14, 567.14 [M+H]⁺.

Step 1h. To a solution of the compound from step 1g (7.800 g, 13.81 mmol) in DCM (125 ml) at rt was added 4 M HCl in 1,4-dioxane (69.0 ml, 276 mmol). The suspension was stirred at rt for 1 h before being poured into a mixture of DCM and saturated NaHCO₃aq. The solid was rinsed into the separatory funnel with DCM and some Et₃N. The two layers were separated. The aqueous layer was extracted with DCM (*1). The combined organic layers were dried over Na₂SO₄ (s), filtered and concentrated. The residue was purified by flash column chromatography (silica, DCM/MeOH/Et₃N) to afford the title compound as yellow foam (5.810 g, 91%) as a single diastereomer. ESI MS m/z=465.01, 467.00 [M+H]⁺.

Example 2

To a solution of Example 1 (50.0 mg, 0.108 mmol) in DCM (1.5 ml) at rt was added triethylamine (45.0 µl, 0.323 mmol), followed by methyl 3-(chlorosulfonyl)benzoate (37.9 mg, 0.161 mmol). The solution was stirred at rt for 1 h. Excess 2-propanol was added to quench the reaction. After 10 min at rt, the mixture was freed of volatiles. The residue was directly purified by flash column chromatography (silica, hexanes/EtOAc) to afford the title compound as yellow foam (57.0 mg, 80%). ESI MS m/z=663.01, 665.01 [M+H]⁺.

Example 3

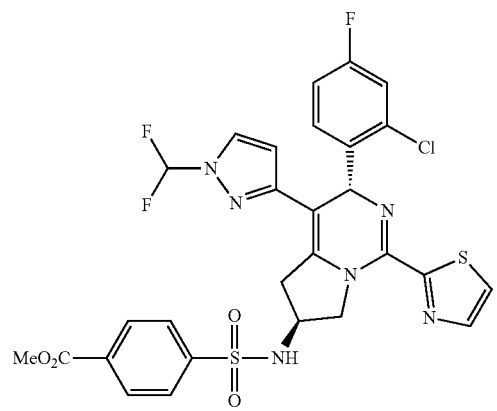 [SMILES: COC(=O)c1ccc(S(=O)(=O)N[C@H]2CC3=C(c4ccn(C(F)F)n4)[C@H](c4ccc(F)cc4Cl)N=C(c4nccs4)N3C2)cc1]

The title compound was prepared following similar procedure as Example 2. ESI MS m/z=663.01, 665.00 [M+H]⁺.

Example 4

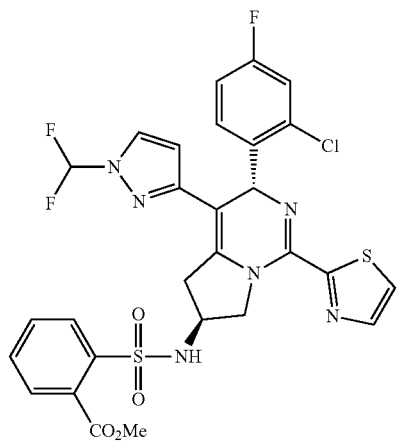 [SMILES: COC(=O)c1ccccc1S(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 2. ESI MS m/z=663.01, 665.00 [M+H]⁺.

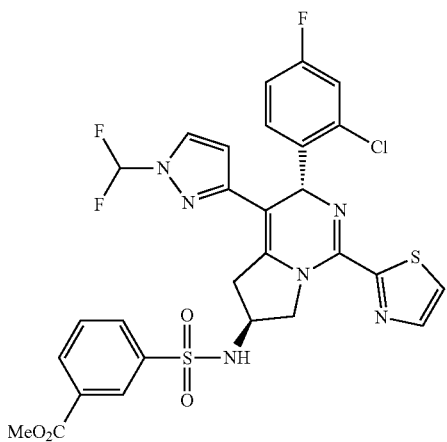

Example 5

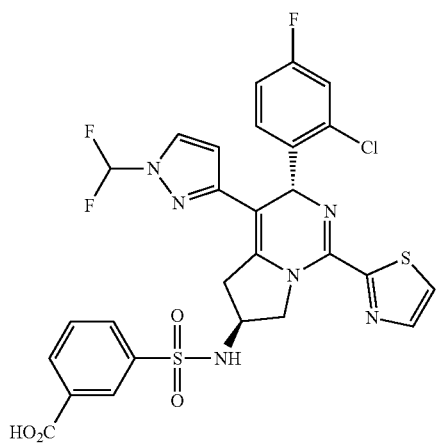 [SMILES: O=C(O)c1cccc(S(=O)(=O)N[C@H]2CC3=C(c4ccn(C(F)F)n4)[C@H](c4ccc(F)cc4Cl)N=C(c4nccs4)N3C2)c1]

To a solution of Example 2 (25.0 mg, 0.038 mmol) in THF (0.5 ml) and MeOH (0.5 ml) at rt was added a solution of lithium hydroxide (5.42 mg, 0.226 mmol) in water (0.150 ml). The mixture was stirred at rt overnight. 0.5 N HCl solution was added until pH~3. The mixture was concentrated with a stream of $N_2$. The aqueous residue was extracted with DCM (*2). The combined organic layers were dried over $Na_2SO_4$ (s), filtered and concentrated. The residue was dried under vacuum to afford the title compound as yellow foam (20.0 mg, 82%). ESI MS m/z=648.98, 650.98 $[M+H]^+$.

Example 7

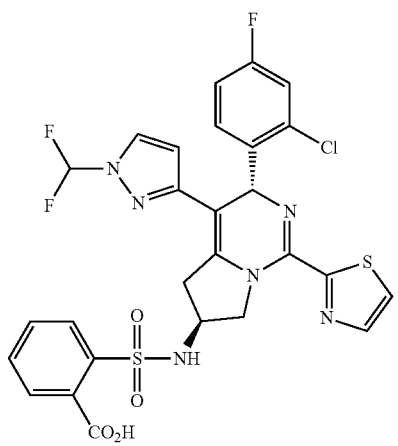

The title compound was prepared following similar procedure as Example 5. ESI MS m/z=648.98, 650.98 $[M+H]^+$.

Example 6

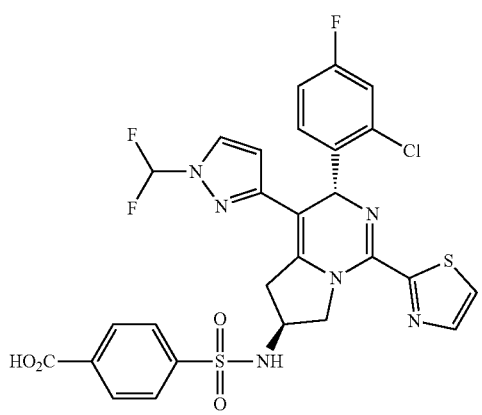 [SMILES: O=C(O)c1ccc(S(=O)(=O)N[C@H]2CC3=C(c4ccn(C(F)F)n4)[C@H](c4ccc(F)cc4Cl)N=C(c4nccs4)N3C2)cc1]

The title compound was prepared following similar procedure as Example 5. ESI MS m/z=648.98, 650.98 $[M+H]^+$.

Example 8

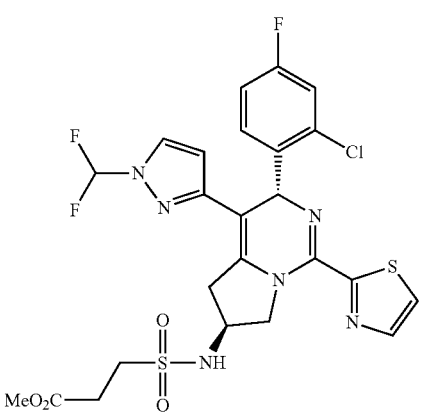 [SMILES: COC(=O)CCS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 2. ESI MS m/z=615.01, 617.01 $[M+H]^+$.

Example 9

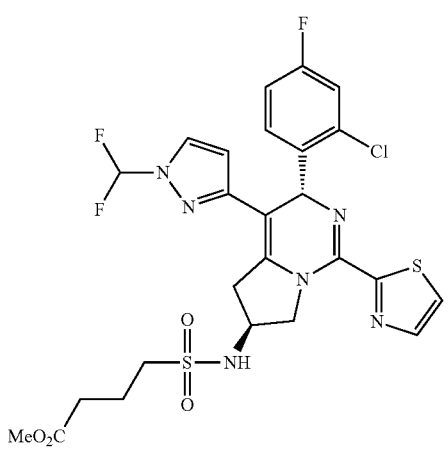 [SMILES: COC(=O)CCCS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 2. ESI MS m/z=629.01, 631.00 [M+H]⁺.

Example 11

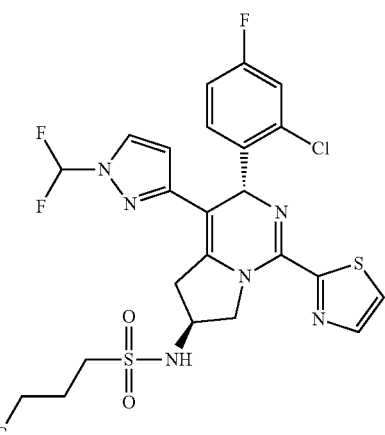

The title compound was prepared following similar procedure as Example 5. ESI MS m/z=615.00, 617.00 [M+H]⁺.

Example 10

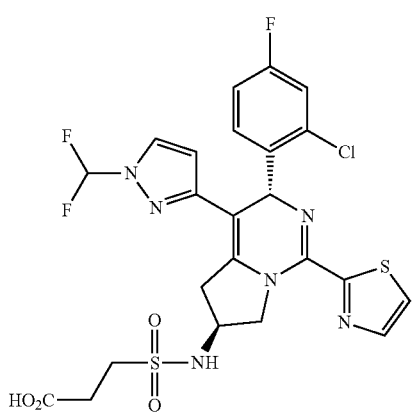 [SMILES: O=C(O)CCS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 5. ESI MS m/z=600.99, 602.98 [M+H]⁺.

Example 12

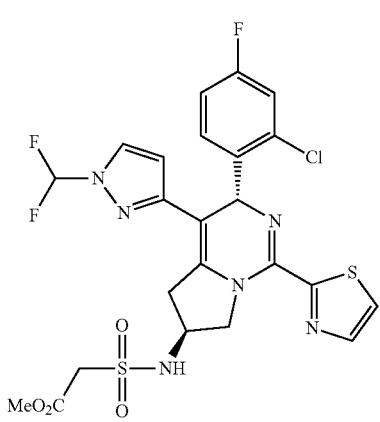 [SMILES: COC(=O)CS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 2. ESI MS m/z=600.97, 602.97 [M+H]⁺.

Example 13

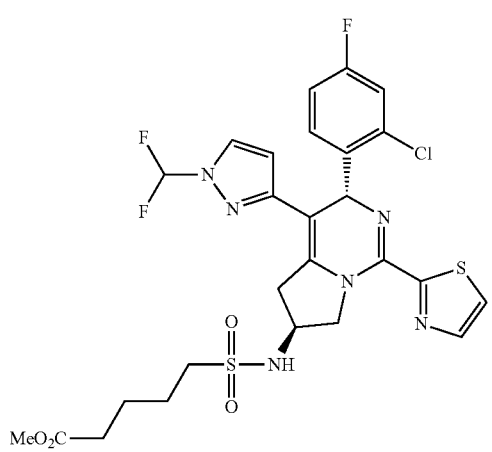 [SMILES: COC(=O)CCCCS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 2. ESI MS m/z=643.02, 645.02 [M+H]⁺.

Example 14

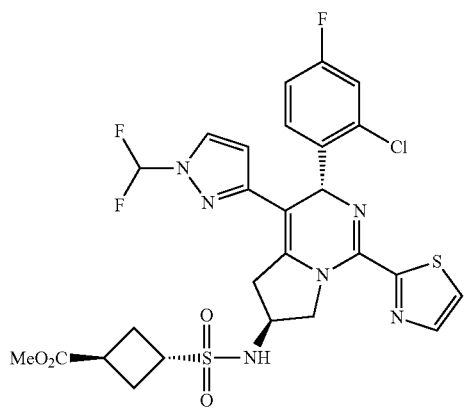 [SMILES: COC(=O)[C@H]1C[C@H](S(=O)(=O)N[C@H]2CC3=C(c4ccn(C(F)F)n4)[C@H](c4ccc(F)cc4Cl)N=C(c4nccs4)N3C2)C1]

The title compound was prepared following similar procedure as Example 2. ESI MS m/z=641.01, 643.01 [M+H]⁺.

Example 15

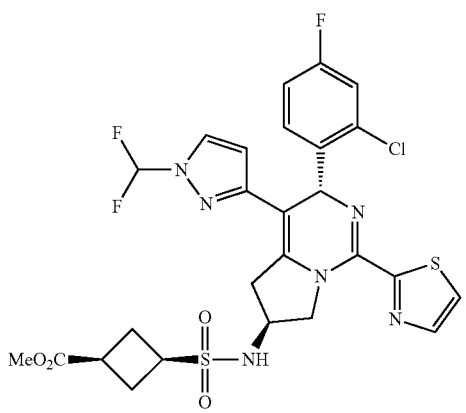 [SMILES: COC(=O)[C@H]1C[C@@H](S(=O)(=O)N[C@H]2CC3=C(c4ccn(C(F)F)n4)[C@H](c4ccc(F)cc4Cl)N=C(c4nccs4)N3C2)C1]

The title compound was isolated from Example 14. ESI MS m/z=641.02, 643.02 [M+H]⁺.

Example 16

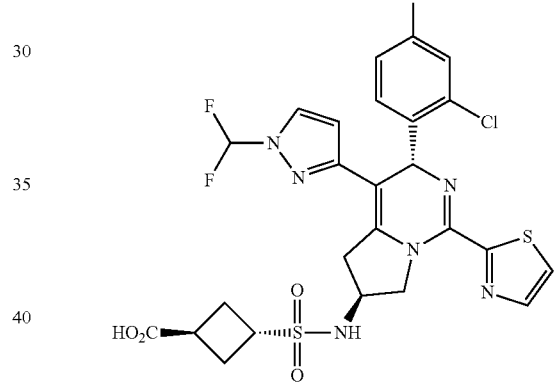

The title compound was prepared following similar procedure as Example 5. ESI MS m/z=626.99, 628.99 [M+H]⁺.

Example 17

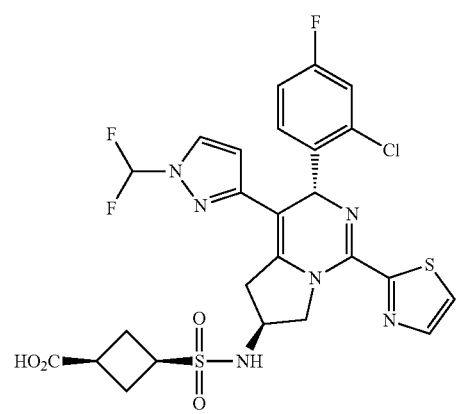 [SMILES: O=C(O)[C@H]1C[C@@H](S(=O)(=O)N[C@H]2CC3=C(c4ccn(C(F)F)n4)[C@H](c4ccc(F)cc4Cl)N=C(c4nccs4)N3C2)C1]

61

The title compound was prepared following similar procedure as Example 5. ESI MS m/z=626.98, 628.98 [M+H]⁺.

Example 18

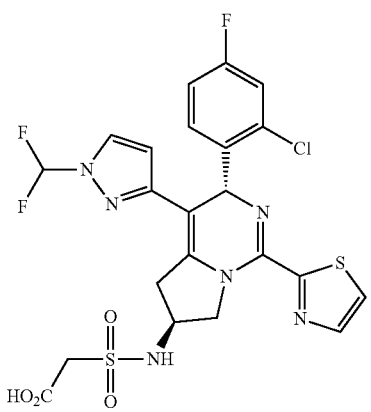 [SMILES: O=C(O)CS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 5. ESI MS m/z=587.06, 589.06 [M+H]⁺.

Example 19

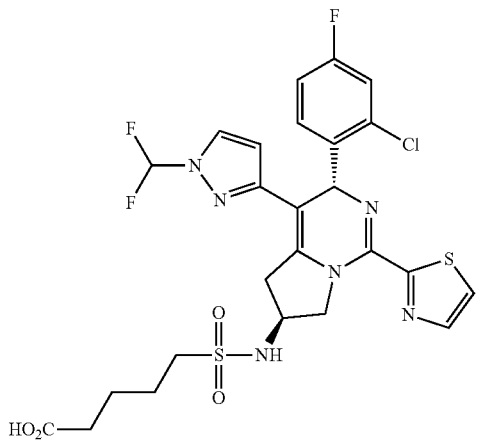 [SMILES: O=C(O)CCCCS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 5. ESI MS m/z=629.10, 631.10 [M+H]⁺.

62

Example 20

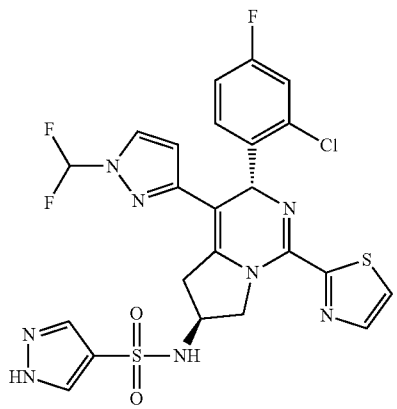 [SMILES: O=S(=O)(N[C@H]1CC2=C(c3ccn(C(F)F)n3)[C@H](c3ccc(F)cc3Cl)N=C(c3nccs3)N2C1)c1cn[nH]c1]

The title compound was prepared following similar procedure as Example 2. ESI MS m/z=595.08, 597.08 [M+H]⁺.

Example 21

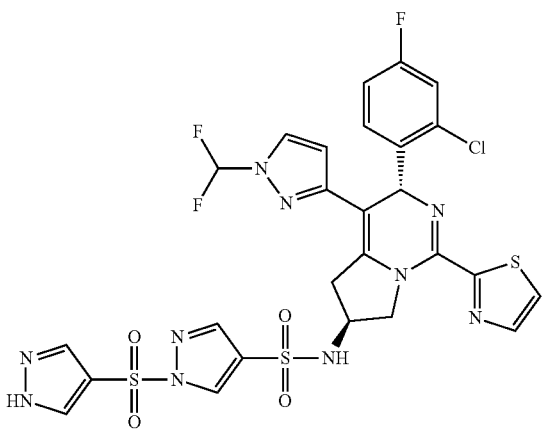 [SMILES: O=S(=O)(N[C@H]1CC2=C(c3ccn(C(F)F)n3)[C@H](c3ccc(F)cc3Cl)N=C(c3nccs3)N2C1)c1cnn(S(=O)(=O)c2cn[nH]c2)c1]

The title compound was isolated from Example 20. ESI MS m/z=725.06, 727.06 [M+H]⁺.

Example 22

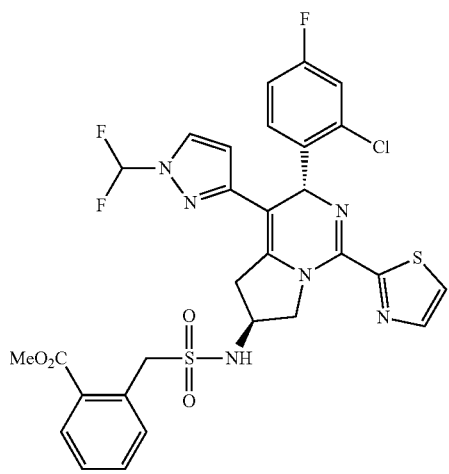 [SMILES: COC(=O)c1ccccc1CS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 2. ESI MS m/z=677.11, 679.10 [M+H]$^+$.

Example 23

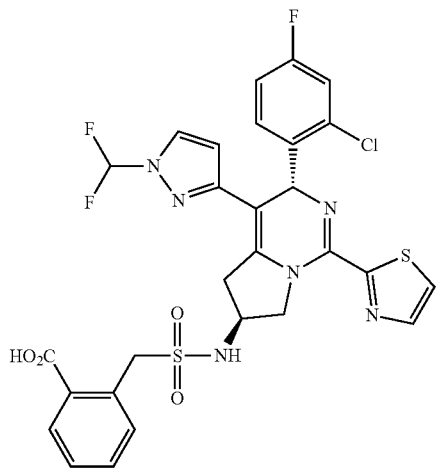 [SMILES: O=C(O)c1ccccc1CS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 5. ESI MS m/z=663.09, 665.09 [M+H]$^+$.

Example 24

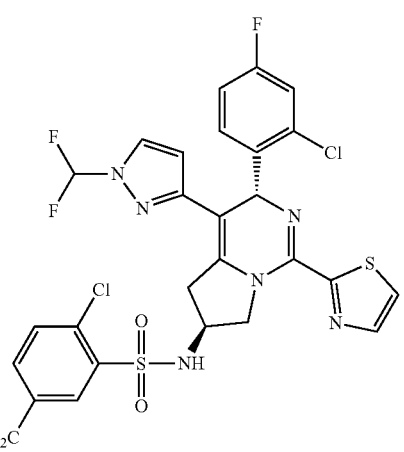

The title compound was prepared following similar procedure as Example 2. ESI MS m/z=697.05, 699.05 [M+H]$^+$.

Example 25

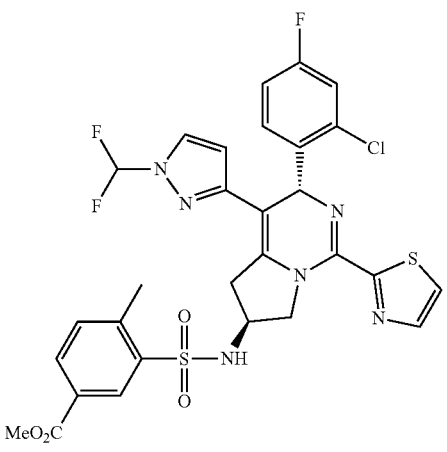 [SMILES: COC(=O)c1ccc(C)c(S(=O)(=O)N[C@H]2CC3=C(c4ccn(C(F)F)n4)[C@H](c4ccc(F)cc4Cl)N=C(c4nccs4)N3C2)c1]

The title compound was prepared following similar procedure as Example 2. ESI MS m/z=677.10, 679.10 [M+H]$^+$.

Example 26

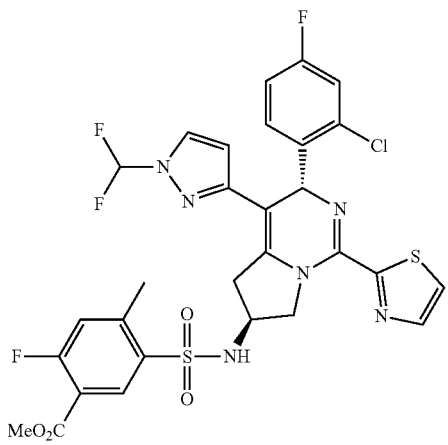 [SMILES: COC(=O)c1cc(S(=O)(=O)N[C@H]2CC3=C(c4ccn(C(F)F)n4)[C@H](c4ccc(F)cc4Cl)N=C(c4nccs4)N3C2)c(C)cc1F]

The title compound was prepared following similar procedure as Example 2. ESI MS m/z=695.09, 697.10 [M+H]+.

Example 28

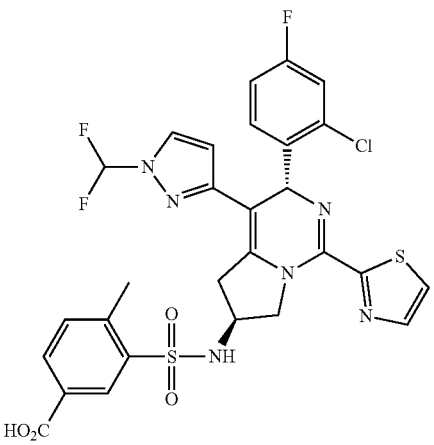

The title compound was prepared following similar procedure as Example 5. ESI MS m/z=663.09, 665.09 [M+H]+.

Example 27

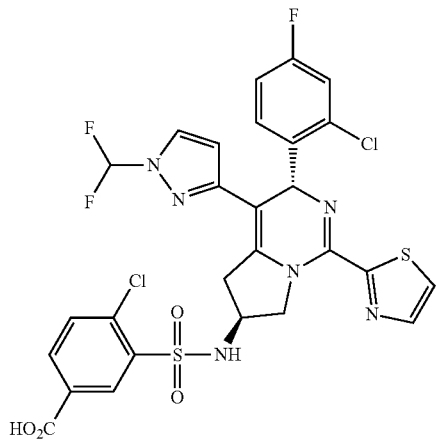 [SMILES: O=C(O)c1ccc(Cl)c(S(=O)(=O)N[C@H]2CC3=C(c4ccn(C(F)F)n4)[C@H](c4ccc(F)cc4Cl)N=C(c4nccs4)N3C2)c1]

The title compound was prepared following similar procedure as Example 5. ESI MS m/z=683.04, 685.04 [M+H]+.

Example 29

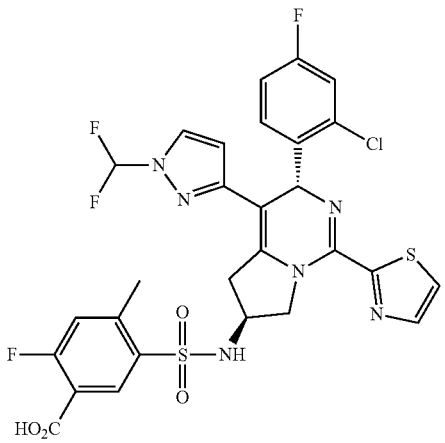 [SMILES: Cc1cc(F)c(C(=O)O)cc1S(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 5. ESI MS m/z=681.08, 683.08 [M+H]+.

Example 30

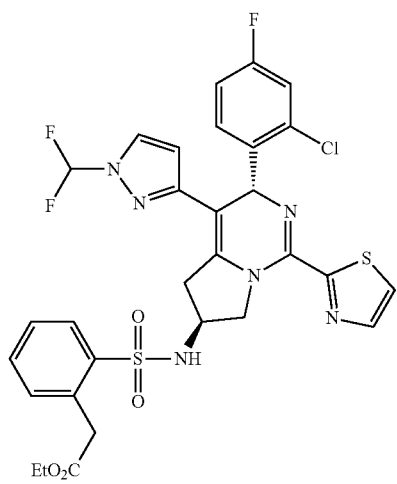

The title compound was prepared following similar procedure as Example 2. ESI MS m/z=691.12, 693.12 [M+H]⁺.

Example 32

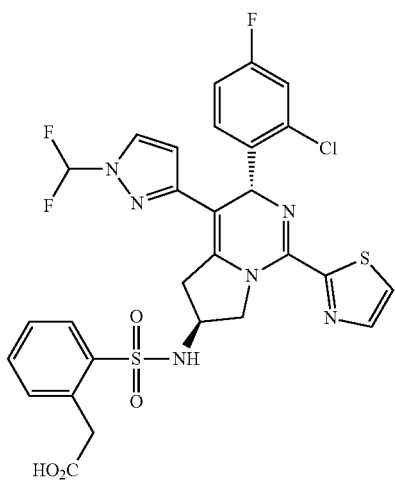

The title compound was prepared following similar procedure as Example 5. ESI MS m/z=663.08, 665.08 [M+H]⁺.

Example 31

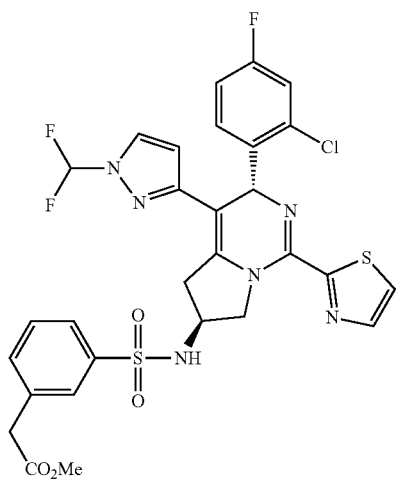 [SMILES: COC(=O)Cc1cccc(S(=O)(=O)N[C@H]2CC3=C(c4ccn(C(F)F)n4)[C@H](c4ccc(F)cc4Cl)N=C(c4nccs4)N3C2)c1]

The title compound was prepared following similar procedure as Example 2. ESI MS m/z=677.10, 679.10 [M+H]⁺.

Example 33

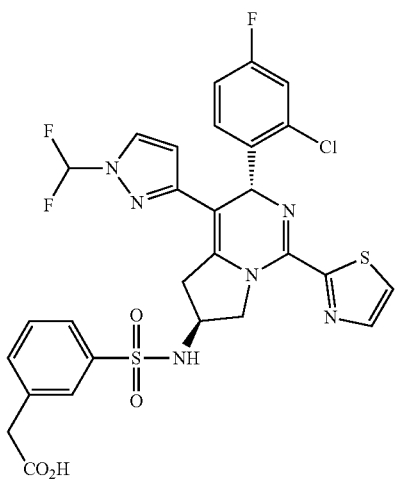 [SMILES: O=C(O)Cc1cccc(S(=O)(=O)N[C@H]2CC3=C(c4ccn(C(F)F)n4)[C@H](c4ccc(F)cc4Cl)N=C(c4nccs4)N3C2)c1]

The title compound was prepared following similar procedure as Example 5. ESI MS m/z=663.08, 665.08 [M+H]⁺.

Example 34

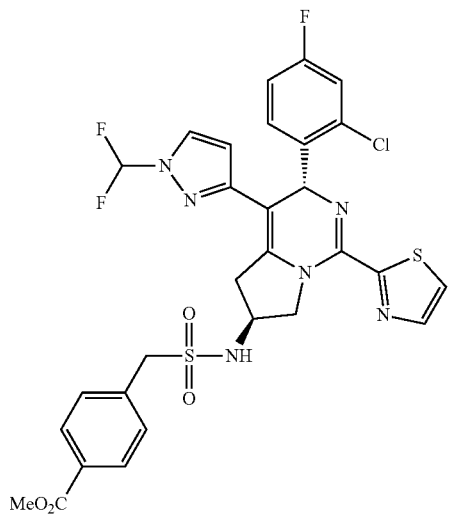 [SMILES: COC(=O)c1ccc(CS(=O)(=O)N[C@H]2CC3=C(c4ccn(C(F)F)n4)[C@H](c4ccc(F)cc4Cl)N=C(c4nccs4)N3C2)cc1]

The title compound was prepared following similar procedure as Example 2. ESI MS m/z=677.10, 679.10 [M+H]+.

Example 35

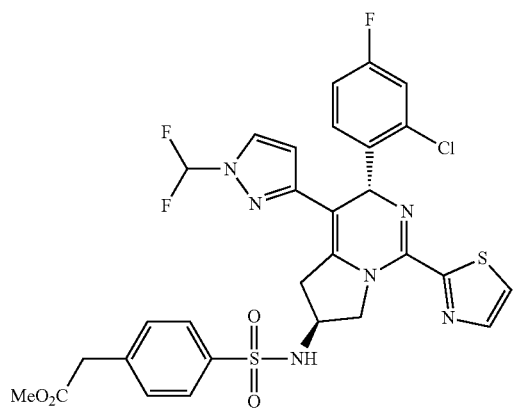 [SMILES: COC(=O)Cc1ccc(S(=O)(=O)N[C@H]2CC3=C(c4ccn(C(F)F)n4)[C@H](c4ccc(F)cc4Cl)N=C(c4nccs4)N3C2)cc1]

The title compound was prepared following similar procedure as Example 2. ESI MS m/z=677.10, 679.10 [M+H]+.

Example 36

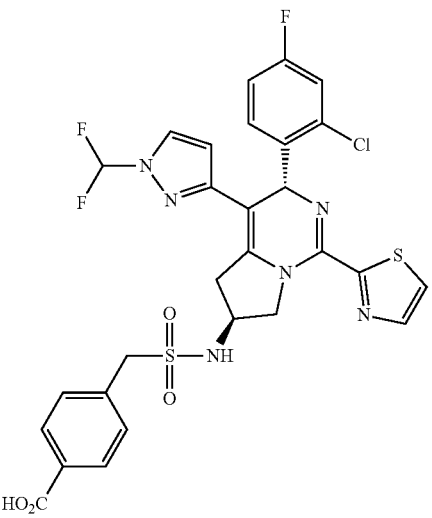 [SMILES: O=C(O)c1ccc(CS(=O)(=O)N[C@H]2CC3=C(c4ccn(C(F)F)n4)[C@H](c4ccc(F)cc4Cl)N=C(c4nccs4)N3C2)cc1]

The title compound was prepared following similar procedure as Example 5. ESI MS m/z=663.08, 665.08 [M+H]+.

Example 37

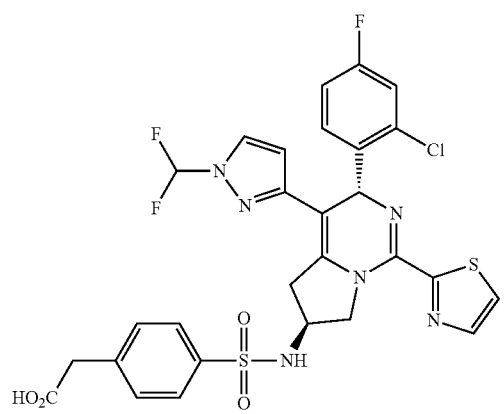 [SMILES: O=C(O)Cc1ccc(S(=O)(=O)N[C@H]2CC3=C(c4ccn(C(F)F)n4)[C@H](c4ccc(F)cc4Cl)N=C(c4nccs4)N3C2)cc1]

The title compound was prepared following similar procedure as Example 5. ESI MS m/z=663.08, 665.08 [M+H]+.

Example 38

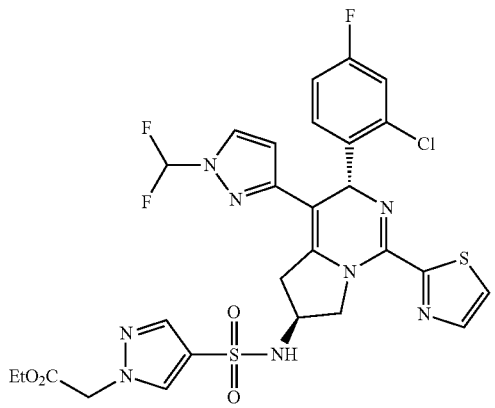 [SMILES: CCOC(=O)Cn1cc(S(=O)(=O)N[C@H]2CC3=C(c4ccn(C(F)F)n4)[C@H](c4ccc(F)cc4Cl)N=C(c4nccs4)N3C2)cn1]

To a solution of Example 20 (30.0 mg, 0.050 mmol) in acetonitrile (1 ml) at rt was added cesium carbonate (32.9 mg, 0.101 mmol), followed by a solution of ethyl bromoacetate (7.30 μl, 0.066 mmol) in acetonitrile (0.1 ml). The mixture quickly turned into a thick suspension which was stirred at rt for 0.5 h. Excess EtOH was added to quench the reaction. After 15 min at rt, the mixture was diluted with DCM and filtered through a short pad of celite. The filtrate was concentrated. The residue was purified by flash column chromatography (silica, hexanes/EtOAc) to afford the title compound as yellow foam (6.0 mg, 17%). ESI MS m/z=681.13, 683.13 [M+H]$^+$.

Example 39

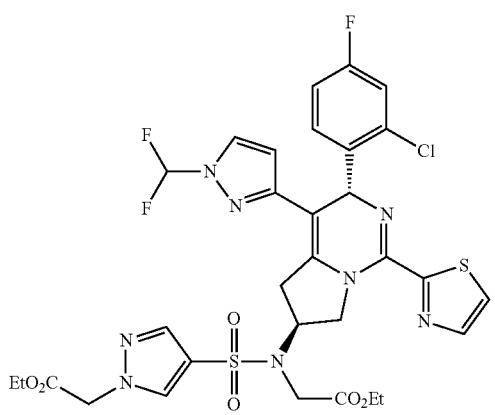 [SMILES: CCOC(=O)CN([C@H]1CC2=C(c3ccn(C(F)F)n3)[C@H](c3ccc(F)cc3Cl)N=C(c3nccs3)N2C1)S(=O)(=O)c1cnn(CC(=O)OCC)c1]

The title compound was isolated from Example 38. ESI MS m/z=767.16, 769.16 [M+H]$^+$.

Example 40

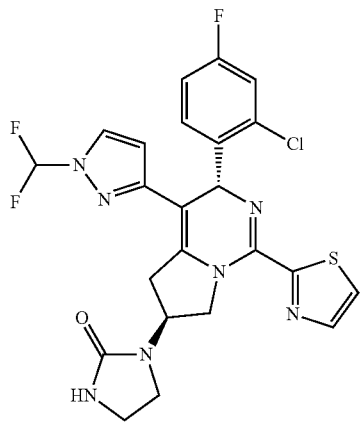 [SMILES: O=C1NCCN1[C@H]1CC2=C(c3ccn(C(F)F)n3)[C@H](c3ccc(F)cc3Cl)N=C(c3nccs3)N2C1]

Step 40a. To a solution of Example 1 (0.300 g, 0.645 mmol) in THF (7 ml) at rt was added 1-chloro-2-isocyanatoethane (0.055 ml, 0.645 mmol). The solution was stirred at rt overnight. The mixture was concentrated by rotavapor and dried under vacuum to afford the desired product as a yellow foam, which was used directly for next step. ESI MS m/z=570.09, 572.09 [M+H]$^+$.

Step 40b. To a solution of the compound from step 40a (0.645 mmol) in THF (8 ml) at rt was added NaH (60% in mineral oil, 0.052 g, 1.290 mmol). The suspension was stirred at rt for 30 min. DMF (4.00 ml) was added at rt. The suspension was stirred at rt for 2 h. Excess triethylamine hydrochloride was added to quench the reaction. The mixture was partitioned with EtOAc and water. The organic layer was washed with brine (*3), dried over Na$_2$SO$_4$ (s), filtered and concentrated. The residue was purified by flash column chromatography (silica, hexanes/EtOAc) to afford the title compound as yellow foam (0.280 g, 81% over 2 steps). ESI MS m/z=534.13, 536.12 [M+H]$^+$.

Example 41

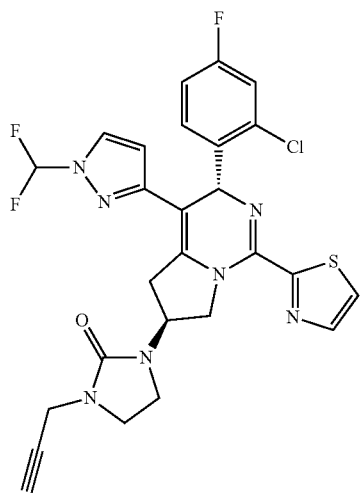 [SMILES: C#CCN1CCN([C@H]2CC3=C(c4ccn(C(F)F)n4)[C@H](c4ccc(F)cc4Cl)N=C(c4nccs4)N3C2)C1=O]

To a solution of Example 40 (0.100 g, 0.187 mmol) in DMF (2 ml) at 0° C. was added NaH (60% in mineral oil,

73

0.015 g, 0.375 mmol). The suspension was stirred at 0° C. for 30 min. Propargyl bromide (80 wt % in toluene, 0.027 ml, 0.243 mmol) was added at 0° C. The suspension was stirred at 0° C. for 1.0 h and then at rt for 0.5 h. Excess triethylamine hydrochloride was added at 0° C. to quench the reaction. The mixture was stirred at rt for 5 min and then diluted with EtOAc and water. The organic layer was washed with brine (*3), dried over Na$_2$SO$_4$ (s), filtered and concentrated. The residue was purified by flash column chromatography (silica, hexanes/acetone) to afford the title compound as yellow foam (97.0 mg, 91%). ESI MS m/z=572.13, 574.12 [M+H]$^+$.

Example 42

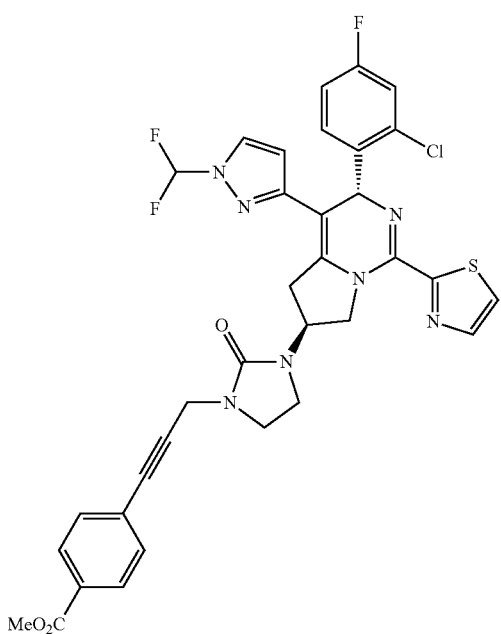 [SMILES: COC(=O)c1ccc(C#CCN2CCN([C@H]3CC4=C(c5ccn(C(F)F)n5)[C@H](c5ccc(F)cc5Cl)N=C(c5nccs5)N4C3)C2=O)cc1]

To a mixture of Example 41 (45.0 mg, 0.079 mmol), methyl 4-iodobenzoate (26.8 mg, 0.102 mmol) and copper (I) iodide (2.247 mg, 0.012 mmol) in THF (1 ml) and triethylamine (110 μl, 0.787 mmol) at rt was added bis(triphenylphosphine)palladium(II) chloride (2.76 mg, 3.93 μmol). The mixture was purged with N$_2$ and then stirred at 35° C. overnight. The mixture was concentrated. The residue was purified by flash column chromatography (silica, hexanes/EtOAc) to afford the title compound as yellow foam (42.0 mg, 76%). ESI MS m/z=706.16, 708.16 [M+H]$^+$.

74

Example 43

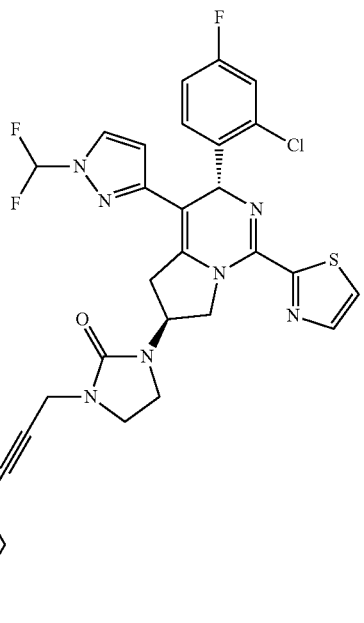

The title compound was prepared following similar procedure as Example 5. ESI MS m/z=692.15, 694.14 [M+H]$^+$.

Example 44

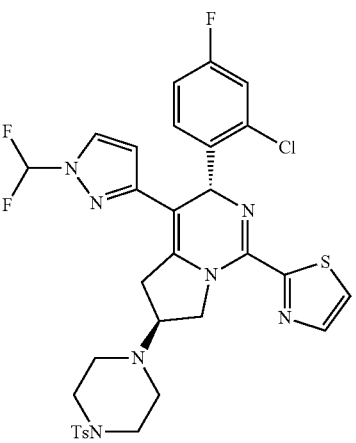 [SMILES: Cc1ccc(S(=O)(=O)N2CCN([C@H]3CC4=C(c5ccn(C(F)F)n5)[C@H](c5ccc(F)cc5Cl)N=C(c5nccs5)N4C3)CC2)cc1]

A mixture of Example 1 (0.300 g, 0.645 mmol) and N,N-bis(2-chloroethyl)-4-methylbenzenesulfonamide (0.210 g, 0.710 mmol) in DIPEA (0.248 ml, 1.419 mmol) was heated at 125° C. overnight before being allowed to cool down to rt. The mixture was dissolved in DCM and water with a little bit of MeOH. Saturated NaHCO$_3$ solution was added. The aqueous layer was extracted with DCM (*1). The combined organic layers were dried over Na$_2$SO$_4$ (s), filtered and concentrated. The residue was purified by flash column chromatography (silica, hexanes/EtOAc) to afford the title compound as yellow foam (0.315 g, 71%). ESI MS m/z=688.15, 690.15 [M+H]$^+$.

Example 45

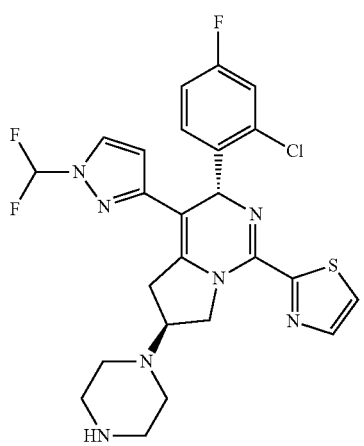 [SMILES: Fc1ccc([C@@H]2N=C(c3nccs3)N3C[C@@H](N4CCNCC4)CC3=C2c2ccn(C(F)F)n2)c(Cl)c1]

A dark green mixture of Example 44 (0.310 g, 0.450 mmol) and 4-hydroxybenzoic acid (0.187 g, 1.351 mmol) in HBr (33% in HOAc, 3.71 ml, 22.52 mmol) was stirred at rt for 2 overnights. The mixture was slowly poured into a cold mixture of DCM and 10% KOH solution. The aqueous layer was extracted with DCM (*2). The combined organic layers were dried over $Na_2SO_4$ (s), filtered and concentrated. The residue was purified by flash column chromatography (silica, DCM/MeOH/$Et_3N$) to afford the title compound as yellow foam (0.177 g, 74%). ESI MS m/z=534.14, 536.14 $[M+H]^+$.

Example 46

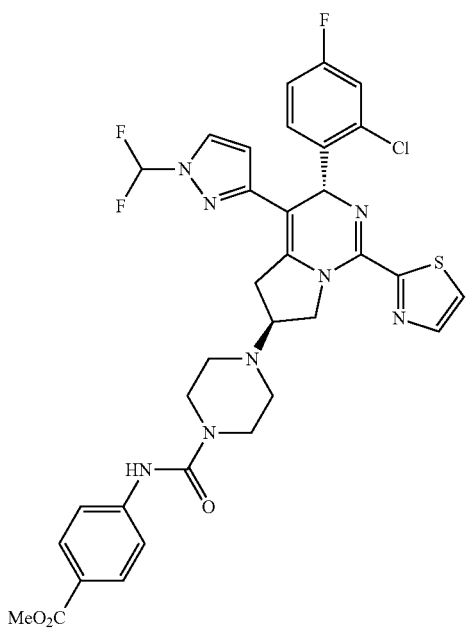 [SMILES: COC(=O)c1ccc(NC(=O)N2CCN([C@H]3CC4=C(c5ccn(C(F)F)n5)[C@H](c5ccc(F)cc5Cl)N=C(c5nccs5)N4C3)CC2)cc1]

To a solution of methyl 4-aminobenzoate (13.59 mg, 0.090 mmol) in DCM (1 ml) at rt was added CDI (14.58 mg, 0.090 mmol). The clear colorless solution was stirred at rt overnight. Example 45 (40.0 mg, 0.075 mmol) was added at rt. The mixture was stirred at rt for 3 h. The mixture was directly purified by flash column chromatography (silica, DCM/MeOH) to afford the title compound as yellow foam (17.5 mg, 33%). ESI MS m/z=711.19, 713.19 $[M+H]^+$.

Example 47

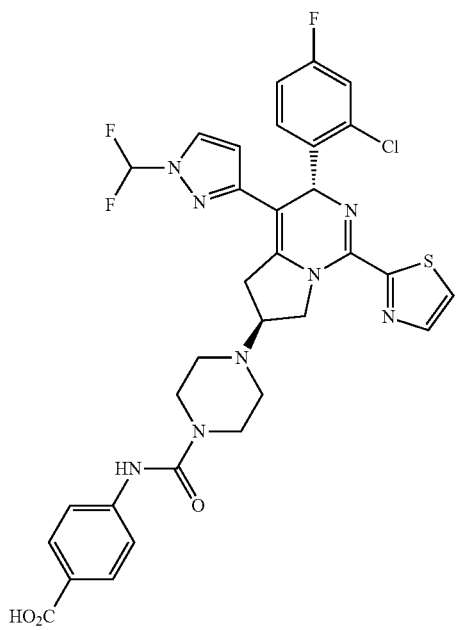 [SMILES: O=C(O)c1ccc(NC(=O)N2CCN([C@H]3CC4=C(c5ccn(C(F)F)n5)[C@H](c5ccc(F)cc5Cl)N=C(c5nccs5)N4C3)CC2)cc1]

The title compound was prepared following similar procedure as Example 5. ESI MS m/z=697.17, 699.17 $[M+H]^+$.

Example 48

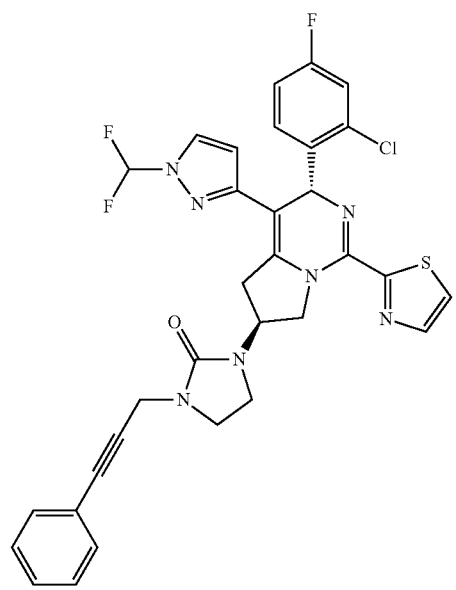 [SMILES: O=C1N(CC#Cc2ccccc2)CCN1[C@H]1CC2=C(c3ccn(C(F)F)n3)[C@H](c3ccc(F)cc3Cl)N=C(c3nccs3)N2C1]

The title compound was prepared following similar procedure as Example 42. ESI MS m/z=648.16, 650.15 $[M+H]^+$.

Example 49

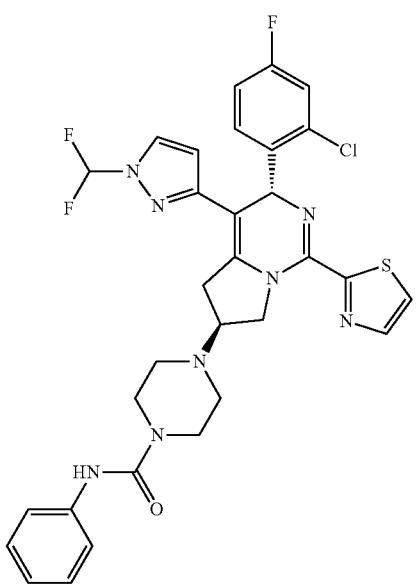 [SMILES: O=C(Nc1ccccc1)N1CCN([C@H]2CC3=C(c4ccn(C(F)F)n4)[C@H](c4ccc(F)cc4Cl)N=C(c4nccs4)N3C2)CC1]

To a solution of Example 45 (20.0 mg, 0.037 mmol) in THF (1 ml) at rt was added phenyl isocyanate (6.14 μl, 0.056 mmol). The clear colorless solution was stirred at rt for 2 h. Excess MeOH was added to quench the reaction. The mixture was concentrated. The residue was purified by flash column chromatography (silica, DCM/MeOH) to afford the title compound as yellow foam (20.0 mg, 82%). ESI MS m/z=653.18, 655.18 [M+H]$^+$.

Example 50

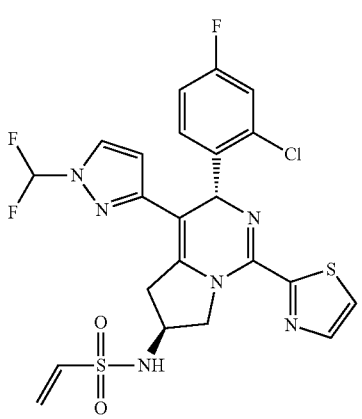 [SMILES: C=CS(=O)(=O)N[C@H]1CC2=C(c3ccn(C(F)F)n3)[C@H](c3ccc(F)cc3Cl)N=C(c3nccs3)N2C1]

To a solution of Example 1 (0.600 g, 1.291 mmol) in DCM (15 ml) at 0° C. was added triethylamine (0.720 ml, 5.16 mmol), followed by 2-chloroethane-1-sulfonyl chloride (0.135 ml, 1.291 mmol). The resulting yellow solution was stirred at 0° C. for 1.0 h. Water was added to quench the reaction. The mixture was allowed to warm up to rt and diluted with DCM and brine. The aqueous layer was extracted with DCM (*1). The combined organic layers were dried over Na$_2$SO$_4$ (s), filtered and concentrated. The residue was purified by flash column chromatography (silica, EtOAc/Hexanes) to afford the title compound as yellow foam (0.655 g, 91%). ESI MS m/z=555.07, 557.06 [M+H]$^+$.

Example 51

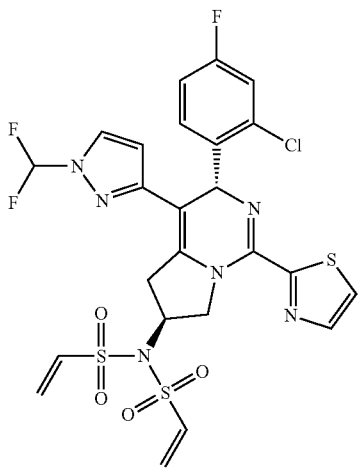 [SMILES: C=CS(=O)(=O)N([C@H]1CC2=C(c3ccn(C(F)F)n3)[C@H](c3ccc(F)cc3Cl)N=C(c3nccs3)N2C1)S(=O)(=O)C=C]

The title compound was isolated from Example 50. ESI MS m/z=645.04, 647.04 [M+H]$^+$.

Example 52

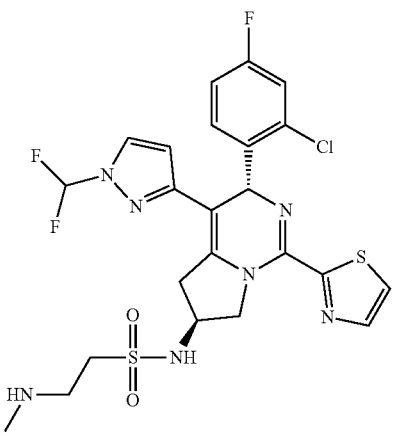 [SMILES: CNCCS(=O)(=O)N[C@H]1CC2=C(c3ccn(C(F)F)n3)[C@H](c3ccc(F)cc3Cl)N=C(c3nccs3)N2C1]

To a solution of Example 50 (30.0 mg, 0.054 mmol) in THF (1 ml) at rt was added methylamine (2 M in THF, 135 μl, 0.270 mmol). The resulting yellow solution was stirred at rt for 1.0 h. More methylamine (2 M in THF, 135 μl, 0.270 mmol) was added. The solution was stirred at rt overnight before being freed of volatiles with a stream of N$_2$. The residue was purified by flash column chromatography (silica, DCM/MeOH) to afford the title compound as yellow foam (24.0 mg, 76%). ESI MS m/z=586.11, 588.10 [M+H]$^+$.

Example 53

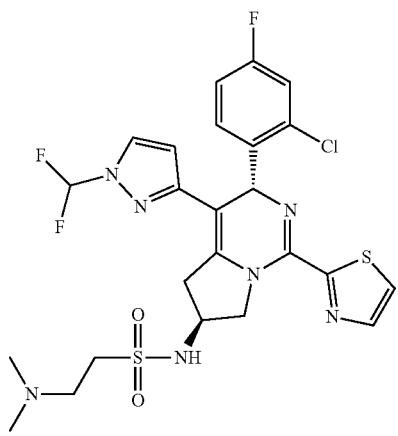 [SMILES: CN(C)CCS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 52. ESI MS m/z=600.12, 602.12 [M+H]⁺.

Example 54

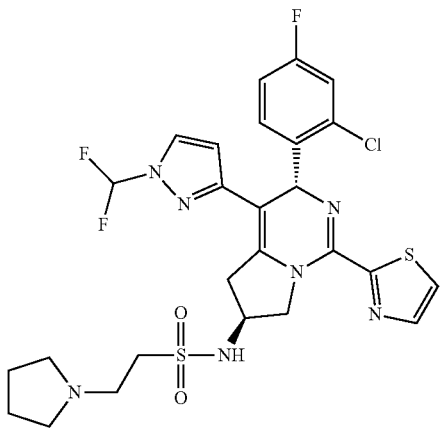 [SMILES: O=S(=O)(CCN1CCCC1)N[C@H]1CC2=C(c3ccn(C(F)F)n3)[C@H](c3ccc(F)cc3Cl)N=C(c3nccs3)N2C1]

The title compound was prepared following similar procedure as Example 52. ESI MS m/z=626.14, 628.14 [M+H]⁺.

Example 55

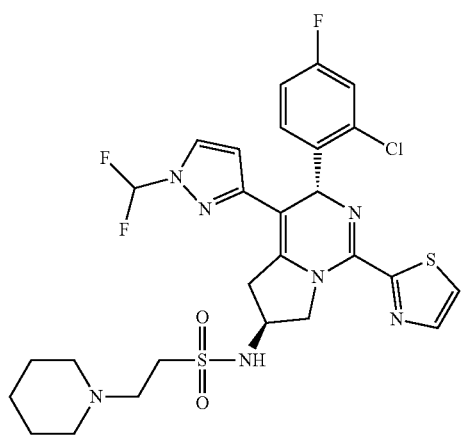 [SMILES: O=S(=O)(CCN1CCCCC1)N[C@H]1CC2=C(c3ccn(C(F)F)n3)[C@H](c3ccc(F)cc3Cl)N=C(c3nccs3)N2C1]

The title compound was prepared following similar procedure as Example 52. ESI MS m/z=640.16, 642.15 [M+H]⁺.

Example 56

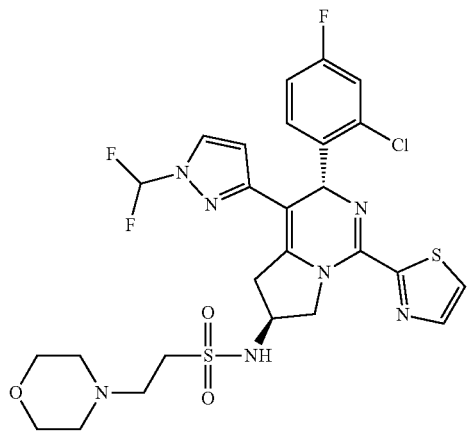 [SMILES: O=S(=O)(CCN1CCOCC1)N[C@H]1CC2=C(c3ccn(C(F)F)n3)[C@H](c3ccc(F)cc3Cl)N=C(c3nccs3)N2C1]

The title compound was prepared following similar procedure as Example 52. ESI MS m/z=642.13, 644.13 [M+H]⁺.

Example 57

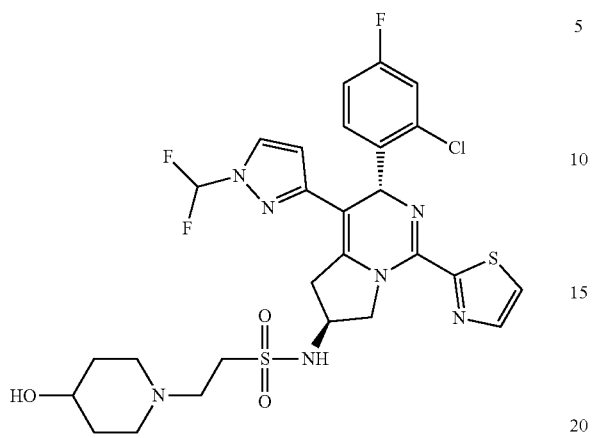

The title compound was prepared following similar procedure as Example 52. ESI MS m/z=656.15, 658.15 [M+H]+.

Example 59

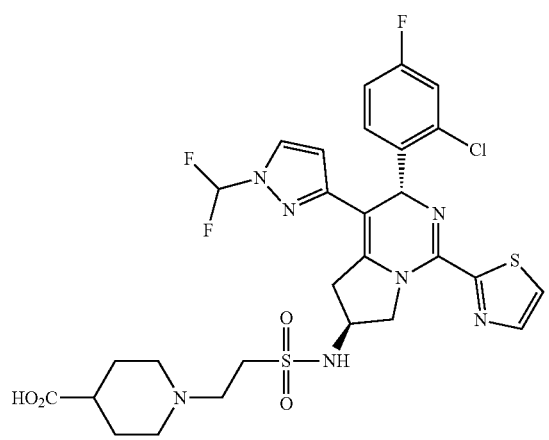 [SMILES: O=C(O)C1CCN(CCS(=O)(=O)N[C@H]2CC3=C(c4ccn(C(F)F)n4)[C@H](c4ccc(F)cc4Cl)N=C(c4nccs4)N3C2)CC1]

The title compound was prepared following similar procedure as Example 5. ESI MS m/z=684.14, 686.14 [M+H]+.

Example 58

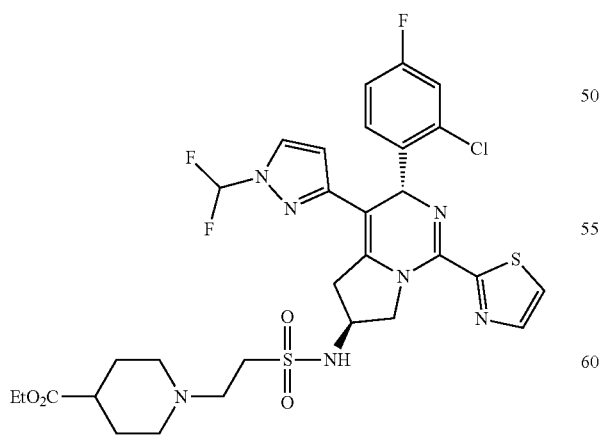

The title compound was prepared following similar procedure as Example 52. ESI MS m/z=712.18, 714.17 [M+H]+.

Example 60

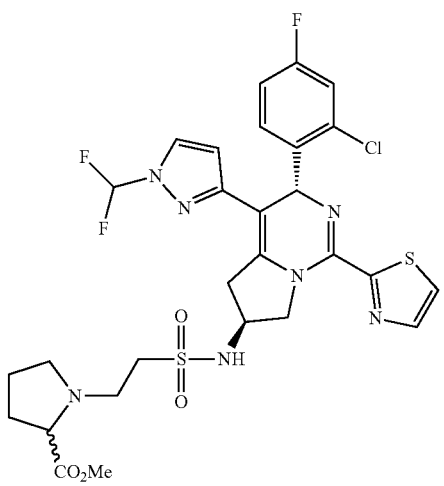 [SMILES: COC(=O)C1CCCN1CCS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 52. ESI MS m/z=684.14, 686.14 [M+H]+.

Example 61

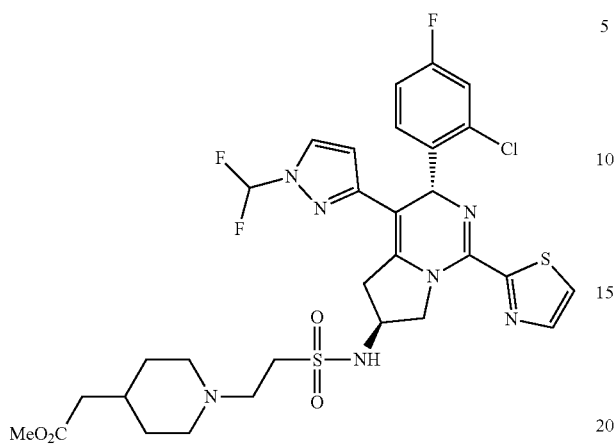

The title compound was prepared following similar procedure as Example 52. ESI MS m/z=712.18, 714.17 [M+H]⁺.

Example 63

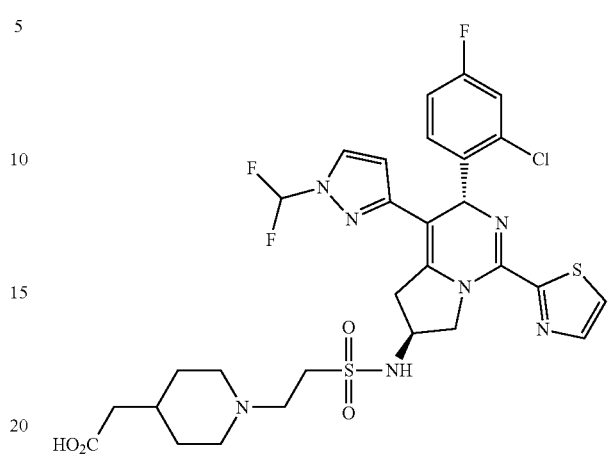

The title compound was prepared following similar procedure as Example 5. ESI MS m/z=698.16, 700.16 [M+H]⁺.

Example 62

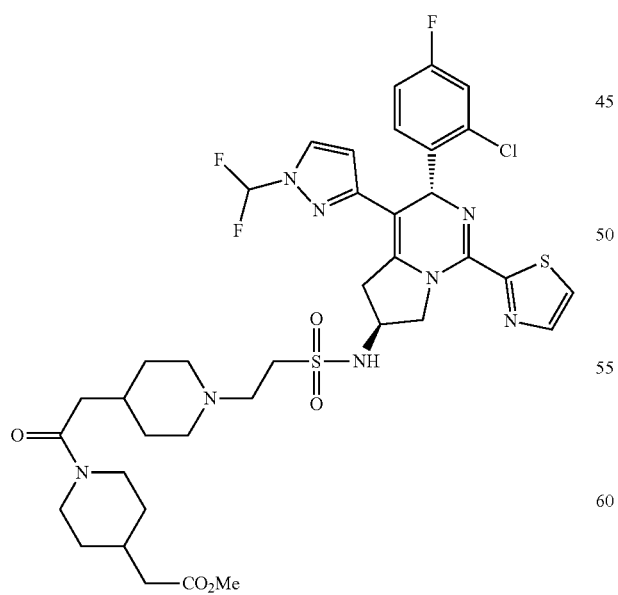

The title compound was isolated from Example 61. ESI MS m/z=837.26, 839.26 [M+H]⁺.

Example 64

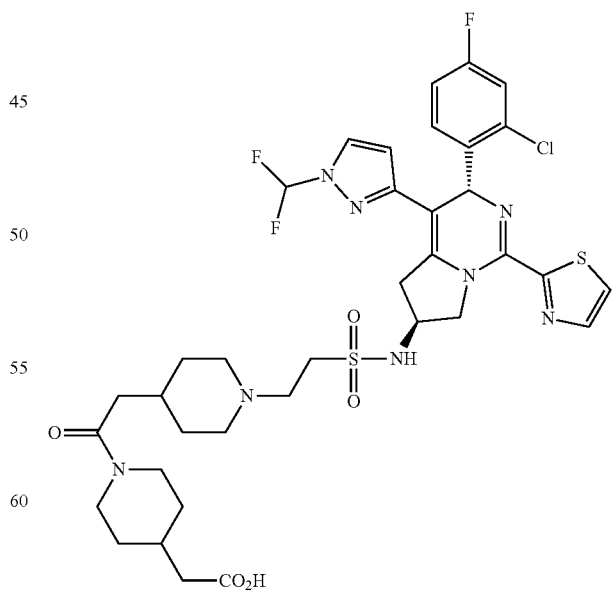

The title compound was prepared following similar procedure as Example 5. ESI MS m/z=823.25, 825.24 [M+H]⁺.

Example 65

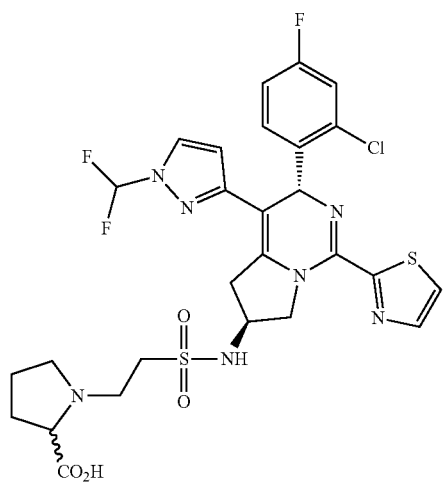 [SMILES: O=C(O)C1CCCN1CCS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 5. ESI MS m/z=670.13, 672.13 [M+H]$^+$.

Example 67

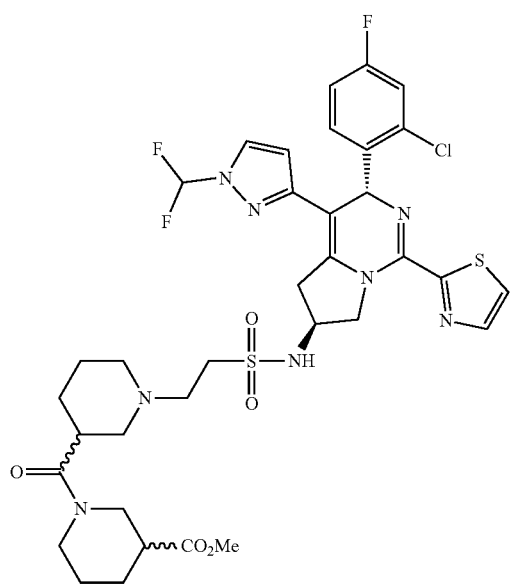

The title compound was isolated from Example 66. ESI MS m/z=809.23, 811.23 [M+H]$^+$.

Example 66

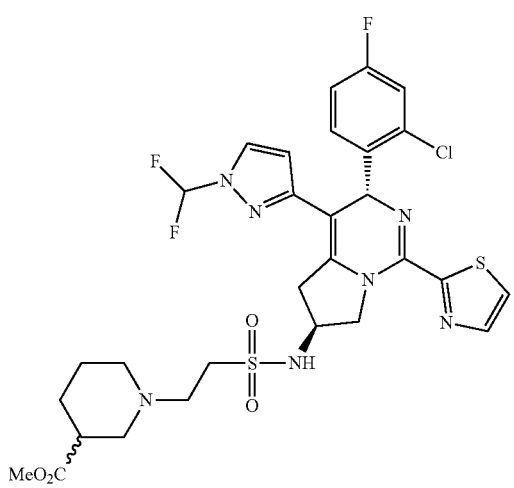 [SMILES: COC(=O)C1CCCN(CCS(=O)(=O)N[C@H]2CC3=C(c4ccn(C(F)F)n4)[C@H](c4ccc(F)cc4Cl)N=C(c4nccs4)N3C2)C1]

The title compound was prepared following similar procedure as Example 52. ESI MS m/z=698.16, 700.16 [M+H]$^+$.

Example 68

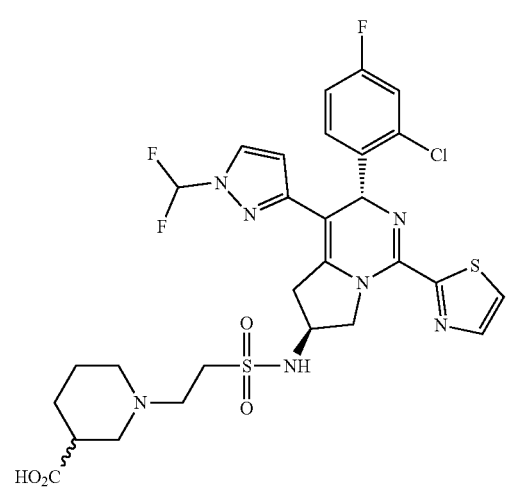 [SMILES: O=C(O)C1CCCN(CCS(=O)(=O)N[C@H]2CC3=C(c4ccn(C(F)F)n4)[C@H](c4ccc(F)cc4Cl)N=C(c4nccs4)N3C2)C1]

The title compound was prepared following similar procedure as Example 5. ESI MS m/z=684.15, 686.14 [M+H]$^+$.

Example 69

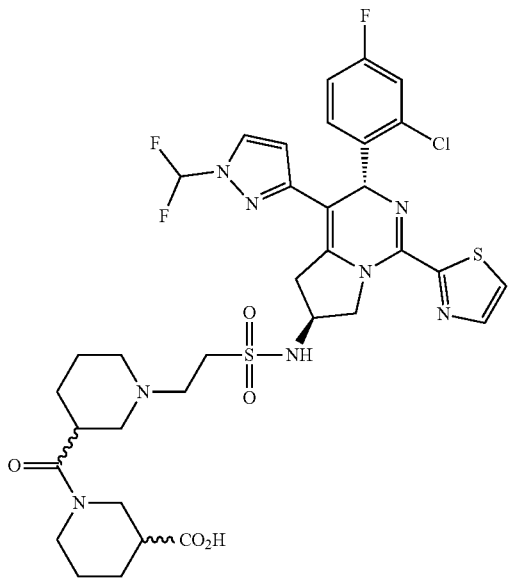 [SMILES: O=C(O)C1CCCN(C(=O)C2CCCN(CCS(=O)(=O)N[C@H]3CC4=C(c5ccn(C(F)F)n5)[C@H](c5ccc(F)cc5Cl)N=C(c5nccs5)N4C3)C2)C1]

The title compound was prepared following similar procedure as Example 5. ESI MS m/z=795.21, 797.21 [M+H]⁺.

Example 70

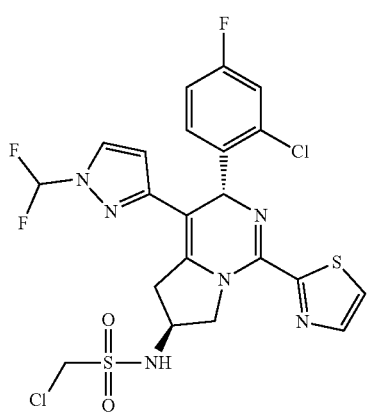 [SMILES: O=S(=O)(CCl)N[C@H]1CC2=C(c3ccn(C(F)F)n3)[C@H](c3ccc(F)cc3Cl)N=C(c3nccs3)N2C1]

The title compound was prepared following similar procedure as Example 2. ESI MS m/z=577.00, 579.00 [M+H]⁺.

Example 71

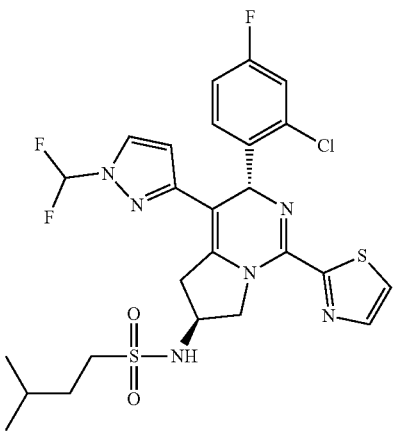 [SMILES: CC(C)CCS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 2. ESI MS m/z=599.10, 601.10 [M+H]⁺.

Example 72

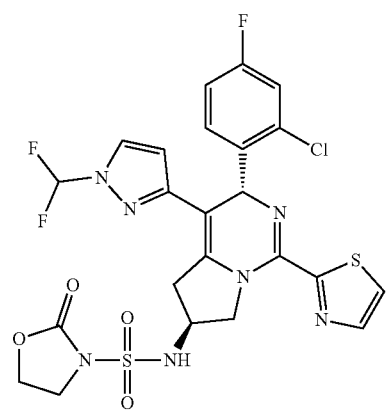 [SMILES: O=C1OCCN1S(=O)(=O)N[C@H]1CC2=C(c3ccn(C(F)F)n3)[C@H](c3ccc(F)cc3Cl)N=C(c3nccs3)N2C1]

To a solution of chlorosulfonyl isocyanate (61.8 μl, 0.710 mmol) in DCM (6 ml) at 0° C. was added a solution of 2-bromoethan-1-ol (50.3 μl, 0.710 mmol) in DCM (0.5 ml). The solution was stirred at 0° C. for 1 h and then at rt for 1 h. A solution of Example 1 (300.0 mg, 0.645 mmol) and triethylamine (180 μl, 1.291 mmol) in DCM (1 ml) was added at rt. The resulting yellow solution was stirred at rt for 1 h. Excess 2-propanol was added to quench the reaction. The mixture was concentrated. The residue was purified by flash column chromatography (silica, EtOAc/Hexanes) to afford the title compound as yellow foam (0.230 g, 58%). ESI MS m/z=614.04, 616.04 [M+H]⁺.

Example 73

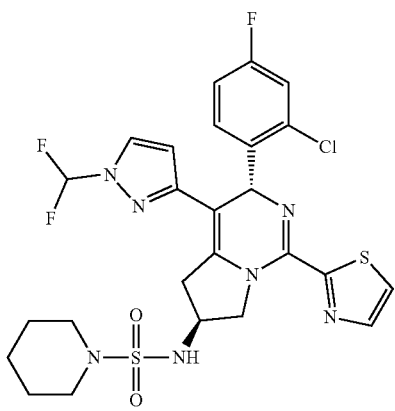 [SMILES: O=S(=O)(N[C@H]1CC2=C(c3ccn(C(F)F)n3)[C@H](c3ccc(F)cc3Cl)N=C(c3nccs3)N2C1)N1CCCCC1]

To a solution of Example 72 (30.0 mg, 0.049 mmol) in acetonitrile (1 ml) at rt was added triethylamine (20.43 μl, 0.147 mmol), followed by a solution of piperidine (5.31 μl, 0.054 mmol) in acetonitrile (0.1 ml). The solution was stirred at 100° C. for 0.5 h using a microwave reactor. The mixture was concentrated. The residue was purified by flash column chromatography (silica, EtOAc/Hexanes) to afford the title compound as yellow foam (22.0 mg, 74%). ESI MS m/z=612.10, 614.09 [M+H]$^+$.

Example 74

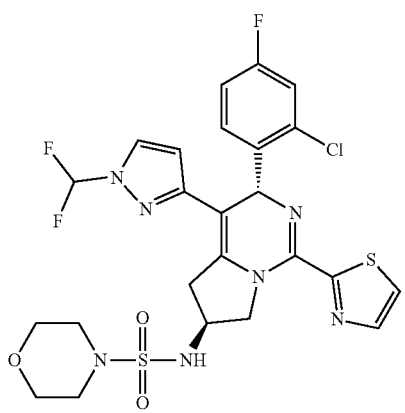 [SMILES: O=S(=O)(N[C@H]1CC2=C(c3ccn(C(F)F)n3)[C@H](c3ccc(F)cc3Cl)N=C(c3nccs3)N2C1)N1CCOCC1]

The title compound was prepared following similar procedure as Example 73. ESI MS m/z=614.07, 616.07 [M+H]$^+$.

Example 75

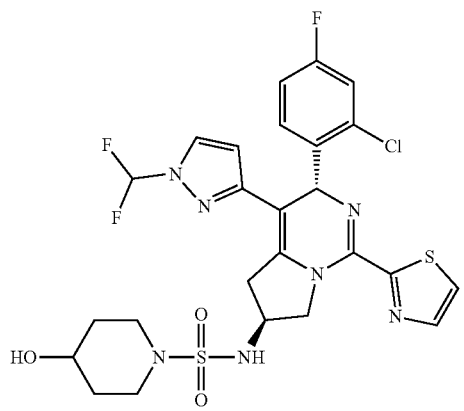 [SMILES: O=S(=O)(N[C@H]1CC2=C(c3ccn(C(F)F)n3)[C@H](c3ccc(F)cc3Cl)N=C(c3nccs3)N2C1)N1CCC(O)CC1]

The title compound was prepared following similar procedure as Example 73. ESI MS m/z=628.09, 630.08 [M+H]$^+$.

Example 76

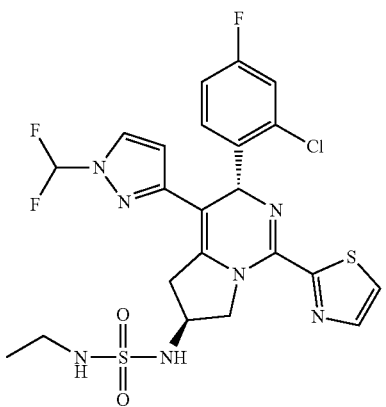 [SMILES: CCNS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 2. ESI MS m/z=572.07, 574.06 [M+H]$^+$.

Example 77

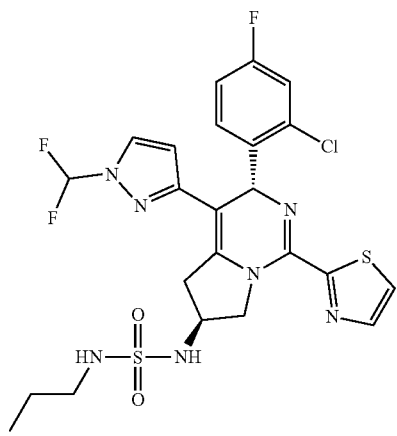 [SMILES: CCCNS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 73. ESI MS m/z=586.08, 588.08 [M+H]⁺.

Example 78

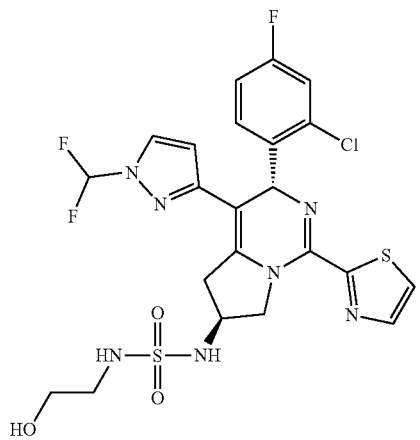

The title compound was prepared following similar procedure as Example 73. ESI MS m/z=588.06, 590.06 [M+H]⁺.

Example 79

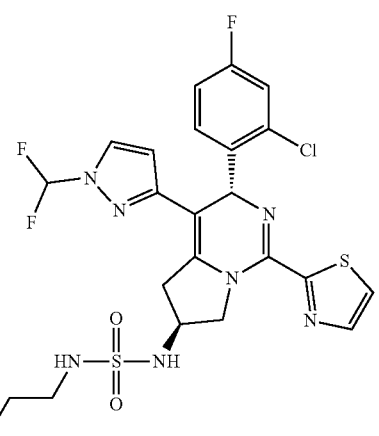

The title compound was prepared following similar procedure as Example 73. ESI MS m/z=602.08, 604.07 [M+H]⁺.

Example 80

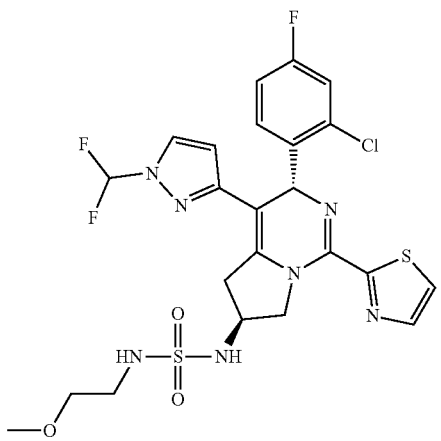 [SMILES: COCCNS(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 73. ESI MS m/z=602.08, 604.08 [M+H]⁺.

Example 81

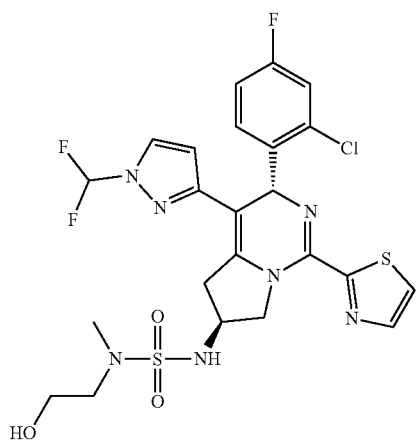 [SMILES: CN(CCO)S(=O)(=O)N[C@H]1CC2=C(c3ccn(C(F)F)n3)[C@H](c3ccc(F)cc3Cl)N=C(c3nccs3)N2C1]

The title compound was prepared following similar procedure as Example 73. ESI MS m/z=602.10, 604.10 [M+H]+.

Example 82

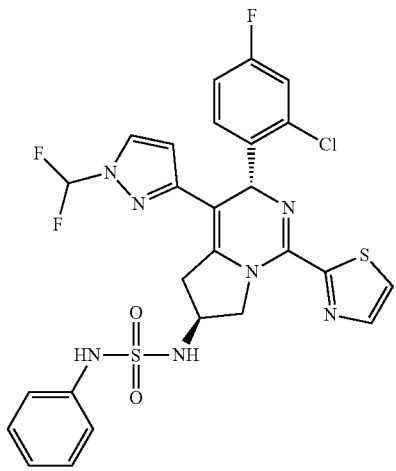 [SMILES: O=S(=O)(Nc1ccccc1)N[C@H]1CC2=C(c3ccn(C(F)F)n3)[C@H](c3ccc(F)cc3Cl)N=C(c3nccs3)N2C1]

The title compound was prepared following similar procedure as Example 73. ESI MS m/z=620.09, 622.09 [M+H]+.

Example 83

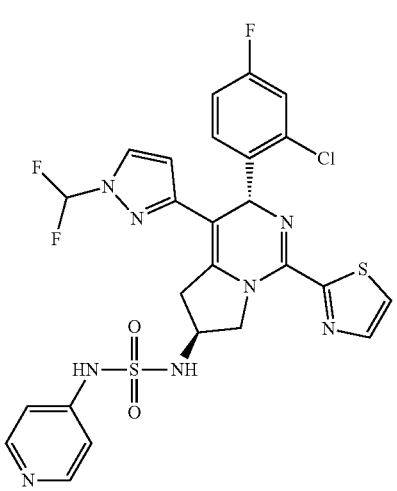 [SMILES: O=S(=O)(Nc1ccncc1)N[C@H]1CC2=C(c3ccn(C(F)F)n3)[C@H](c3ccc(F)cc3Cl)N=C(c3nccs3)N2C1]

The title compound was prepared following similar procedure as Example 73. ESI MS m/z=621.09, 623.08 [M+H]+.

Example 87

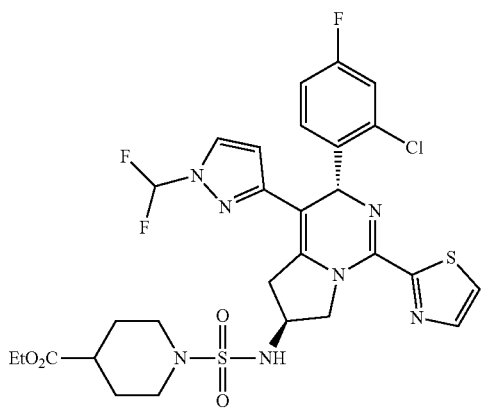 [SMILES: CCOC(=O)C1CCN(S(=O)(=O)N[C@H]2CC3=C(c4ccn(C(F)F)n4)[C@H](c4ccc(F)cc4Cl)N=C(c4nccs4)N3C2)CC1]

The title compound was prepared following similar procedure as Example 73. ESI MS m/z=684.13, 686.12 [M+H]+.

Example 88

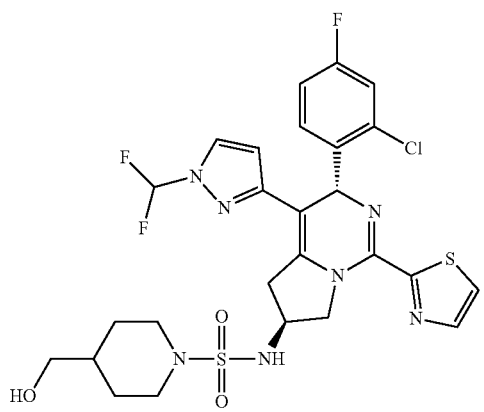 [SMILES: O=S(=O)(N[C@H]1CC2=C(c3ccn(C(F)F)n3)[C@H](c3ccc(F)cc3Cl)N=C(c3nccs3)N2C1)N1CCC(CO)CC1]

The title compound was prepared following similar procedure as Example 73. ESI MS m/z=642.11, 644.10 [M+H]+.

Example 89

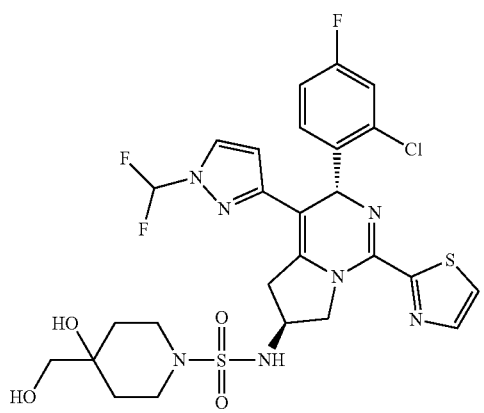 [SMILES: O=S(=O)(N[C@H]1CC2=C(c3ccn(C(F)F)n3)[C@H](c3ccc(F)cc3Cl)N=C(c3nccs3)N2C1)N1CCC(O)(CO)CC1]

The title compound was prepared following similar procedure as Example 73. ESI MS m/z=658.10, 660.10 [M+H]+.

Example 90

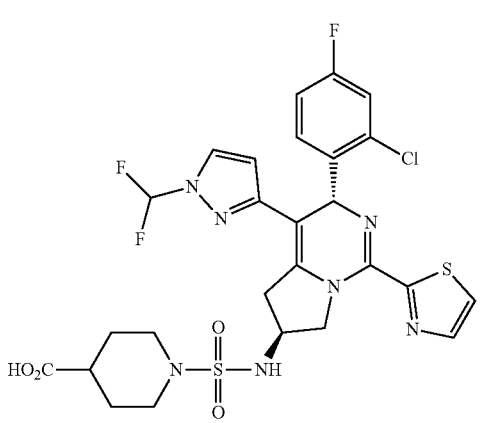 [SMILES: O=C(O)C1CCN(S(=O)(=O)N[C@H]2CC3=C(c4ccn(C(F)F)n4)[C@H](c4ccc(F)cc4Cl)N=C(c4nccs4)N3C2)CC1]

The title compound was prepared following similar procedure as Example 5. ESI MS m/z=656.09, 658.08 [M+H]+.

Example 91

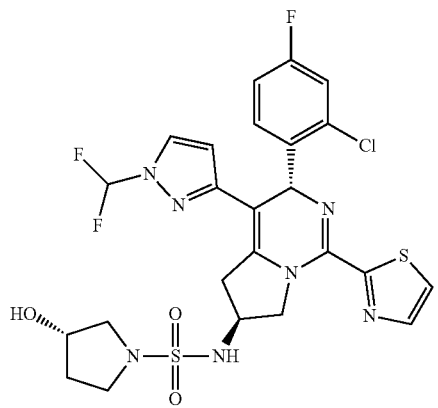 [SMILES: O=S(=O)(N[C@H]1CC2=C(c3ccn(C(F)F)n3)[C@H](c3ccc(F)cc3Cl)N=C(c3nccs3)N2C1)N1CC[C@H](O)C1]

The title compound was prepared following similar procedure as Example 73. ESI MS m/z=614.07, 616.07 [M+H]+.

Example 92

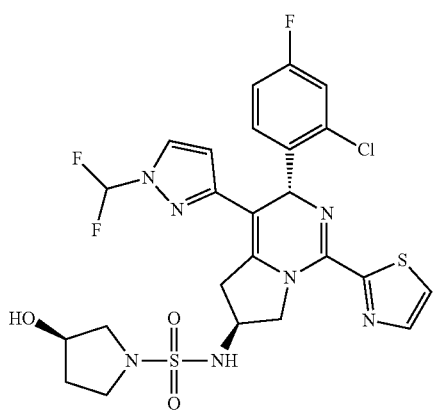 [SMILES: O=S(=O)(N[C@H]1CC2=C(c3ccn(C(F)F)n3)[C@H](c3ccc(F)cc3Cl)N=C(c3nccs3)N2C1)N1CC[C@@H](O)C1]

The title compound was prepared following similar procedure as Example 73. ESI MS m/z=614.08, 616.07 [M+H]+.

Example 94

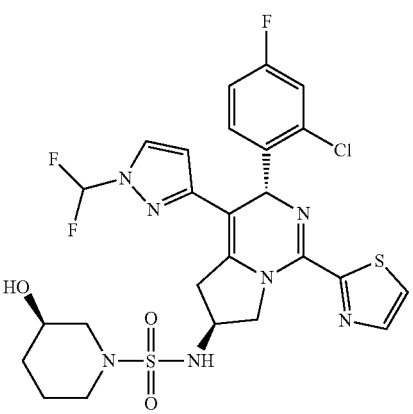

The title compound was prepared following similar procedure as Example 73. ESI MS m/z=628.08, 630.09 [M+H]+.

Example 93

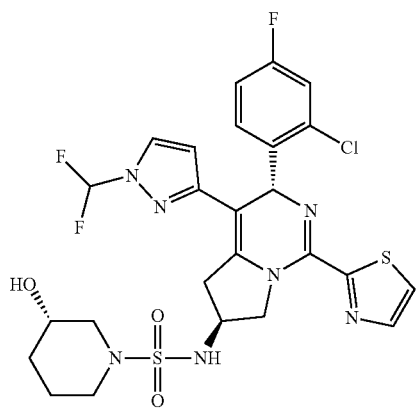 [SMILES: O=S(=O)(N[C@H]1CC2=C(c3ccn(C(F)F)n3)[C@H](c3ccc(F)cc3Cl)N=C(c3nccs3)N2C1)N1CCC[C@H](O)C1]

The title compound was prepared following similar procedure as Example 73. ESI MS m/z=628.10, 630.09 [M+H]+.

Example 95

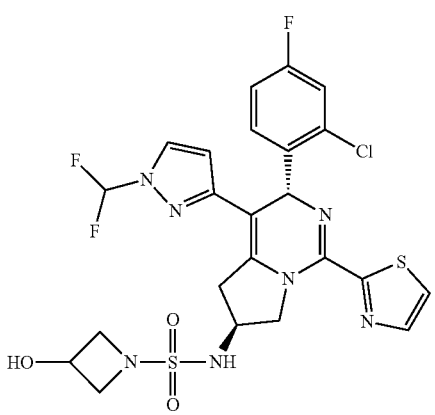 [SMILES: O=S(=O)(N[C@H]1CC2=C(c3ccn(C(F)F)n3)[C@H](c3ccc(F)cc3Cl)N=C(c3nccs3)N2C1)N1CC(O)C1]

The title compound was prepared following similar procedure as Example 73. ESI MS m/z=600.05, 602.05 [M+H]+.

Example 96

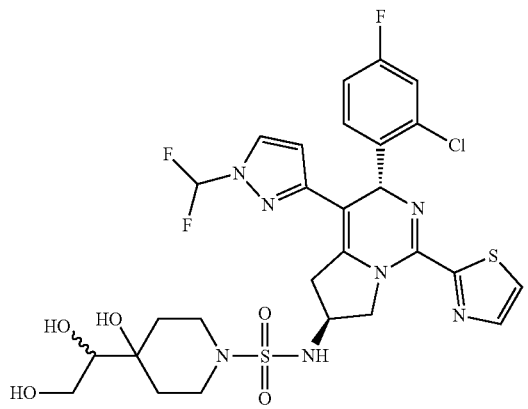 [SMILES: O=S(=O)(N[C@H]1CC2=C(c3ccn(C(F)F)n3)[C@H](c3ccc(F)cc3Cl)N=C(c3nccs3)N2C1)N1CCC(O)(C(O)CO)CC1]

Step 96a. To a clear solution of 4-hydroxy-4-vinyl-piperidine-1-carboxylic acid benzyl ester (0.200 g, 0.765 mmol) in THF (6 ml) and water (0.600 ml) at rt was added NMO (0.448 g, 3.83 mmol), followed by osmium tetroxide (2.5 wt % in t-butanol, 0.480 ml, 0.038 mmol) dropwise. The mixture was stirred at rt overnight. Saturated $Na_2S_2O_3$ solution was added to quench the reaction. After 20 min at rt, the mixture was diluted with DCM. The aqueous layer was back-extracted with DCM (*3). The combined organic layers were dried over $Na_2SO_4$ (s), filtered and concentrated. The residue was purified by flash column chromatography (silica, EtOAc/Hexanes) to afford the desired compound as yellow foam (0.204 g, 90%). ESI MS m/z=296.14 [M+H]+.

Step 96b. To a clear solution of the compound from step 96a (0.204 g, 0.691 mmol) in MeOH (5 ml) was added 10% Pd—C (0.074 g, 0.069 mmol). The mixture was flushed with $H_2$ and stirred at rt with a $H_2$ balloon for 3 h. The suspension was filtered through a short pad of celite, washing with MeOH. The filtrate was concentrated. The residue was dried under vacuum to afford the desired compound as yellow foam (0.115 g, 100%), which was used directly for next step.

Step 96c. To a solution of Example 72 (0.030 g, 0.049 mmol) in acetonitrile (1 ml) at rt was added triethylamine (0.034 ml, 0.244 mmol), followed by a solution of the compound from step 96b (10.24 mg, 0.064 mmol) in ACN/DMF/MeOH (2/1/1, 0.2 ml). The solution was stirred at 105° C. for 0.5 h using a microwave reactor. The solution was freed of volatiles with a stream of $N_2$. The residue was purified by flash column chromatography (silica, acetone/Hexanes) to afford the title compound as yellow foam (5.0 mg, 15%). ESI MS m/z=688.11, 690.11 [M+H]+.

Example 97

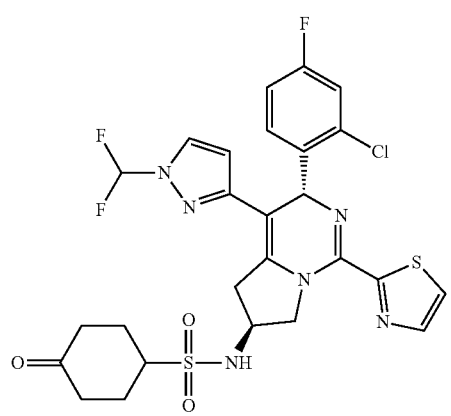 [SMILES: O=C1CCC(S(=O)(=O)N[C@H]2CC3=C(c4ccn(C(F)F)n4)[C@H](c4ccc(F)cc4Cl)N=C(c4nccs4)N3C2)CC1]

The title compound was prepared following similar procedure as Example 2. ESI MS m/z=625.09, 627.08 [M+H]+.

Example 98

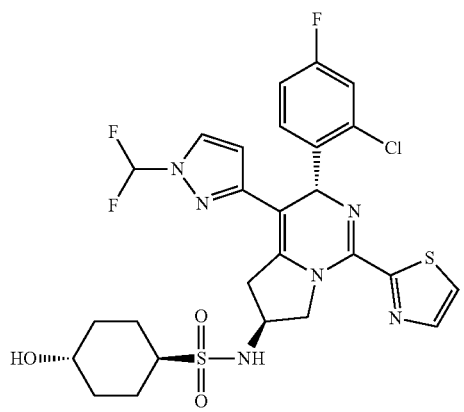 [SMILES: O=S(=O)(N[C@H]1CC2=C(c3ccn(C(F)F)n3)[C@H](c3ccc(F)cc3Cl)N=C(c3nccs3)N2C1)[C@H]1CC[C@H](O)CC1]

Step 98a. To a solution of Example 97 (0.080 g, 0.128 mmol) in MeOH (3 ml) at 0° C. was added $NaBH_4$ (7.26 mg, 0.192 mmol) The mixture was stirred at 0° C. for 0.5 h. Saturated $NH_4Cl$ solution was added to quench the reaction. The mixture was diluted with DCM and water and allowed to warm up to rt. The aqueous layer was back-extracted with DCM (*1).

The combined organic layers were dried over $Na_2SO_4$ (s), filtered and concentrated. The residue was purified by flash column chromatography (silica, acetone/Hexanes) to afford the title compound as yellow foam (62.0 mg, 77%). ESI MS m/z=627.10, 629.10 [M+H]+.

Example 99

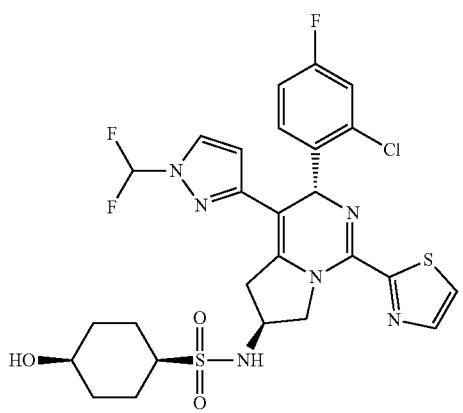 [SMILES: O=S(=O)(N[C@H]1CC2=C(c3ccn(C(F)F)n3)[C@H](c3ccc(F)cc3Cl)N=C(c3nccs3)N2C1)[C@H]1CC[C@@H](O)CC1]

The title compound was isolated from Example 98. ESI MS m/z=627.10, 629.10 [M+H]+.

Example 100

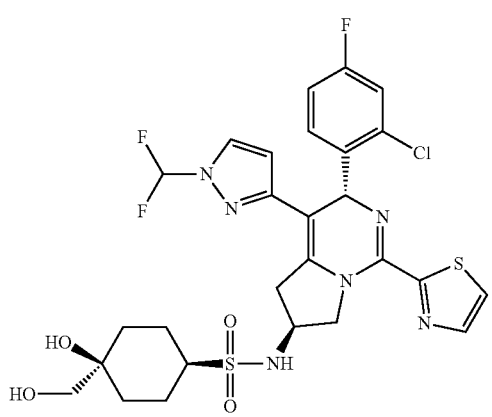 [SMILES: O=S(=O)(N[C@H]1CC2=C(c3ccn(C(F)F)n3)[C@H](c3ccc(F)cc3Cl)N=C(c3nccs3)N2C1)[C@H]1CC[C@](O)(CO)CC1]

Step 100a. To a solution of trimethylsulfoxinium iodide (0.070 g, 0.320 mmol) in DMSO (3 ml) at rt was added potassium tert-butoxide (0.054 g, 0.480 mmol). The mixture was stirred at rt for 0.5 h. A solution of Example 97 (0.100 g, 0.160 mmol) in DMSO (1.0 ml) was added. The mixture was stirred at rt for 2 h. Saturated NH₄Cl solution was added to quench the reaction. The mixture was diluted with EtOAc. The organic layer was washed with water (*2), brine (*1), dried over Na₂SO₄ (s), filtered and concentrated. The residue was purified by flash column chromatography (silica, EtOAc/cyclohexane) to afford the desired compound as yellow foam (95.0 mg, 93%). ESI MS m/z=639.11, 641.10 [M+H]+.

Step 100b. To a solution of the compound from step 100a (95.0 mg, 0.149 mmol) in THF (1.2 ml) and water (0.400 ml) at rt was added TFA (45.8 µl, 0.595 mmol). The mixture was stirred at rt for 3 h. Saturated NaHCO₃ solution (0.4 ml) was added to quench the reaction, followed by a solution of NaOH (23.78 mg, 0.595 mmol) in water (0.05 ml). The mixture was stirred at rt for 15 min before being diluted with DCM and water. The aqueous layer was extracted with DCM (*1). The combined organic layers were dried over Na₂SO₄ (s), filtered and concentrated. The residue was purified by flash column chromatography (silica, acetone/Hexanes) to afford the title compound as yellow foam (94.0 mg, 96%). ESI MS m/z=657.12, 659.11 [M+H]+.

Example 101

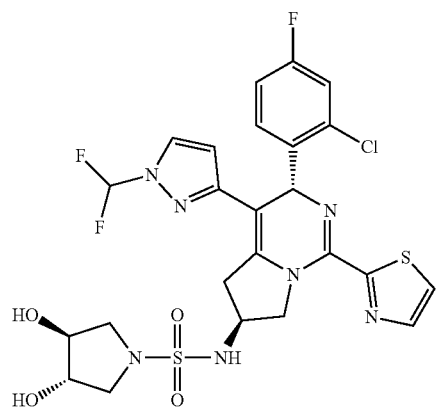 [SMILES: O=S(=O)(N[C@H]1CC2=C(c3ccn(C(F)F)n3)[C@H](c3ccc(F)cc3Cl)N=C(c3nccs3)N2C1)N1C[C@H](O)[C@@H](O)C1]

The title compound was prepared following similar procedure as Example 73. ESI MS m/z=630.07, 632.07 [M+H]+.

Example 102

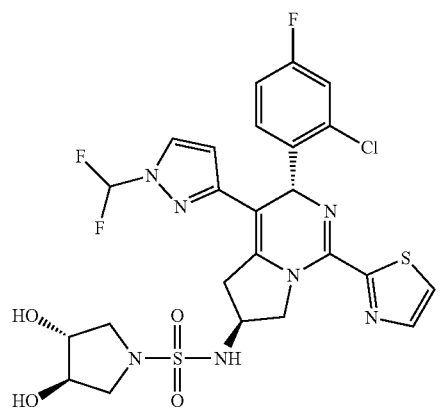 [SMILES: O=S(=O)(N[C@H]1CC2=C(c3ccn(C(F)F)n3)[C@H](c3ccc(F)cc3Cl)N=C(c3nccs3)N2C1)N1C[C@@H](O)[C@H](O)C1]

The title compound was prepared following similar procedure as Example 73. ESI MS m/z=630.07, 632.07 [M+H]+.

Example 103

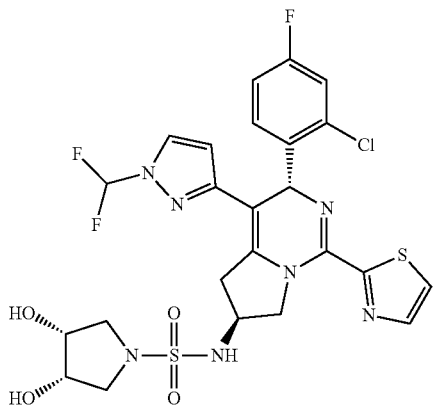 [SMILES: O=S(=O)(N[C@H]1CC2=C(c3ccn(C(F)F)n3)[C@H](c3ccc(F)cc3Cl)N=C(c3nccs3)N2C1)N1C[C@@H](O)[C@@H](O)C1]

The title compound was prepared following similar procedure as Example 73. ESI MS m/z=630.08, 632.08 [M+H]$^+$.

Example 104

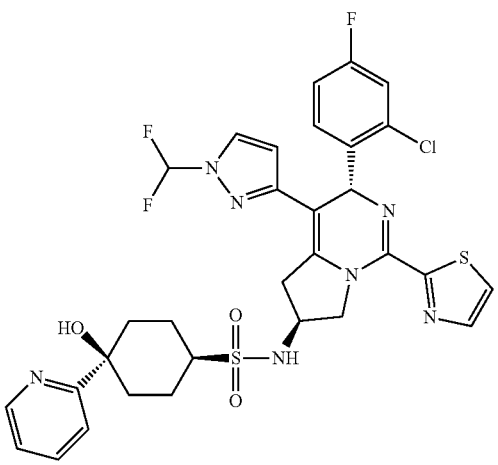 [SMILES: O=S(=O)(N[C@H]1CC2=C(c3ccn(C(F)F)n3)[C@H](c3ccc(F)cc3Cl)N=C(c3nccs3)N2C1)[C@H]1CC[C@](O)(c2ccccn2)CC1]

Step 104a. To a solution of 2-bromopyridine (0.031 ml, 0.317 mmol) in THF (1.2 ml) at −78° C. was added BuLi (2.5 M in hexanes, 0.127 ml, 0.317 mmol). The mixture was stirred at −78° C. for 1.0 h. A solution of Example 97 (0.033 g, 0.053 mmol) in THF (0.3 ml) was added. The mixture was stirred at −78° C. for 0.5 h. Saturated NH$_4$Cl solution was added to quench the reaction. The mixture was diluted with DCM and water and allowed to warm up to rt. The aqueous layer was back-extracted with DCM (*1). The combined organic layers were dried over Na$_2$SO$_4$ (s), filtered and concentrated. The residue was purified by flash column chromatography (silica, EtOAc/cyclohexane) to afford the title compound as yellow foam (20.0 mg, 54%). ESI MS m/z=704.14, 706.14 [M+H]$^+$.

Example 105

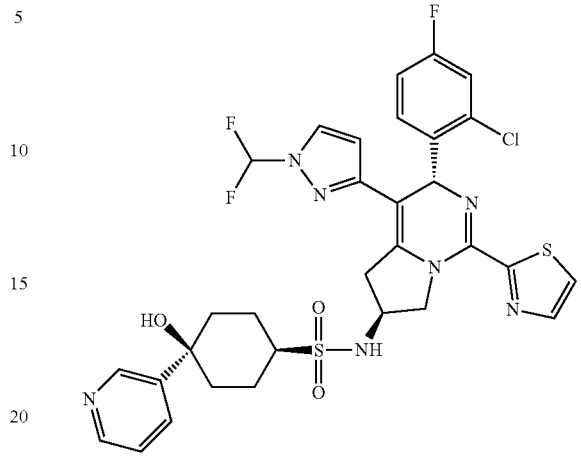

The title compound was prepared following similar procedure as Example 104. ESI MS m/z=704.13, 706.13 [M+H]$^+$.

Example 106

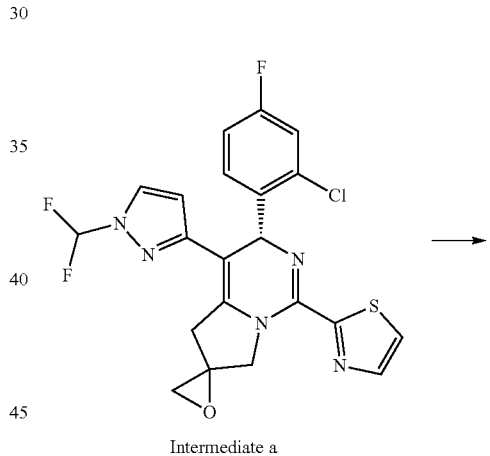

Intermediate a

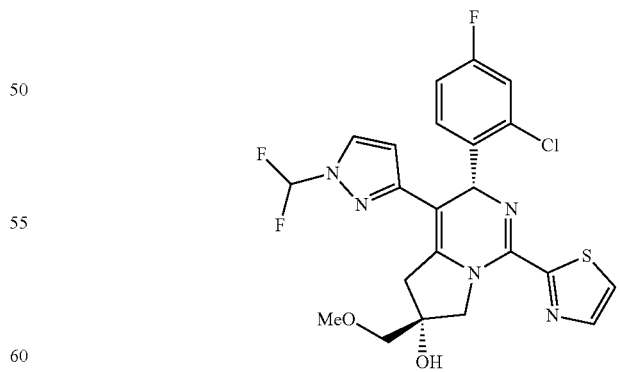

To a solution of intermediate a (prepared according to U.S. Ser. No. 16/210,472, 34 mg, 0.071 mmol) in MeOH (0.5 ml) at rt was added Sc(OTf)$_3$ (10 mg, 0.02 mmol). It was stirred at rt for 2 days. To the reaction mixture was added sat. aqueous NaHCO$_3$ solution, extracted with EtOAc,

Example 107

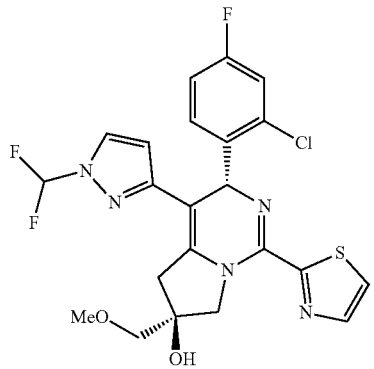 [SMILES: COC[C@]1(O)CC2=C(c3ccn(C(F)F)n3)[C@H](c3ccc(F)cc3Cl)N=C(c3nccs3)N2C1]

The tentatively assigned title compound (10 mg) was isolated from Example 106. ESI MS m/z=510.07, 512.07 [M+H]+.

Example 108

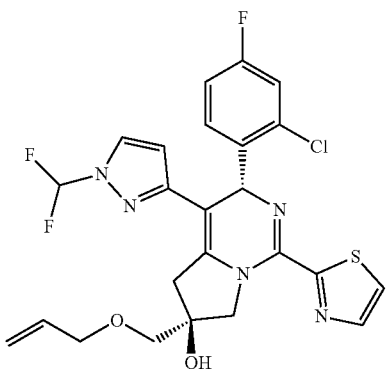 [SMILES: C=CCOC[C@]1(O)CC2=C(c3ccn(C(F)F)n3)[C@H](c3ccc(F)cc3Cl)N=C(c3nccs3)N2C1]

The tentatively assigned title compound was prepared following the general procedure of Example 106. ESI MS m/z=536.11, 538.11 [M+H]+.

Example 109

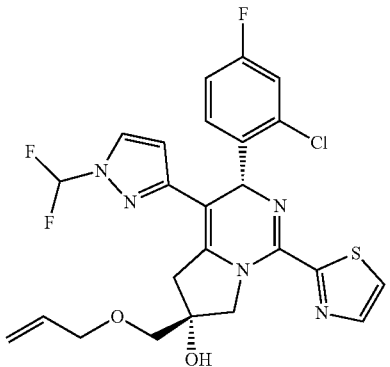 [SMILES: C=CCOC[C@@]1(O)CC2=C(c3ccn(C(F)F)n3)[C@H](c3ccc(F)cc3Cl)N=C(c3nccs3)N2C1]

The tentatively assigned title compound was prepared following the general procedure of Example 106. ESI MS m/z=536.11, 538.11 [M+H]+.

Example 110

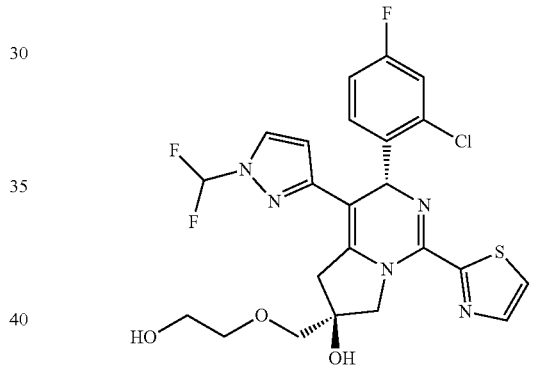

The tentatively assigned title compound was prepared following the general procedure of Example 106. ESI MS m/z=540.11, 542.11 [M+H]+.

Example 111

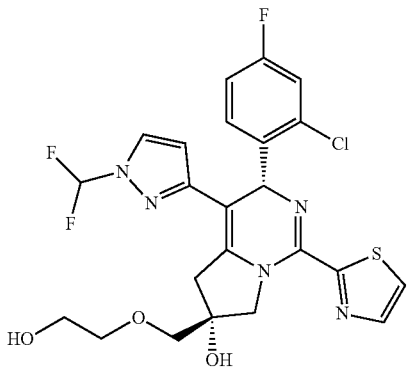 [SMILES: OCCOC[C@@]1(O)CC2=C(c3ccn(C(F)F)n3)[C@H](c3ccc(F)cc3Cl)N=C(c3nccs3)N2C1]

The tentatively assigned title compound was prepared following the general procedure of Example 106. ESI MS m/z=540.11, 542.11 [M+H]+.

Example 112

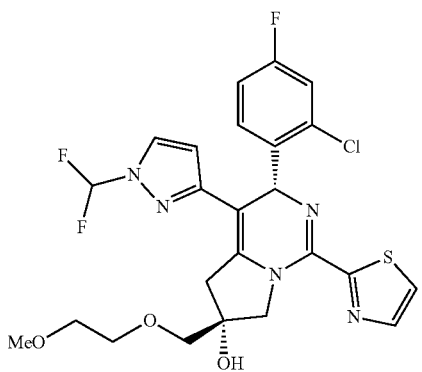 [SMILES: COCCOC[C@@]1(O)CC2=C(c3ccn(C(F)F)n3)[C@H](c3ccc(F)cc3Cl)N=C(c3nccs3)N2C1]

The tentatively assigned title compound was prepared following the general procedure of Example 106. ESI MS m/z=554.13, 556.13 [M+H]+.

Example 113

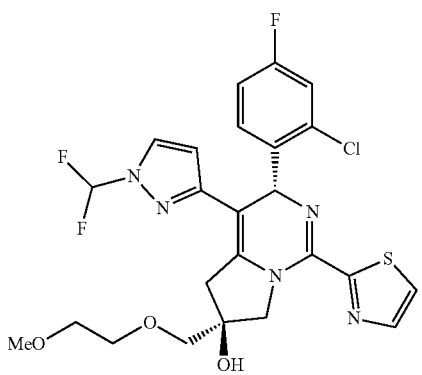 [SMILES: COCCOC[C@]1(O)CC2=C(c3ccn(C(F)F)n3)[C@H](c3ccc(F)cc3Cl)N=C(c3nccs3)N2C1]

The tentatively assigned title compound was prepared following the general procedure of Example 106. ESI MS m/z=554.13, 556.13 [M+H]+.

Example 114

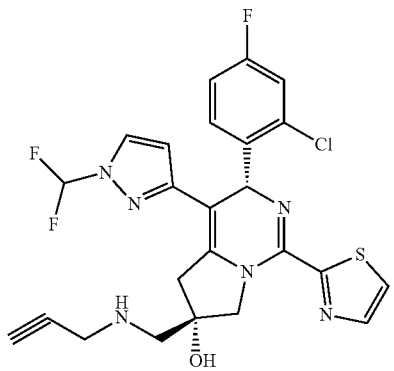 [SMILES: C#CCNC[C@@]1(O)CC2=C(c3ccn(C(F)F)n3)[C@H](c3ccc(F)cc3Cl)N=C(c3nccs3)N2C1]

To a solution of intermediate a (prepared according to U.S. Ser. No. 16/210,472, 78 mg, 0.163 mmol) in EtOH (0.5 ml) at rt was added propargyl amine (90 mg, 1.63 mmol). It was stirred at rt for 16 h. The reaction mixture was extracted with DCM, washed with water and brine. The organic layer was dried (Na₂SO₄), filtered, concentrated. The crude product was separated by prep-TLC (silica, hexanes/EtOAc) to give tentatively assigned title compound (34 mg, 39%). ESI MS m/z=533.04, 535.04 [M+H]+.

Example 115

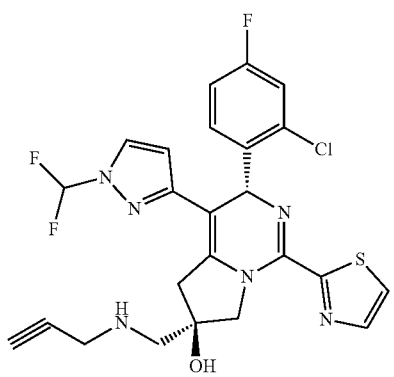 [SMILES: C#CCNC[C@]1(O)CC2=C(c3ccn(C(F)F)n3)[C@H](c3ccc(F)cc3Cl)N=C(c3nccs3)N2C1]

The tentatively assigned title compound (20 mg) was isolated from Example 114. ESI MS m/z=533.04, 535.04 [M+H]+.

Example 116

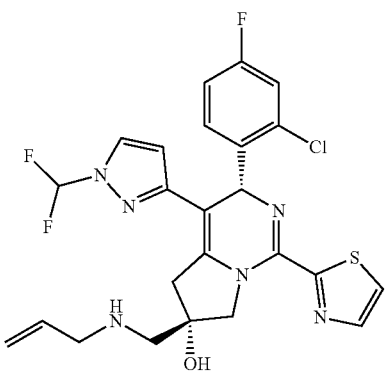 [SMILES: C=CCNC[C@@]1(O)CC2=C(c3ccn(C(F)F)n3)[C@H](c3ccc(F)cc3Cl)N=C(c3nccs3)N2C1]

The tentatively assigned title compound was prepared following the general procedure of Example 114. ESI MS m/z=535.06, 537.06 [M+H]+.

Example 117

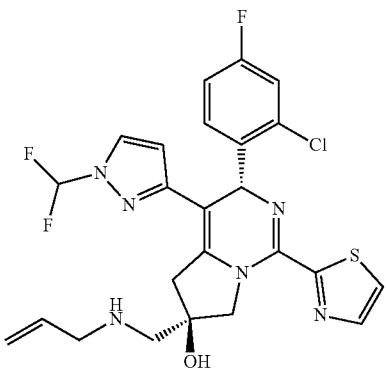 [SMILES: C=CCNC[C@]1(O)CC2=C(c3ccn(C(F)F)n3)[C@H](c3ccc(F)cc3Cl)N=C(c3nccs3)N2C1]

The tentatively assigned title compound was prepared following the general procedure of Example 114. ESI MS m/z=535.06, 537.06 [M+H]+.

Example 118

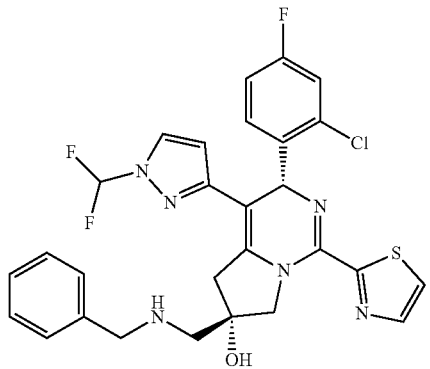 [SMILES: O[C@]1(CNCc2ccccc2)CC2=C(c3ccn(C(F)F)n3)[C@H](c3ccc(F)cc3Cl)N=C(c3nccs3)N2C1]

The tentatively assigned title compound was prepared following the general procedure of Example 114. ESI MS m/z=585.06, 587.05 [M+H]+.

Example 119

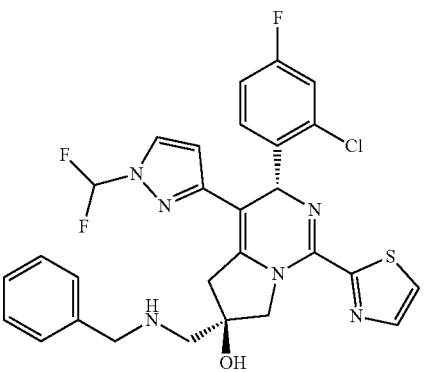 [SMILES: O[C@@]1(CNCc2ccccc2)CC2=C(c3ccn(C(F)F)n3)[C@H](c3ccc(F)cc3Cl)N=C(c3nccs3)N2C1]

The tentatively assigned title compound was prepared following the general procedure of Example 114. ESI MS m/z=585.06, 587.05 [M+H]+.

Example 120

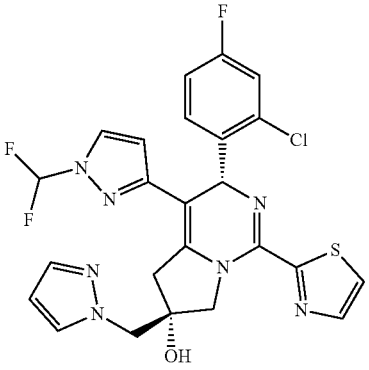 [SMILES: O[C@]1(Cn2cccn2)CC2=C(c3ccn(C(F)F)n3)[C@H](c3ccc(F)cc3Cl)N=C(c3nccs3)N2C1]

The tentatively assigned title compound was prepared following the general procedure of Example 114. ESI MS m/z=546.04, 548.04 [M+H]+.

Example 121

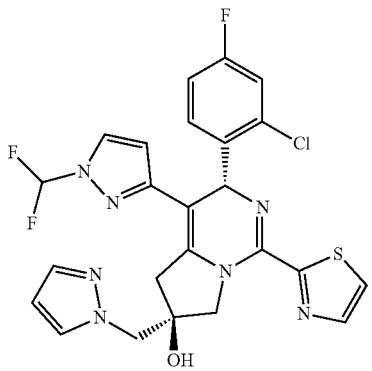 [SMILES: O[C@@]1(Cn2cccn2)CC2=C(c3ccn(C(F)F)n3)[C@H](c3ccc(F)cc3Cl)N=C(c3nccs3)N2C1]

The tentatively assigned title compound was prepared following the general procedure of Example 114. ESI MS m/z=546.04, 548.04 [M+H]+.

Example 122

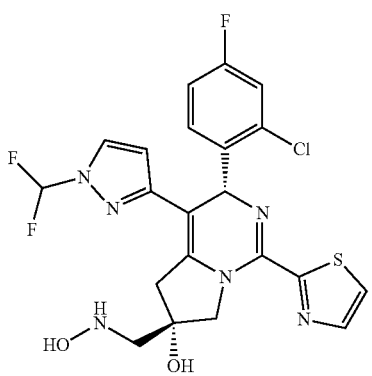 [SMILES: ONC[C@@]1(O)CC2=C(c3ccn(C(F)F)n3)[C@H](c3ccc(F)cc3Cl)N=C(c3nccs3)N2C1]

To a solution of intermediate a (prepared according to U.S. Ser. No. 16/210,472, 48 mg, 0.10 mmol) in EtOH (0.7 ml) at rt was added hydroxyamine hydrochloride (69 mg, 1.0 mmol) and Et$_3$N (71 mg, 0.70 mmol). It was stirred at rt for 16 h. To the reaction mixture was added sat. aqueous NaHCO$_3$ solution, extracted with EtOAc, washed with water and brine. The organic layer was dried (Na$_2$SO$_4$), filtered, concentrated. The crude product was separated by prep-HPLC to give tentatively assigned title compound (6.1 mg, 12%). MS m/z=511.02, 513.02 [M+H]+.

Example 123

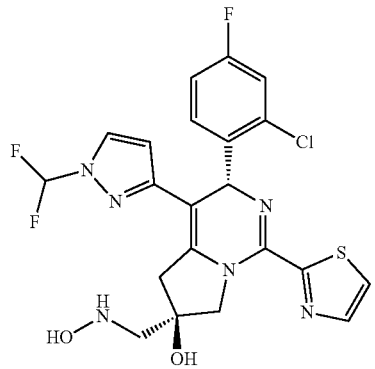 [SMILES: ONC[C@]1(O)CC2=C(c3ccn(C(F)F)n3)[C@H](c3ccc(F)cc3Cl)N=C(c3nccs3)N2C1]

The tentatively assigned title compound was isolated from Example 122. MS m/z=511.02, 513.02 [M+H]+.

Example 124

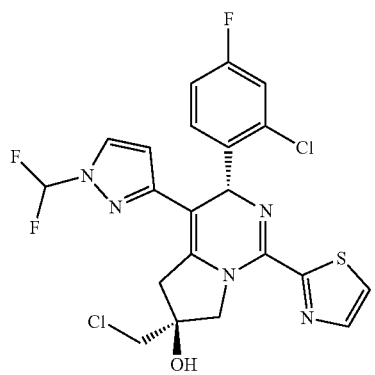 [SMILES: O[C@@]1(CCl)CC2=C(c3ccn(C(F)F)n3)[C@H](c3ccc(F)cc3Cl)N=C(c3nccs3)N2C1]

The tentatively assigned title compound was isolated from Example 122. MS m/z=514.0, 516.0 [M+H]+.

Example 125

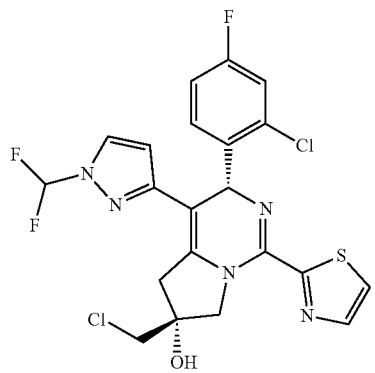 [SMILES: O[C@]1(CCl)CC2=C(c3ccn(C(F)F)n3)[C@H](c3ccc(F)cc3Cl)N=C(c3nccs3)N2C1]

The tentatively assigned title compound was isolated from Example 122. MS m/z=514.0, 516.0 [M+H]+.

Example 126

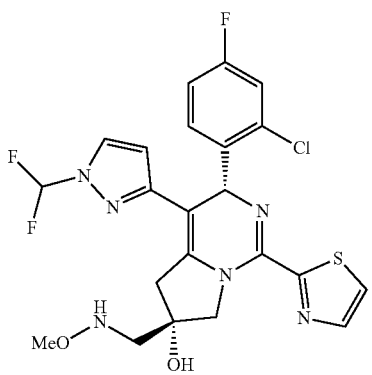 [SMILES: CONC[C@@]1(O)CC2=C(c3ccn(C(F)F)n3)[C@H](c3ccc(F)cc3Cl)N=C(c3nccs3)N2C1]

The tentatively assigned title compound was prepared following the general procedure of Example 122. ESI MS m/z=525.04, 527.4 [M+H]⁺.

Example 127

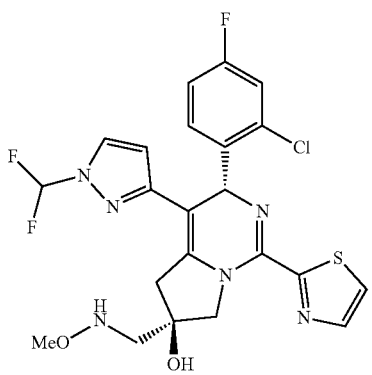 [SMILES: CONC[C@]1(O)CC2=C(c3ccn(C(F)F)n3)[C@H](c3ccc(F)cc3Cl)N=C(c3nccs3)N2C1]

The tentatively assigned title compound was prepared following the general procedure of Example 122. ESI MS m/z=525.04, 527.4 [M+H]⁺.

Example 128

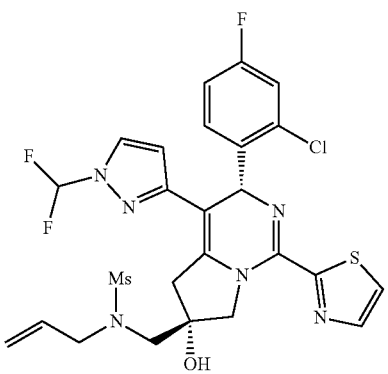 [SMILES: C=CCN(C[C@@]1(O)CC2=C(c3ccn(C(F)F)n3)[C@H](c3ccc(F)cc3Cl)N=C(c3nccs3)N2C1)S(C)(=O)=O]

To a solution of example 116 (10 mg, 0.019 mmol) and Et₃N (5.67 mg, 0.056 mmol) in DCM (0.5 mL) was added MSCl (2.1 mg, 0.019 mmol) at 0° C. and stirred for 1 h. The mixture was extracted with EtOAc, washed with water and brine. The organic layer was dried (Na₂SO₄), filtered and concentrated. The crude product was chromatographed (silica, hexanes/EtOAc) to give the title compound (4.0 mg, 35%). ESI-MS m/z=613.12, 615.12 [M+H]⁺.

Example 129

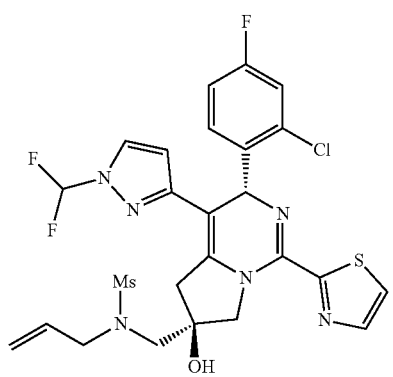 [SMILES: C=CCN(C[C@]1(O)CC2=C(c3ccn(C(F)F)n3)[C@H](c3ccc(F)cc3Cl)N=C(c3nccs3)N2C1)S(C)(=O)=O]

The tentatively assigned title compound was prepared following the general procedure of Example 128. 613.12, 615.12 [M+H]⁺.

Example 130

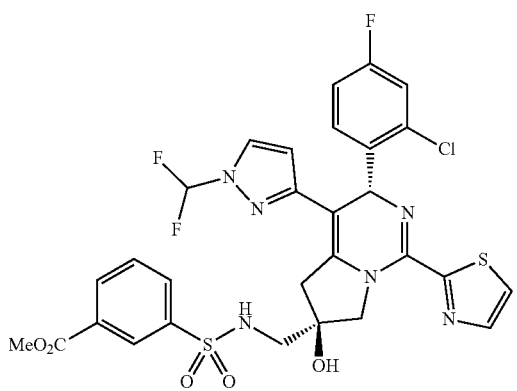 [SMILES: COC(=O)c1cccc(S(=O)(=O)NC[C@]2(O)CC3=C(c4ccn(C(F)F)n4)[C@H](c4ccc(F)cc4Cl)N=C(c4nccs4)N3C2)c1]

Step 130a. A solution of the intermediate a (prepared according to U.S. Ser. No. 16/210,472, 290 mg, 0.607 mmol) in 7 N NH₃ in MeOH (1.0 mL, 7 mmol) was stirred at rt for 16 h. It was concentrated to give the crude product which was used directly without purification. MS m/z=495.10, 497.10 [M+H]⁺.

Step 130b. To a solution of compound from step 130a (100 mg, 0.202 mmol) and Et₃N (61.3 mg, 0.606 mmol) in DCM (1.0 mL) was added methyl 3-(chlorosulfonyl)benzoate (42.7 mg, 0.182 mmol) at 0° C. and stirred for 1 h. The mixture was diluted with EtOAc, washed with water and brine. The organic layer was dried (Na₂SO₄), filtered and concentrated. The crude product was chromatographed (silica, hexanes/EtOAc) to give the tentatively assigned title compound (62 mg, 44%). ESI-MS m/z=693.11, 695.11 [M+H]⁺.

Example 131

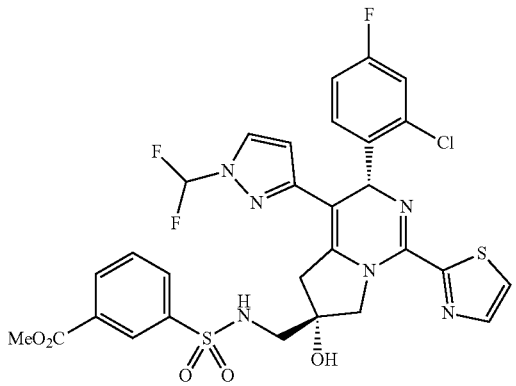 [SMILES: COC(=O)c1cccc(S(=O)(=O)NC[C@@]2(O)CC3=C(c4ccn(C(F)F)n4)[C@H](c4ccc(F)cc4Cl)N=C(c4nccs4)N3C2)c1]

The tentatively assigned title compound (35 mg) was isolated from Example 130. ESI MS m/z=693.11, 695.11 [M+H]+.

Example 132

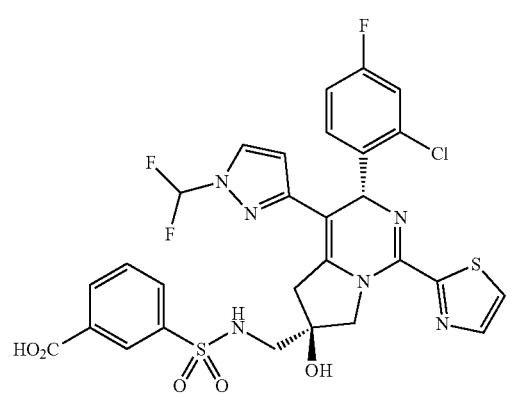 [SMILES: O=C(O)c1cccc(S(=O)(=O)NC[C@]2(O)CC3=C(c4ccn(C(F)F)n4)[C@H](c4ccc(F)cc4Cl)N=C(c4nccs4)N3C2)c1]

To a solution of Example 130 (21 mg, 0.030 mmol) in THF/MeOH (0.5/0.5 ml) at 0° C. was added a solution of LiOH (0.30 mL 0.5 M, 0.15 mmol). The mixture was stirred at 0° C. for 1 h. 0.5 N HCl solution was added to quench the reaction. The mixture was diluted with DCM and water until aqueous layer pH~2. The aqueous layer was extracted with DCM (*2). The combined organic layers were dried over Na$_2$SO$_4$ (s), filtered and concentrated. The residue was dried under vacuum to afford the tentatively assigned title compound (16 mg, 78%) as yellow solid. ESI MS m/z=679.07, 681.07 [M+H]+.

Example 133

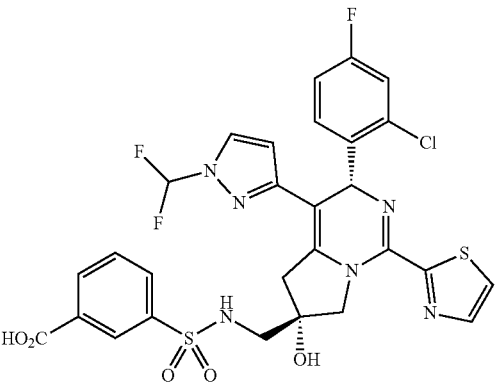 [SMILES: O=C(O)c1cccc(S(=O)(=O)NC[C@@]2(O)CC3=C(c4ccn(C(F)F)n4)[C@H](c4ccc(F)cc4Cl)N=C(c4nccs4)N3C2)c1]

The tentatively assigned title compound was prepared following the general procedure of Example 132. ESI MS m/z=679.07, 681.07 [M+H]+.

Example 134

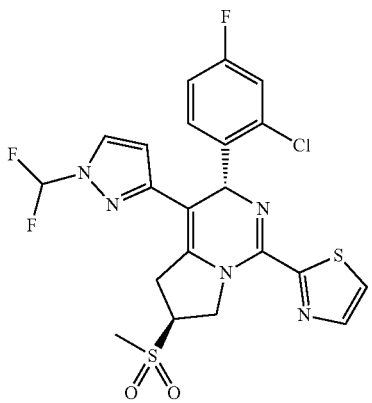 [SMILES: CS(=O)(=O)[C@H]1CC2=C(c3ccn(C(F)F)n3)[C@H](c3ccc(F)cc3Cl)N=C(c3nccs3)N2C1]

Step 134a. To a solution of Intermediate 1 (1.86 g, 3.29 mmol) and Methyl methanesulfonylacetate (1.0 g, 6.57 mmol) in DMF (10 mL) was added Cs$_2$CO$_3$ (1.61 g, 4.93 mmol). The reaction was stirred overnight at room temperature. The reaction was extracted with EtOAc, washed with water and brine. The organic layer was dried (Na$_2$SO$_4$), filtered and concentrated. The crude product was chromatographed (silica, hexane/ethyl acetate) to give the desired compound as a yellow foam (1.18 g, 56.4%). ESI-MS m/z=636.0, 638.0 [M+H]+.

Step 134b. A solution of the compound from step 134a (1.18 g, 1.85 mmol), 1-(difluoromethyl)-4-(4,4,5,5-tetramethyl-1,3,2-dioxaborolan-2-yl)-1H-pyrazole (0.678 g, 2.78 mmol), Pd(OAc)$_2$ (21 mg, 0.093 mmol), S-Phos (76 mg, 0.185 mmol) and potassium phosphate (0.786 g, 3.71 mmol) in THF-water (20 mL/1 mL) at rt was degassed and stirred at rt under N$_2$ for 18 h. It was diluted with EtOAc, washed with water, brine, dry over Na$_2$SO$_4$, filtered and concentrated. The crude product was chromatographed (silica, hexane/EtOAc) to give the desired compound as yellow foam (1.1 g, 88%). ESI-MS m/z=674.12, 676.12 [M+H]+.

Step 134c. A solution of the compound from step 134b (0.163 g, 0.242 mmol) in methanol (2.0 ml) at 0° C. was added sodium borohydride (0.046 g, 1.21 mmol) portionwise. It was stirred at 0° C. for 1 h and rt for 3 h. The reaction was quenched with sat. aqueous NH₄Cl solution, extracted with EtOAc, washed with water and brine. The organic layer was dried (Na₂SO₄), filtered and concentrated. The crude product was chromatographed (silica, hexanes/EtOAc) to give the desired compound as yellow gum (95 mg, 61%). ESI-MS m/z=646.12, 648.12 [M+H]⁺.

Step 134d. To a solution of the compound from step 134c (120 mg, 0.186 mmol) in dichloromethane (1.5 ml) at 0° C. was added TFA (1.5 mL, 19.5 mmol). It was stirred at rt for 1 h. The reaction mixture was then concentrated. To the reaction mixture was added DCM (2 mL), MeOH (1 mL) and NaOH (1 mL, 2M), extracted with EtOAc, washed with water and brine. The organic layer was dried (Na₂SO₄), filtered and concentrated to give the desired compound as yellow foam (90 mg, 89%). ESI-MS m/z=546.06, 548.06 [M+H]⁺.

Step 134f. To a solution of the compound from step 134d (0.080 g, 0.147 mmol) and Et₃N (59 mg, 0.586 mmol) in DCM (2.0 mL) at 0° C. was added mesyl chloride (33.6 mg, 0.293 mmol). The reaction mixture was stirred for 16 h at the rt. The reaction was extracted with EtOAc, washed with water and brine. The organic layer was dried (Na₂SO₄), filtered and concentrated. The crude product was chromatographed (silica, hexanes/EtOAc) to give tentatively assigned title compound (30 mg, 39%). ESI MS m/z=528.05, 530.05 [M+H]⁺.

Example 135

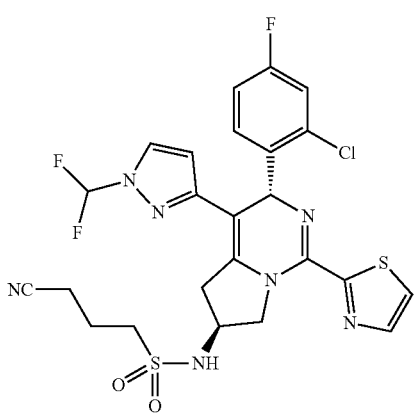 [SMILES: N#CCCCS(=O)(=O)N[C@H]1CC2=C(c3ccn(C(F)F)n3)[C@H](c3ccc(F)cc3Cl)N=C(c3nccs3)N2C1]

To a solution of Example 1 (200 mg, 0.430 mmol) and Et₃N (131 mg, 1.29 mmol) in DCM (1.0 mL) was added 3-cyanopropane-1-sulfonyl chloride (87 mg, 0.516 mmol) at 0° C. and stirred for 2 h. The mixture was extracted with EtOAc, washed with water and brine. The organic layer was dried (Na₂SO₄), filtered and concentrated. The crude product was chromatographed (silica, hexanes/EtOAc) to give the title compound (211 mg, 82%). ESI MS m/z=596.09, 598.09 [M+H]⁺.

Example 136

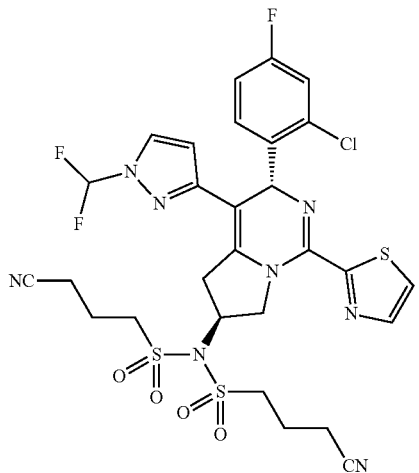 [SMILES: N#CCCCS(=O)(=O)N([C@H]1CC2=C(c3ccn(C(F)F)n3)[C@H](c3ccc(F)cc3Cl)N=C(c3nccs3)N2C1)S(=O)(=O)CCCC#N]

The title compound was isolated from Example 135. ESI MS m/z=727.09, 729.09 [M+H]⁺.

Example 137

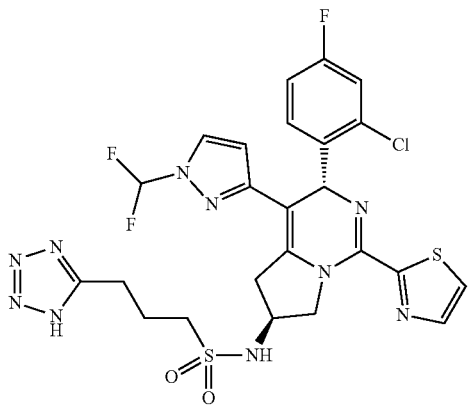 [SMILES: O=S(=O)(CCCc1nnn[nH]1)N[C@H]1CC2=C(c3ccn(C(F)F)n3)[C@H](c3ccc(F)cc3Cl)N=C(c3nccs3)N2C1]

A mixture of Example 135 (80 mg, 0.134 mmol), NaN₃ (43.6 mg, 0.671 mmol) and NH₄Cl (43.1 mg, 0.805 mmol) in DMF (1.0 mL) was stirred at 85° C. for 20 h. The mixture was diluted with EtOAc, washed with water and brine. The organic layer was dried (Na₂SO₄), filtered and concentrated. The crude product was purified by prep-HPLC (MeCN/water) to give the title compound (22 mg, 25%). ESI MS m/z=639.11, 641.11 [M+H]⁺.

Example 138

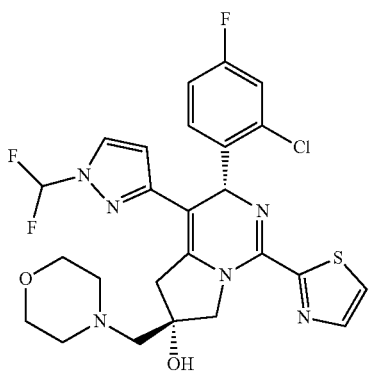 [SMILES: O[C@]1(CN2CCOCC2)CC2=C(c3ccn(C(F)F)n3)[C@H](c3ccc(F)cc3Cl)N=C(c3nccs3)N2C1]

The tentatively assigned title compound was prepared following the general procedure of Example 114. ESI MS m/z=565.14, 567.14 [M+H]$^+$.

Example 139

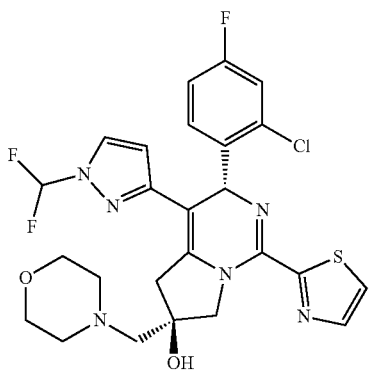 [SMILES: O[C@@]1(CN2CCOCC2)CC2=C(c3ccn(C(F)F)n3)[C@H](c3ccc(F)cc3Cl)N=C(c3nccs3)N2C1]

The tentatively assigned title compound was prepared following the general procedure of Example 114. ESI MS m/z=565.14, 567.14 [M+H]$^+$.

Example 140

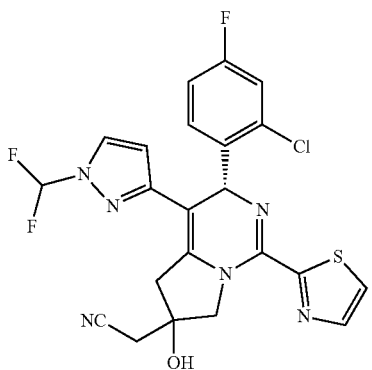 [SMILES: N#CCC1(O)CC2=C(c3ccn(C(F)F)n3)[C@H](c3ccc(F)cc3Cl)N=C(c3nccs3)N2C1]

A mixture of intermediate a (prepared according to U.S. Ser. No. 16/210,472, 137 mg, 0.287 mmol), KCN (74.7 mg, 0.671 mmol) and NH$_4$Cl (30.7 mg, 0.573 mmol) in DMF (1.0 mL) was stirred at 80° C. for 20 h. The mixture was diluted with EtOAc, washed with water and brine. The organic layer was dried (Na$_2$SO$_4$), filtered and concentrated. The crude product was purified by chromatography (silica, hexanes/EtOAc) to give the title compounds (74 mg, 51%) as a mixture of two diastereomers (ratio 1/1). ESI MS m/z 505.09, 507.09 [M+H]$^+$.

Example 141

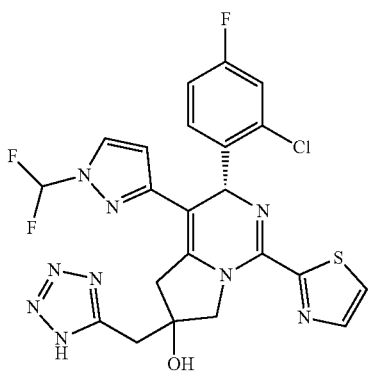 [SMILES: OC1(Cc2nnn[nH]2)CC2=C(c3ccn(C(F)F)n3)[C@H](c3ccc(F)cc3Cl)N=C(c3nccs3)N2C1]

A solution of azidotrimethylsilane (30.8 μl, 0.232 mmol), dibutylstannanone (38.5 mg, 0.154 mmol) and example 140 (39 mg, 0.077 mmol) in toluene (1.0 mL) was stirred at 70° C. for 3 days. It was cooled to rt and chromatographed (silica, DCM/MeOH) to give the title compounds (13 mg, 30%) as a mixture of two diastereomers (ratio 1/2). ESI MS m/z 548.10, 550.10 [M+H]$^+$.

Example 142

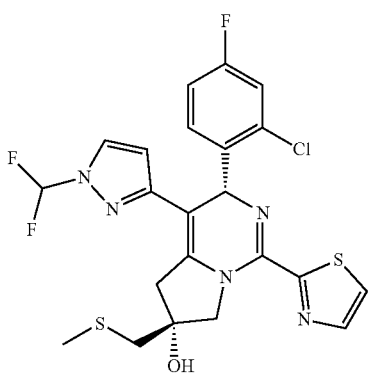 [SMILES: CSC[C@@]1(O)CC2=C(c3ccn(C(F)F)n3)[C@H](c3ccc(F)cc3Cl)N=C(c3nccs3)N2C1]

To a solution of intermediate a (prepared according to U.S. Ser. No. 16/210,472, 45 mg, 0.094 mmol) and triphenylsilanethiol (30.3 mg, 0.104 mmol) in MeOH (0.3 mL) was added Et$_3$N (15.75 0.113 mmol) in MeOH (0.1 mL). After being stirred at rt for 1 h, sodium methoxide (6.09 mg, 0.113 mmol) and MeI (7.05 μl, 0.113 mmol) was added and the mixture was stirred at rt for 1 more hour. It was quenched with aqueous NH$_4$Cl solution, extracted with EtOAc, washed with water, brine, dry over Na$_2$SO$_4$, filtered, concentrated and chromatographed (silica, hexanes/EtOAc) to give the tentatively assigned title compounds (21 mg, 42%). ESI MS m/z 526.08, 528.07 [M+H]⁺.

Example 143

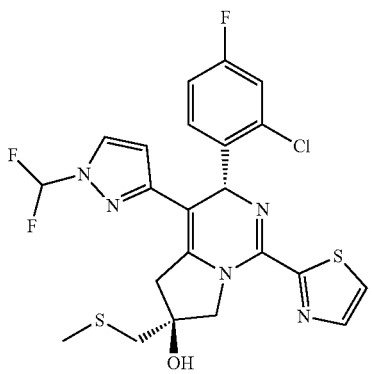 [SMILES: CSC[C@]1(O)CC2=C(c3ccn(C(F)F)n3)[C@H](c3ccc(F)cc3Cl)N=C(c3nccs3)N2C1]

The tentatively assigned title compound was isolated from Example 142. ESI-MS m/z=526.08 528.08 [M+H]⁺.

Example 144

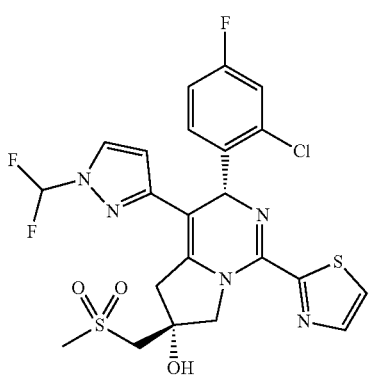 [SMILES: CS(=O)(=O)C[C@@]1(O)CC2=C(c3ccn(C(F)F)n3)[C@H](c3ccc(F)cc3Cl)N=C(c3nccs3)N2C1]

A mixture of example 142 and sodium perborate tetrahydrate (11.41 mg, 0.074 mmol) in AcOH (0.2 mL) was stirred at 45° C. for 3 h. It was diluted with EtOAc, washed with sat. aqueous NaHCO₃, brine, dry over Na₂SO₄, filtered, concentrated and chromatographed (silica, hexanes/EtOAc) to give the tentatively assigned title compound (9.0 mg, 65%). ESI MS m/z 558.06, 560.06 [M+H]⁺.

Example 145

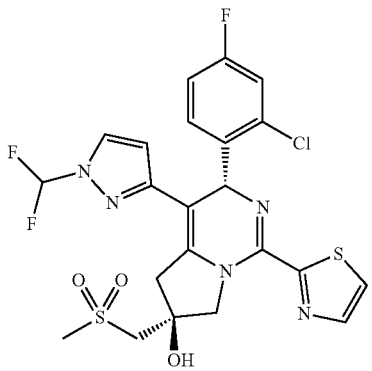 [SMILES: CS(=O)(=O)C[C@]1(O)CC2=C(c3ccn(C(F)F)n3)[C@H](c3ccc(F)cc3Cl)N=C(c3nccs3)N2C1]

The tentatively assigned title compound was prepared following the general procedure of Example 144. ESI MS m/z=558.06, 560.06 [M+H]⁺.

Example 146

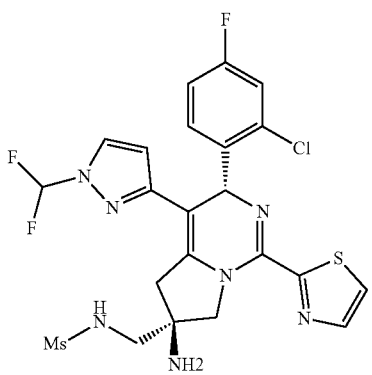

Step 146a. To a solution of Intermediate 1 (100 g, 176 mmol) and 3-(tert-butyl) 4-methyl (2R,4S)-2-(tert-butyl) oxazolidine-3,4-dicarboxylate (101 g, 352 mmol) in THF (250 mL) and DMPU (100 mL) cooled to −40° C. under N₂ was added LiHMDS (1 M in THF, 299 mL, 299 mmol) in 20 min with stirring. The reaction mixture was stirred at −40° C. for 0.5 hours before being quenched by H₂O (100 mL) at −40° C. and being allowed to warm up to 10° C. The reaction mixture was partitioned between EtOAc and water. The organic layer was washed with H₂O (*1), brine (*1), dried over Na₂SO₄ (s), filtered, and concentrated. The residue was chromatographed (silica, Hexanes/EtOAc) to give the desired compound (119 g, 79%) as yellow solid. ESI MS m/z=771.35, 773.35 [M+H]⁺.

Step 146b. To a solution of the compound from Step 146a (119 g, 83% purity, 127 mmol) and 1-(difluoromethyl)-3-(4,4,5,5-tetramethyl-1,3,2-dioxaborolan-2-yl)-1H-pyrazole (46.7 g, 191 mmol) in THF (500 mL) under Ar at rt was added a solution of K₃PO₄ (53.8 g, 254 mmol) in H₂O (125 mL) and DTBPF PdCl₂ (4.13 g, 6.35 mmol). The reaction mixture was degassed and heated at 50° C. for 3 h under Ar before being allowed to cooled down to rt. The reaction mixture was partitioned between EtOAc and water. The organic layer was washed with H₂O (*1), brine (*1), dried over Na₂SO₄ (s), filtered, and concentrated. The residue was chromatographed (silica, Hexanes/EtOAc) to give the desired compound (85.0 g, 83%) as yellow solid. ESI MS m/z=809.45, 811.45 [M+H]⁺.

Step 146c. To a solution of the compound from Step 146b (7.000 g, 8.65 mmol) in acetonitrile (70 ml) at rt was added boron trifluoride etherate (5.48 ml, 43.2 mmol) dropwise. The mixture was stirred at rt for 5 h. Water (7 ml) was added at 0° C. to quench the reaction. The mixture was allowed to warm up to rt. 1 N HCl solution (50 ml) was added at rt. The clear yellow solution was stirred at rt overnight before being concentrated by rotavapor. The aqueous residue was diluted with MTBE and 1 N HCl solution. The organic layer was extracted with 1 N HCl solution (*2). The combined aqueous layers were basicified to pH~8 with saturated K₂CO₃ solution, extracted with DCM (*4). The combined DCM extract was dried over Na₂SO₄ (s), filtered and concentrated. The residue was dried under vacuum to afford the desired product as a yellow solid, which was used directly for next step. ESI MS m/z=541.11, 543.10 [M+H]⁺.

Step 146d. To a solution of the compound from Step 146c (crude product, 8.65 mmol) in THF (90 ml) at 0° C. was added a solution of Boc-anhydride (2.410 ml, 10.38 mmol) in THF (10 ml) dropwise. After 10 min at 0° C., the cooling bath was removed and the mixture was stirred at rt for 20 h. More (Boc)₂O (0.226 g) was added. The solution was stirred at rt for 3 h before being concentrated. The residue was dissolved in DCM (150 ml) and cool down to 0° C. Triethylamine (6.03 ml, 43.3 mmol) was added at 0° C., followed by a solution of methanesulfonyl chloride (1.348 ml, 17.30 mmol) in DCM (10 ml). The mixture was stirred at 0° C. for 1 h. The cooling bath was removed and the mixture was allowed to warm up and stirred at 40° C. for 15 h. Excess i-PrOH was added to quench the reaction. The mixture was concentrated. The residue was chromatographed (silica, Hexanes/EtOAc) to give the desired compound (4.10 g, 77% over 2 steps) as yellow solid. ESI MS m/z=623.14, 625.14 [M+H]⁺.

Step 146e. To a solution of the compound from Step 146d (0.32 g, 0.514 mmol) in MeOH (5 ml) at 0° C. was added sodium borohydride (0.039 g, 1.03 mmol). The mixture was stirred at 0° C. for 1 h. More sodium borohydride (0.039 g, 1.03 mmol) was added at 0° C. The mixture was stirred at 0° C. for 1 h. Saturated NH₄Cl solution was added to quench the reaction at 0° C. The mixture was diluted with EtOAc and water and allowed to warm up to rt. The organic layer was washed with brine (*1), dried over Na₂SO₄ (s), filtered and concentrated. The residue was chromatographed (silica, Hexanes/EtOAc) to give the desired compound (0.142 g, 46%) as yellow solid. ESI MS m/z=595.07, 597.07 [M+H]⁺.

Step 146f. To a solution of the compound from Step 146e (0.53 g, 0.89 mmol) in DMSO (3.0 ml) at rt was added IBX (0.375 g, 1.34 mmol). The mixture was stirred at rt for 4 h. More IBX (0.375 g, 1.34 mmol) was added at rt. The mixture was stirred at rt overnight. Saturated Na₂S₂O₃ solution was added to quench the reaction. The mixture was diluted with DCM and water. The aqueous layer was backextracted with DCM (*1). The combined organic layers were dried over Na₂SO₄ (s), filtered and concentrated. The residue was chromatographed (silica, Hexanes/EtOAc) to give the desired compound (0.21 g, 40%) as yellow solid. ESI MS m/z=593.13, 595.13 [M+H]⁺.

Step 146g. To a solution of the compound from Step 146f (210 mg, 0.354 mmol), AcOH (106 mg, 1.78 mmol) and allylamine (101 mg, 1.78 mmol) in DCM (2.0 ml) at rt was added sodium triactoxyborohydride (75 mg, 0.354 mmol). The mixture was stirred at rt for 1 h. More sodium triactoxyborohydride (75 mg, 0.354 mmol). was added at rt. The mixture was stirred at rt overnight. Saturated NaHCO₃ solution was added to quench the reaction. The mixture was diluted with DCM and water. The aqueous layer was backextracted with DCM (*1). The combined organic layers were dried over Na₂SO₄ (s), filtered and concentrated. The residue was chromatographed (silica, Hexanes/EtOAc) to give the desired compound (118 mg, 52.5%) as yellow solid. ESI MS m/z=634.19, 636.19 [M+H]⁺.

Step 146h. To a solution of compound from Step 146g (80 mg, 0.126 mmol) and Et₃N (88 µl, 0.631 mmol in DCM (1.7 mL) at 0° C. was added MsCl (29.5 µl, 0.378 mmol) and stirred for 1 h. It was quenched with water, extracted with EtOAc, washed with water, brine, dry over Na₂SO₄, filtered, concentrated and chromatographed (silica, Hexanes/EtOAc) to give desired compound (70 mg, 78%). ESI MS m/z=712.17, 714.17 [M+H]⁺.

Step 146i. A solution of compound from Step 146h (42 mg, 0.059 mmol), Pd(Ph₃p)₄ (13.63 mg, 0.012 mmol) and 1,3-dimethylpyrimidine-2,4,6(1H,3H,5H)-trione (92 mg, 0.590 mmol) in MeCN (1.5 mL) was degassed and stirred at 75° C. for 20 h. It was cooled to rt, diluted with EtOAC, washed with water, brine, dry over Na₂SO₄, filtered, concentrated and chromatographed (silica, Hexanes/EtOAc) to give desired compound (35 mg, 88%). ESI MS m/z=672.15, 674.14 [M+H]⁺.

Step 146j. To a solution of compound from step 146i (32 mg, 0.048 mmol) in DCM (1.0 mL) was added TFA (1.0 mL) and stirred at rt for 2 h. it was concentrated, treated with 10% K₂CO₃, extracted with DCM, washed with brine, dry over Na₂SO₄, filtered, conc to give the title compound (22 mg, 81%). ESI MS m/z=572.09, 574.09 [M+H]⁺.

Example 147

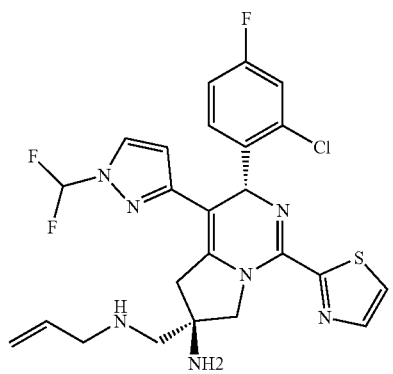 [SMILES: C=CCNC[C@]1(N)CC2=C(c3ccn(C(F)F)n3)[C@H](c3ccc(F)cc3Cl)N=C(c3nccs3)N2C1]

To a solution of the compound from Step 146g (26 mg, 0.041 mmol) in DCM (1.0 ml) at rt was added TFA (1.0 mL) dropwise. The mixture was stirred at rt for 2 h. The mixture was concentrated under vacuum. The mixture was dissolved in DCM (10 mL) and saturated NaHCO₃ solution with some 30% K₂CO₃ solution added. The aqueous layer was extracted with DCM (*1). The combined organic layers were dried over Na₂SO₄ (s), filtered and concentrated. The residue was dried under vacuum to afford the crude compound (0.020 g, 91%) as yellow solid. ESI MS m/z 534.14, 536.14 [M+H]⁺.

Example 148

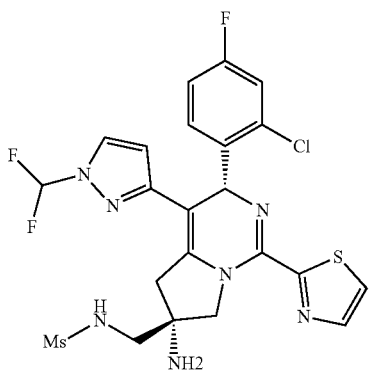

The title compound was prepared following the general procedure of Example 146. ESI MS m/z=572.09, 574.09 [M+H]$^+$.

Example 150

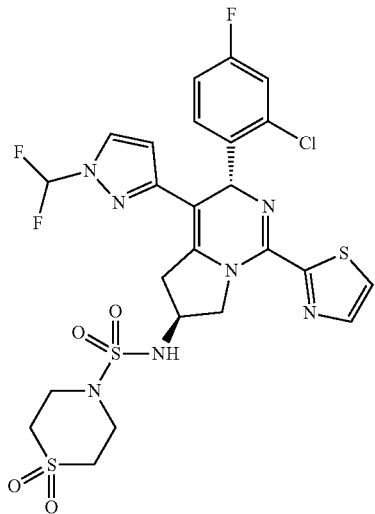 [SMILES: O=S1(=O)CCN(S(=O)(=O)N[C@H]2CC3=C(c4ccn(C(F)F)n4)[C@H](c4ccc(F)cc4Cl)N=C(c4nccs4)N3C2)CC1]

The title compound was prepared following the general procedure of Example 73. ESI MS m/z=662.04, 664.04 [M+H]$^+$.

Example 149

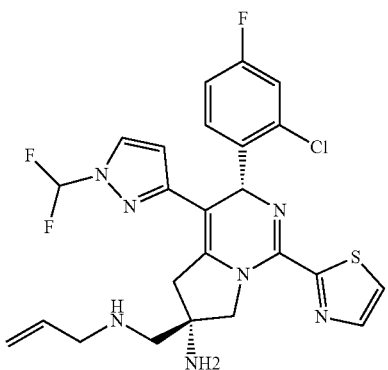

The title compound was prepared following the general procedure of Example 147. ESI MS m/z=534.14, 536.14 [M+H]$^+$.

Example 151

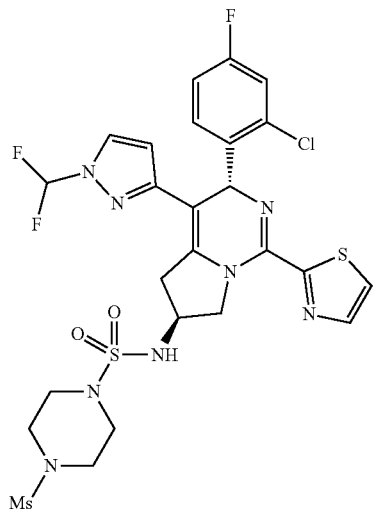 [SMILES: CS(=O)(=O)N1CCN(S(=O)(=O)N[C@H]2CC3=C(c4ccn(C(F)F)n4)[C@H](c4ccc(F)cc4Cl)N=C(c4nccs4)N3C2)CC1]

The title compound was prepared following the general procedure of Example 73. ESI MS m/z=691.06, 693.06 [M+H]$^+$.

Example 152

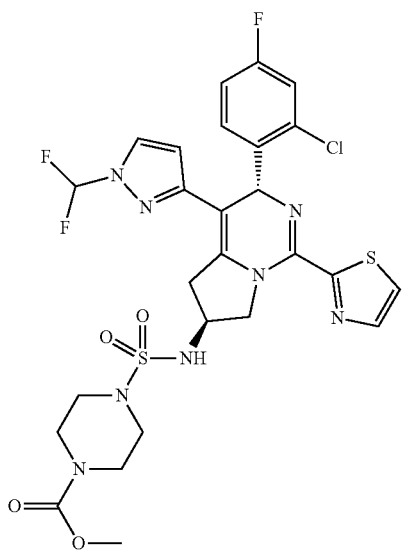 [SMILES: COC(=O)N1CCN(S(=O)(=O)N[C@H]2CC3=C(c4ccn(C(F)F)n4)[C@H](c4ccc(F)cc4Cl)N=C(c4nccs4)N3C2)CC1]

The title compound was prepared following the general procedure of Example 73. ESI MS m/z=671.09, 673.09 [M+H]+.

Example 154

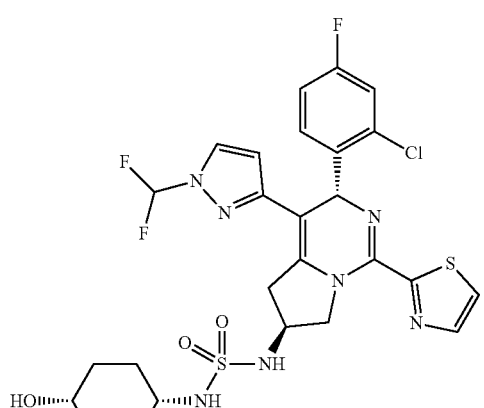

The title compound was prepared following the general procedure of Example 73. ESI MS m/z=642.11, 644.11 [M+H]+.

Example 153

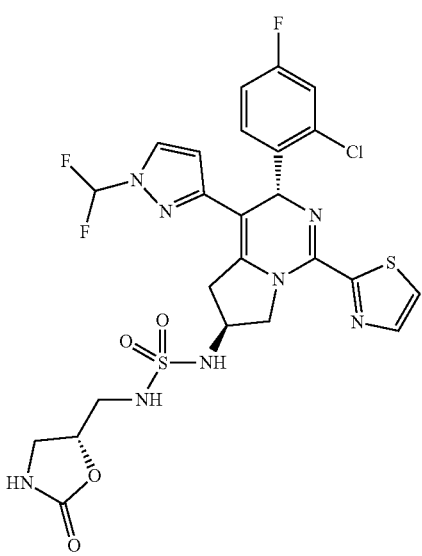 [SMILES: O=C1NC[C@H](CNS(=O)(=O)N[C@H]2CC3=C(c4ccn(C(F)F)n4)[C@H](c4ccc(F)cc4Cl)N=C(c4nccs4)N3C2)O1]

The tentatively assigned title compound was prepared following the general procedure of Example 73. ESI MS m/z=671.09, 673.09 [M+H]+.

Example 155

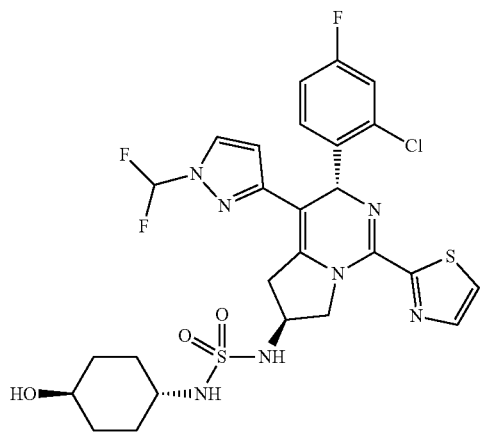 [SMILES: O=S(=O)(N[C@H]1CC2=C(c3ccn(C(F)F)n3)[C@H](c3ccc(F)cc3Cl)N=C(c3nccs3)N2C1)N[C@H]1CC[C@H](O)CC1]

The title compound was prepared following the general procedure of Example 73. ESI MS m/z=642.11, 644.11 [M+H]+.

Example 156

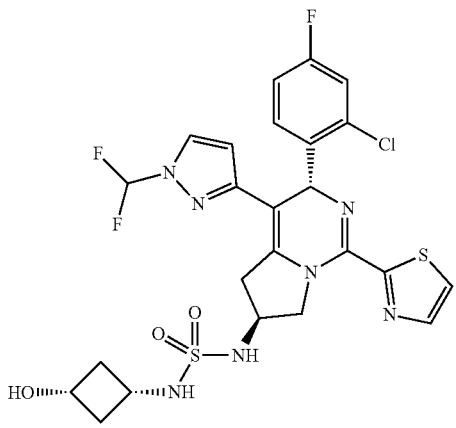 [SMILES: O=S(=O)(N[C@H]1CC2=C(c3ccn(C(F)F)n3)[C@H](c3ccc(F)cc3Cl)N=C(c3nccs3)N2C1)N[C@H]1C[C@@H](O)C1]

The title compound was prepared following the general procedure of Example 73. ESI MS m/z=614.08, 616.08 [M+H]$^+$.

Example 157

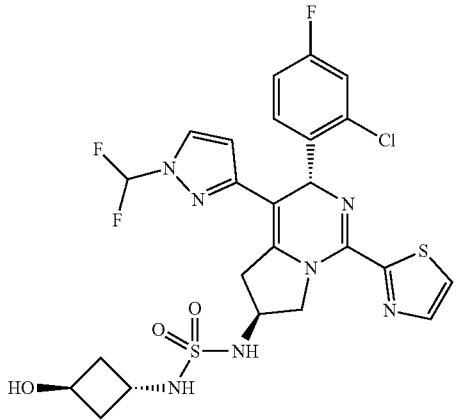 [SMILES: O=S(=O)(N[C@H]1CC2=C(c3ccn(C(F)F)n3)[C@H](c3ccc(F)cc3Cl)N=C(c3nccs3)N2C1)N[C@H]1C[C@H](O)C1]

The title compound was prepared following the general procedure of Example 73. ESI MS m/z=614.08, 616.08 [M+H]$^+$.

Example 158

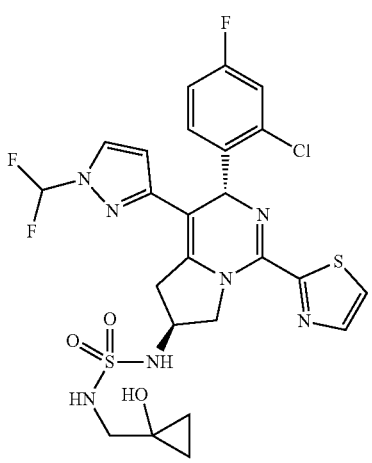 [SMILES: O=S(=O)(NCC1(O)CC1)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=614.09, 616.09 [M+H]$^+$.

Example 159

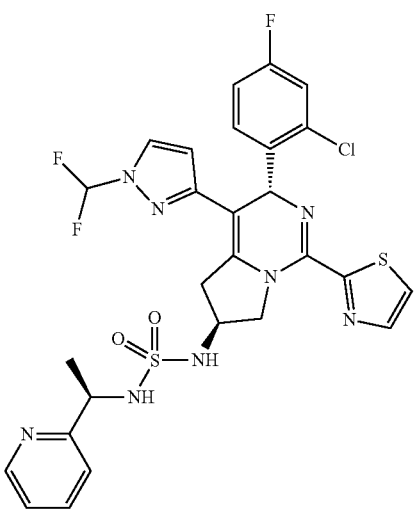 [SMILES: C[C@@H](NS(=O)(=O)N[C@H]1CC2=C(c3ccn(C(F)F)n3)[C@H](c3ccc(F)cc3Cl)N=C(c3nccs3)N2C1)c1ccccn1]

The title compound was prepared following the general procedure of Example 73. ESI MS m/z=649.10, 651.10 [M+H]$^+$.

Example 160

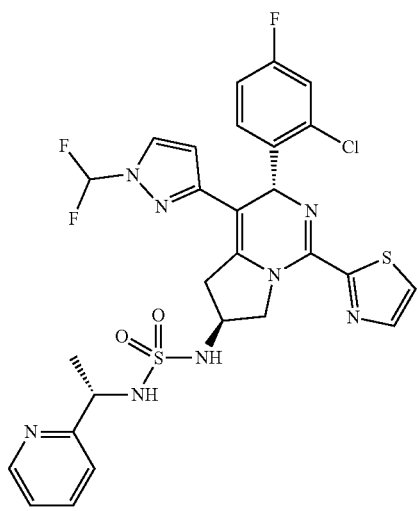 [SMILES: C[C@H](NS(=O)(=O)N[C@H]1CC2=C(c3ccn(C(F)F)n3)[C@H](c3ccc(F)cc3Cl)N=C(c3nccs3)N2C1)c1ccccn1]

The title compound was prepared following the general procedure of Example 73. ESI MS m/z=649.10, 651.10 [M+H]+.

Example 162

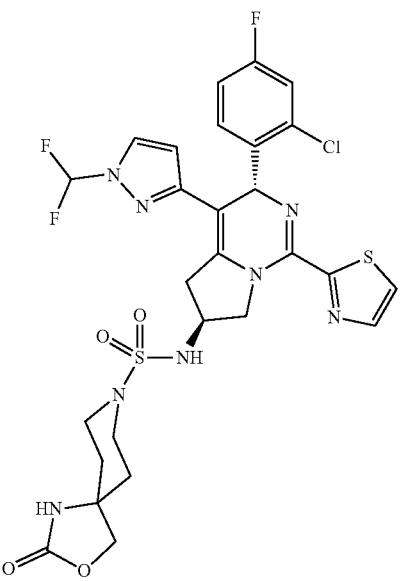

The title compound was prepared following the general procedure of Example 73. ESI MS m/z=683.10, 685.10 [M+H]+.

Example 161

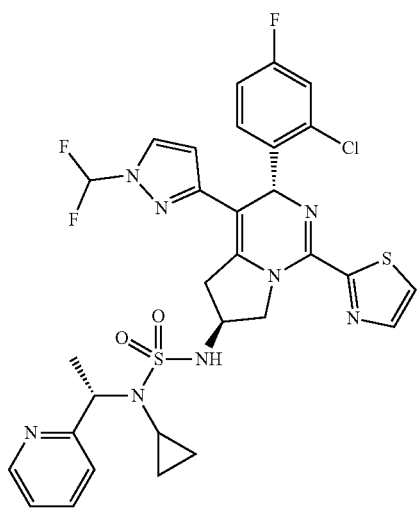 [SMILES: C[C@@H](c1ccccn1)N(C1CC1)S(=O)(=O)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=675.10, 677.10 [M+H]+.

Example 163

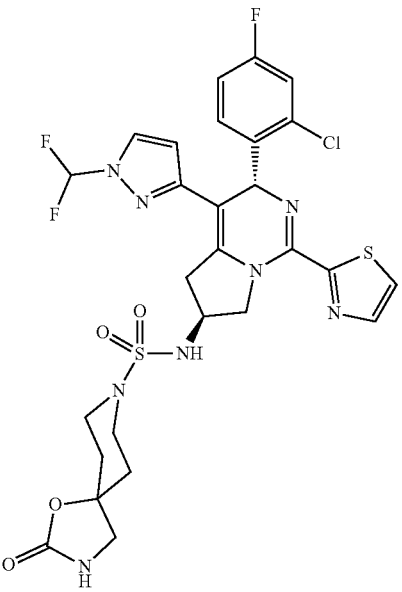 [SMILES: O=C1NCC2(CCN(S(=O)(=O)N[C@H]3CC4=C(c5ccn(C(F)F)n5)[C@H](c5ccc(F)cc5Cl)N=C(c5nccs5)N4C3)CC2)O1]

The title compound was prepared following the general procedure of Example 73. ESI MS m/z=683.11, 685.11 [M+H]+.

Example 164

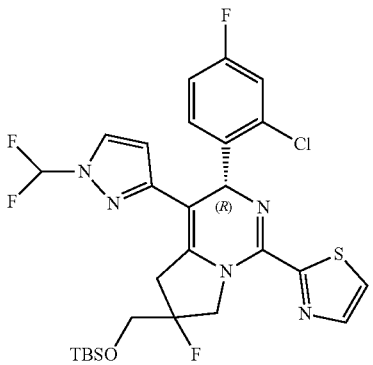

Step 164a. To a stirred mixture of Intermediate 1 (4.0 g, 7.1 mmol, 1.0 eq.) and dimethyl 2-fluoromalonate (2.12 g, 14.1 mmol, 2.0 eq.) in DMF (30 mL) was added NaH (60% in mineral oil, 566 mg, 14.1 mmol, 2.0 eq.) in portions at 0° C. The reaction mixture was stirred at rt for 1 hour. The reaction mixture was quenched by addition of sat.NH$_4$Cl (aq) at 0° C. Then the mixture was extracted with EtOAc. The combined organic phase was washed with brine, dried over Na$_2$SO$_4$ and concentrated. The crude product was chromatographed (silica gel, EtOAc/petroleum ether) to give the desired compound (3.4 g, 75.7%) as a yellow solid. ESI MS m/z=636.00, 638.00 [M+H]$^+$.

Step 164b. To a stirred mixture of the compound from Step 164a (2.80 g, 4.41 mmol, 1.0 eq.), 1-(difluoromethyl)-3-(4,4,5,5-tetramethyl-1,3,2-dioxaborolan-2-yl)-1H-pyrazole (1.61 g, 6.60 mmol, 1.5 eq.) in THF (30 mL) was added a solution of K$_3$PO$_4$ (1.87 g, 8.82 mmol, 2.0 eq.) in H$_2$O (30 mL) and Pd(DTBPF)C$_{12}$ (287 mg, 0.44 mmol, 0.1 eq.) at rt under N$_2$. Then the reaction mixture was stirred at 50° C. for 4 hours under N$_2$. The reaction was cooled to rt. The organic layer was concentrated under reduced pressure. The crude product was chromatographed (silica gel, EtOAc/petroleum ether) to give the desired compound (2.80 g, 94.5%) as red semi-solid. ESI MS m/z=672.05, 674.05 [M+H]$^+$.

Step 164c. To a stirred mixture of the compound from step 164b (2.80 g, 4.17 mmol, 1.0 eq.) in MeOH (30 mL) was added NaBH$_4$ (788 mg, 20.83 mmol, 5.0 eq.) at 0° C. Then the reaction mixture was stirred for 2 hour at rt. The reaction was quenched with water. The resulting mixture was extracted with EtOAc and washed with brine, dried over Na$_2$SO$_4$ and concentrated under reduced pressure. The crude product was chromatographed (silica gel, EtOAc/petroleum ether) to give the desired compound (2.0 g, 77.9%) as a yellow solid. ESI MS m/z=616.10, 618.10 [M+H]$^+$.

Step 164d. To a stirred mixture of the compound from Step 164c (300 mg, 0.49 mmol, 1.0 eq.) and TBSCl (73 mg, 0.49 mmol, 1.0 eq.) in DCM (3 mL) was added imidazole (66 mg, 0.98 mmol, 2.0 eq) at rt. The resulting mixture was stirred for 16 h at rt. The reaction mixture was diluted with water (30 mL), extracted with EtOAc (3×30 mL). The combined organic layers were dried over Na$_2$SO$_4$. After filtration, the filtrate was concentrated under vacuum. The residue was chromatographed (silica gel, EtOAc/petroleum ether) to give the desired compound (200 mg, 56.2%) as a yellow solid. ESI MS m/z=730.60, 732.60 [M+H]$^+$.

Step 164e. To a stirred mixture of the compound from Step 164d (150 mg, 0.20 mmol, 1.0 eq.) in CH$_2$Cl$_2$ (2 mL) were added MSCl (35 mg, 0.30 mmol, 1.5 eq.) and Et$_3$N (41 mg, 0.40 mmol, 2.0 eq.) dropwise at rt. The resulting mixture was stirred for 2 hour at rt. The resulting mixture was diluted with EtOAc (30 mL), washed with water (2×20 mL), dried over anhydrous Na$_2$SO$_4$, concentrated under vacuum to give the desired product (150 mg) as a crude product, which was used directly in next step without further purification. ESI MS m/z=808.20, 810.20 [M+H]$^+$.

Step 164f. To a stirred mixture of the compound from Step 164e (150 mg, crude) in CH$_2$Cl$_2$ (1 mL) was added TFA (0.5 mL). The resulting mixture was stirred for 1 hour at rt. The resulting mixture was concentrated under vacuum. The residue was dissolved in EtOAc (30 mL), washed with NaHCO$_3$aq. (1×10 mL), water (2×10 mL) and dried over anhydrous Na$_2$SO$_4$. The filtrate was concentrated under vacuum to give the desired product (110 mg) as a crude product, which was used in next step without further purification. ESI MS m/z=708.15, 710.15 [M+H]$^+$.

Step 164g. To a stirred mixture of the compound from Step 164f (110 mg, crude) in CH$_2$Cl$_2$ (1 mL) was added TEA (50 mg, 0.50 mmol) at rt. The resulting mixture was stirred for 6 hour at 40° C. The resulting mixture was diluted with EtOAc (30 mL). The resulting mixture was washed with water (1×10 mL) and dried over anhydrous Na$_2$SO$_4$, concentrated under vacuum. The crude product was chromatographed (silica gel, EtOAc/petroleum ether) to give the title product (80 mg, 84%). ESI MS m/z=612.30, 614.30 [M+H]$^+$.

Example 165

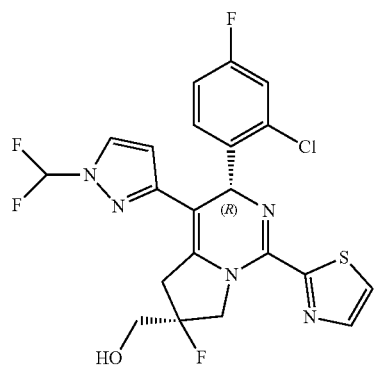

To a stirred mixture of Example 164 (80 mg, crude) in THF (1 mL) was added a solution of 12 N HCl (0.3 mL) at rt. The resulting mixture was stirred for 1 hour at rt. The resulting mixture was diluted with EA (30 mL). The resulting mixture was washed with NaHCO$_3$aq. (1×10 mL), water (2×10 mL) and dried over anhydrous Na$_2$SO$_4$, concentrated under vacuum. The crude product was purified by Prep-HPLC to afford the title product (15.0 mg) as a yellow solid. ESI MS m/z=498.20, 500.20 [M+H]$^+$.

Example 166

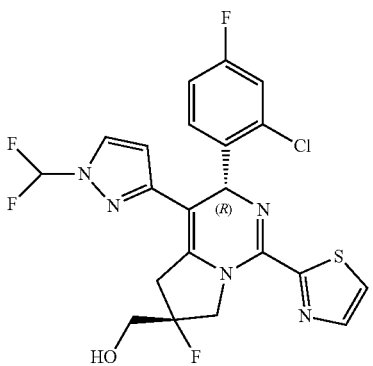

The title compound (28.8 mg) as a yellow solid was also isolated from Example 165. ESI MS m/z=498.15, 500.15 [M+H]⁺.

Example 167

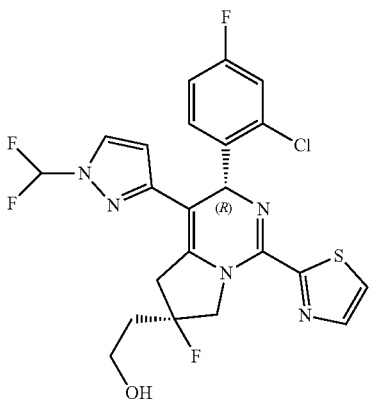

Step 167a. To a stirred mixture of the compound from Step 164d (3.00 g, 4.12 mmol, 1.00 eq.) in DCM (40 ml) was added Dess-Martin periodinate (2.09 g, 4.94 mmol, 1.20 eq.) at rt. The reaction mixture was stirred at rt for 1 h. The reaction mixture was concentrated under reduced pressure. The crude product was chromatographed (silica gel, EtOAc/petroleum ether) to give the desired compound (2.37 g, 79%) as a yellow solid. ESI MS m/z=728.30, 730.30 [M+H]⁺.

Step 167b. To a stirred mixture of methyltriphenylphosphonium bromide (1.67 g, 4.7 mmol, 2.0 eq.) in THF (4 ml) was added n-BuLi (2.5 M) (1.4 mL, 3.51 mmol, 2.7 eq.) dropwise at −10° C. under N₂. The reaction mixture was stirred at −10° C. for 0.5 h. Then to the above mixture was added a solution of the compound from Step 167a (1.7 g, 2.34 mmol, 1.0 eq.) in THF (10 ml). The resulting mixture was stirred for another 1 hour at rt. The reaction mixture was quenched with NH₄Cl aq solution. The resulting mixture was extracted with EtOAc (50 mL*3). The combined organic layers were washed with brine and dried over Na₂SO₄ and concentrated under reduced pressure. The crude product was chromatographed (silica gel, EtOAc/petroleum ether) to give the desired compound (630 mg, 35%) as a yellow solid. ESI MS m/z=726.20, 728.20 [M+H]⁺.

Step 167c. To a stirred mixture of the compound from Step 167b (580 mg, 0.8 mmol) in THF (6 mL) was added BH₃.THF (1 M) (2.40 mL, 2.4 mmol, 3 eq.) at 0° C. The resulting mixture was stirred for 2 hour at 0° C. To the above mixture was added H₂O (130 mg, 7.2 mmol, 9 eq.) at 0° C., then 3N NaOH solution (2.4 mL, 7.2 mmol, 9 eq.) and H₂O₂ (30%)(1.90, 16.8 mmol, 21 eq.). The resulting mixture was stirred for 2 hour at rt. The resulting mixture was diluted with water, extracted with EtOAc (30 mL×3). The combined organic layers were washed with brine and dried over anhydrous Na₂SO₄, and concentrated under reduced pressure. The residue was chromatographed (silica gel, EtOAc/petroleum ether) to give the desire product (175 mg, 29.5%) as a yellow solid. ESI MS m/z=744.30, 746.30 [M+H]⁺.

Step 167d. To a stirred mixture of the compound from Step 167c (175 mg, 0.24 mmol) and pivaloyl chloride (58 mg, 0.48 mmol, 2 eq.) in CH₂Cl₂ (3 ml) was added DMAP (59 mg, 0.48 mmol, 2 eq.) at rt. The reaction mixture was stirred for 1 h at rt. The resulting mixture was diluted with water and extracted with EtOAc (20 mL×3), the combined organic layers were washed with brine and dried over anhydrous Na₂SO₄, and concentrated under reduced pressure. The residue was chromatographed (silica gel, EtOAc/petroleum ether) to give the desire product (140 mg, 71.8%) as a yellow solid. ESI MS m/z=828.30, 830.30 [M+H]⁺.

Step 167e. To a stirred mixture of the compound from Step 167d (140 mg, 0.17 mmol, 1.0 eq.) in THF (2 ml) was added a solution of 1M TBAF (0.5 mL, 0.50 mmol, 3 eq.) at rt. The reaction mixture was stirred at rt for 1 h. The resulting mixture was diluted with water, extracted with EtOAc (20 mL*3). The combined organic layers were washed with brine and dried over anhydrous Na₂SO₄, and concentrated under reduced pressure. The residue was chromatographed (silica gel, EtOAc/petroleum ether) to give the desire product (100 mg, 82.9%) as a yellow solid. ESI MS m/z=714.25, 716.25 [M+H]⁺.

Step 167f. To a stirred mixture of the compound from Step 167e (100 mg, 0.14 mmol, 1.0 eq.) in CH₂Cl₂ (1 ml) and pyridine (1 mL) was added TsCl (53 mg, 0.28 mmol, 2 eq.) at rt. The reaction mixture was stirred at rt for 16 h. The resulting mixture was diluted with water, extracted with EtOAc (20 mL*3). The combined organic layers were washed with brine and dried over anhydrous Na₂SO₄, and concentrated under reduced pressure. The residue was chromatographed (silica gel, EtOAc/petroleum ether) to give the desire product (100 mg, 82%) as a yellow solid. ESI MS m/z=868.05, 870.05 [M+H]⁺.

Step 167g. To a stirred mixture of the compound from Step 167f (100 mg, 0.12 mmol, 1.0 eq.) in CH₂Cl₂ (1 ml) was added TFA (0.3 mL) at rt. The reaction mixture was stirred for 2 h at rt. The resulting was quenched with NaHCO₃aq. solution The resulting mixture was diluted with water, extracted with EtOAc (20 mL*3). The combined organic layers were washed with brine and dried over anhydrous Na₂SO₄, and concentrated under reduced pressure to give the desire product (95 mg, crude) as a yellow solid. ESI MS m/z=768.10, 770.10 [M+H]⁺.

Step 167h. To a stirred mixture of the compound from Step 167g (95 mg, crude) in CH₂Cl₂ (2 ml) was added TEA (40 mg, 0.40 mmol) at rt. The reaction mixture was stirred at 40° C. for 5 h. The reaction mixture was concentrated under reduced pressure. The crude product was chromatographed (silica gel, EtOAc/petroleum ether) to give the desire product (50 mg) as a yellow solid. ESI MS m/z=596.15, 598.15 [M+H]⁺.

Step 167i. To a stirred mixture of the compound from Step 167h (50 mg, 0.08 mmol, 1 eq.) in CH₂Cl₂ (2 mL) was added a solution of 1.5 M DIBAL-H (0.16 mL, 0.24 mmol, 3 eq.) at −78° C. under N₂. The reaction mixture was stirred for 2 hours at −78° C. The reaction mixture was quenched with ice brine and extracted with EtOAc (*3). The combined organic layers were washed with brine and dried over anhydrous Na₂SO₄, and concentrated under reduced pressure. The residue was purified by Pre-HPLC to give the title compound (4.6 mg, 10.7%) as a yellow solid. ESI MS m/z=512.10, 514.10 [M+H]⁺.

Example 168

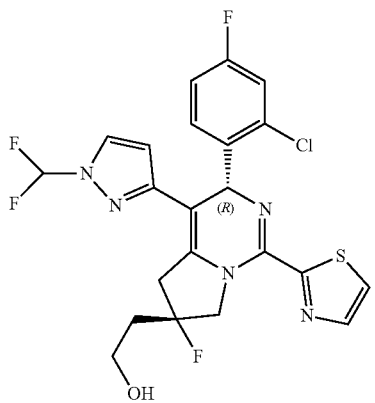

The title product (1.2 mg, 2.8%) as a yellow solid was also isolated Example 167. ESI MS m/z=512.15, 514.15 [M+H]⁺.

Example 169

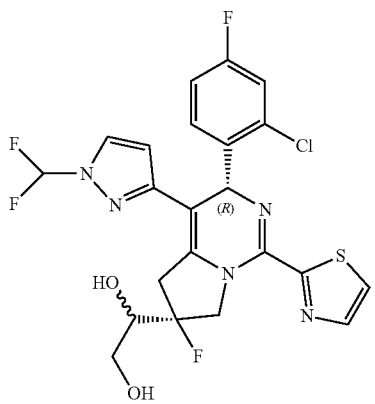

Step 169a. To a stirred mixture of MeOCH₂OCH₂SnBu₃ (1.51 g, 4.13 mmol, 3 eq.) in THF (10 mL) was added n-BuLi (2.5 M) (1.48 mL, 3.7 mmol, 2.7 eq.) at −78° C. After 30 minutes at −78° C. a solution of the compound from Step 167a (1 g, 1.38 mmol, 1 eq.) in THF (3 mL) was added dropwise at −78° C. The resulting mixture was stirred for another 1 h at −78° C. The reaction mixture was quenched with ice brine and extracted with EtOAc (50 mL*3). The combined organic layers were washed with brine and dried over anhydrous Na₂SO₄, and concentrated under reduced pressure. The residue was chromatographed (silica gel, EtOAc/petroleum ether) to give the desire product (250 mg, 22.6%) as a yellow solid. ESI MS m/z=804.30, 806.30 [M+H]⁺.

Step 169b. To a stirred mixture of the compound from Step 169a (250 mg, 0.31 mmol, 1.00 eq.) in THF (3 mL) was added TBAF (1 M in THF, 0.6 mL, 0.6 mmol, 2 eq.) at rt. The reaction mixture was stirred for 1 hour at rt. The resulting mixture was diluted with water and extracted with EtOAc (*3). The combined organic layers were washed with brine and dried over anhydrous Na₂SO₄, and concentrated under reduced pressure. The residue was chromatographed (silica gel, EtOAc/petroleum ether) to give the desire product (170 mg, 79.2%) as a yellow solid. ESI MS m/z=690.15, 692.15 [M+H]⁺.

Step 169c. To a stirred mixture of the compound from Step 169b (170 mg, 0.25 mmol, 1.0 eq.) in CH₂Cl₂ (1 ml) and pyridine (1 mL) was added TsCl (94 mg, 0.50 mmol, 2 eq.) at rt.

The reaction mixture was stirred for 48 hours at rt. The resulting mixture was diluted with water and extracted with EtOAc (20 mL×3). The combined organic layers were washed with brine and dried over anhydrous Na₂SO₄, and concentrated under reduced pressure. The residue was chromatographed (silica gel, EtOAc/petroleum ether) to give the desire product (100 mg, 48.1%) as a yellow solid. ESI MS m/z=844.20, 846.20 [M+H]⁺.

Step 169d. To a stirred mixture of the compound from Step 169c (100 mg, 0.12 mmol, 1.00 eq.) in CH₂Cl₂ (1.5 mL) was added TFA (0.3 mL) at rt. The reaction mixture was stirred at rt for 2 h. The resulting mixture was quenched with saturated NaHCO₃aq. solution and extracted with EtOAc (*3). The combined organic layers were washed with brine and dried over anhydrous Na₂SO₄, and concentrated under reduced pressure to give the desire product (100 mg) as a crude product, which was used in next step directly without further purification. ESI MS m/z=700.10, 702.10 [M+H]⁺.

Step 169e. To a stirred mixture of the compound from Step 169d (100 mg, crude) in CH₂Cl₂ (2 mL) was added TEA (43 mg, 0.43 mmol) at rt. The reaction mixture was stirred at 40° C. for 16 hour. The reaction mixture was concentrated under reduced pressure. The crude product was purified by Prep-HPLC to give the title compound (12.7 mg, 16.9%) as a yellow solid. ESI MS m/z=528.15, 530.15 [M+H]⁺.

Example 170

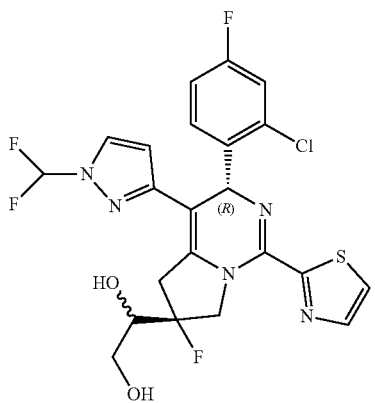

The title compound (2.6 mg, 3.5%) as a yellow solid was also isolated from Example 169. ESI MS m/z=528.15, 530.15 [M+H]⁺.

Example 171

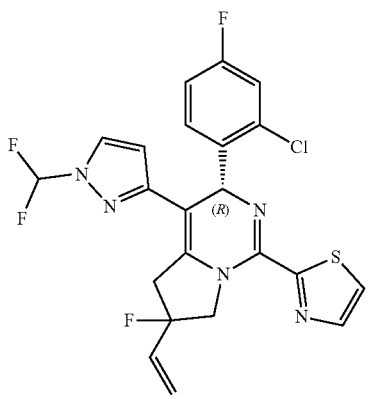

To a stirred mixture of the compound from Step 167b (280 mg, 0.39 mmol) in MeOH (3 ml) was added HCl (1.00 ml) at rt The resulting mixture was stirred at rt for 16 hours. The reaction was quenched with NaHCO$_3$aq. solution. The resulting mixture was extracted with EtOAc (20 mL*3). The combined organic layers were washed with brine and dried over anhydrous Na$_2$SO$_4$, and concentrated under reduced pressure. The residue was dissolved in CH$_2$Cl$_2$ (3 mL). To the above mixture were added TEA (118 mg, 1.17 mmol) and MSCl (53 mg, 0.47 mmol) at rt. The resulting mixture was stirred at rt for 16 hours. The resulting mixture was concentrated under reduced pressure. The residue was purified by Prep-HPLC to give the title product (6.2 mg) as a yellow solid. ESI MS m/z=494.15, 496.15 [M+H]$^+$.

Example 172

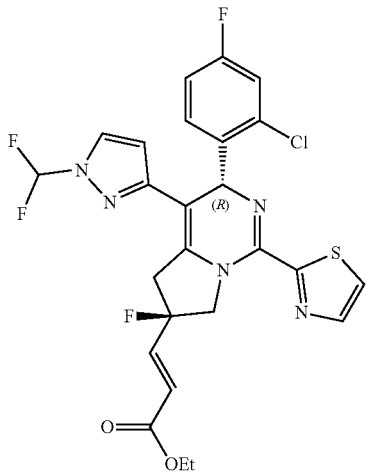

Step 172a. To a stirred mixture of ethyl 2-(diethoxyphosphoryl)acetate (231 mg, 1.03 mmol, 1.5 eq.) in THF (5 mL) was added t-BuOK (100 mg, 0.89 mmol, 1.3 eq.) at rt. The resulting mixture was stirred for 30 min at rt. To the reaction mixture was added the compound from Step 167a (500 mg, 0.69 mmol, 1.00 eq.). The resulting mixture was stirred for another 2 hours at rt. The reaction was quenched by the addition of NH$_4$Cl aq. solution. The resulting mixture was extracted with EtOAc (3×50 mL). The combined organic layers were washed with brine and dried over anhydrous Na$_2$SO$_4$, and concentrated under reduced pressure. The residue was chromatographed (silica gel, EtOAc/petroleum ether) to give the desire product (360 mg, 65.7%) as a yellow solid. ESI MS m/z=798.25, 800.25 [M+H]$^+$.

Step 172b. To a stirred mixture of the compound from Step 172a (300 mg, 0.38 mmol, 1.0 eq.) in THF (2 mL) was added HCl (0.5 mL) at rt. The resulting mixture was stirred for 30 min at rt. The mixture was quenched with NaHCO$_3$aq. solution. The resulting mixture was extracted with EtOAc (2×30 mL). The combined organic layers were washed with brine and dried over anhydrous Na$_2$SO$_4$, and concentrated under reduced pressure to give the desire product (250 mg) as a crude product, which was used directly in next step without further purification. ESI MS m/z=684.10, 686.10 [M+H]$^+$.

Step 172c. To a stirred mixture of the compound from Step 172b (250 mg, crude) in CH$_2$Cl$_2$ (3 mL) were added TsCl (105 mg, 0.55 mmol) and TEA (111 mg, 1.1 mmol) at rt. The resulting mixture was stirred for 16 h at rt. The resulting mixture was concentrated under reduced pressure. The residue was chromatographed (silica gel, EtOAc/petroleum ether) to give the desire product (210 mg) as a yellow solid. ESI MS m/z=838.20, 840.20 [M+H]$^+$.

Step 172d. To a stirred mixture of the compound from Step 172c (210 mg, 0.25 mmol) in CH$_2$Cl$_2$ (1.5 mL) was added TFA (0.5 mL) at rt. The resulting mixture was stirred for 2 hours at rt. The resulting mixture was concentrated under vacuum to give the desired product (210 mg) as a crude product, which was used directly in next step without further purification. ESI MS m/z=738.25, 740.25 [M+H]$^+$.

Step 172e. To a stirred mixture of the compound from Step 172d (210 mg, crude) in CH$_2$Cl$_2$ (2 mL) was added TEA (144 mg, 1.4 mmol) at rt. The resulting mixture was stirred for 24 h at rt. The resulting mixture was concentrated under reduced pressure and chromatographed (silica gel, EtOAc/petroleum ether) to give the desire product (135 mg) as a yellow solid. ESI MS m/z=566.05, 568.05 [M+H]$^+$.

Step 172f. The compound from Step 172e was purified by Prep-HPLC to afford the title compound (4.8 mg) as a yellow solid. ESI MS m/z=566.10, 568.10 [M+H]$^+$.

Example 173

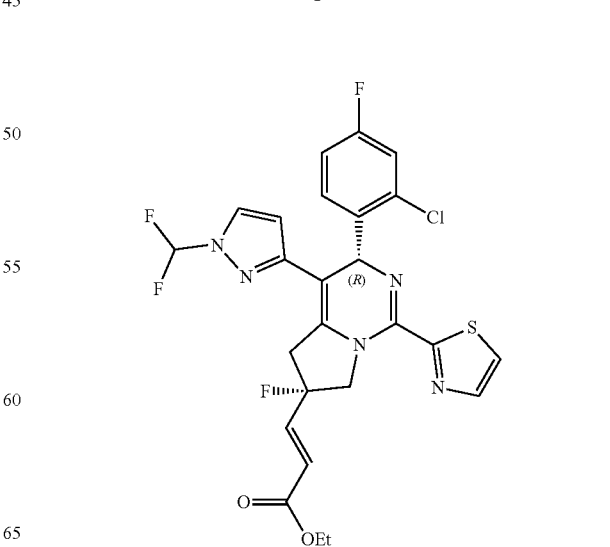

The title compound (0.8 mg, 2.67%) as a yellow solid was also isolated from Example 172. ESI MS m/z [M+H]$^P$=566.10.

Example 174

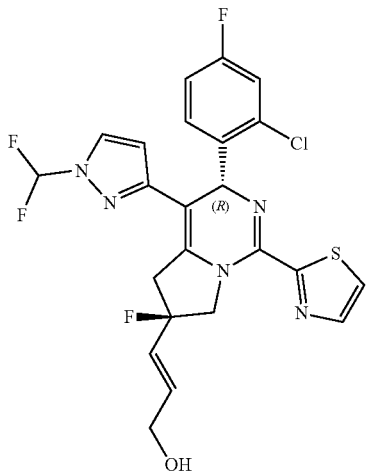

To a stirred mixture of the compound from Step 172e (105 mg, 0.19 mmol, 1.0 eq.) in THF (1 mL) was added a solution of 1.5 M DIBAL-H (0.37 mL, 0.56 mmol, 3.0 eq.) dropwise at −78° C. The resulting mixture was stirred for 5 hours at −78° C. The reaction was quenched with NH$_4$Cl aq. solution at −78° C. The resulting mixture was extracted with EtOAc (3*20 mL). The combined organic layers were washed with brine, dried over anhydrous Na$_2$SO$_4$, and concentrated under reduced pressure. The residue was purified by Pre-HPLC to give the title product (5.9 mg) as a yellow solid. ESI MS m/z=524.05, 526.05 [M+H]$^+$.

Example 175

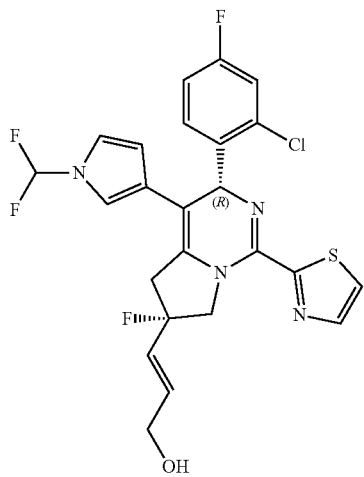

The title product (2.4 mg) as a yellow solid was also isolated from Example 174. ESI MS m/z=524.10, 526.10 [M+H]$^+$.

Example 176

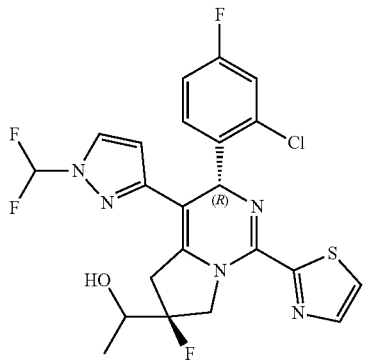

Step 176a. To a stirred mixture of the compound from Step 167a (400 mg, 0.55 mmol, 1.0 eq.) in THF (4 mL) was added bromo(methyl)magnesium (0.82 mL, 0.82 mmol, 1.5 eq.) dropwise at −78° C. The resulting mixture was stirred for 2 hours at −78° C. Then the reaction was quenched by the addition of NH$_4$Cl aq. solution (10 mL) at −78° C. The resulting mixture was extracted with EtOAc (2*30 mL). The combined organic layers were washed with brine and dried over anhydrous Na$_2$SO$_4$, and concentrated under reduced pressure. The residue was chromatographed (silica gel, EtOAc/petroleum ether) to give the desire product (250 mg, 61.2%) as a yellow solid. ESI MS m/z=744.20, 746.20 [M+H]$^+$.

Step 176b. To a stirred mixture of the compound from Step 176a (200 mg, 0.27 mmol, 1.0 eq.) in THF (2 mL) was added HCl (0.4 mL) at rt. The resulting mixture was stirred for 30 min at rt. The reaction was quenched by the addition of NaHCO$_3$aq. solution. The resulting mixture was extracted with EtOAc (3*30 mL). The combined organic layers were washed with brine and dried over anhydrous Na$_2$SO$_4$, and concentrated under reduced pressure to give the desired product (170 mg) as a crude product, which was used in the next step directly without further purification. ESI MS m/z=630.10, 632.10 [M+H]$^+$.

Step 176c. To a stirred mixture of the compound from Step 176b (170 mg, crude) in DCM (1 mL) and pyridine (1 mL) was added TsCl (52 mg, 0.27 mmol) at rt The resulting mixture was stirred for 16 h at rt. The resulting mixture was diluted with EA (50 mL). The resulting mixture was washed with HCl (1M) (1×10 mL), water (1×10 mL), brine (1×10 mL) and dried over anhydrous Na$_2$SO$_4$. After filtration, the filtrate was concentrated under reduced pressure. The residue was chromatographed by Prep-TLC (EA/PE=1/1) to afford PH-ETA-D2-143-3(85 mg) as a yellow solid. ESI MS m/z=784.30, 786.30 [M+H]$^+$.

Step 176d. To a stirred mixture of the compound from Step 176c (85 mg, 0.11 mmol, 1.0 eq.) in CH$_2$Cl$_2$ (1 mL) was added TFA (0.3 mL) at rt. The resulting mixture was stirred for 2 h at rt. The resulting mixture was washed with NaHCO$_3$aq. (1×10 mL), water (1×10 mL), brine (1×10 mL), dried over anhydrous Na$_2$SO$_4$, and concentrated to give the desired product (85 mg) as a crude product, which was used in next step directly without further purification. ESI MS m/z=684.05, 686.05 [M+H]$^+$.

Step 176e. To a stirred mixture of the compound from Step 176d (85 mg, crude) in CH$_2$Cl$_2$ (1 mL) was added TEA (38 mg, 0.38 mmol) at rt. The resulting mixture was stirred for 24 hours at rt. The resulting mixture was concentrated and purified by Prep-HPLC to give the title compound (19.8 mg) as a yellow solid. ESI MS m/z=512.05, 514.05 [M+H]⁺.

Example 177

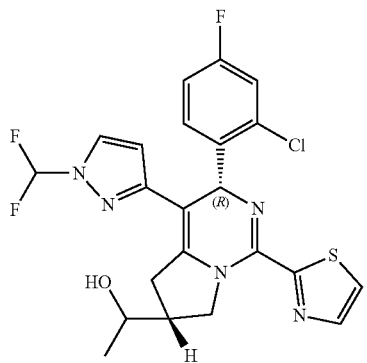

The title compound (4.0 mg) as a yellow solid was also isolated from Example 176. ESI MS m/z=512.15, 514.15 [M+H]⁺.

Example 178

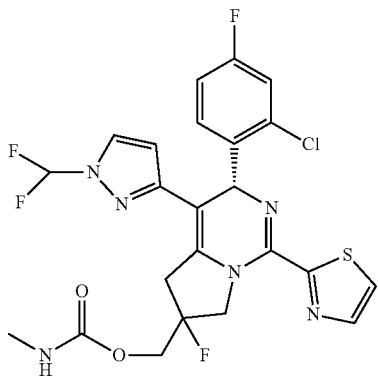 [SMILES: CNC(=O)OCC1(F)CC2=C(c3ccn(C(F)F)n3)[C@H](c3ccc(F)cc3Cl)N=C(c3nccs3)N2C1]

Step 178a. To a stirred mixture of Example 164 (120 mg, crude) in THF (1 mL) was added a solution of 12 N HCl (0.3 mL) at rt. The resulting mixture was stirred for 1 hour at rt. The resulting mixture was diluted with EA (30 mL). The resulting mixture was washed with NaHCO₃ aq. (1×10 mL), water (2×10 mL) and dried over anhydrous Na₂SO₄, concentrated under vacuum to afford the desired product (90 mg) as a yellow solid. ESI MS m/z=498.20, 500.20 [M+H]⁺.

Step 178b. To a stirred mixture of from Step 178a (90 mg, 0.18 mmol, 1.0 eq.) and MeNH₂.HCl (15 mg, 0.22 mmol, 1.2 eq.) in DCM (3 mL) was added CDI (58 mg, 0.36 mmol, 2.0 eq.) and TEA (55 mg, 0.54 mmol, 3.0 eq.) at rtrt. The reaction mixture was stirred for 1 h at rt. The reaction mixture was concentrated under reduced pressure. The crude product was purified by Prep-HPLC to give the title compound (51.3 mg, 46.0%) as a yellow solid. ESI MS m/z=555.15, 557.15 [M+H]⁺.

Example 179

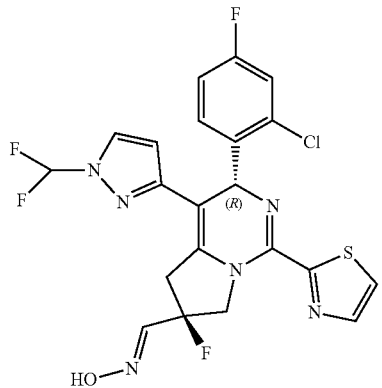

Step 179a. To a stirred mixture of DMSO (156 mg, 2.00 mmol, 2 eq.) in CH₂Cl₂ (3 mL) was added (COCl)₂ (189 mg, 1.5 mmol, 1.5 eq.) dropwise at −78° C. The resulting mixture was stirred for 20 min at −78° C. Then a solution of the compound from Step 178a (500 mg, 1.0 mmol, 1 eq.) in DCM (5 mL) dropwise at −78° C., followed by the addition of TEA (404 mg, 4.0 mmol, 4 eq.). The resulting mixture was stirred for 30 min at −78° C. then warmed up to room temperature. The reaction was quenched by the addition of water and extracted with EtOAc (50 mL×3). The combined organic layers were dried over anhydrous Na₂SO₄ and concentrated reduced pressure. The residue was purified (silica gel, EtOAc/petroleum ether) to give the desired product (300 mg, 60%) as a yellow solid. ESI MS m/z=514.10, 516.10 [M+H]⁺.

Step 179b. To a stirred mixture of the compound from Step 179a (100 mg, 0.19 mmol, 1 eq.) and NH₂OH.HCl (41 mg, 0.58 mmol, 3 eq.) in CH₂Cl₂ (2 mL) was added TEA (59 mg, 0.58 mmol, 3 eq.) and 4 A Molecular Sieves (50 mg) at room temperature. The resulting mixture was stirred for 16 h at room temperature. The resulting mixture was diluted with water and extracted with EtOAc (*3). The combined organic layers were dried over anhydrous Na₂SO₄ and concentrated reduced pressure. The residue was purified by Pre-HPLC to give the title compound (7.2 mg) as a yellow solid. ESI MS m/z=511.05, 513.05 [M+H]⁺.

Example 180

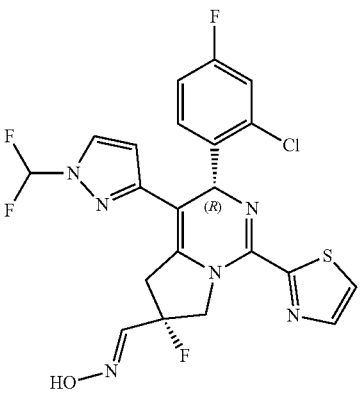

The title compound (11.0 mg) as a yellow solid was also isolated from Example 179. ESI MS m/z=511.05, 513.05 [M+H]+.

Example 181

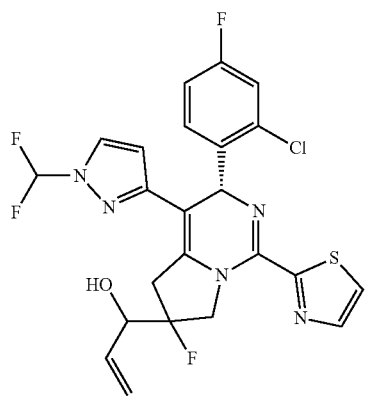 [SMILES: C=CC(O)C1(F)CC2=C(c3ccn(C(F)F)n3)[C@H](c3ccc(F)cc3Cl)N=C(c3nccs3)N2C1]

The compound from Step 179a (100 mg, 0.20 mmol, 1 eq.) was dissolved in acetonitrile, and the resulting mixture was lyophilized for 16 hours under vacuum to give the desired product (100 mg) as a crude yellow solid, which was used in next step directly.

Step 181b. To a stirred solution of the compound from Step 181a (100 mg, crude) in anhydrous THF (1 mL) was added bromo(ethenyl)magnesium (0.6 mL, 0.60 mmol) dropwise at −78° C. The resulting mixture was stirred for 2 hours at −78° C. The reaction was quenched with NH$_4$Cl aq. solution at −78° C. The aqueous layer was extracted with EtOAc (*3). The combined organic layers were dried over anhydrous Na$_2$SO$_4$ and concentrated. The residue was purified by Pre-HPLC to give the title compound (3.7 mg, 3.50%) as a yellow solid. ESI MS m/z=524.20, 526.20 [M+H]+.

Example 182

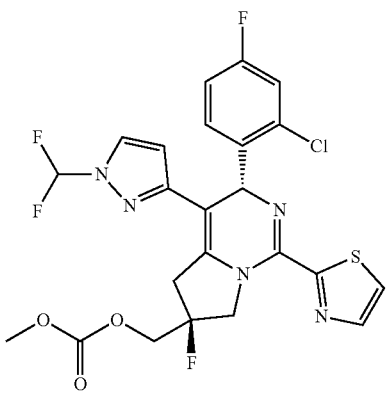 [SMILES: COC(=O)OC[C@]1(F)CC2=C(c3ccn(C(F)F)n3)[C@H](c3ccc(F)cc3Cl)N=C(c3nccs3)N2C1]

To a stirred solution of the compound from Step 178a (50.0 mg, 0.10 mmol) and CDI (32.6 mg, 0.20 mmol, 2 eq.) in CH$_2$Cl$_2$ (0.50 mL) was added TEA (31 mg, 0.31 mmol, 3 eq.) at r.t. The resulting mixture was stirred for 2 h at rt. The reaction was quenched by the addition of MeOH. The resulting mixture was concentrated under vacuum. The residue was purified by Prep-HPLC to afford the title compound (6.0 mg, 15.0%) as a yellow solid. ESI MS m/z=556.15, 558.15 [M+H]+.

Example 183

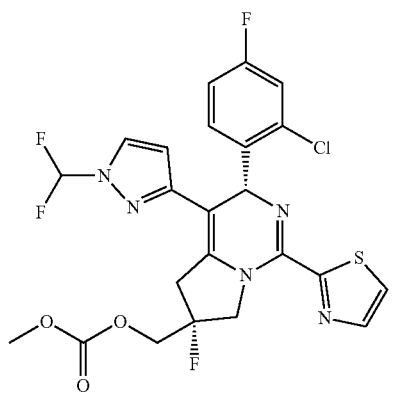 [SMILES: COC(=O)OC[C@@]1(F)CC2=C(c3ccn(C(F)F)n3)[C@H](c3ccc(F)cc3Cl)N=C(c3nccs3)N2C1]

The title compound (17.1 mg, 42.7%) as a yellow solid was also isolated from Example 182. ESI MS m/z=556.15, 558.15 [M+H]+.

Example 184

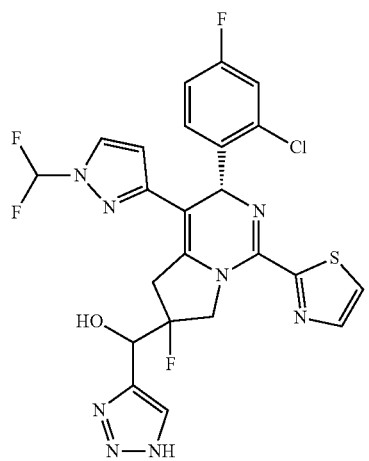 [SMILES: OC(c1c[nH]nn1)C1(F)CC2=C(c3ccn(C(F)F)n3)[C@H](c3ccc(F)cc3Cl)N=C(c3nccs3)N2C1]

Step 184a. To a stirred solution of the compound from Step 179a (700 mg, 0.97 mmol, 1 eq.) in THF (69 mL) was added 0.5 M (2-lithioethynyl)trimethylsilane (5.8 mL, 2.9 mmol, 3 eq.) dropwise at −78° C. The resulting mixture was stirred for 1 hour at −78° C. The reaction was quenched by the addition of water (10 mL) at −78° C. The aqueous layer was extracted with EtOAc (30 mL×3).). The combined organic layers were dried over anhydrous Na$_2$SO$_4$ and concentrated reduced pressure. The residue was purified (silica gel, EtOAc/petroleum ether) to give the desired product (400 mg) as a yellow solid. ESI MS m/z=826.45, 828.45 [M+H]+.

Step 184b. To a stirred mixture of the compound from Step 184a (400 mg, 0.48 mmol, 1 eq.) in THF (4 mL) was added 12 N HCl (1 mL) at room temperature. The resulting mixture was stirred for 30 minutes at room temperature. The mixture was quenched with saturated NaHCO$_3$aq. solution. The resulting mixture was extracted with EtOAc (20 mL×3).). The combined organic layers were dried over anhydrous Na$_2$SO$_4$ and concentrated reduced pressure. The residue was purified (silica gel, EtOAc/petroleum ether) to give the desired product (310 mg) as a light yellow solid. ESI MS m/z=712.25, 714.25 [M+H]$^+$.

Step 184c. To a stirred mixture of the compound from Step 184b (310 mg, 0.44 mmol, 1 eq.) and TsCl (83 mg, 0.44 mmol, 1 eq.) in CH$_2$Cl$_2$ (5 mL) were added Et$_3$N (133 mg, 1.32 mmol, 3 eq.) and DMAP (5 mg, 0.04 mmol, 0.1 eq.) at room temperature. The resulting mixture was stirred for 1 hour at room temperature. The resulting mixture was diluted with water (20 mL). The aqueous layer was extracted with CH$_2$Cl$_2$ (15 mL*3).). The combined organic layers were dried over anhydrous Na$_2$SO$_4$ and concentrated reduced pressure.

The residue was purified (silica gel, EtOAc/petroleum ether) to give the desired product (95 mg) as a light yellow solid. ESI MS m/z=866.35, 868.35 [M+H]$^+$.

Step 184d. To a stirred mixture of the compound from Step 184c (135 mg, 0.16 mmol, 1 eq.) in CH$_2$Cl$_2$ (1 mL) was added TFA (0.3 mL) at room temperature. The resulting mixture was stirred for 3 hour at r.t. The mixture was quenched with saturated NaHCO$_3$(aq.). The resulting mixture was extracted with EtOAc (20 mL*3). The combined organic layers were dried over anhydrous Na$_2$SO$_4$ and concentrated reduced pressure to give the desired product (95 mg) as a light yellow solid (100 mg), which was used in next step directly without further purification. ESI MS m/z=766.15, 768.15 [M+H]$^+$.

Step 184e. To a stirred mixture of the compound from Step 184d (100 mg, 0.13 mmol, 1 eq.) in CH$_2$Cl$_2$ (1 mL) was added TEA (40 mg, 0.39 mmol, 3 eq.) at room temperature. The resulting mixture was stirred for overnight at room temperature. The resulting mixture was diluted with water (10 mL), extracted with CH$_2$Cl$_2$ (10 mL×3). The combined organic layers were dried over anhydrous Na$_2$SO$_4$ and concentrated reduced pressure. The residue was purified (silica gel, EtOAc/petroleum ether) to give the desired product (60 mg) as a light yellow solid. ESI MS m/z=594.10, 596.10 [M+H]$^+$.

Step 184f. To a stirred solution of the compound from Step 184e (50 mg, 0.08 mmol, 1 eq.) in THF (0.5 mL) was added 1M TBAF (0.13 mL, 0.13 mmol, 1.5 eq.) dropwise at room temperature. The resulting mixture was stirred for 10 min at room temperature. The resulting mixture was diluted with water (10 mL), extracted with EA (10 mL*3). The combined organic layers were dried over anhydrous Na$_2$SO$_4$ and concentrated reduced pressure. The residue was purified (silica gel, EtOAc/petroleum ether) to give the desired product (40 mg) as a brown solid. ESI MS m/z=522.05, 524.05 [M+H]$^+$.

Step 184g. Into a 8 mL sealed tube were added a solution of the compound from Step 184f (40 mg, 0.08 mmol, 1 eq.) in t-BuOH (0.5 mL), sodium ascorbate (30 mg, 0.15 mmol, 2 eq.), Cu$_2$SO$_4$ (12 mg, 0.08 mmol, 1 eq.), NaN$_3$ (5.5 mg, 0.08 mmol, 1.1 eq.) and H$_2$O (0.5 mL) at rt. The resulting mixture was stirred for 3 h at rt. The resulting mixture was diluted with water (10 mL). The precipitated solids were collected by filtration. The residue was purified by Prep-HPLC to give the title compound (2.3 mg, 5.31%) as a yellow solid. ESI MS m/z=565.10, 567.10 [M+H]$^+$.

Example 185

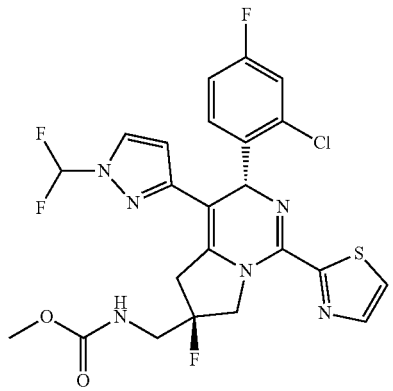 [SMILES: COC(=O)NC[C@]1(F)CC2=C(c3ccn(C(F)F)n3)[C@H](c3ccc(F)cc3Cl)N=C(c3nccs3)N2C1]

Step 185a. To a stirred solution of the compound from Step 179a (600 mg, 0.82 mmol, 1.0 eq.) and in NH$_3$/MeOH (7M, 5 mL) was added NH$_4$OAc (635 mg, 8.2 mmol, 10 eq.) at rt. The resulting mixture was stirred for 1 hour at rt. Then NaBH$_3$CN (155 mg, 2.47 mmol, 3.0 eq.) was added in portions at room temperature. The resulting mixture was stirred for additional 2 hours at room temperature. The resulting mixture was quenched by the addition of water (30 mL). The resulting mixture was extracted with EtOAc (3×50 mL). The combined organic layers were dried over anhydrous Na$_2$SO$_4$ and concentrated reduced pressure. The residue was purified (silica gel, EtOAc/petroleum ether) to give the desired product (190 mg, 31.6%) as a yellow solid. ESI MS m/z=729.25, 731.25 [M+H]$^+$.

Step 185b. To a solution of the compound from Step 185a (190 mg, 0.26 mmol, 1.0 eq.) in CH$_2$Cl$_2$ (2 mL) was added CDI (85 mg, 0.52 mmol, 2.0 eq.) at room temperature. The resulting mixture was stirred for 2 hours at room temperature. Then MeOH (1 mL) was added at room temperature. The resulting mixture was stirred for additional 16 hours at 40° C. The resulting mixture was concentrated under vacuum and purified (silica gel, EtOAc/petroleum ether) to give the desired product (125 mg, 60.9%) as a yellow solid. ESI MS m/z=787.25, 789.25 [M+H]$^+$.

Step 185c. To a solution of the compound from Step 185b (125 mg, 0.16 mmol, 1.0 eq.) in THF (1 mL) was added 12N HCl (0.2 mL) at room temperature. The resulting mixture was stirred for 30 min at room temperature. The reaction was quenched with saturated NaHCO$_3$(aq.). The aqueous layer was extracted with EtOAc (10 mL*3). The combined organic layers were dried over anhydrous Na$_2$SO$_4$ and concentrated under reduced pressure to give the desired product (100 mg) as a crude product, which was used in the next step directly without further purification. ESI MS m/z=673.15, 675.15 [M+H]$^+$.

Step 185d. To a stirred solution of the compound from Step 185c (100 mg, crude) in CH$_2$Cl$_2$ (1 mL) were added TsCl (85 mg, 0.45 mmol) and TEA (75 mg, 0.74 mmol) and at room temperature. The resulting mixture was stirred for 16 h at room temperature. The resulting mixture was concentrated under vacuum and purified (silica gel, EtOAc/petroleum ether) to give the desired product (80 mg) as a yellow solid. ESI MS m/z=827.25, 829.25 [M+H]$^+$.

Step 185e. To a stirred solution of the compound from Step 185d (80 mg, 0.1 mmol, 1.0 eq.) in CH$_2$Cl$_2$ (1 mL) was added TFA (0.3 mL) at room temperature. The resulting mixture was stirred for 1 hour at room temperature. The combined organic layers were dried over anhydrous Na$_2$SO$_4$ and concentrated under reduced pressure to give the desired product (80 mg) as a crude product, which was used in the next step directly without further purification. ESI MS m/z=727.20, 729.20 [M+H]$^+$.

Step 185f. To a stirred solution of the compound from Step 185e (80 mg, crude) in DCM (1 mL) was added TEA (100 mg, 1.0 mmol) at room temperature. The resulting mixture was stirred for 15 hours at room temperature. The resulting mixture was concentrated under reduced pressure and purified (silica gel, EtOAc/petroleum ether) to give the desired product (40 mg) as a yellow solid. ESI MS m/z=555.10, 557.10 [M+H]$^+$.

Step 185g. The solution of the compound from Step 185f (40 mg) was purified by Prep-HPLC to give the title compound (12.5 mg) as a yellow solid. ESI MS m/z=555.20, 557.20 [M+H]$^+$.

Example 186

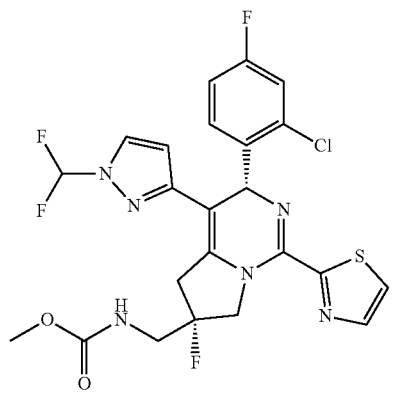 [SMILES: COC(=O)NC[C@@]1(F)CC2=C(c3ccn(C(F)F)n3)[C@H](c3ccc(F)cc3Cl)N=C(c3nccs3)N2C1]

The title compound (3.3 mg) as a yellow solid was also isolated from Example 185. ESI MS m/z=555.15, 557.15 [M+H]$^+$.

Example 187

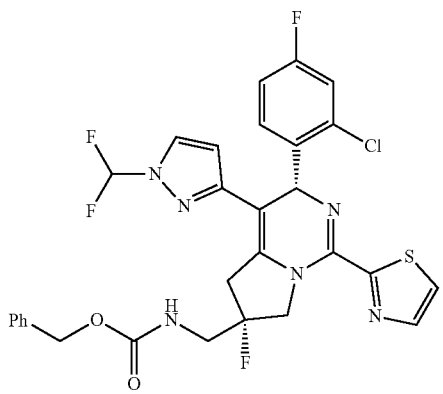 [SMILES: O=C(NC[C@@]1(F)CC2=C(c3ccn(C(F)F)n3)[C@H](c3ccc(F)cc3Cl)N=C(c3nccs3)N2C1)OCc1ccccc1]

The title compound was prepared following the general procedure of Example 185. ESI MS m/z=631.05, 633.05 [M+H]$^+$.

Example 188

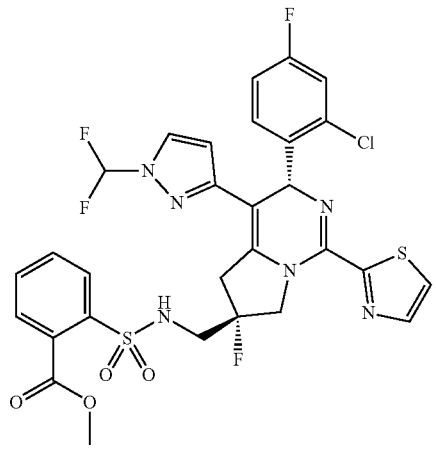 [SMILES: COC(=O)c1ccccc1S(=O)(=O)NC[C@@]1(F)CC2=C(c3ccn(C(F)F)n3)[C@H](c3ccc(F)cc3Cl)N=C(c3nccs3)N2C1]

Step 188a. To a stirred solution of PPh$_3$ (3 equiv) in THF was added DEAD (3 equiv) dropwise at 0° C. The mixture was stirred for 30 min at room temperature. To the above mixture was added the compound from Step 178a (1 equiv) and methyl 2-(N-(tert-butoxycarbonyl)sulfamoyl)benzoate (2 equiv) in THF dropwise at 0° C. The resulting mixture was stirred for additional 15 hours at room temperature. The reaction mixture was diluted with water at room temperature and extracted with EtOAc. The resulting mixture was concentrated under vacuum and purified (silica gel, EtOAc/petroleum ether) to give the desired product as a yellow solid. ESI MS m/z=795.20, 797.20 [M+H]$^+$.

Step 188b. To a stirred solution of the compound from Step 188a in DCM (3 mL) was added TFA (1 mL) at room temperature. The resulting mixture was stirred for 3 hours at room temperature. The resulting mixture was concentrated under vacuum and purified by Prep-HPLC to give the title compound. ESI MS m/z=694.95, 696.95 [M+H]$^+$.

Example 189

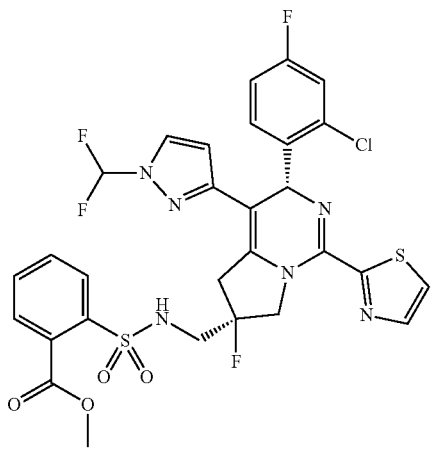 [SMILES: COC(=O)c1ccccc1S(=O)(=O)NC[C@]1(F)CC2=C(c3ccn(C(F)F)n3)[C@H](c3ccc(F)cc3Cl)N=C(c3nccs3)N2C1]

The title compound was also isolated from Example 188. ESI MS m/z=695.15, 697.15 [M+H]$^+$.

Example 190

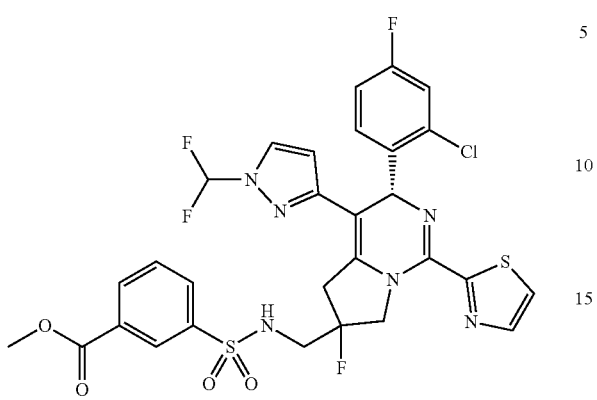

The title compound was prepared following the general procedure of Example 188. ESI MS m/z=695.20, 697.20 [M+H]⁺.

Example 191

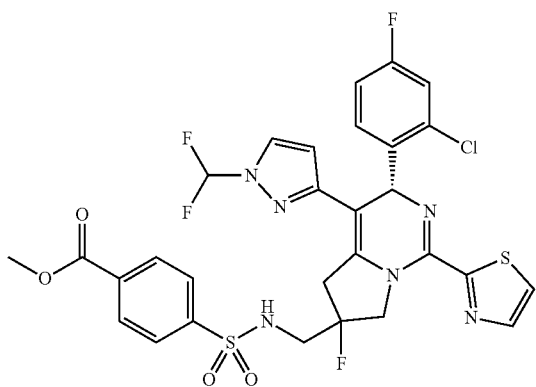 [SMILES: COC(=O)c1ccc(S(=O)(=O)NCC2(F)CC3=C(c4ccn(C(F)F)n4)[C@H](c4ccc(F)cc4Cl)N=C(c4nccs4)N3C2)cc1]

The title compound was prepared following the general procedure of Example 188. ESI MS m/z=695.20, 697.20 [M+H]⁺.

Example 192

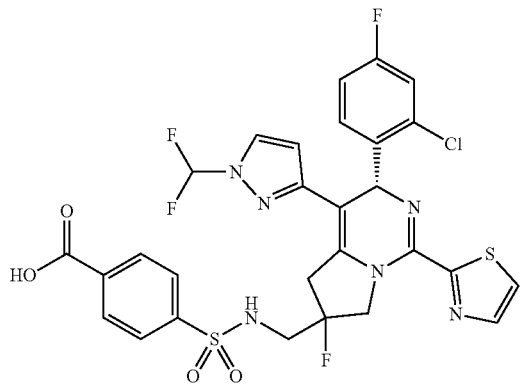 [SMILES: O=C(O)c1ccc(S(=O)(=O)NCC2(F)CC3=C(c4ccn(C(F)F)n4)[C@H](c4ccc(F)cc4Cl)N=C(c4nccs4)N3C2)cc1]

The title compound was prepared following the general procedure of Example 5. ESI MS m/z=681.15, 683.15 [M+H]⁺.

Example 193

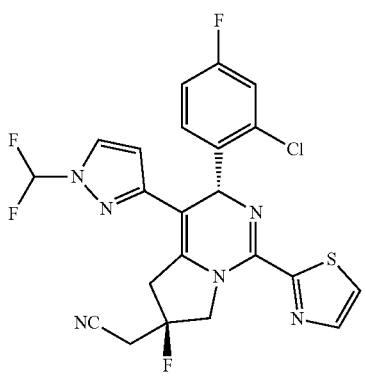 [SMILES: N#CC[C@]1(F)CC2=C(c3ccn(C(F)F)n3)[C@H](c3ccc(F)cc3Cl)N=C(c3nccs3)N2C1]

To a stirred mixture of the compound from Step 178a (250 mg, 0.50 mmol, 1 eq.), acetone cyanohydrin (106 mg, 1.25 mmol, 2.5 equiv) and PPh₃ (395 mg, 1.5 mmol, 3.0 equiv) in THF (5 mL) was added DEAD (218 mg, 1.25 mmol, 2.5 equiv) dropwise at 0° C. The resulting mixture was stirred for overnight at room temperature. The reaction mixture was diluted with water, and extracted with EA (20 mL*3). The combined organic layers were washed with brine, dried over Na₂SO₄, and concentrated under reduced pressure. The crude product was purified by Prep-HPLC to give the title compound (1.3 mg) as a yellow solid. ESI MS m/z=507.20, 509.20 [M+H]⁺.

Example 194

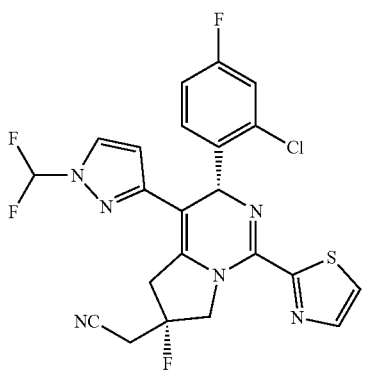 [SMILES: N#CC[C@@]1(F)CC2=C(c3ccn(C(F)F)n3)[C@H](c3ccc(F)cc3Cl)N=C(c3nccs3)N2C1]

The title compound was isolated from Example 193. ESI MS m/z=507.20, 509.20 [M+H]⁺.

Example 195

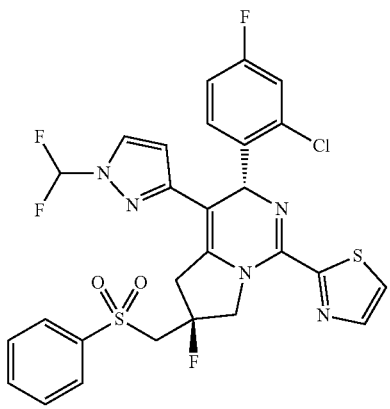 [SMILES: O=S(=O)(C[C@]1(F)CC2=C(c3ccn(C(F)F)n3)[C@H](c3ccc(F)cc3Cl)N=C(c3nccs3)N2C1)c1ccccc1]

Step 195a. To a stirred mixture of the compound from Step 178a (300 mg, 0.52 mmol) in DCM (5 mL) were added MsCl (69 mg, 0.61 mmol) and TEA (122 mg, 1.21 mmol) at 0° C. The resulting mixture was stirred for 1 hour at room temperature. The resulting mixture was diluted with water and extracted with EA (30 mL*3). The organic layer was washed with brine and dried over anhydrous $Na_2SO_4$. The resulting mixture was concentrated under vacuum and purified (silica gel, EtOAc/petroleum ether) to give the desired product (270 mg, 77.8%) as a yellow solid. ESI MS m/z=576.00, 578.00 $[M+H]^+$.

Step 195b. To a stirred mixture of the compound from Step 195a (270 mg, 0.47 mmol, 1 eq.) in DMF (2 mL) was added sodium benzenethiolate (310 mg, 2.35 mmol, 5 eq.) at 0° C. The resulting mixture was stirred at r.t. for 16 h. The resulting mixture was diluted with water and extracted with EA (30 mL×3). The resulting mixture was concentrated under vacuum and purified (silica gel, EtOAc/petroleum ether) to give the desired product (150 mg, 61.6%) as a yellow solid. ESI MS m/z=590.15, 592.15 $[M+H]^+$.

Step 195c. To a stirred mixture of the compound from Step 195b (120 mg, 0.20 mmol) in NMP (3 mL) was added m-CPBA (121 mg, 0.60 mmol, 3 eq., 85% purity) at 0° C. The resulting mixture was stirred for 2 h at 0° C. The resulting mixture was diluted with water and extracted with EtOAc (20 mL×3). The resulting mixture was concentrated under vacuum and purified by Pre-HPLC to give the title product afford the title compound (4.3 mg) as a yellow solid. ESI MS m/z=622.20, 624.20 $[M+H]^+$.

Example 196

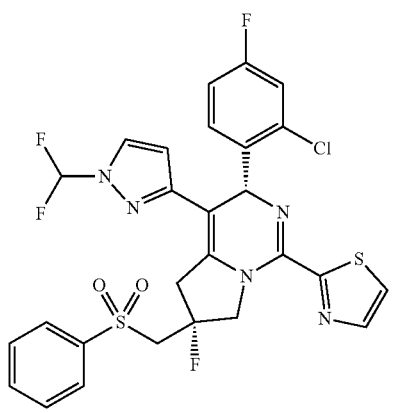 [SMILES: O=S(=O)(C[C@@]1(F)CC2=C(c3ccn(C(F)F)n3)[C@H](c3ccc(F)cc3Cl)N=C(c3nccs3)N2C1)c1ccccc1]

The title compound was isolated from Example 195. ESI MS m/z=622.20, 624.20 $[M+H]^+$.

Example 197

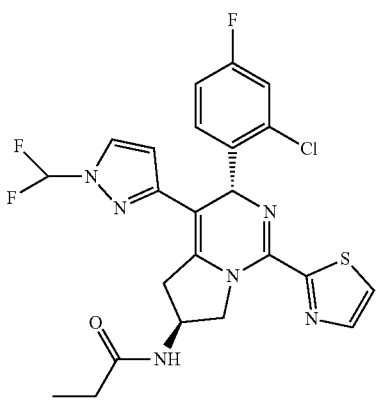 [SMILES: CCC(=O)N[C@H]1CC2=C(c3ccn(C(F)F)n3)[C@H](c3ccc(F)cc3Cl)N=C(c3nccs3)N2C1]

To a stirred mixture of Example 1 (20.00 mg, 0.038 mmol) in DCM were added TEA (11.6 mg, 0.115 mmol, 3.0 equiv) and propionyl chloride (10.6 mg, 0.115 mmol, 3 equiv) at 0° C. The resulting mixture was stirred for 1.5 h at 0° C. The resulting mixture was concentrated under reduced pressure. The crude product was purified by Prep-HPLC to afford the title compound (8.2 mg, 37%). ESI MS m/z=521.15, 523.15 $[M+H]^+$.

Example 198

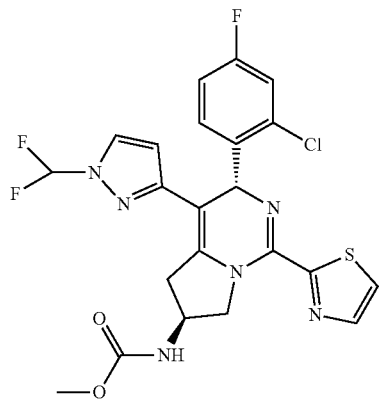 [SMILES: COC(=O)N[C@H]1CC2=C(c3ccn(C(F)F)n3)[C@H](c3ccc(F)cc3Cl)N=C(c3nccs3)N2C1]

The title compound was prepared following the general procedure of Example 197. ESI MS m/z=523.10, 524.10 [M+H]+.

Example 200

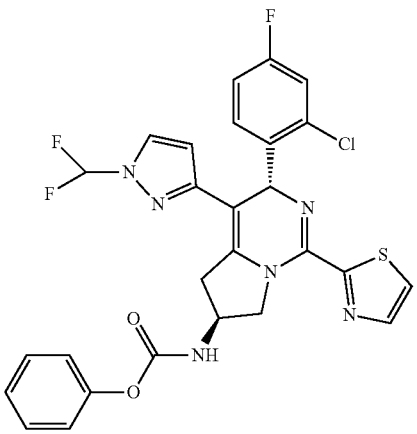

The title compound was prepared following the general procedure of Example 197. ESI MS m/z=585.20, 587.20 [M+H]+.

Example 199

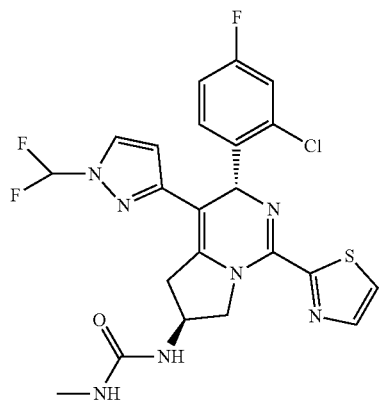 [SMILES: CNC(=O)N[C@H]1CC2=C(c3ccn(C(F)F)n3)[C@H](c3ccc(F)cc3Cl)N=C(c3nccs3)N2C1]

The title compound was prepared following the general procedure of Example 197. ESI MS m/z=522.20, 524.20 [M+H]+.

Example 201

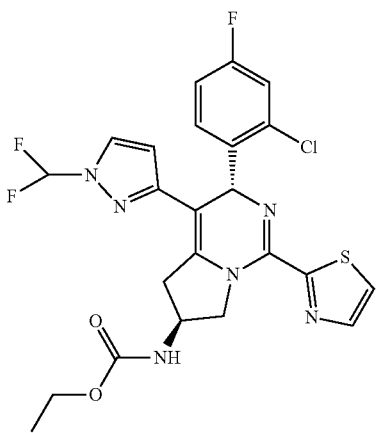 [SMILES: CCOC(=O)N[C@H]1CC2=C(c3ccn(C(F)F)n3)[C@H](c3ccc(F)cc3Cl)N=C(c3nccs3)N2C1]

The title compound was prepared following the general procedure of Example 197. ESI MS m/z=537.15, 539.15 [M+H]+.

Example 202

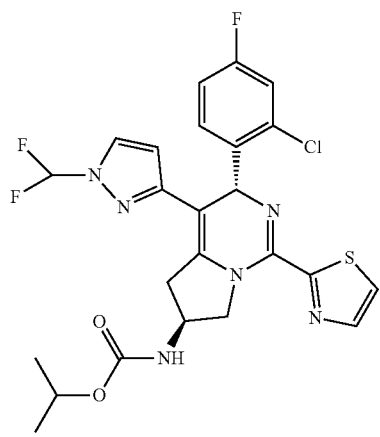 [SMILES: CC(C)OC(=O)N[C@H]1CC2=C(c3ccn(C(F)F)n3)[C@H](c3ccc(F)cc3Cl)N=C(c3nccs3)N2C1]

The title compound was prepared following the general procedure of Example 197. ESI MS m/z=551.15, 553.15 [M+H]+.

Example 204

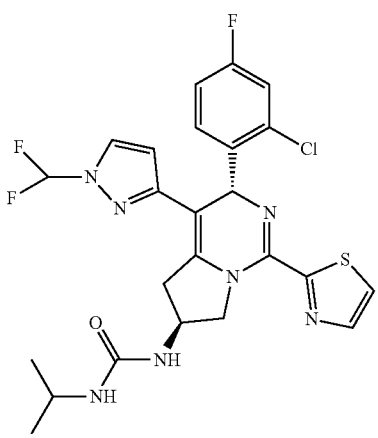

The title compound was prepared following the general procedure of Example 197. ESI MS m/z=550.20, 552.20 [M+H]+.

Example 203

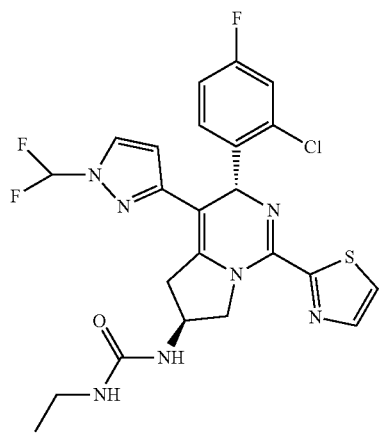 [SMILES: CCNC(=O)N[C@H]1CC2=C(c3ccn(C(F)F)n3)[C@H](c3ccc(F)cc3Cl)N=C(c3nccs3)N2C1]

The title compound was prepared following the general procedure of Example 197. ESI MS m/z=536.15, 538.15 [M+H]+.

Example 205

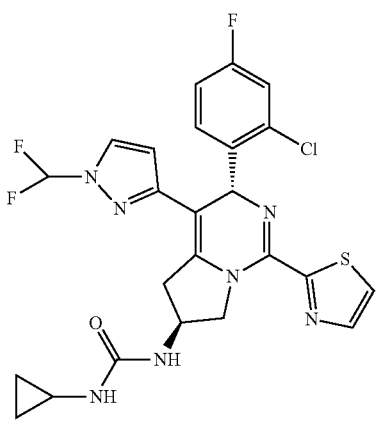 [SMILES: O=C(NC1CC1)N[C@H]1CC2=C(c3ccn(C(F)F)n3)[C@H](c3ccc(F)cc3Cl)N=C(c3nccs3)N2C1]

The title compound was prepared following the general procedure of Example 197. ESI MS m/z=548.20, 550.20 [M+H]+.

Example 206

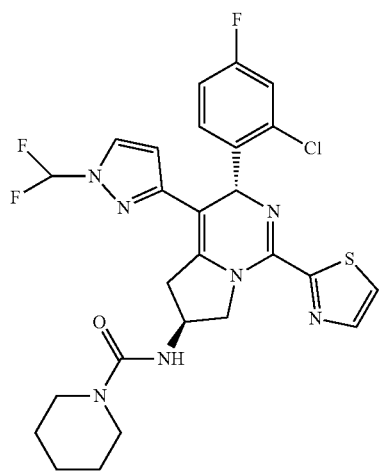 [SMILES: O=C(N[C@H]1CC2=C(c3ccn(C(F)F)n3)[C@H](c3ccc(F)cc3Cl)N=C(c3nccs3)N2C1)N1CCCCC1]

The title compound was prepared following the general procedure of Example 197. ESI MS m/z=576.25, 578.25 [M+H]+.

Example 208

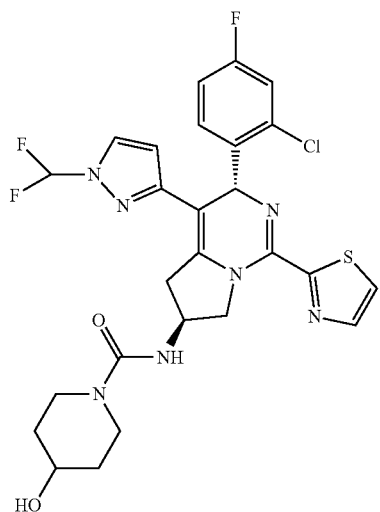

The title compound was prepared following the general procedure of Example 197. ESI MS m/z=592.25, 594.25 [M+H]+.

Example 207

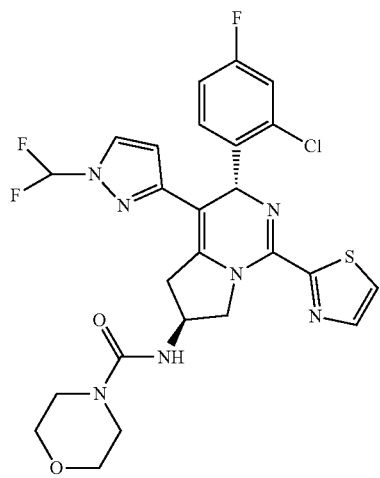 [SMILES: O=C(N[C@H]1CC2=C(c3ccn(C(F)F)n3)[C@H](c3ccc(F)cc3Cl)N=C(c3nccs3)N2C1)N1CCOCC1]

The title compound was prepared following the general procedure of Example 197. ESI MS m/z=578.25, 580.25 [M+H]+.

Example 209

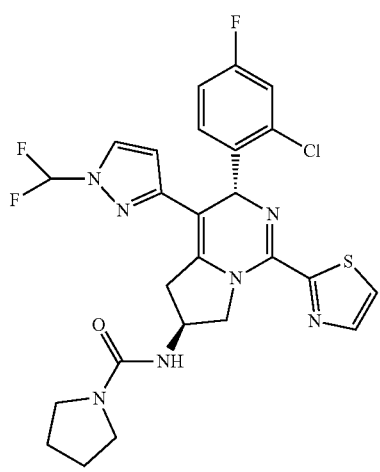 [SMILES: O=C(N[C@H]1CC2=C(c3ccn(C(F)F)n3)[C@H](c3ccc(F)cc3Cl)N=C(c3nccs3)N2C1)N1CCCC1]

The title compound was prepared following the general procedure of Example 197. ESI MS m/z=562.20, 564.20 [M+H]+.

Example 210

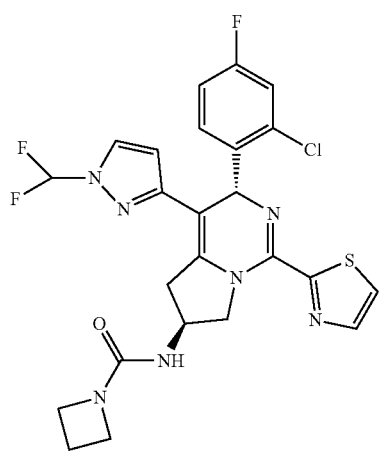 [SMILES: O=C(N[C@H]1CC2=C(c3ccn(C(F)F)n3)[C@H](c3ccc(F)cc3Cl)N=C(c3nccs3)N2C1)N1CCC1]

The title compound was prepared following the general procedure of Example 197. ESI MS m/z=548.20, 550.20 [M+H]+.

Example 211

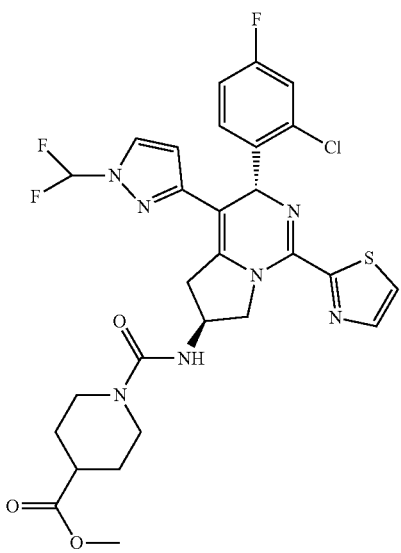 [SMILES: COC(=O)C1CCN(C(=O)N[C@H]2CC3=C(c4ccn(C(F)F)n4)[C@H](c4ccc(F)cc4Cl)N=C(c4nccs4)N3C2)CC1]

The title compound was prepared following the general procedure of Example 197. ESI MS m/z=634.25, 636.25 [M+H]+.

Example 212

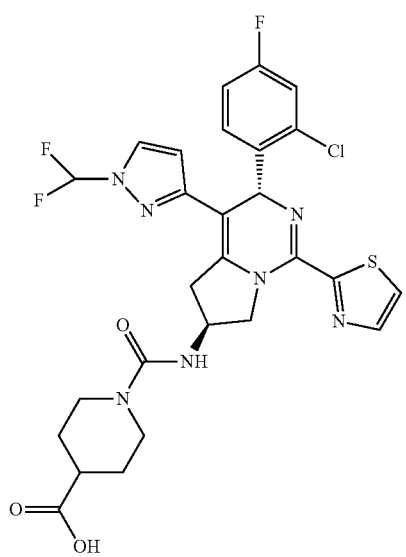 [SMILES: O=C(O)C1CCN(C(=O)N[C@H]2CC3=C(c4ccn(C(F)F)n4)[C@H](c4ccc(F)cc4Cl)N=C(c4nccs4)N3C2)CC1]

The title compound was prepared following the general procedure of Example 197. ESI MS m/z=620.10, 622.10 [M+H]+.

Example 213

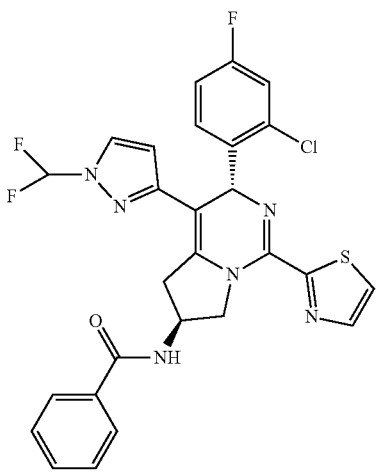 [SMILES: O=C(N[C@H]1CC2=C(c3ccn(C(F)F)n3)[C@H](c3ccc(F)cc3Cl)N=C(c3nccs3)N2C1)c1ccccc1]

The title compound was prepared following the general procedure of Example 197. ESI MS m/z=569.20, 571.20 [M+H]+.

Example 214

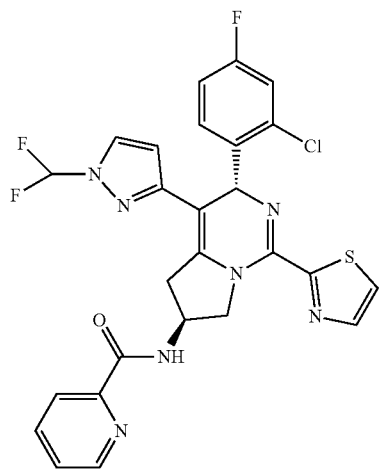 [SMILES: O=C(N[C@H]1CC2=C(c3ccn(C(F)F)n3)[C@H](c3ccc(F)cc3Cl)N=C(c3nccs3)N2C1)c1ccccn1]

The title compound was prepared following the general procedure of Example 197. ESI MS m/z=570.20, 572.20 [M+H]+.

Example 217

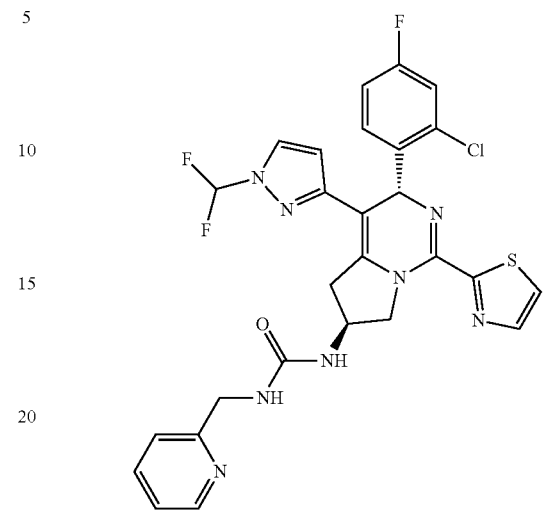

The title compound was prepared following the general procedure of Example 197. ESI MS m/z=599.10, 601.10 [M+H]+.

Example 216

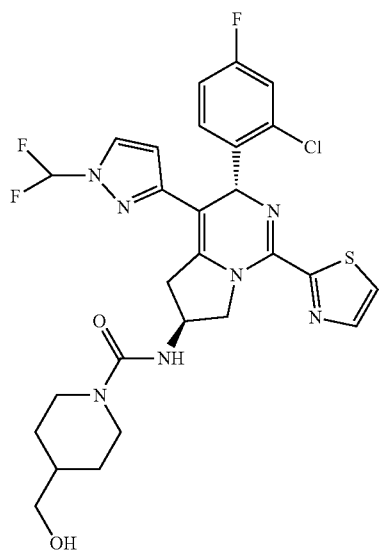 [SMILES: O=C(N[C@H]1CC2=C(c3ccn(C(F)F)n3)[C@H](c3ccc(F)cc3Cl)N=C(c3nccs3)N2C1)N1CCC(CO)CC1]

The title compound was prepared following the general procedure of Example 197. ESI MS m/z=606.25, 608.25 [M+H]+.

Example 218

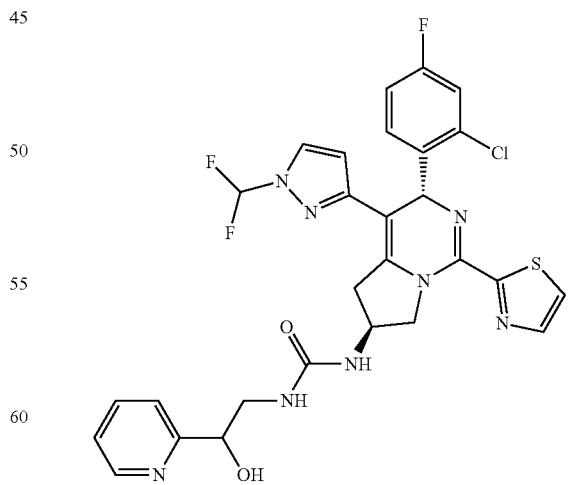

The title compound was prepared following the general procedure of Example 197. ESI MS m/z=629.10, 631.10 [M+H]+.

Example 219

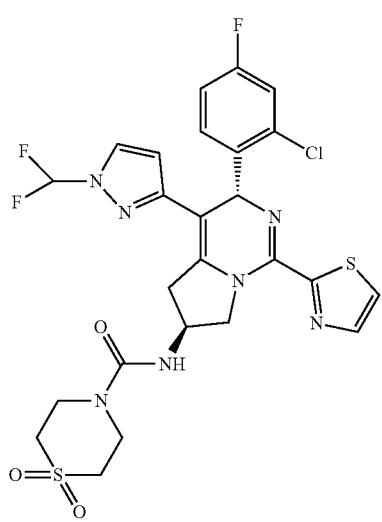 [SMILES: O=C(N[C@H]1CC2=C(c3ccn(C(F)F)n3)[C@H](c3ccc(F)cc3Cl)N=C(c3nccs3)N2C1)N1CCS(=O)(=O)CC1]

The title compound was prepared following the general procedure of Example 197. ESI MS m/z=626.00, 628.00 [M+H]⁺.

Example 220

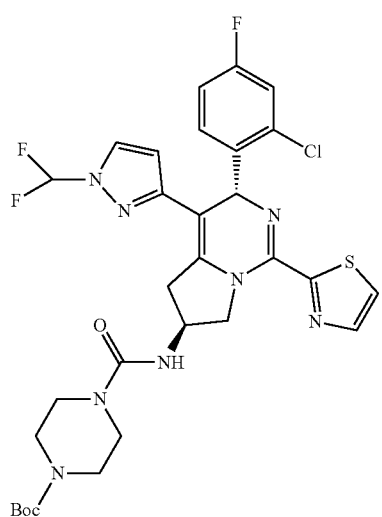

The title compound was prepared following the general procedure of Example 197. ESI MS m/z=677.25, 679.25 [M+H]⁺.

Example 221

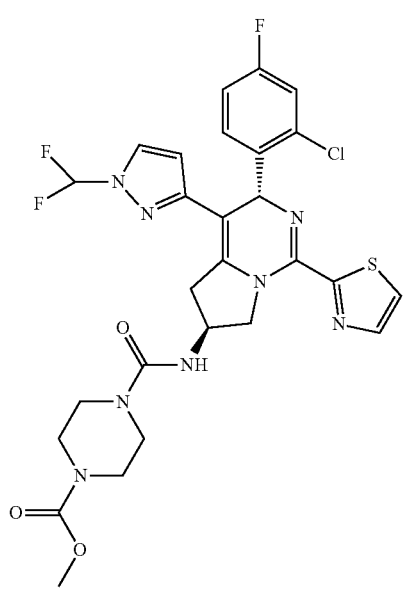 [SMILES: COC(=O)N1CCN(C(=O)N[C@H]2CC3=C(c4ccn(C(F)F)n4)[C@H](c4ccc(F)cc4Cl)N=C(c4nccs4)N3C2)CC1]

The title compound was prepared following the general procedure of Example 197. ESI MS m/z=635.05, 637.05 [M+H]⁺.

Example 222

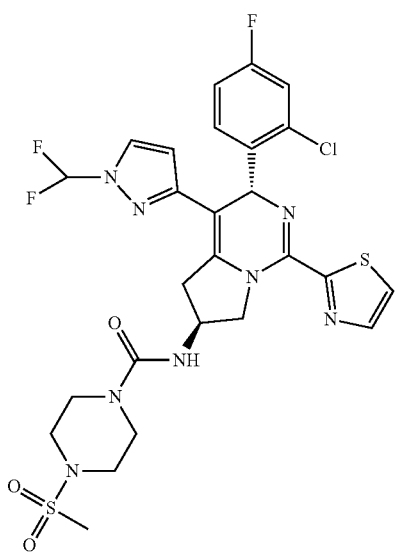 [SMILES: CS(=O)(=O)N1CCN(C(=O)N[C@H]2CC3=C(c4ccn(C(F)F)n4)[C@H](c4ccc(F)cc4Cl)N=C(c4nccs4)N3C2)CC1]

The title compound was prepared following the general procedure of Example 197. ESI MS m/z=655.05, 657.05 [M+H]⁺.

Example 223

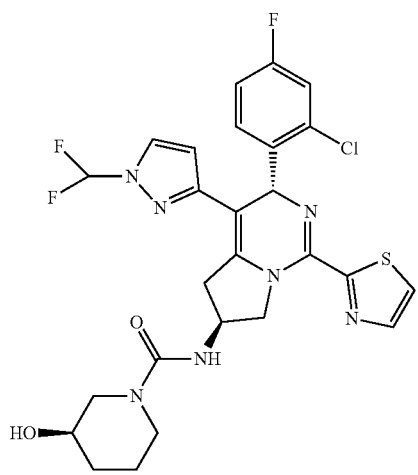 [SMILES: O=C(N[C@H]1CC2=C(c3ccn(C(F)F)n3)[C@H](c3ccc(F)cc3Cl)N=C(c3nccs3)N2C1)N1CCC[C@@H](O)C1]

The title compound was prepared following the general procedure of Example 197. ESI MS m/z=592.15, 594.15 [M+H]⁺.

Example 224

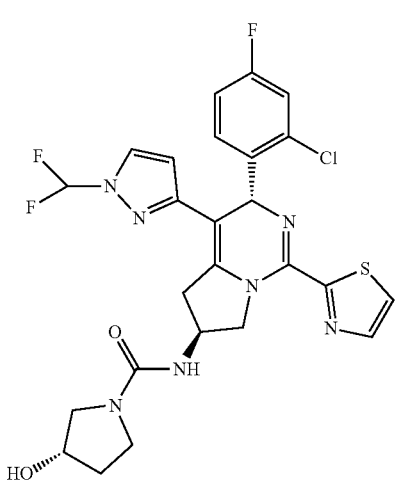 [SMILES: O=C(N[C@H]1CC2=C(c3ccn(C(F)F)n3)[C@H](c3ccc(F)cc3Cl)N=C(c3nccs3)N2C1)N1CC[C@H](O)C1]

The title compound was prepared following the general procedure of Example 197. ESI MS m/z=578.10, 580.10 [M+H]⁺.

Example 225

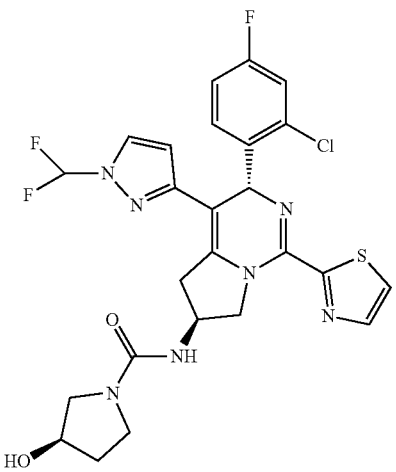 [SMILES: O=C(N[C@H]1CC2=C(c3ccn(C(F)F)n3)[C@H](c3ccc(F)cc3Cl)N=C(c3nccs3)N2C1)N1CC[C@@H](O)C1]

The title compound was prepared following the general procedure of Example 197. ESI MS m/z=578.15, 580.15 [M+H]⁺.

Example 226

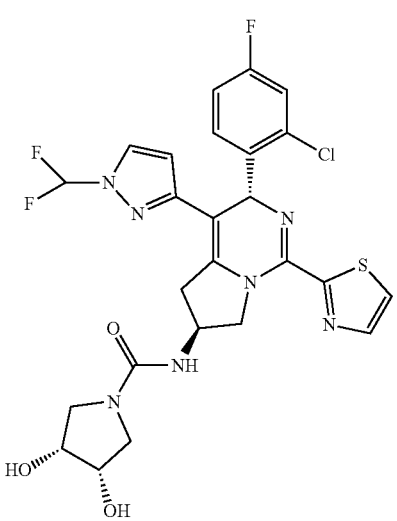 [SMILES: O=C(N[C@H]1CC2=C(c3ccn(C(F)F)n3)[C@H](c3ccc(F)cc3Cl)N=C(c3nccs3)N2C1)N1C[C@@H](O)[C@@H](O)C1]

The title compound was prepared following the general procedure of Example 197. ESI MS m/z=594.15, 596.15 [M+H]⁺.

Example 227

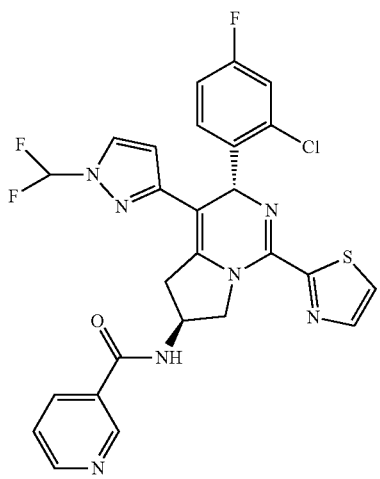 [SMILES: O=C(N[C@H]1CC2=C(c3ccn(C(F)F)n3)[C@H](c3ccc(F)cc3Cl)N=C(c3nccs3)N2C1)c1cccnc1]

The title compound was prepared following the general procedure of Example 197. ESI MS m/z=570.05, 572.05 [M+H]⁺.

Example 228

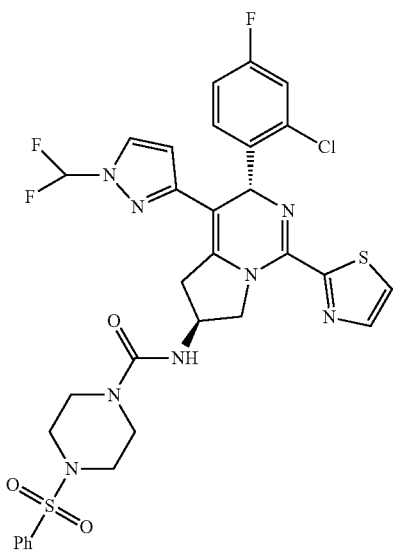 [SMILES: O=C(N[C@H]1CC2=C(c3ccn(C(F)F)n3)[C@H](c3ccc(F)cc3Cl)N=C(c3nccs3)N2C1)N1CCN(S(=O)(=O)c2ccccc2)CC1]

The title compound was prepared following the general procedure of Example 197. ESI MS m/z=717.20, 719.20 [M+H]⁺.

Example 229

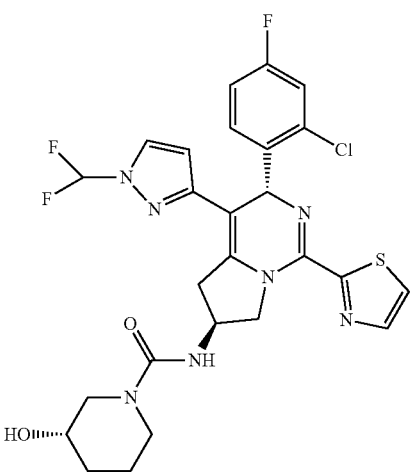 [SMILES: O=C(N[C@H]1CC2=C(c3ccn(C(F)F)n3)[C@H](c3ccc(F)cc3Cl)N=C(c3nccs3)N2C1)N1CCC[C@H](O)C1]

The title compound was prepared following the general procedure of Example 197. ESI MS m/z=592.10, 594.10 [M+H]⁺.

Example 230

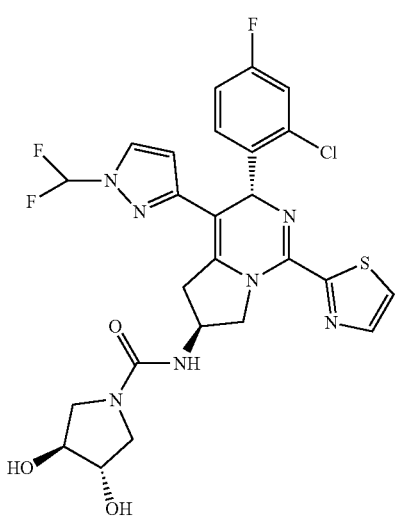 [SMILES: O=C(N[C@H]1CC2=C(c3ccn(C(F)F)n3)[C@H](c3ccc(F)cc3Cl)N=C(c3nccs3)N2C1)N1C[C@H](O)[C@@H](O)C1]

The title compound was prepared following the general procedure of Example 197. ESI MS m/z=594.15, 596.15 [M+H]⁺.

Example 231

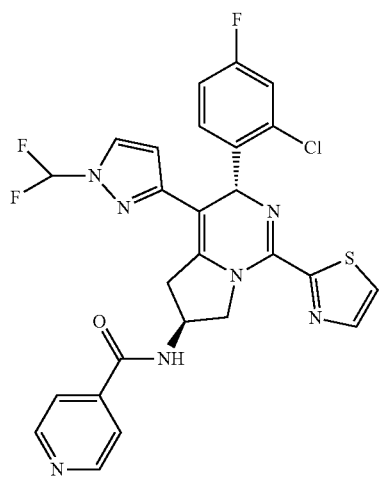 [SMILES: O=C(N[C@H]1CC2=C(c3ccn(C(F)F)n3)[C@H](c3ccc(F)cc3Cl)N=C(c3nccs3)N2C1)c1ccncc1]

The title compound was prepared following the general procedure of Example 197. ESI MS m/z=570.10, 572.10 [M+H]+.

Example 233

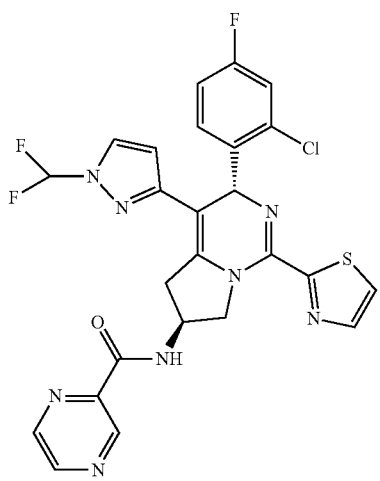

The title compound was prepared following the general procedure of Example 197. ESI MS m/z=571.10, 573.10 [M+H]+.

Example 232

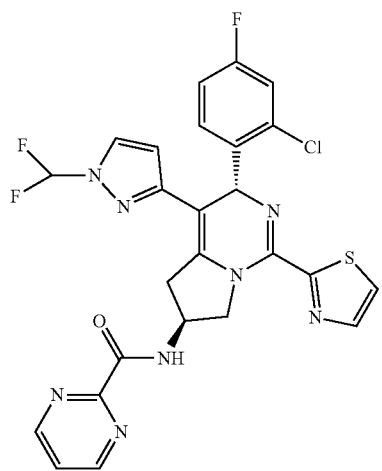 [SMILES: O=C(N[C@H]1CC2=C(c3ccn(C(F)F)n3)[C@H](c3ccc(F)cc3Cl)N=C(c3nccs3)N2C1)c1ncccn1]

The title compound was prepared following the general procedure of Example 197. ESI MS m/z=571.00, 573.00 [M+H]+.

Example 234

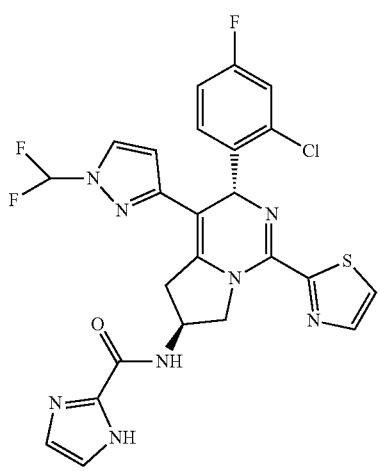 [SMILES: O=C(N[C@H]1CC2=C(c3ccn(C(F)F)n3)[C@H](c3ccc(F)cc3Cl)N=C(c3nccs3)N2C1)c1ncc[nH]1]

The title compound was prepared following the general procedure of Example 197. ESI MS m/z=559.05, 561.05 [M+H]+.

Example 235

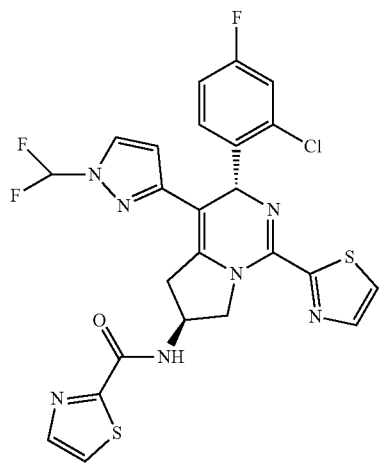 [SMILES: O=C(N[C@H]1CC2=C(c3ccn(C(F)F)n3)[C@H](c3ccc(F)cc3Cl)N=C(c3nccs3)N2C1)c1nccs1]

The title compound was prepared following the general procedure of Example 197. ESI MS m/z=576.00, 578.00 [M+H]$^+$.

Example 236

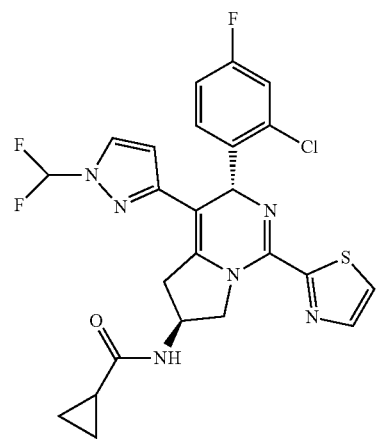 [SMILES: O=C(N[C@H]1CC2=C(c3ccn(C(F)F)n3)[C@H](c3ccc(F)cc3Cl)N=C(c3nccs3)N2C1)C1CC1]

The title compound was prepared following the general procedure of Example 197. ESI MS m/z=533.05, 535.05 [M+H]$^+$.

Example 237

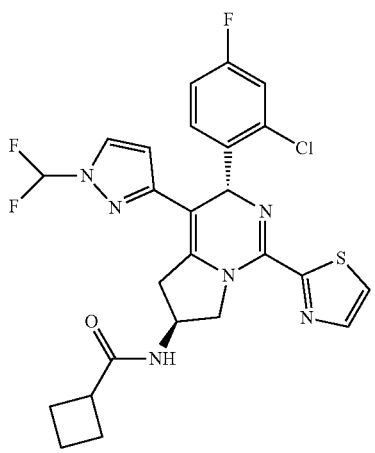 [SMILES: O=C(N[C@H]1CC2=C(c3ccn(C(F)F)n3)[C@H](c3ccc(F)cc3Cl)N=C(c3nccs3)N2C1)C1CCC1]

The title compound was prepared following the general procedure of Example 197. ESI MS m/z=547.05, 549.05 [M+H]$^+$.

Example 238

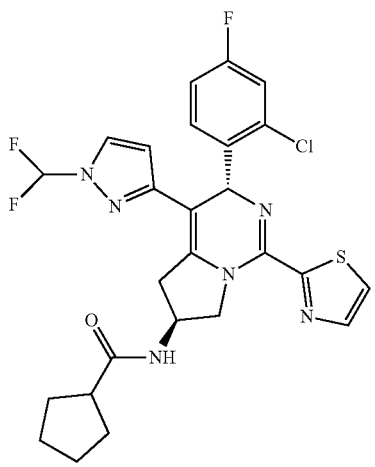 [SMILES: O=C(N[C@H]1CC2=C(c3ccn(C(F)F)n3)[C@H](c3ccc(F)cc3Cl)N=C(c3nccs3)N2C1)C1CCCC1]

The title compound was prepared following the general procedure of Example 197. ESI MS m/z=561.05, 563.05 [M+H]$^+$.

Example 239

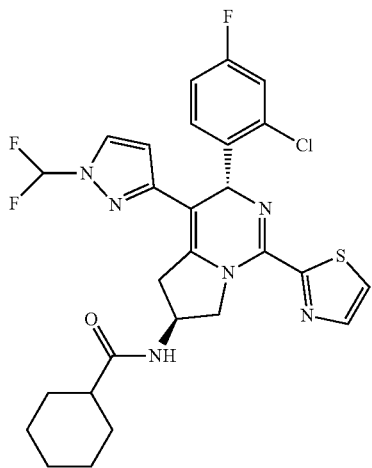 [SMILES: O=C(N[C@H]1CC2=C(c3ccn(C(F)F)n3)[C@H](c3ccc(F)cc3Cl)N=C(c3nccs3)N2C1)C1CCCCC1]

The title compound was prepared following the general procedure of Example 197. ESI MS m/z=575.10, 577.10 [M+H]+.

Example 240

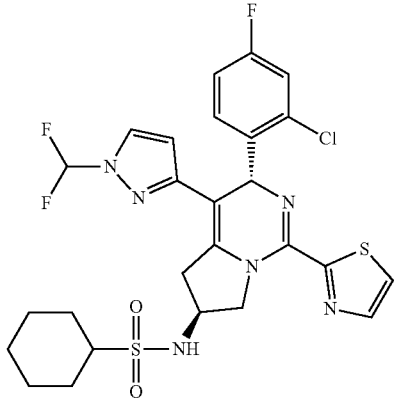 [SMILES: O=S(=O)(N[C@H]1CC2=C(c3ccn(C(F)F)n3)[C@H](c3ccc(F)cc3Cl)N=C(c3nccs3)N2C1)C1CCCCC1]

The title compound was prepared following the general procedure of Example 2. ESI MS m/z=611.11, 613.11 [M+H]+.

Example 241

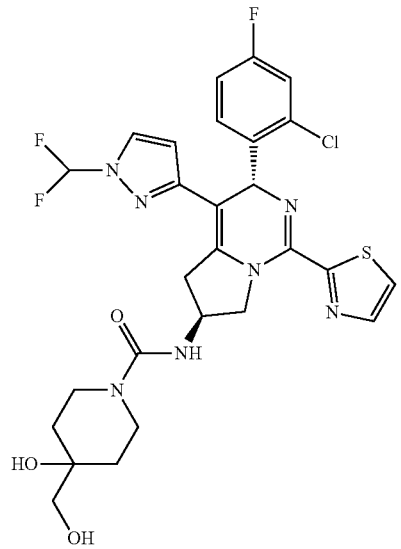 [SMILES: O=C(N[C@H]1CC2=C(c3ccn(C(F)F)n3)[C@H](c3ccc(F)cc3Cl)N=C(c3nccs3)N2C1)N1CCC(O)(CO)CC1]

The title compound was prepared following the general procedure of Example 197. ESI MS m/z=622.10, 624.10 [M+H]+.

Example 242

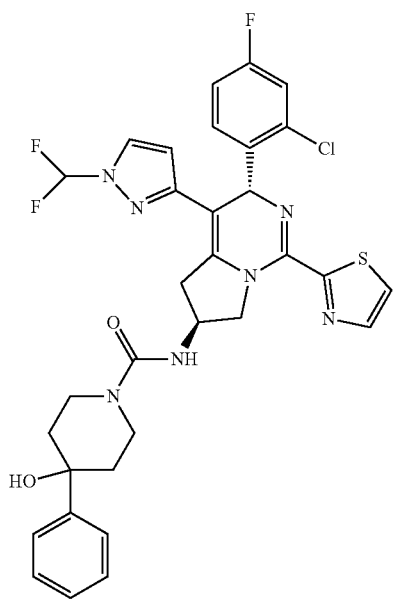 [SMILES: O=C(N[C@H]1CC2=C(c3ccn(C(F)F)n3)[C@H](c3ccc(F)cc3Cl)N=C(c3nccs3)N2C1)N1CCC(O)(c2ccccc2)CC1]

The title compound was prepared following the general procedure of Example 197. ESI MS m/z=668.10, 670.10 [M+H]+.

Example 243

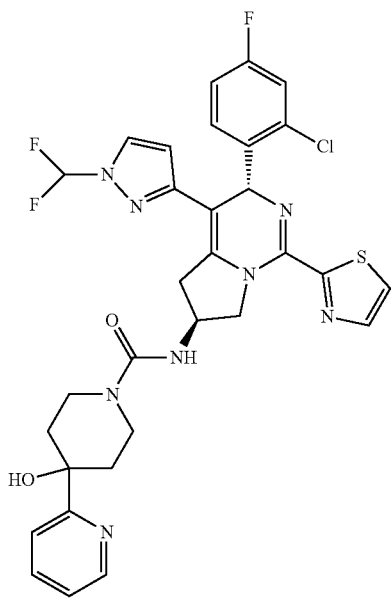 [SMILES: O=C(N[C@H]1CC2=C(c3ccn(C(F)F)n3)[C@H](c3ccc(F)cc3Cl)N=C(c3nccs3)N2C1)N1CCC(O)(c2ccccn2)CC1]

The title compound was prepared following the general procedure of Example 197. ESI MS m/z=669.05, 671.05 [M+H]+.

Example 244

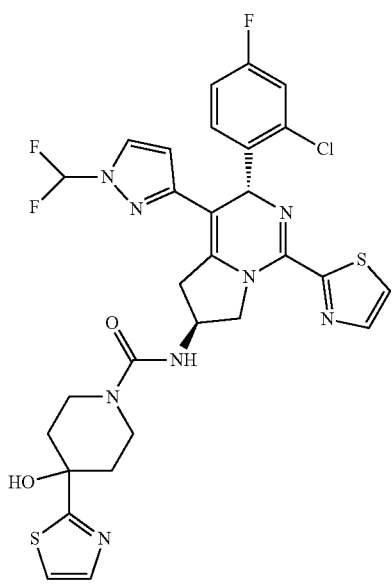

The title compound was prepared following the general procedure of Example 197. ESI MS m/z=675.05, 677.05 [M+H]+.

Example 245

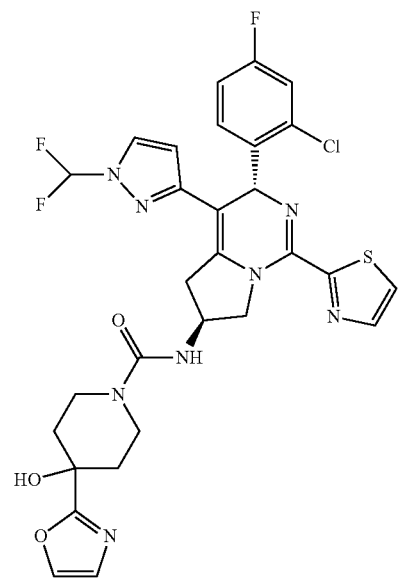 [SMILES: O=C(N[C@H]1CC2=C(c3ccn(C(F)F)n3)[C@H](c3ccc(F)cc3Cl)N=C(c3nccs3)N2C1)N1CCC(O)(c2ncco2)CC1]

The title compound was prepared following the general procedure of Example 197. ESI MS m/z=659.15, 661.15 [M+H]+.

Example 246

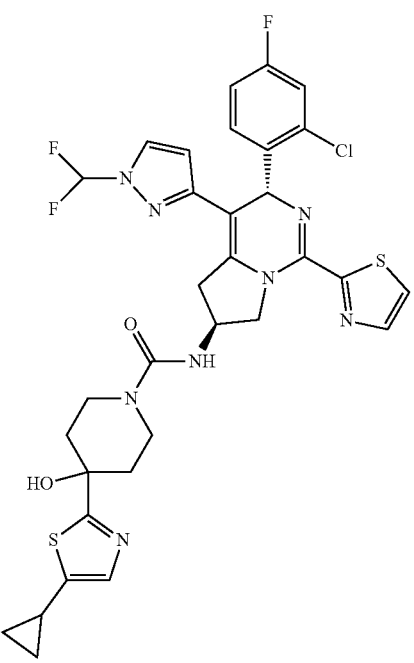 [SMILES: O=C(N[C@H]1CC2=C(c3ccn(C(F)F)n3)[C@H](c3ccc(F)cc3Cl)N=C(c3nccs3)N2C1)N1CCC(O)(c2ncc(C3CC3)s2)CC1]

The title compound was prepared following the general procedure of Example 197. ESI MS m/z=715.10, 717.10 [M+H]+.

Example 247

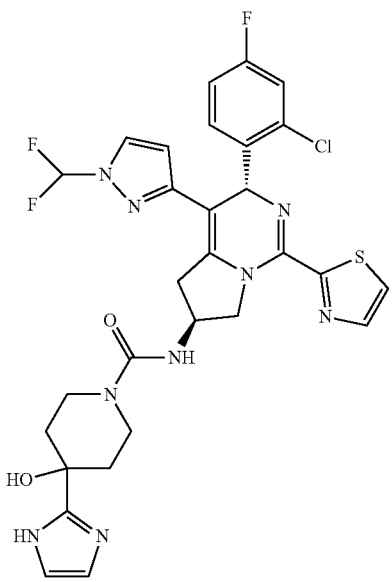

The title compound was prepared following the general procedure of Example 197. ESI MS m/z=658.15, 660.15 [M+H]⁺.

Example 249

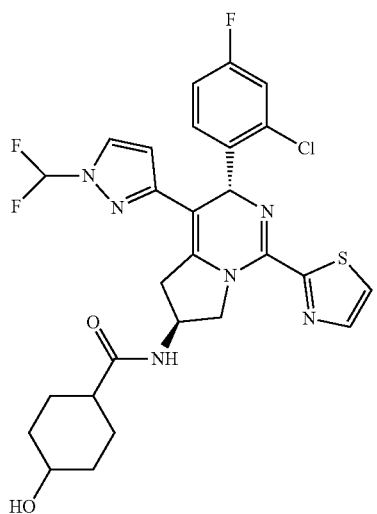

The title compound was prepared following the general procedure of Example 197. ESI MS m/z=591.20, 593.20 [M+H]⁺.

Example 248

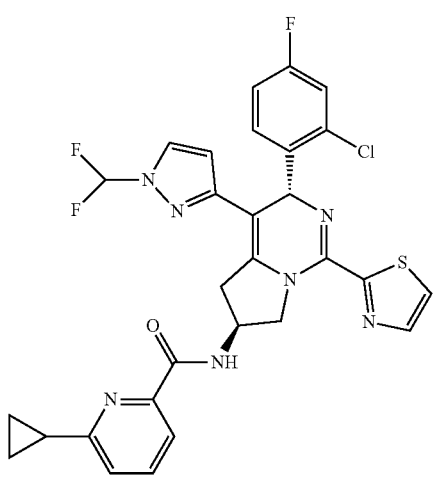 [SMILES: O=C(N[C@H]1CC2=C(c3ccn(C(F)F)n3)[C@H](c3ccc(F)cc3Cl)N=C(c3nccs3)N2C1)c1cccc(C2CC2)n1]

The title compound was prepared following the general procedure of Example 197. ESI MS m/z=610.15, 612.15 [M+H]⁺.

Example 250

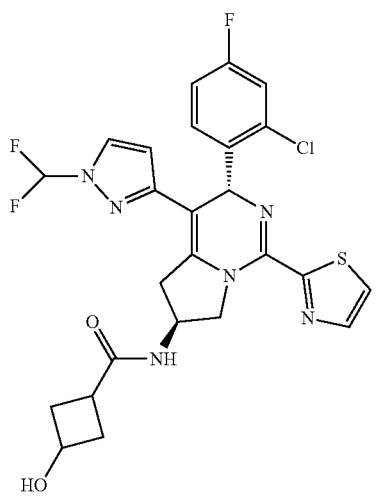 [SMILES: O=C(N[C@H]1CC2=C(c3ccn(C(F)F)n3)[C@H](c3ccc(F)cc3Cl)N=C(c3nccs3)N2C1)C1CC(O)C1]

The title compound was prepared following the general procedure of Example 197. ESI MS m/z=563.20, 565.20 [M+H]⁺.

Example 251

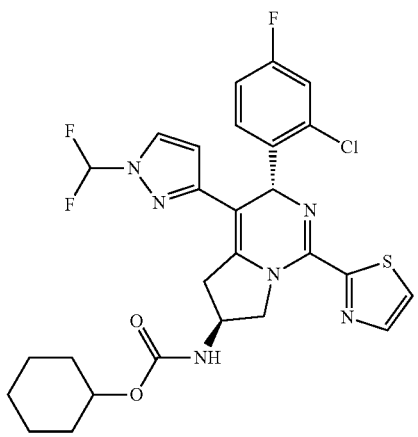 [SMILES: O=C(N[C@H]1CC2=C(c3ccn(C(F)F)n3)[C@H](c3ccc(F)cc3Cl)N=C(c3nccs3)N2C1)OC1CCCCC1]

The title compound was prepared following the general procedure of Example 197. ESI MS m/z=591.15, 593.15 [M+H]+.

Example 253

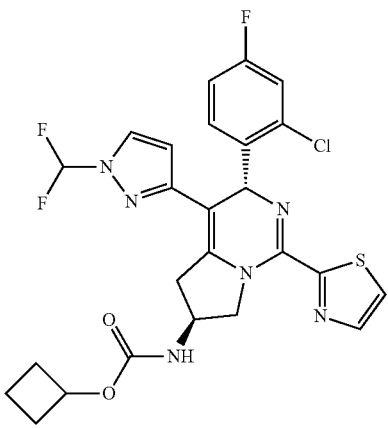

The title compound was prepared following the general procedure of Example 197. ESI MS m/z=563.15, 565.15 [M+H]+.

Example 252

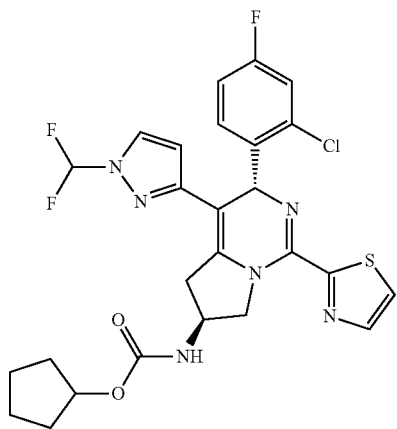 [SMILES: O=C(N[C@H]1CC2=C(c3ccn(C(F)F)n3)[C@H](c3ccc(F)cc3Cl)N=C(c3nccs3)N2C1)OC1CCCC1]

The title compound was prepared following the general procedure of Example 197. ESI MS m/z=577.15, 579.15 [M+H]+.

Example 254

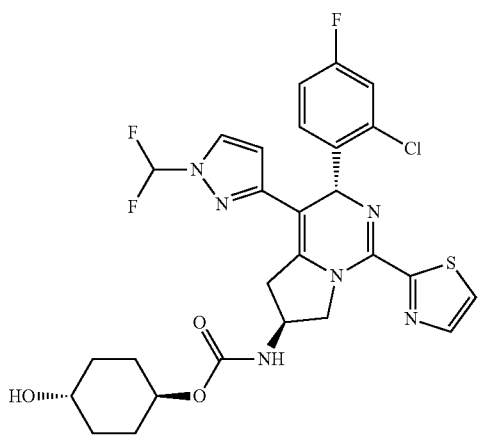 [SMILES: O=C(N[C@H]1CC2=C(c3ccn(C(F)F)n3)[C@H](c3ccc(F)cc3Cl)N=C(c3nccs3)N2C1)O[C@H]1CC[C@H](O)CC1]

The title compound was prepared following the general procedure of Example 197. ESI MS m/z=607.30, 609.17 [M+H]+.

Example 255

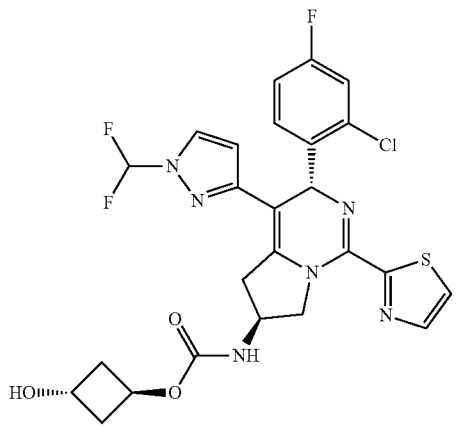 [SMILES: O=C(N[C@H]1CC2=C(c3ccn(C(F)F)n3)[C@H](c3ccc(F)cc3Cl)N=C(c3nccs3)N2C1)O[C@H]1C[C@H](O)C1]

The title compound was prepared following the general procedure of Example 197. ESI MS m/z=579.10, 581.10 [M+H]+.

Example 256

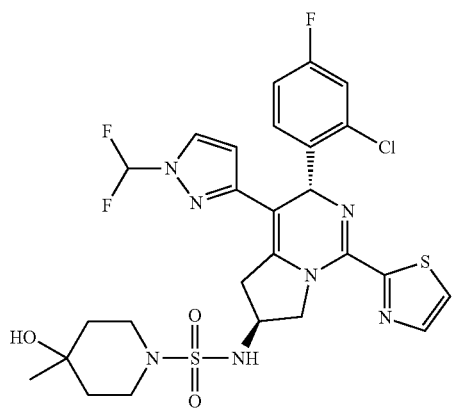 [SMILES: CC1(O)CCN(S(=O)(=O)N[C@H]2CC3=C(c4ccn(C(F)F)n4)[C@H](c4ccc(F)cc4Cl)N=C(c4nccs4)N3C2)CC1]

The title compound was prepared following the general procedure of Example 73. ESI MS m/z=642.00, 644.00 [M+H]+.

Example 257

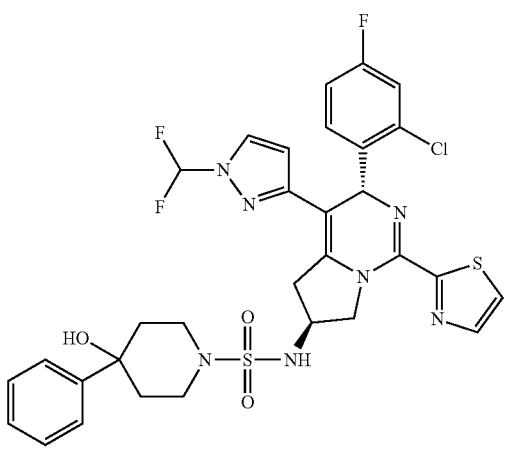 [SMILES: O=S(=O)(N[C@H]1CC2=C(c3ccn(C(F)F)n3)[C@H](c3ccc(F)cc3Cl)N=C(c3nccs3)N2C1)N1CCC(O)(c2ccccc2)CC1]

The title compound was prepared following the general procedure of Example 73. ESI MS m/z=704.05, 706.05 [M+H]+.

Example 258

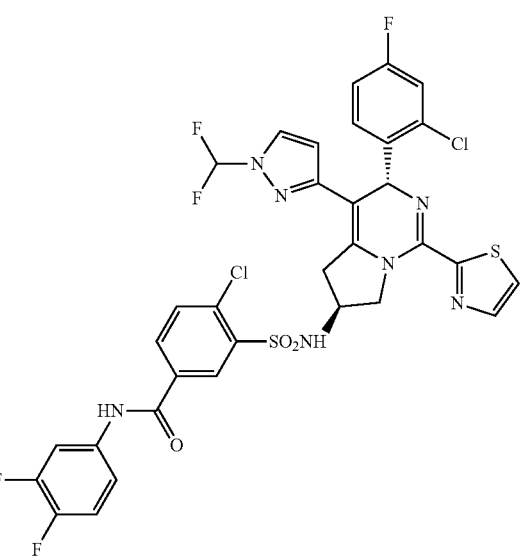

The title compound was prepared following the general procedure of Example 2. ESI MS m/z=794.03, 796.03 [M+H]+.

Example 259

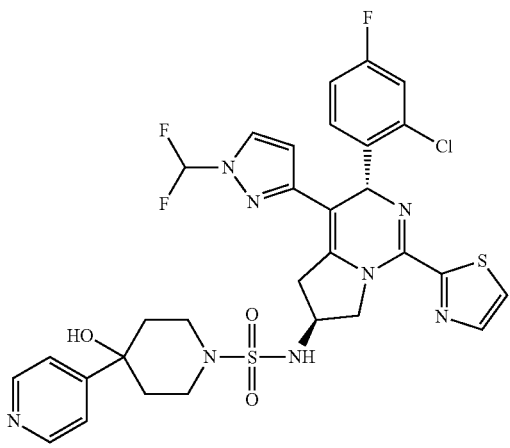 [SMILES: O=S(=O)(N[C@H]1CC2=C(c3ccn(C(F)F)n3)[C@H](c3ccc(F)cc3Cl)N=C(c3nccs3)N2C1)N1CCC(O)(c2ccncc2)CC1]

The title compound was prepared following the general procedure of Example 73. ESI MS m/z=705.05, 707.05 [M+H]$^+$.

Example 260

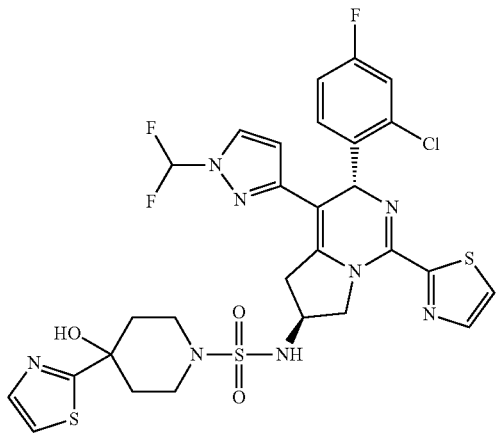

The title compound was prepared following the general procedure of Example 73. ESI MS m/z=710.95, 712.95 [M+H]$^+$.

Example 261

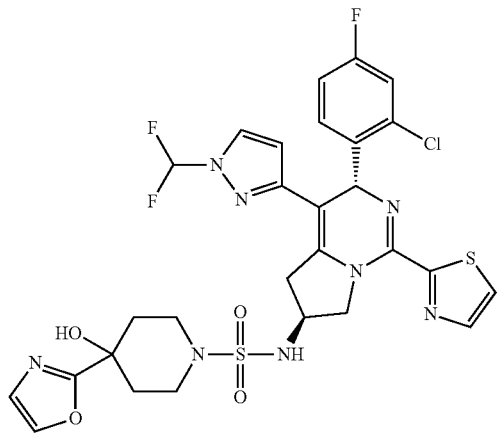 [SMILES: O=S(=O)(N[C@H]1CC2=C(c3ccn(C(F)F)n3)[C@H](c3ccc(F)cc3Cl)N=C(c3nccs3)N2C1)N1CCC(O)(c2nccs2)CC1]

The title compound was prepared following the general procedure of Example 73. ESI MS m/z=695.00, 697.00 [M+H]$^+$.

Example 262

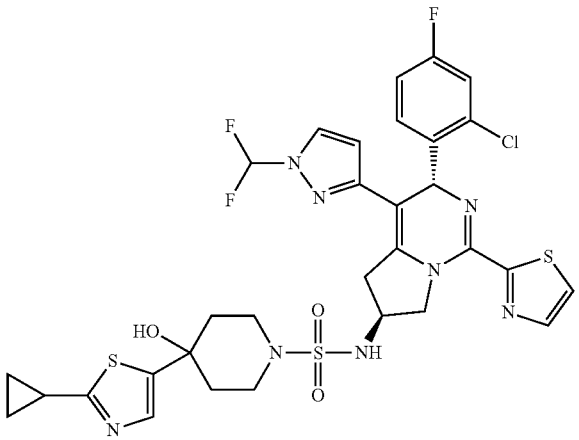 [SMILES: O=S(=O)(N[C@H]1CC2=C(c3ccn(C(F)F)n3)[C@H](c3ccc(F)cc3Cl)N=C(c3nccs3)N2C1)N1CCC(O)(c2cnc(C3CC3)s2)CC1]

The title compound was prepared following the general procedure of Example 73. ESI MS m/z=751.10, 753.10 [M+H]$^+$.

Example 263

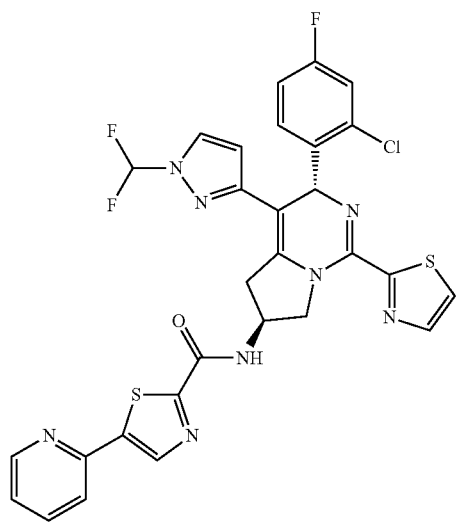 [SMILES: O=C(N[C@H]1CC2=C(c3ccn(C(F)F)n3)[C@H](c3ccc(F)cc3Cl)N=C(c3nccs3)N2C1)c1ncc(-c2ccccn2)s1]

The title compound was prepared following the general procedure of Example 197. ESI MS m/z=653.00, 655.00 [M+H]+.

Example 265

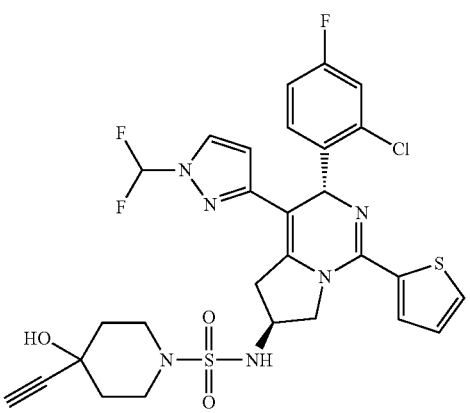

The title compound was prepared following the general procedure of Example 73. ESI MS m/z=652.05, 654.05 [M+H]+.

Example 264

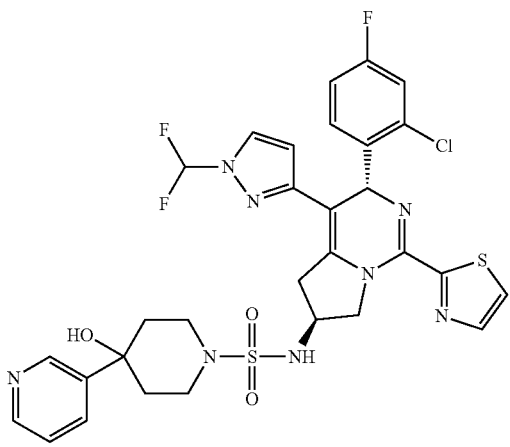 [SMILES: O=S(=O)(N[C@H]1CC2=C(c3ccn(C(F)F)n3)[C@H](c3ccc(F)cc3Cl)N=C(c3nccs3)N2C1)N1CCC(O)(c2cccnc2)CC1]

The title compound was prepared following the general procedure of Example 73. ESI MS m/z=705.10, 707.10 [M+H]+.

Example 266

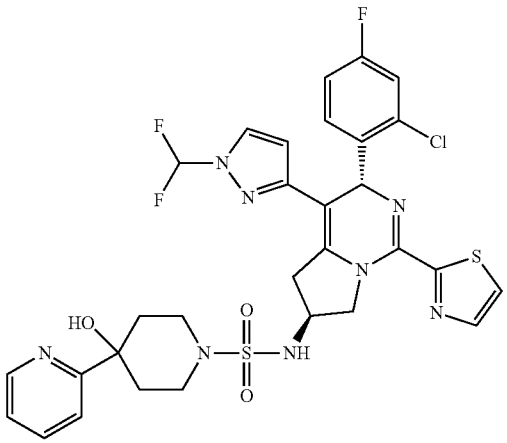 [SMILES: O=S(=O)(N[C@H]1CC2=C(c3ccn(C(F)F)n3)[C@H](c3ccc(F)cc3Cl)N=C(c3nccs3)N2C1)N1CCC(O)(c2ccccn2)CC1]

The title compound was prepared following the general procedure of Example 73. ESI MS m/z=705.05, 707.05 [M+H]+.

Example 267

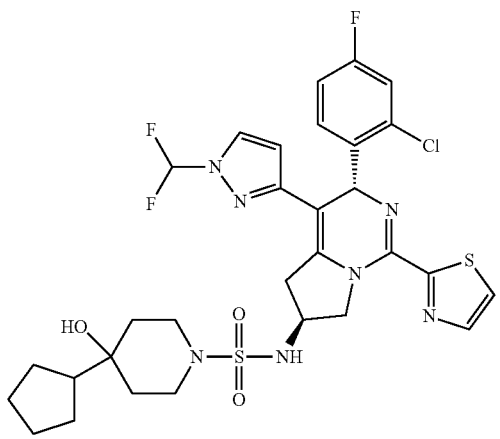 [SMILES: O=S(=O)(N[C@H]1CC2=C(c3ccn(C(F)F)n3)[C@H](c3ccc(F)cc3Cl)N=C(c3nccs3)N2C1)N1CCC(O)(C2CCCC2)CC1]

The title compound was prepared following the general procedure of Example 73. ESI MS m/z=696.05, 698.05 [M+H]+.

Example 269

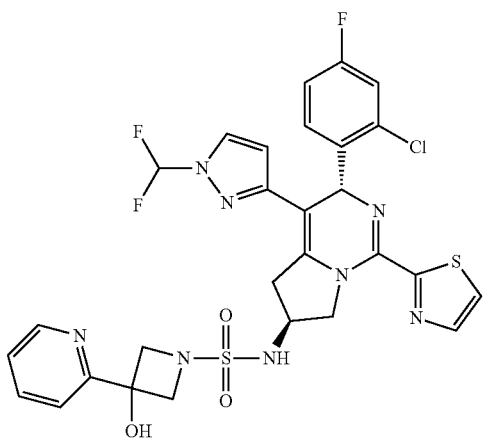

The title compound was prepared following the general procedure of Example 73. ESI MS m/z=677.29.679.15 [M+H]+.

Example 268

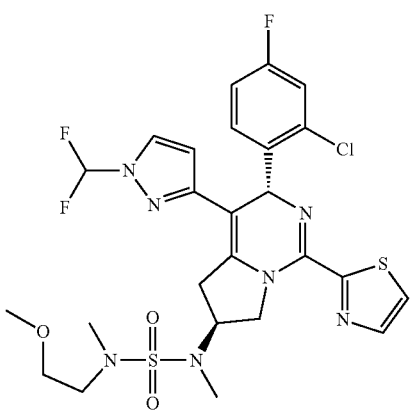 [SMILES: COCCN(C)S(=O)(=O)N(C)[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=630.32, 632.19 [M+H]+.

Example 270

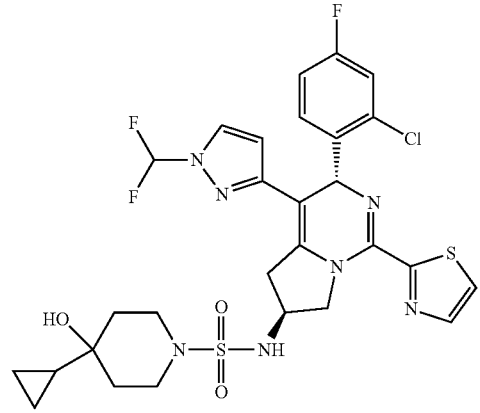 [SMILES: O=S(=O)(N[C@H]1CC2=C(c3ccn(C(F)F)n3)[C@H](c3ccc(F)cc3Cl)N=C(c3nccs3)N2C1)N1CCC(O)(C2CC2)CC1]

The title compound was prepared following the general procedure of Example 73. ESI MS m/z=668.20, 670.20 [M+H]+.

Example 271

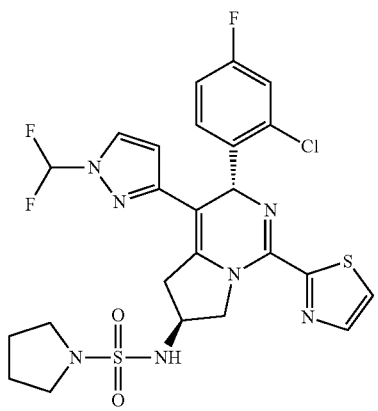 [SMILES: O=S(=O)(N[C@H]1CC2=C(c3ccn(C(F)F)n3)[C@H](c3ccc(F)cc3Cl)N=C(c3nccs3)N2C1)N1CCCC1]

The title compound was prepared following the general procedure of Example 73. ESI MS m/z=598.10, 600.10 [M+H]+.

Example 272

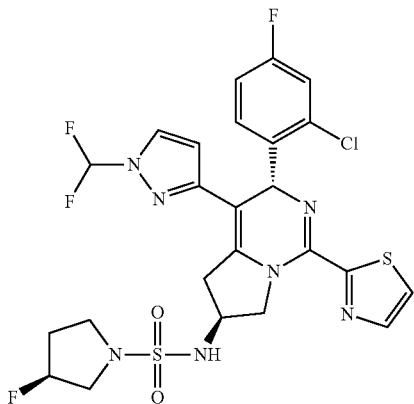 [SMILES: O=S(=O)(N[C@H]1CC2=C(c3ccn(C(F)F)n3)[C@H](c3ccc(F)cc3Cl)N=C(c3nccs3)N2C1)N1CC[C@H](F)C1]

The title compound was prepared following the general procedure of Example 73. ESI MS m/z=616.05, 618.05 [M+H]+.

Example 273

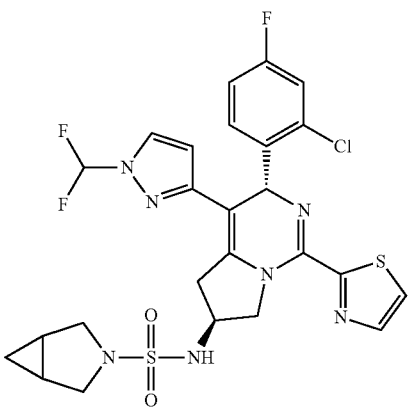 [SMILES: O=S(=O)(N[C@H]1CC2=C(c3ccn(C(F)F)n3)[C@H](c3ccc(F)cc3Cl)N=C(c3nccs3)N2C1)N1CC2CC2C1]

The title compound was prepared following the general procedure of Example 73. ESI MS m/z=610.10, 612.10 [M+H]+.

Example 274

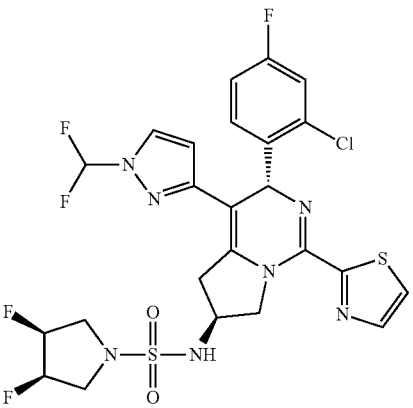 [SMILES: O=S(=O)(N[C@H]1CC2=C(c3ccn(C(F)F)n3)[C@H](c3ccc(F)cc3Cl)N=C(c3nccs3)N2C1)N1C[C@@H](F)[C@@H](F)C1]

The title compound was prepared following the general procedure of Example 73. ESI MS m/z=634.10, 636.10 [M+H]+.

Example 275

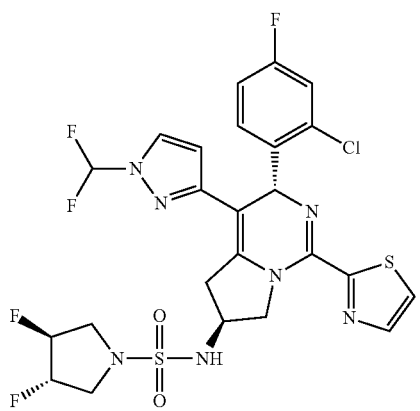 [SMILES: O=S(=O)(N[C@H]1CC2=C(c3ccn(C(F)F)n3)[C@H](c3ccc(F)cc3Cl)N=C(c3nccs3)N2C1)N1C[C@H](F)[C@@H](F)C1]

The title compound was prepared following the general procedure of Example 73. ESI MS m/z=634.05, 636.05 [M+H]+.

Example 276

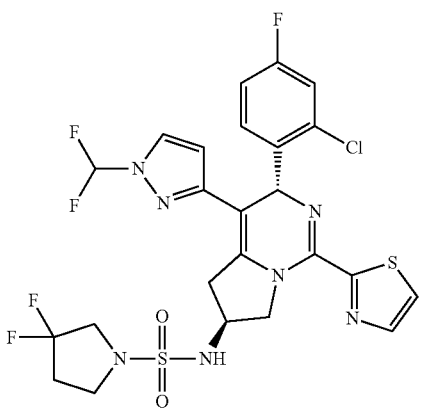 [SMILES: O=S(=O)(N[C@H]1CC2=C(c3ccn(C(F)F)n3)[C@H](c3ccc(F)cc3Cl)N=C(c3nccs3)N2C1)N1CCC(F)(F)C1]

The title compound was prepared following the general procedure of Example 73. ESI MS m/z=634.10, 636.10 [M+H]+.

Example 277

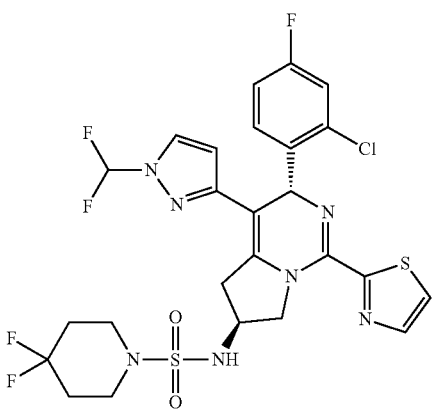 [SMILES: O=S(=O)(N[C@H]1CC2=C(c3ccn(C(F)F)n3)[C@H](c3ccc(F)cc3Cl)N=C(c3nccs3)N2C1)N1CCC(F)(F)CC1]

The title compound was prepared following the general procedure of Example 73. ESI MS m/z=648.05, 650.05 [M+H]+.

Example 278

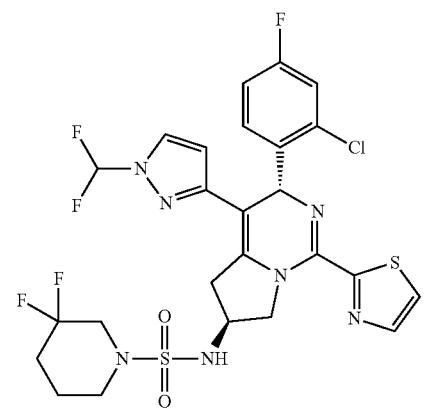 [SMILES: O=S(=O)(N[C@H]1CC2=C(c3ccn(C(F)F)n3)[C@H](c3ccc(F)cc3Cl)N=C(c3nccs3)N2C1)N1CCCC(F)(F)C1]

The title compound was prepared following the general procedure of Example 73. ESI MS m/z=648.10, 650.10 [M+H]+.

Example 279

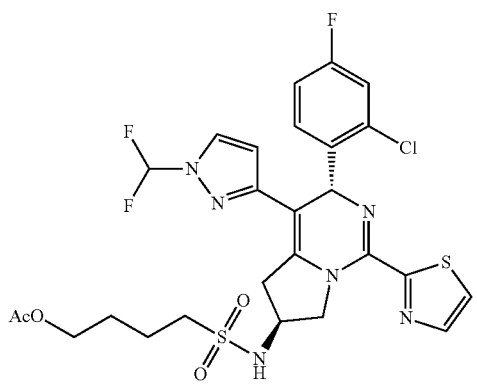 [SMILES: CC(=O)OCCCCS(=O)(=O)N[C@H]1CC2=C(c3ccn(C(F)F)n3)[C@H](c3ccc(F)cc3Cl)N=C(c3nccs3)N2C1]

The title compound was prepared following the general procedure of Example 2. ESI MS m/z=643.13, 645.13 [M+H]$^+$.

Example 280

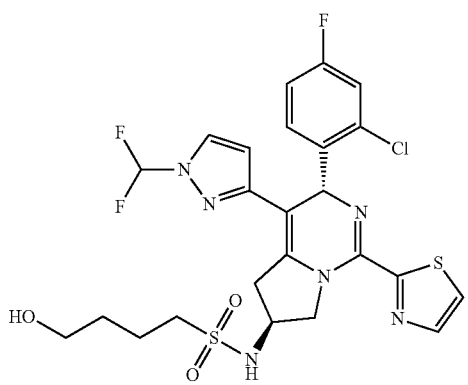 [SMILES: O=S(=O)(CCCCO)N[C@H]1CC2=C(c3ccn(C(F)F)n3)[C@H](c3ccc(F)cc3Cl)N=C(c3nccs3)N2C1]

The title compound was prepared following the general procedure of Example 5. ESI MS m/z=600.94, 602.94 [M+H]$^+$.

Example 281

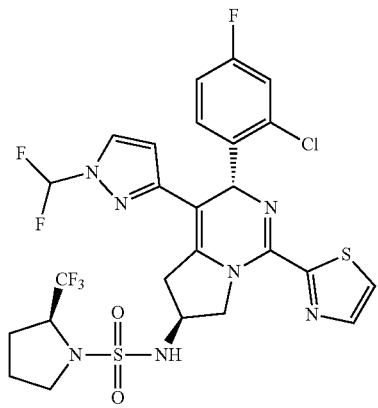 [SMILES: O=S(=O)(N[C@H]1CC2=C(c3ccn(C(F)F)n3)[C@H](c3ccc(F)cc3Cl)N=C(c3nccs3)N2C1)N1CCC[C@H]1C(F)(F)F]

The title compound was prepared following the general procedure of Example 73. ESI MS m/z=666.10, 668.10 [M+H]$^+$.

Example 282

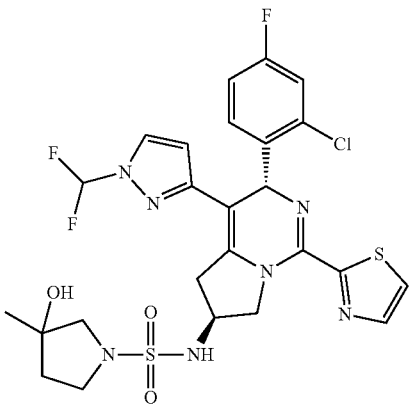 [SMILES: CC1(O)CCN(S(=O)(=O)N[C@H]2CC3=C(c4ccn(C(F)F)n4)[C@H](c4ccc(F)cc4Cl)N=C(c4nccs4)N3C2)C1]

The title compound was prepared following the general procedure of Example 73. ESI MS m/z=628.05, 630.05 [M+H]$^+$.

Example 283

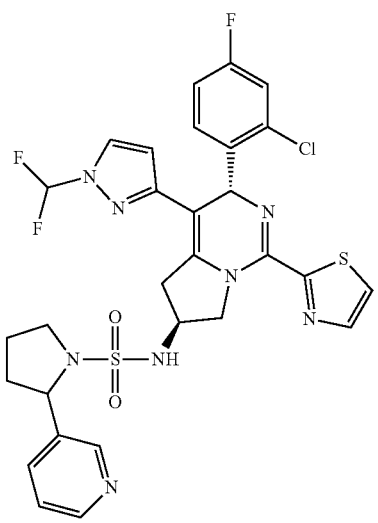 [SMILES: O=S(=O)(N[C@H]1CC2=C(c3ccn(C(F)F)n3)[C@H](c3ccc(F)cc3Cl)N=C(c3nccs3)N2C1)N1CCCC1c1cccnc1]

The title compound was prepared following the general procedure of Example 73. ESI MS m/z=675.10, 677.10 [M+H]$^+$.

Example 284

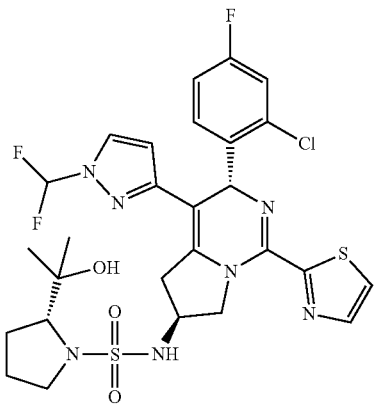 [SMILES: CC(C)(O)[C@H]1CCCN1S(=O)(=O)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=656.15, 658.15 [M+H]+.

Example 286

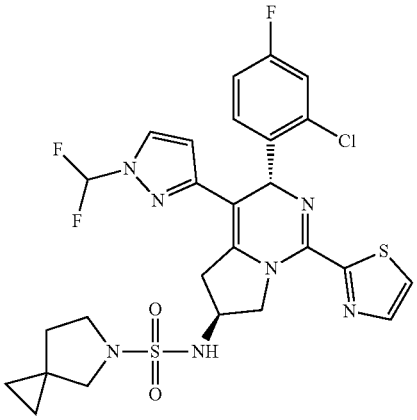

The title compound was prepared following the general procedure of Example 73. ESI MS m/z=624.10, 626.10 [M+H]+.

Example 285

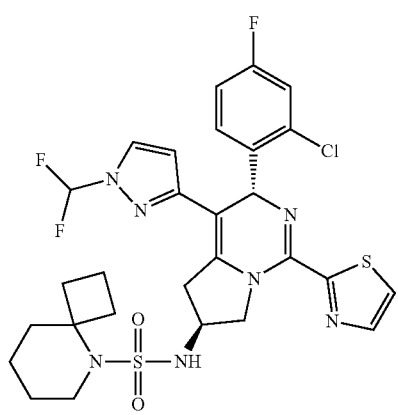 [SMILES: O=S(=O)(N[C@H]1CC2=C(c3ccn(C(F)F)n3)[C@H](c3ccc(F)cc3Cl)N=C(c3nccs3)N2C1)N1CCCCC12CCC2]

The title compound was prepared following the general procedure of Example 73. ESI MS m/z=652.10, 654.10 [M+H]+.

Example 287

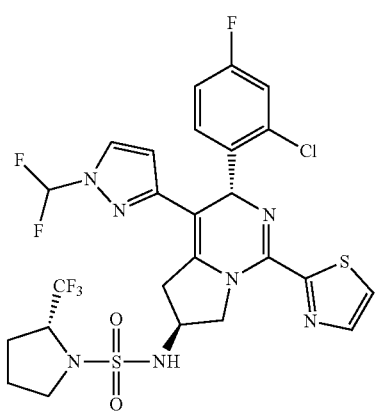 [SMILES: O=S(=O)(N[C@H]1CC2=C(c3ccn(C(F)F)n3)[C@H](c3ccc(F)cc3Cl)N=C(c3nccs3)N2C1)N1CCC[C@@H]1C(F)(F)F]

The title compound was prepared following the general procedure of Example 73. ESI MS m/z=666.05, 668.05 [M+H]+.

Example 288

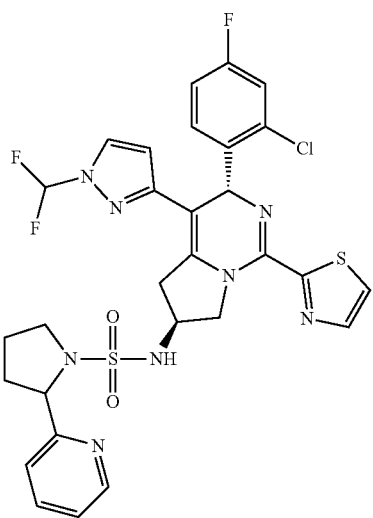 [SMILES: O=S(=O)(N[C@H]1CC2=C(c3ccn(C(F)F)n3)[C@H](c3ccc(F)cc3Cl)N=C(c3nccs3)N2C1)N1CCCC1c1ccccn1]

The title compound was prepared following the general procedure of Example 73. ESI MS m/z=675.10, 677.10 [M+H]+.

Example 290

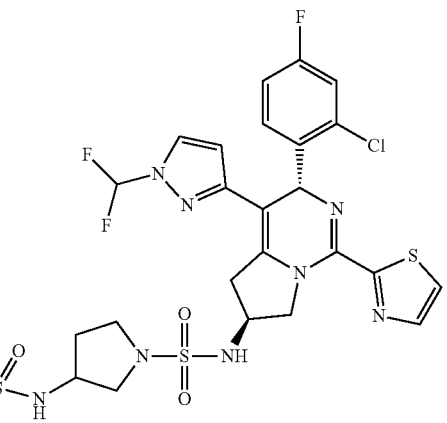

The title compound was prepared following the general procedure of Example 73. ESI MS m/z=691.05, 693.05 [M+H]+.

Example 289

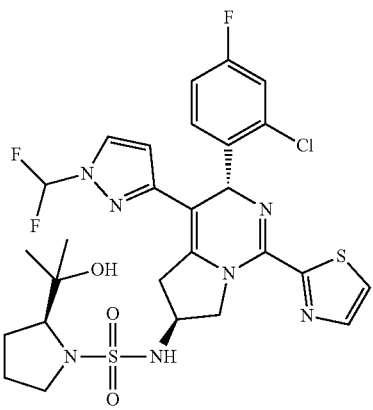 [SMILES: CC(C)(O)[C@@H]1CCCN1S(=O)(=O)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=656.15, 658.15 [M+H]+.

Example 291

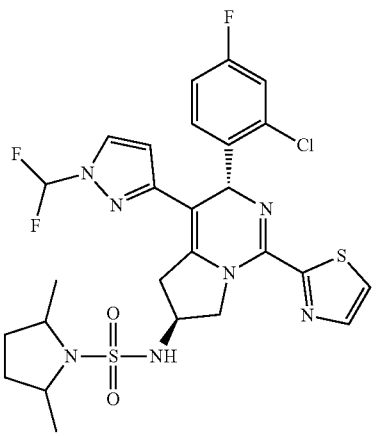 [SMILES: CC1CCC(C)N1S(=O)(=O)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=626.15, 628.15 [M+H]+.

Example 292

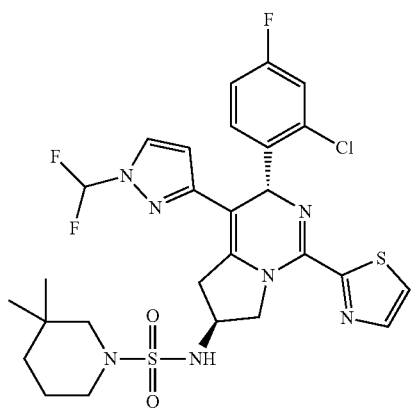 [SMILES: CC1(C)CCCN(S(=O)(=O)N[C@H]2CC3=C(c4ccn(C(F)F)n4)[C@H](c4ccc(F)cc4Cl)N=C(c4nccs4)N3C2)C1]

The title compound was prepared following the general procedure of Example 73. ESI MS m/z=640.15, 642.15 [M+H]+.

Example 294

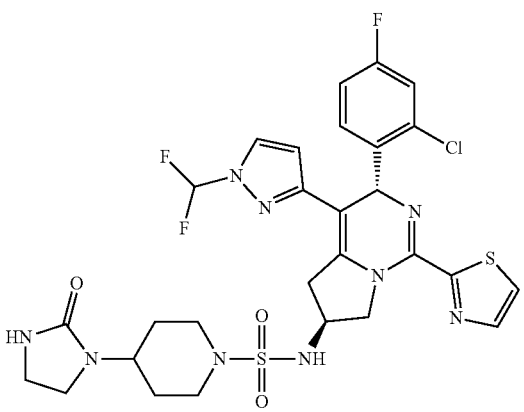

The title compound was prepared following the general procedure of Example 73. ESI MS m/z=696.15, 698.15 [M+H]+.

Example 293

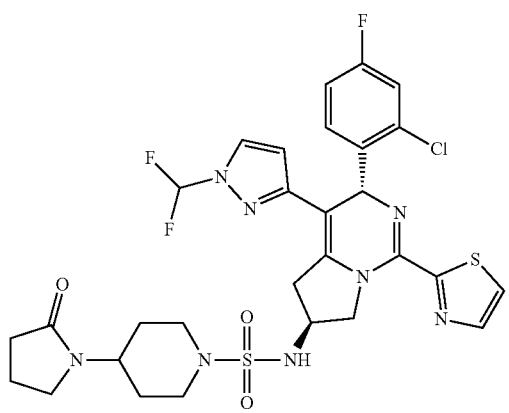 [SMILES: O=C1CCCN1C1CCN(S(=O)(=O)N[C@H]2CC3=C(c4ccn(C(F)F)n4)[C@H](c4ccc(F)cc4Cl)N=C(c4nccs4)N3C2)CC1]

The title compound was prepared following the general procedure of Example 73. ESI MS m/z=695.15, 697.15 [M+H]+.

Example 295

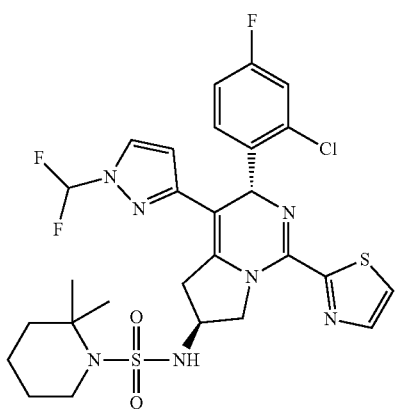 [SMILES: CC1(C)CCCCN1S(=O)(=O)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=640.10, 642.10 [M+H]+.

Example 296

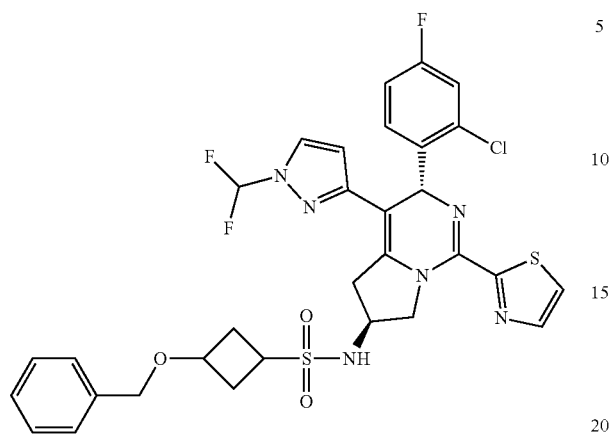

The title compound was prepared following the general procedure of Example 2. ESI MS m/z=689.35, 691.20 [M+H]+.

Example 298

The title compound was prepared following the general procedure of Example 2. ESI MS m/z=610.97, 612.97 [M+H]+.

Example 297

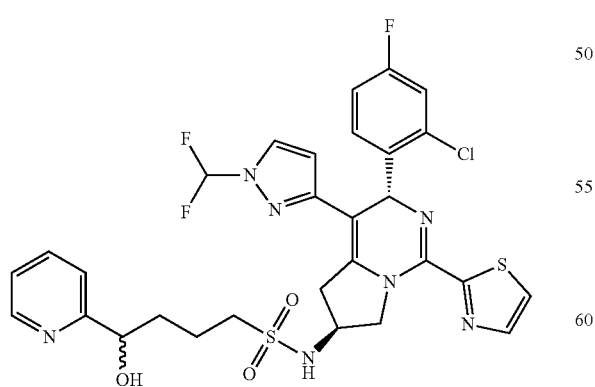

The title compound was prepared following the general procedure of Example 104. ESI MS m/z=678.15, 680.15 [M+H]+.

Example 299

The title compound was prepared following the general procedure of Example 73. ESI MS m/z=626.10, 628.10 [M+H]+.

205
Example 300

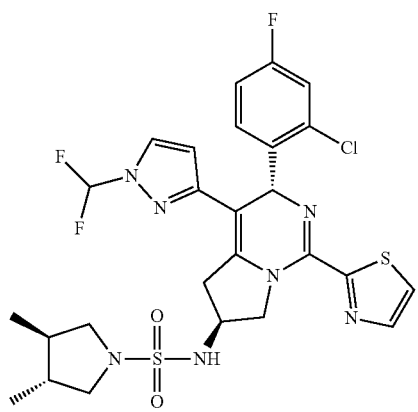 [SMILES: C[C@H]1CN(S(=O)(=O)N[C@H]2CC3=C(c4ccn(C(F)F)n4)[C@H](c4ccc(F)cc4Cl)N=C(c4nccs4)N3C2)C[C@@H]1C]

The title compound was prepared following the general procedure of Example 73. ESI MS m/z=626.05, 628.05 [M+H]⁺.

Example 301

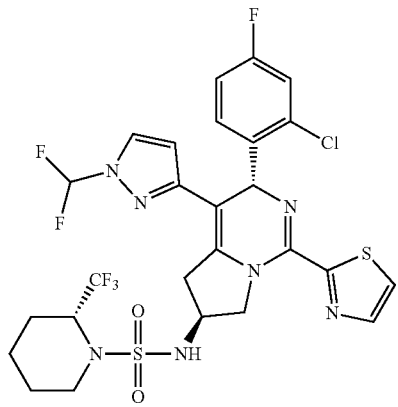 [SMILES: O=S(=O)(N[C@H]1CC2=C(c3ccn(C(F)F)n3)[C@H](c3ccc(F)cc3Cl)N=C(c3nccs3)N2C1)N1CCCC[C@@H]1C(F)(F)F]

The title compound was prepared following the general procedure of Example 73. ESI MS m/z=680.05, 682.05 [M+H]⁺.

206
Example 302

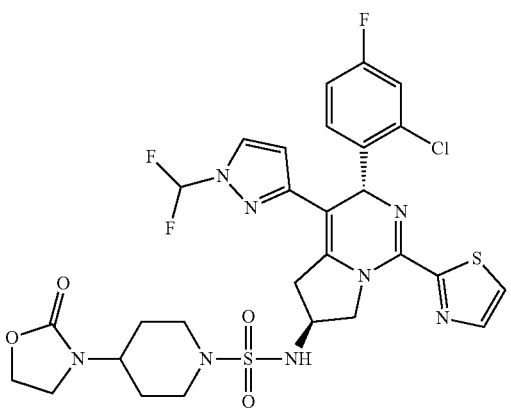 [SMILES: O=C1OCCN1C1CCN(S(=O)(=O)N[C@H]2CC3=C(c4ccn(C(F)F)n4)[C@H](c4ccc(F)cc4Cl)N=C(c4nccs4)N3C2)CC1]

The title compound was prepared following the general procedure of Example 73. ESI MS m/z=697.15, 699.15 [M+H]⁺.

Example 303

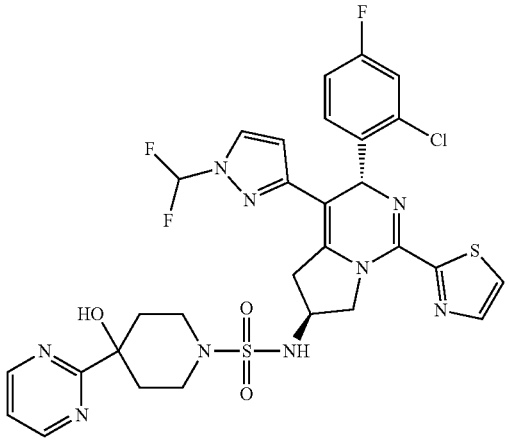 [SMILES: O=S(=O)(N[C@H]1CC2=C(c3ccn(C(F)F)n3)[C@H](c3ccc(F)cc3Cl)N=C(c3nccs3)N2C1)N1CCC(O)(c2ncccn2)CC1]

The title compound was prepared following the general procedure of Example 73. ESI MS m/z=706.10, 708.10 [M+H]⁺.

Example 304

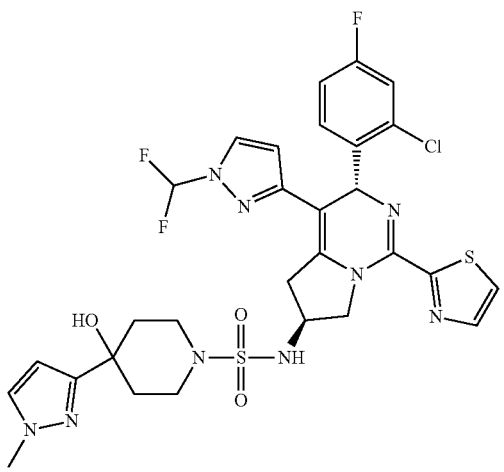 [SMILES: Cn1ccc(C2(O)CCN(S(=O)(=O)N[C@H]3CC4=C(c5ccn(C(F)F)n5)[C@H](c5ccc(F)cc5Cl)N=C(c5nccs5)N4C3)CC2)n1]

The title compound was prepared following the general procedure of Example 73. ESI MS m/z=708.15, 710.15 [M+H]+.

Example 306

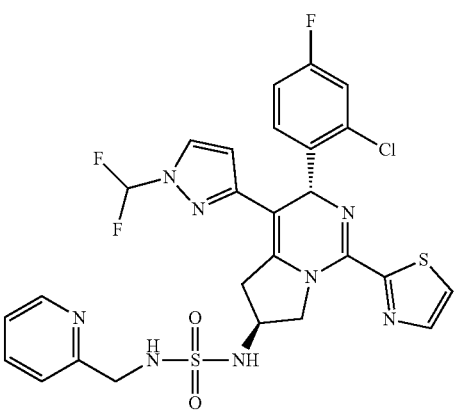

The title compound was prepared following the general procedure of Example 73. ESI MS m/z=635.10, 637.10 [M+H]+.

Example 305

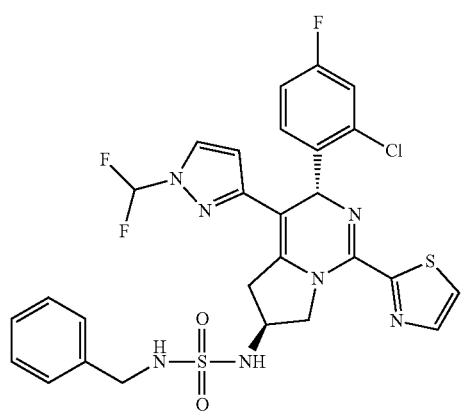 [SMILES: O=S(=O)(NCc1ccccc1)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=634.10, 636.10 [M+H]+.

Example 307

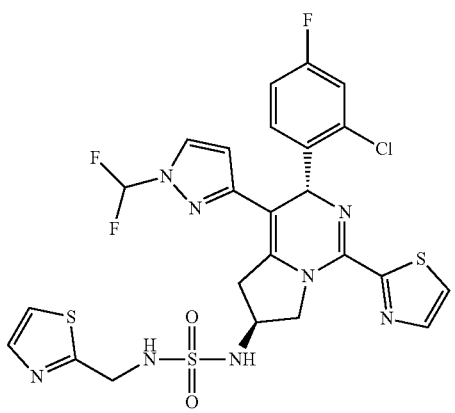 [SMILES: O=S(=O)(NCc1nccs1)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=640.90, 642.90 [M+H]+.

Example 308

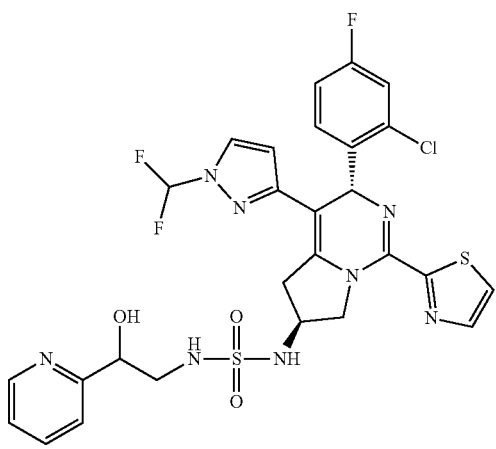 [SMILES: O=S(=O)(NCC(O)c1ccccn1)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=665.10, 667.10 [M+H]$^+$.

Example 309

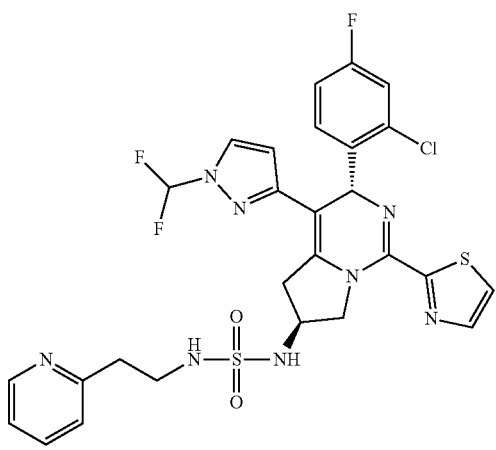 [SMILES: O=S(=O)(NCCc1ccccn1)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=649.10 651.10 [M+H]$^+$.

Example 310

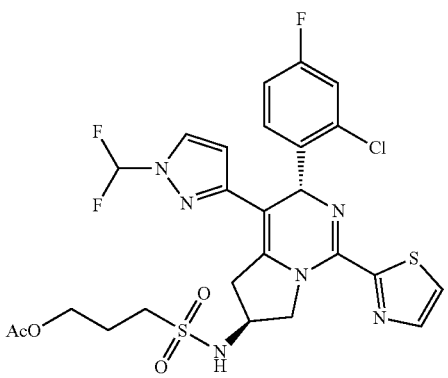 [SMILES: CC(=O)OCCCS(=O)(=O)N[C@H]1CC2=C(c3ccn(C(F)F)n3)[C@H](c3ccc(F)cc3Cl)N=C(c3nccs3)N2C1]

The title compound was prepared following the general procedure of Example 2. ESI MS m/z=628.93, 630.92 [M+H]$^+$.

Example 311

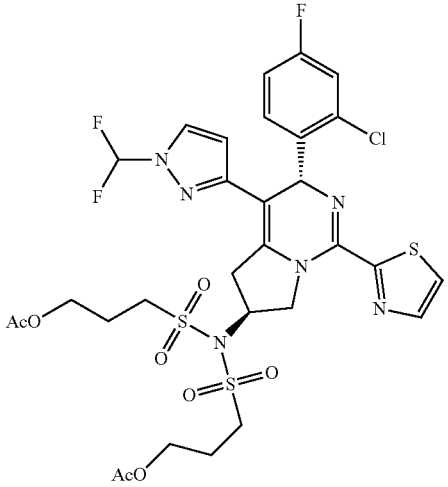 [SMILES: CC(=O)OCCCS(=O)(=O)N([C@H]1CC2=C(c3ccn(C(F)F)n3)[C@H](c3ccc(F)cc3Cl)N=C(c3nccs3)N2C1)S(=O)(=O)CCCOC(C)=O]

The title compound was isolated from Example 310. ESI MS m/z=792.92, 794.92 [M+H]$^+$.

211

Example 312

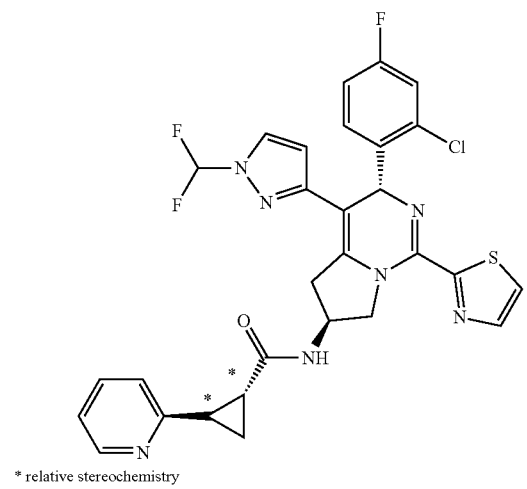

* relative stereochemistry

The title compound was prepared following the general procedure of Example 197. ESI MS m/z=609.98, 611.98 [M+H]⁺.

212

Example 313

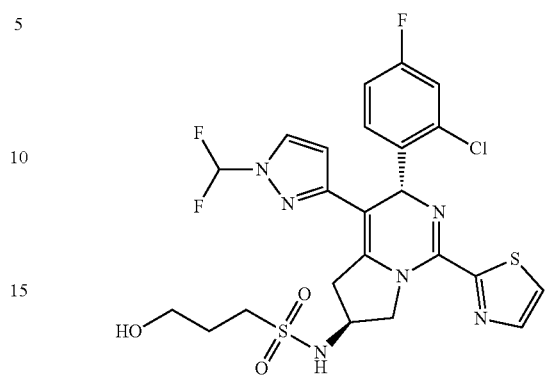

The title compound was prepared following the general procedure of Example 5. ESI MS m/z=586.93, 588.93 [M+H]⁺.

Example 313

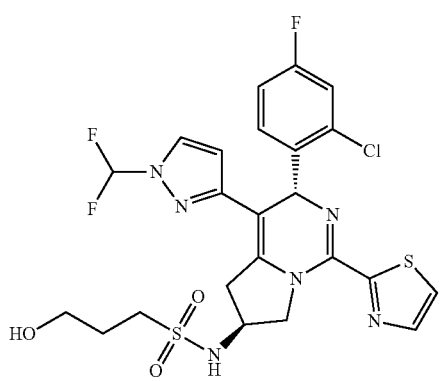 [SMILES: O=S(=O)(CCCO)N[C@H]1CC2=C(c3ccn(C(F)F)n3)[C@H](c3ccc(F)cc3Cl)N=C(c3nccs3)N2C1]

The title compound was prepared following the general procedure of Example 5. ESI MS m/z=586.93, 588.93 [M+H]⁺.

Example 314

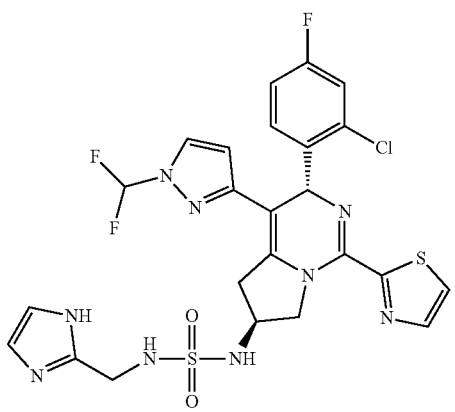 [SMILES: O=S(=O)(NCc1ncc[nH]1)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=624.15, 626.15 [M+H]⁺.

213

Example 315

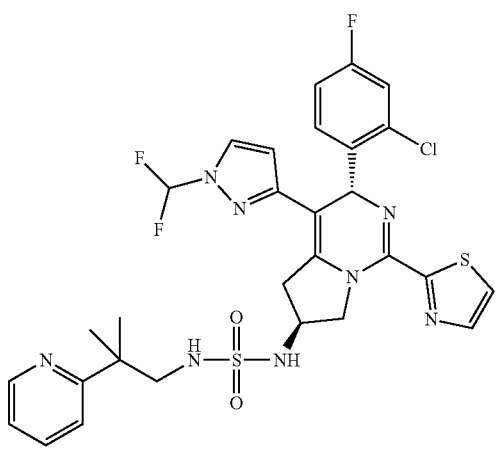 [SMILES: CC(C)(CNS(=O)(=O)N[C@H]1CC2=C(c3ccn(C(F)F)n3)[C@H](c3ccc(F)cc3Cl)N=C(c3nccs3)N2C1)c1ccccn1]

The title compound was prepared following the general procedure of Example 73. ESI MS m/z=677.20, 679.20 [M+H]⁺.

Example 316

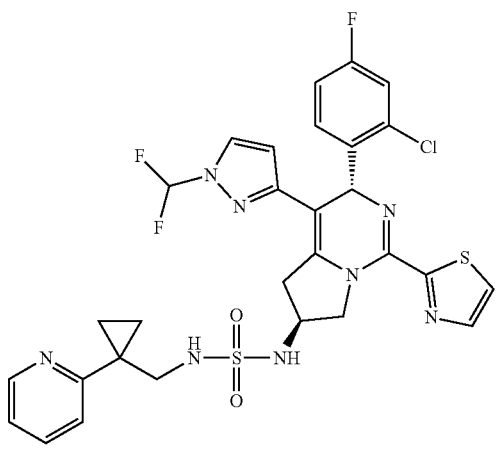 [SMILES: O=S(=O)(NCC1(c2ccccn2)CC1)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=675.10, 677.10 [M+H]⁺.

214

Example 317

The title compound was prepared following the general procedure of Example 73. ESI MS m/z=636.05, 638.05 [M+H]⁺.

Example 318

The title compound was prepared following the general procedure of Example 73. ESI MS m/z=663.05, 665.05 [M+H]⁺.

215
Example 319

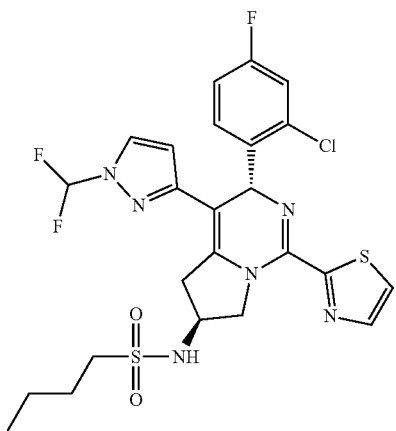 [SMILES: CCCCS(=O)(=O)N[C@H]1CC2=C(c3ccn(C(F)F)n3)[C@H](c3ccc(F)cc3Cl)N=C(c3nccs3)N2C1]

The title compound was prepared following the general procedure of Example 2. ESI MS m/z=585.10, 587.10 [M+H]$^+$.

216
Example 321

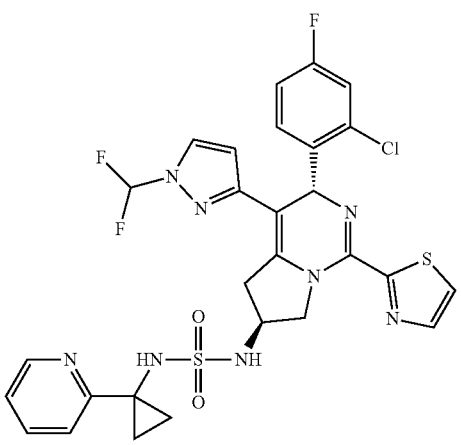

The title compound was prepared following the general procedure of Example 73. ESI MS m/z=661.10, 663.10 [M+H]$^+$.

Example 320

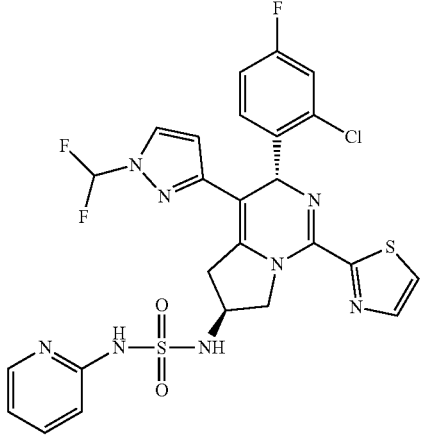 [SMILES: O=S(=O)(Nc1ccccn1)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=621.10, 623.10 [M+H]$^+$.

Example 322

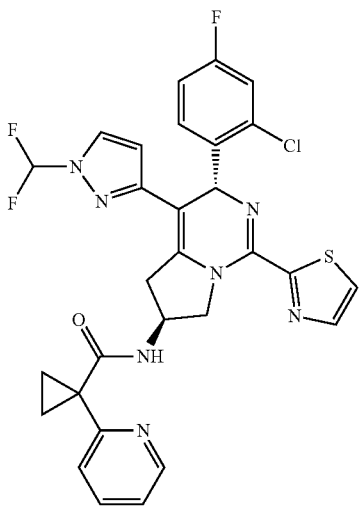 [SMILES: O=C(N[C@H]1CC2=C(c3ccn(C(F)F)n3)[C@H](c3ccc(F)cc3Cl)N=C(c3nccs3)N2C1)C1(c2ccccn2)CC1]

The title compound was prepared following the general procedure of Example 197. ESI MS m/z=610.15, 612.15 [M+H]$^+$.

Example 323

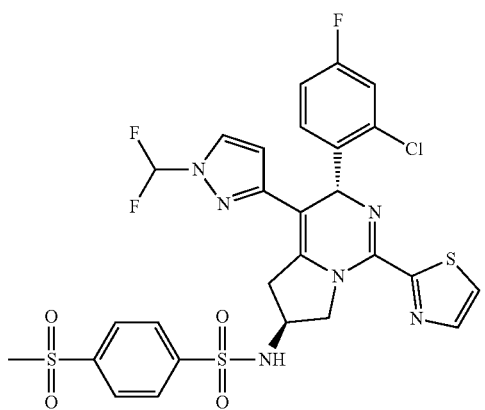 [SMILES: CS(=O)(=O)c1ccc(S(=O)(=O)N[C@H]2CC3=C(c4ccn(C(F)F)n4)[C@H](c4ccc(F)cc4Cl)N=C(c4nccs4)N3C2)cc1]

The title compound was prepared following the general procedure of Example 2. ESI MS m/z=683.07, 685.07 [M+H]$^+$.

Example 325

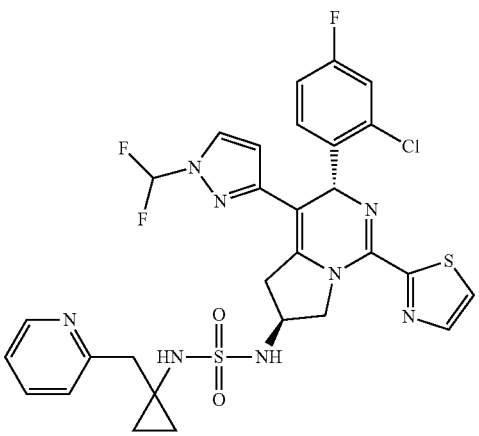

The title compound was prepared following the general procedure of Example 73. ESI MS m/z=675.10, 677.10 [M+H]$^+$.

Example 324

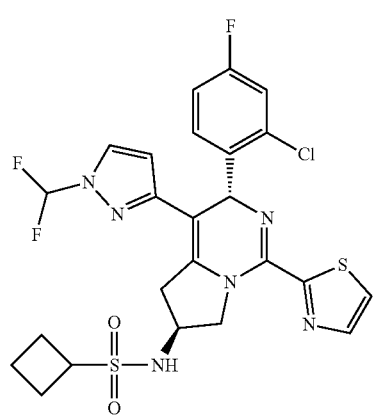 [SMILES: O=S(=O)(N[C@H]1CC2=C(c3ccn(C(F)F)n3)[C@H](c3ccc(F)cc3Cl)N=C(c3nccs3)N2C1)C1CCC1]

The title compound was prepared following the general procedure of Example 2. ESI MS m/z=583.10, 585.10 [M+H]$^+$.

Example 326

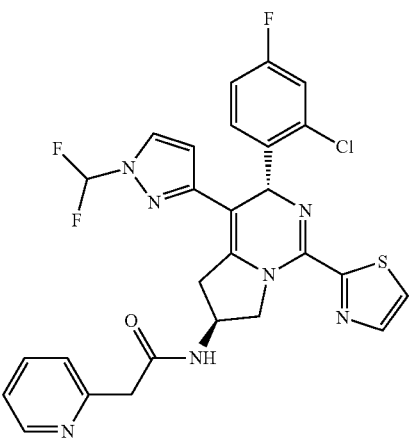 [SMILES: O=C(Cc1ccccn1)N[C@H]1CC2=C(c3ccn(C(F)F)n3)[C@H](c3ccc(F)cc3Cl)N=C(c3nccs3)N2C1]

The title compound was prepared following the general procedure of Example 197. ESI MS m/z=584.05, 586.05 [M+H]$^+$.

Example 327

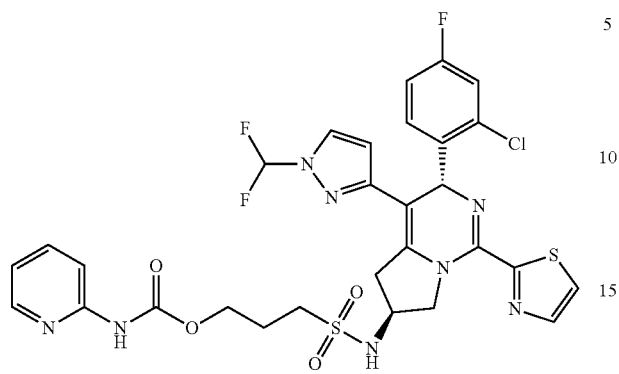

The title compound was prepared following the general procedure of Example 2. ESI MS m/z=707.14, 709.14 [M+H]⁺.

Example 328

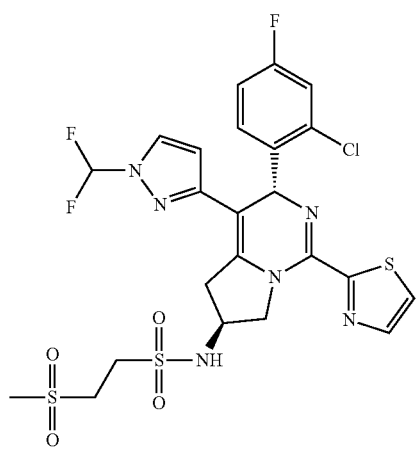 [SMILES: CS(=O)(=O)CCS(=O)(=O)N[C@H]1CC2=C(c3ccn(C(F)F)n3)[C@H](c3ccc(F)cc3Cl)N=C(c3nccs3)N2C1]

The title compound was prepared following the general procedure of Example 2. ESI MS m/z=635.07, 637.07 [M+H]⁺.

Example 329

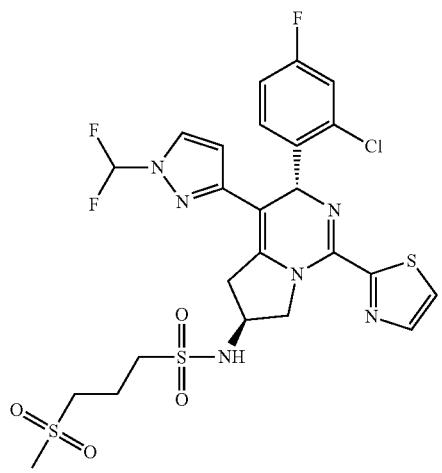 [SMILES: CS(=O)(=O)CCCS(=O)(=O)N[C@H]1CC2=C(c3ccn(C(F)F)n3)[C@H](c3ccc(F)cc3Cl)N=C(c3nccs3)N2C1]

The title compound was prepared following the general procedure of Example 2. ESI MS m/z=649.09, 651.08 [M+H]⁺.

Example 330

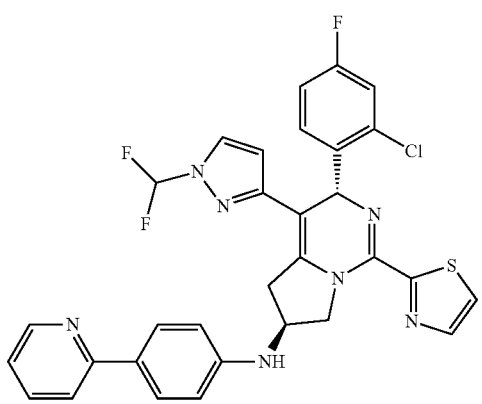 [SMILES: Fc1ccc([C@@H]2N=C(c3nccs3)N3C[C@@H](Nc4ccc(-c5ccccn5)cc4)CC3=C2c2ccn(C(F)F)n2)c(Cl)c1]

The title compound was prepared following the general procedure of Example 197. ESI MS m/z=618.05, 620.05 [M+H]⁺.

Example 331

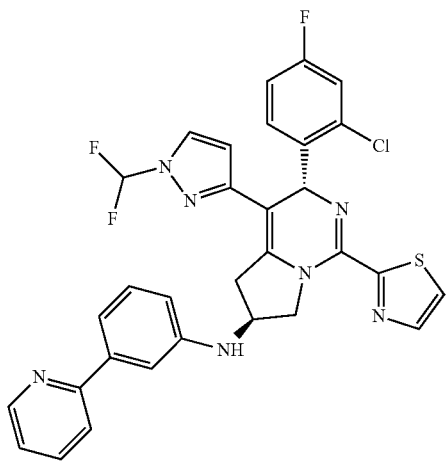 [SMILES: Fc1ccc([C@@H]2N=C(c3nccs3)N3C[C@@H](Nc4cccc(-c5ccccn5)c4)CC3=C2c2ccn(C(F)F)n2)c(Cl)c1]

The title compound was prepared following the general procedure of Example 197. ESI MS m/z=618.10, 620.10 [M+H]+.

Example 333

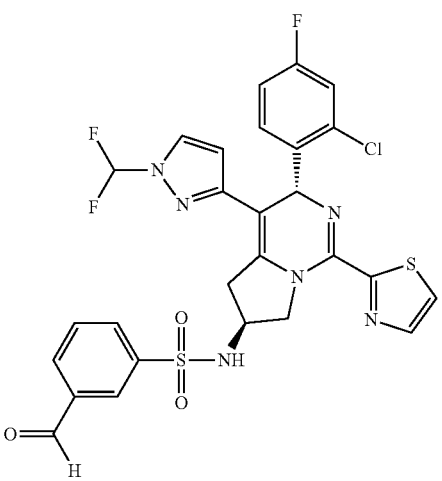

The title compound was prepared following the general procedure of Example 2. ESI MS m/z=633.08, 635.08 [M+H]+.

Example 332

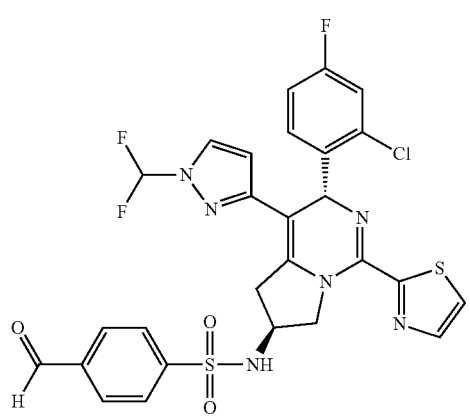 [SMILES: O=Cc1ccc(S(=O)(=O)N[C@H]2CC3=C(c4ccn(C(F)F)n4)[C@H](c4ccc(F)cc4Cl)N=C(c4nccs4)N3C2)cc1]

The title compound was prepared following the general procedure of Example 2. ESI MS m/z=633.09, 635.08 [M+H]+.

Example 334

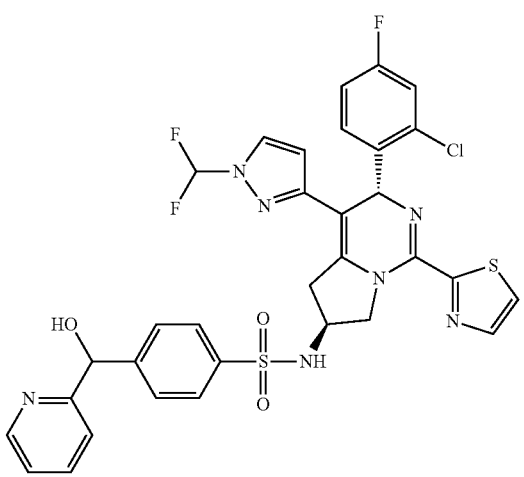 [SMILES: O=S(=O)(N[C@H]1CC2=C(c3ccn(C(F)F)n3)[C@H](c3ccc(F)cc3Cl)N=C(c3nccs3)N2C1)c1ccc(C(O)c2ccccn2)cc1]

The title compound was prepared following the general procedure of Example 104. ESI MS m/z=712.14, 714.14 [M+H]+.

Example 335

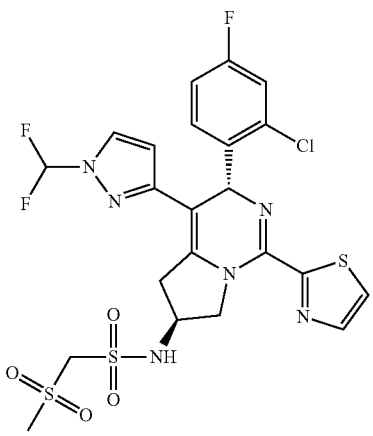 [SMILES: CS(=O)(=O)CS(=O)(=O)N[C@H]1CC2=C(c3ccn(C(F)F)n3)[C@H](c3ccc(F)cc3Cl)N=C(c3nccs3)N2C1]

The title compound was prepared following the general procedure of Example 2. ESI MS m/z=621.05, 623.05 [M+H]$^+$.

Example 336

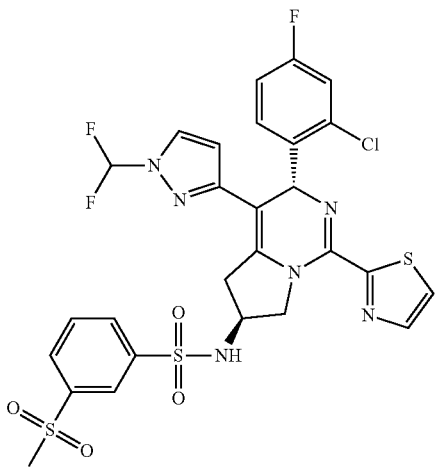 [SMILES: CS(=O)(=O)c1cccc(S(=O)(=O)N[C@H]2CC3=C(c4ccn(C(F)F)n4)[C@H](c4ccc(F)cc4Cl)N=C(c4nccs4)N3C2)c1]

The title compound was prepared following the general procedure of Example 2. ESI MS m/z=683.07, 685.07 [M+H]$^+$.

Example 337

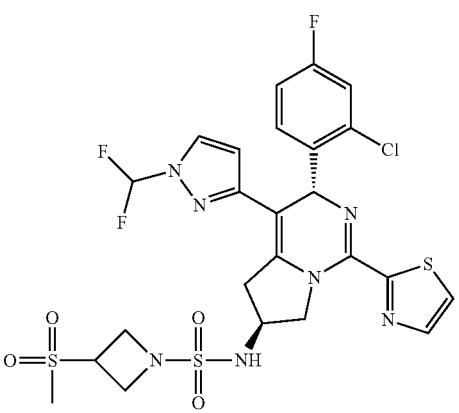 [SMILES: CS(=O)(=O)C1CN(S(=O)(=O)N[C@H]2CC3=C(c4ccn(C(F)F)n4)[C@H](c4ccc(F)cc4Cl)N=C(c4nccs4)N3C2)C1]

The title compound was prepared following the general procedure of Example 73. ESI MS m/z=662.10, 664.10 [M+H]$^+$.

Example 338

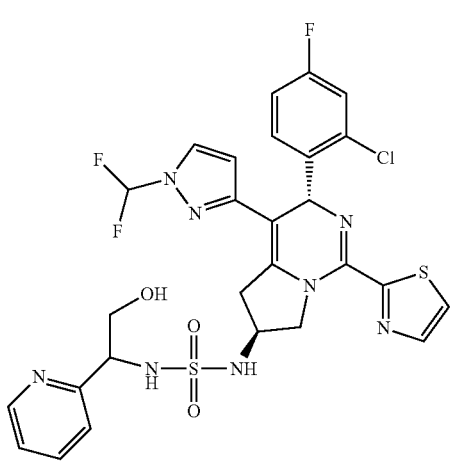 [SMILES: O=S(=O)(NC(CO)c1ccccn1)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=665.05, 667.05 [M+H]$^+$.

Example 339

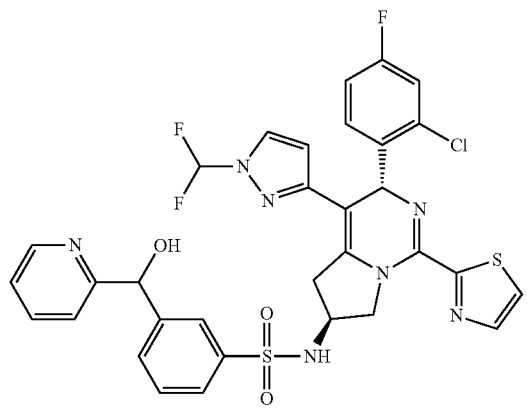 [SMILES: O=S(=O)(N[C@H]1CC2=C(c3ccn(C(F)F)n3)[C@H](c3ccc(F)cc3Cl)N=C(c3nccs3)N2C1)c1cccc(C(O)c2ccccn2)c1]

The title compound was prepared following the general procedure of Example 104. ESI MS m/z=712.14, 714.14 [M+H]+.

Example 340

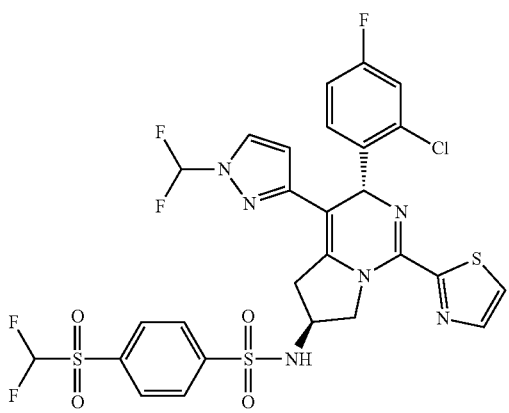 [SMILES: O=S(=O)(N[C@H]1CC2=C(c3ccn(C(F)F)n3)[C@H](c3ccc(F)cc3Cl)N=C(c3nccs3)N2C1)c1ccc(S(=O)(=O)C(F)F)cc1]

The title compound was prepared following the general procedure of Example 2. ESI MS m/z=719.06, 721.06 [M+H]+.

Example 341

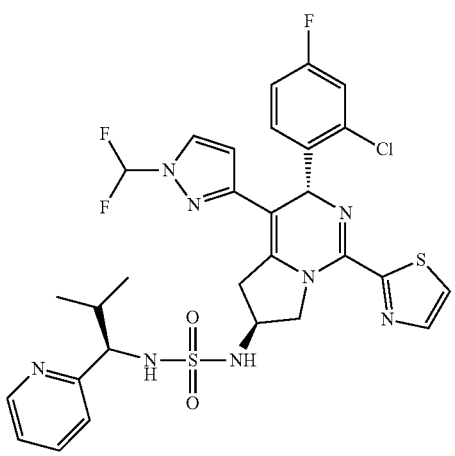 [SMILES: CC(C)[C@@H](NS(=O)(=O)N[C@H]1CC2=C(c3ccn(C(F)F)n3)[C@H](c3ccc(F)cc3Cl)N=C(c3nccs3)N2C1)c1ccccn1]

The title compound was prepared following the general procedure of Example 73. ESI MS m/z=677.10, 679.10 [M+H]+.

Example 342

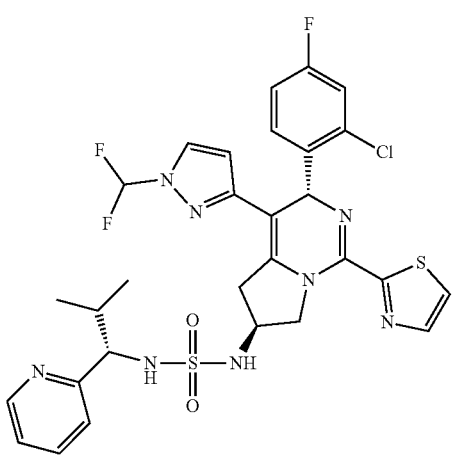 [SMILES: CC(C)[C@H](NS(=O)(=O)N[C@H]1CC2=C(c3ccn(C(F)F)n3)[C@H](c3ccc(F)cc3Cl)N=C(c3nccs3)N2C1)c1ccccn1]

The title compound was prepared following the general procedure of Example 73. ESI MS m/z=677.20, 679.20 [M+H]+.

Example 343

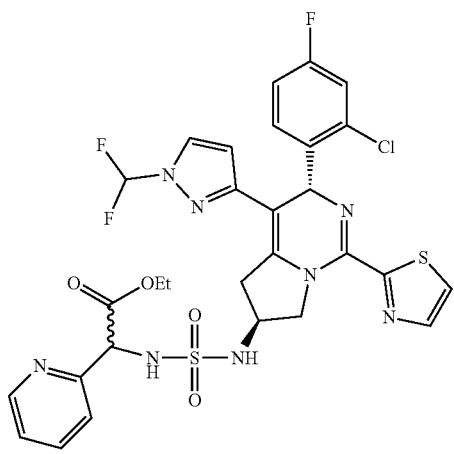 [SMILES: CCOC(=O)C(NS(=O)(=O)N[C@H]1CC2=C(c3ccn(C(F)F)n3)[C@H](c3ccc(F)cc3Cl)N=C(c3nccs3)N2C1)c1ccccn1]

The title compound was prepared following the general procedure of Example 73. ESI MS m/z=707.05, 709.05 [M+H]$^+$.

Example 345

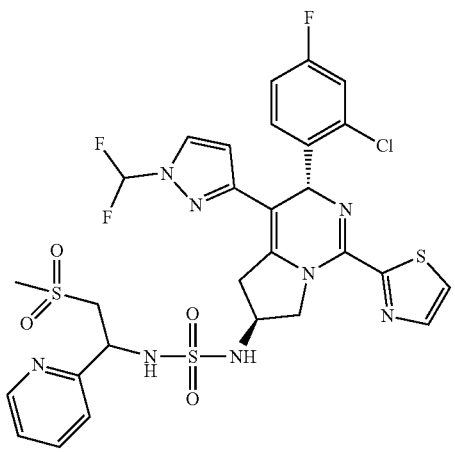

The title compound was prepared following the general procedure of Example 73. ESI MS m/z=727.00, 729.00 [M+H]$^+$.

Example 344

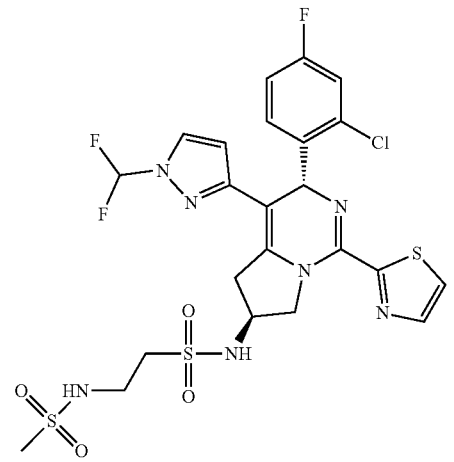 [SMILES: CS(=O)(=O)NCCS(=O)(=O)N[C@H]1CC2=C(c3ccn(C(F)F)n3)[C@H](c3ccc(F)cc3Cl)N=C(c3nccs3)N2C1]

The title compound was prepared following the general procedure of Example 2. ESI MS m/z=650.08, 652.08 [M+H]$^+$.

Example 346

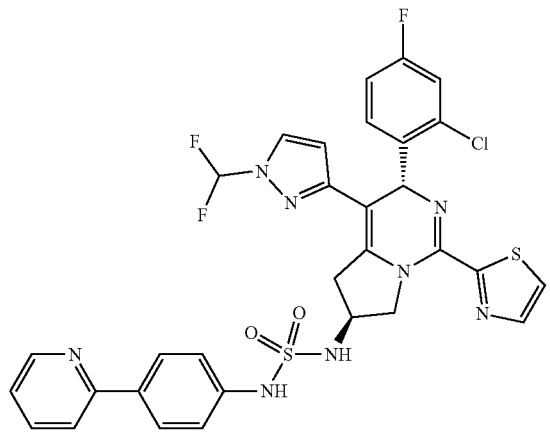 [SMILES: O=S(=O)(Nc1ccc(-c2ccccn2)cc1)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=697.05, 681.05 [M+H]$^+$.

Example 347

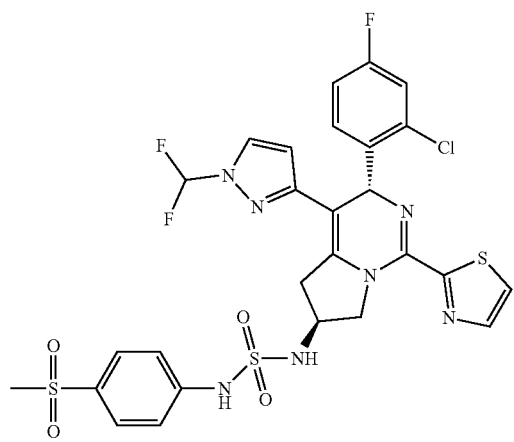 [SMILES: CS(=O)(=O)c1ccc(NS(=O)(=O)N[C@H]2CC3=C(c4ccn(C(F)F)n4)[C@H](c4ccc(F)cc4Cl)N=C(c4nccs4)N3C2)cc1]

The title compound was prepared following the general procedure of Example 73. ESI MS m/z=698.10, 700.10 [M+H]+.

Example 349

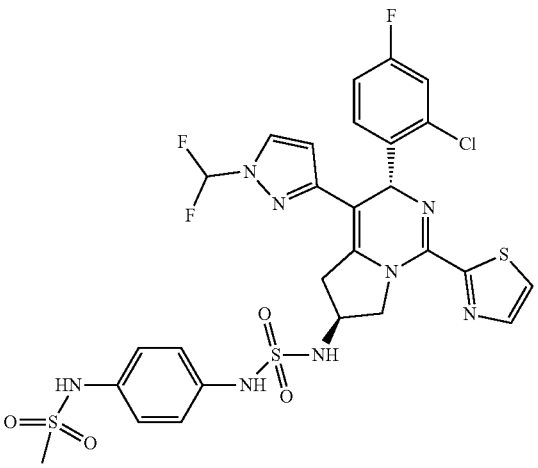

The title compound was prepared following the general procedure of Example 73. ESI MS m/z=713.00, 715.00 [M+H]+.

Example 348

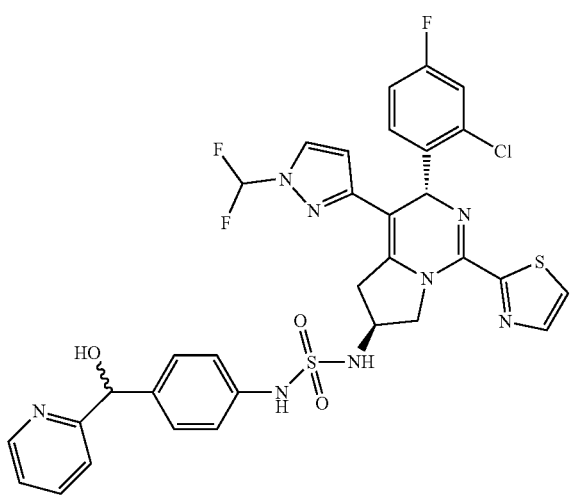 [SMILES: O=S(=O)(Nc1ccc(C(O)c2ccccn2)cc1)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=727.00, 729.00 [M+H]+.

Example 350

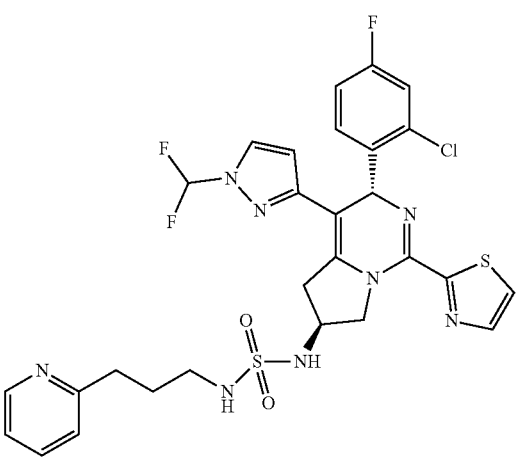 [SMILES: O=S(=O)(NCCCc1ccccn1)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=663.15, 665.15 [M+H]+.

231

Example 351

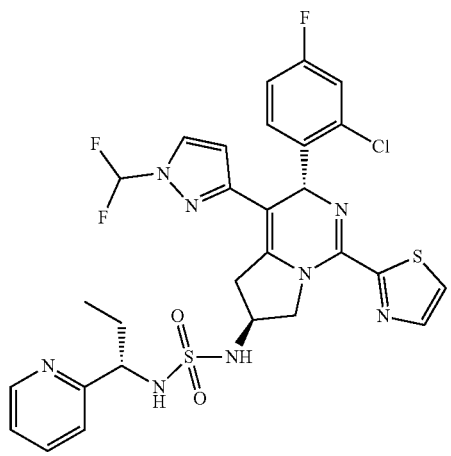 [SMILES: CC[C@H](NS(=O)(=O)N[C@H]1CC2=C(c3ccn(C(F)F)n3)[C@H](c3ccc(F)cc3Cl)N=C(c3nccs3)N2C1)c1ccccn1]

The title compound was prepared following the general procedure of Example 73. ESI MS m/z=663.10, 665.10 [M+H]⁺.

Example 352

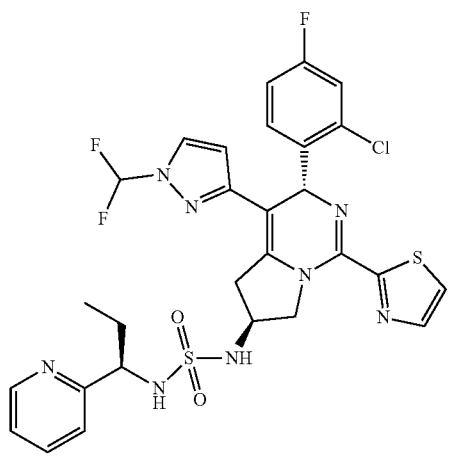 [SMILES: CC[C@@H](NS(=O)(=O)N[C@H]1CC2=C(c3ccn(C(F)F)n3)[C@H](c3ccc(F)cc3Cl)N=C(c3nccs3)N2C1)c1ccccn1]

The title compound was prepared following the general procedure of Example 73. ESI MS m/z=663.10, 665.10 [M+H]⁺.

232

Example 353

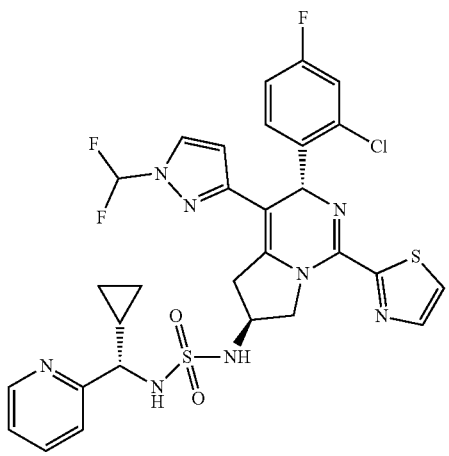 [SMILES: O=S(=O)(N[C@H]1CC2=C(c3ccn(C(F)F)n3)[C@H](c3ccc(F)cc3Cl)N=C(c3nccs3)N2C1)N[C@H](c1ccccn1)C1CC1]

The title compound was prepared following the general procedure of Example 73. ESI MS m/z=675.10, 677.10 [M+H]⁺.

Example 354

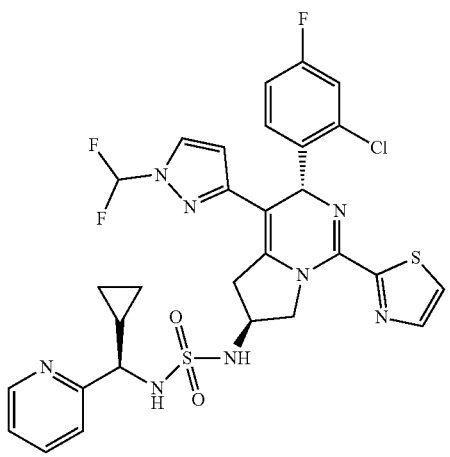 [SMILES: O=S(=O)(N[C@H]1CC2=C(c3ccn(C(F)F)n3)[C@H](c3ccc(F)cc3Cl)N=C(c3nccs3)N2C1)N[C@@H](c1ccccn1)C1CC1]

The title compound was prepared following the general procedure of Example 73. ESI MS m/z=675.10, 677.10 [M+H]⁺.

Example 355

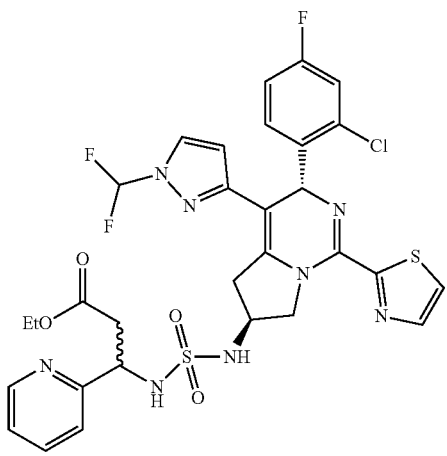 [SMILES: O=C(O)CC(NS(=O)(=O)N[C@H]1CC2=C(c3ccn(C(F)F)n3)[C@H](c3ccc(F)cc3Cl)N=C(c3nccs3)N2C1)c1ccccn1]

The title compound was prepared following the general procedure of Example 73. ESI MS m/z=721.30, 723.30 [M+H]$^+$.

Example 356

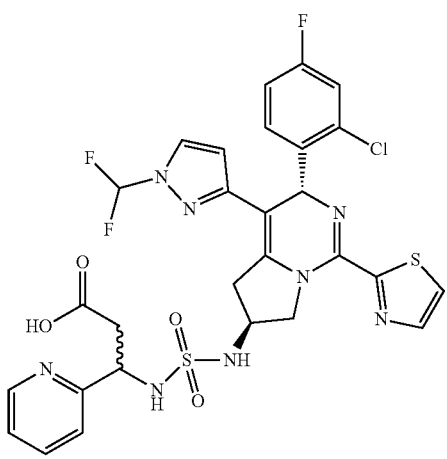

The title compound was prepared following the general procedure of Example 5. ESI MS m/z=693.25, 695.25 [M+H]$^+$.

Example 357

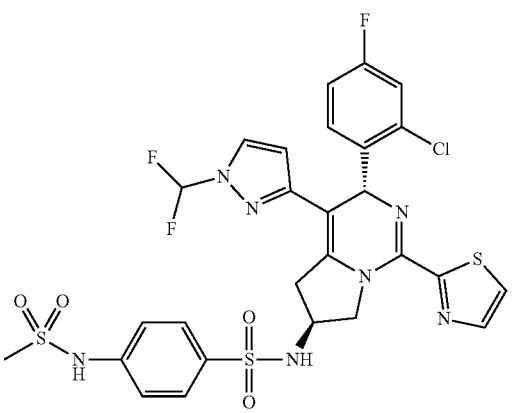 [SMILES: CS(=O)(=O)Nc1ccc(S(=O)(=O)N[C@H]2CC3=C(c4ccn(C(F)F)n4)[C@H](c4ccc(F)cc4Cl)N=C(c4nccs4)N3C2)cc1]

The title compound was prepared following the general procedure of Example 2. ESI MS m/z=698.10, 700.10 [M+H]$^+$.

Example 358

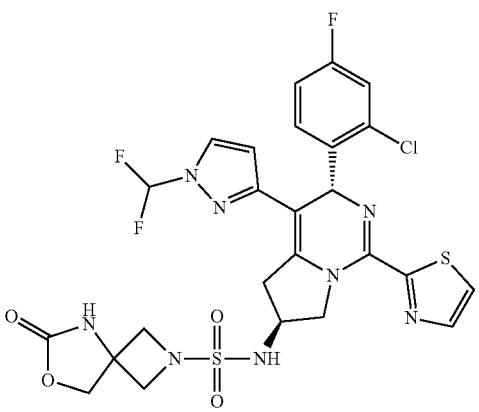 [SMILES: O=C1NC2(CO1)CN(S(=O)(=O)N[C@H]1CC3=C(c4ccn(C(F)F)n4)[C@H](c4ccc(F)cc4Cl)N=C(c4nccs4)N3C1)C2]

The title compound was prepared following the general procedure of Example 73. ESI MS m/z=655.18, 657.07 [M+H]$^+$.

Example 359

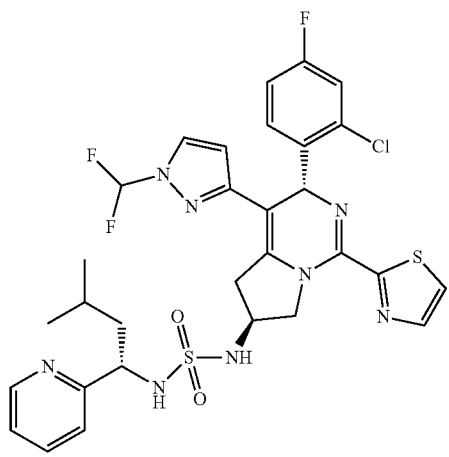 [SMILES: CC(C)C[C@H](NS(=O)(=O)N[C@H]1CC2=C(c3ccn(C(F)F)n3)[C@H](c3ccc(F)cc3Cl)N=C(c3nccs3)N2C1)c1ccccn1]

The title compound was prepared following the general procedure of Example 73. ESI MS m/z=691.10, 693.10 [M+H]+.

Example 360

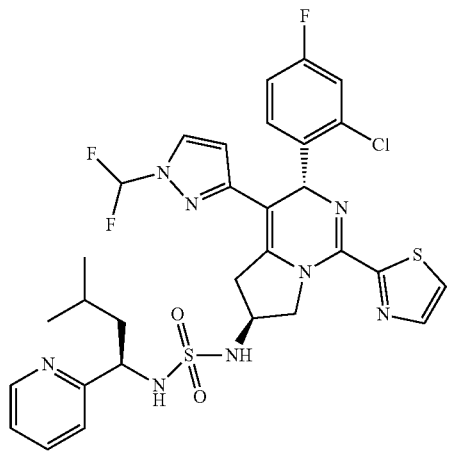 [SMILES: CC(C)C[C@@H](NS(=O)(=O)N[C@H]1CC2=C(c3ccn(C(F)F)n3)[C@H](c3ccc(F)cc3Cl)N=C(c3nccs3)N2C1)c1ccccn1]

The title compound was prepared following the general procedure of Example 73. ESI MS m/z=691.15, 693.15 [M+H]+.

Example 361

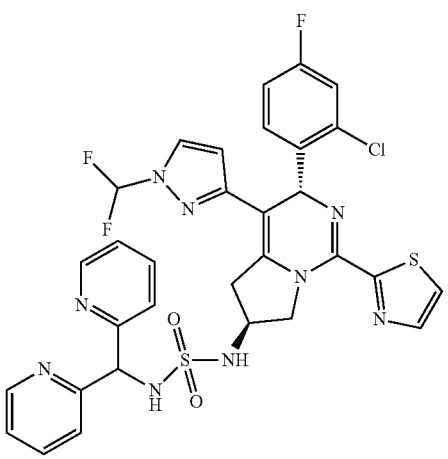 [SMILES: O=S(=O)(NC(c1ccccn1)c1ccccn1)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=712.20, 714.20 [M+H]+.

Example 362

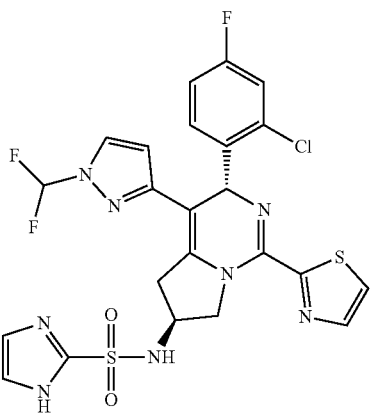 [SMILES: O=S(=O)(N[C@H]1CC2=C(c3ccn(C(F)F)n3)[C@H](c3ccc(F)cc3Cl)N=C(c3nccs3)N2C1)c1ncc[nH]1]

The title compound was prepared following the general procedure of Example 2. ESI MS m/z=595.01, 596.90 [M+H]+.

Example 363

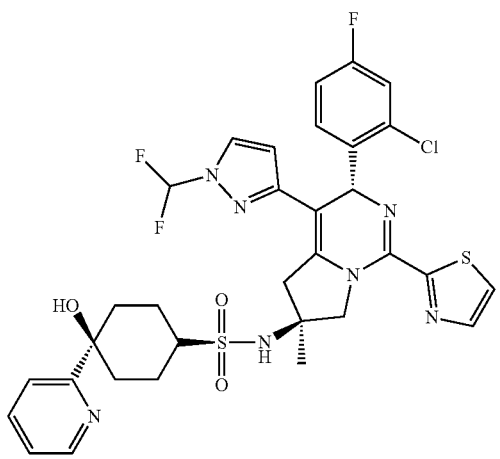

The title compound was prepared following the general procedure of Example 2. ESI MS m/z=718.27, 720.22 [M+H]⁺.

Example 364

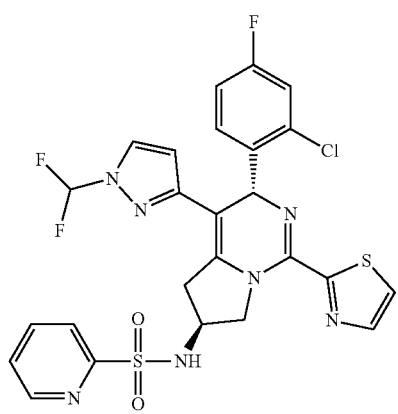 [SMILES: O=S(=O)(N[C@H]1CC2=C(c3ccn(C(F)F)n3)[C@H](c3ccc(F)cc3Cl)N=C(c3nccs3)N2C1)c1ccccn1]

The title compound was prepared following the general procedure of Example 2. ESI MS m/z=606.10, 607.98 [M+H]⁺.

Example 365

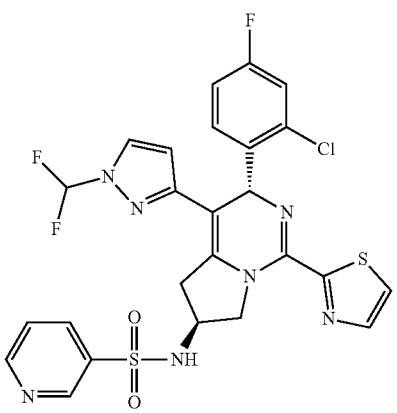 [SMILES: O=S(=O)(N[C@H]1CC2=C(c3ccn(C(F)F)n3)[C@H](c3ccc(F)cc3Cl)N=C(c3nccs3)N2C1)c1cccnc1]

The title compound was prepared following the general procedure of Example 2. ESI MS m/z=606.03, 607.91 [M+H]⁺.

Example 366

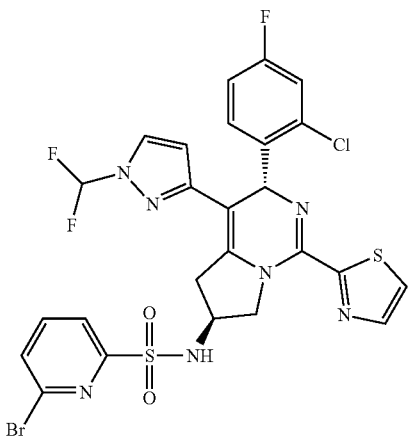 [SMILES: O=S(=O)(N[C@H]1CC2=C(c3ccn(C(F)F)n3)[C@H](c3ccc(F)cc3Cl)N=C(c3nccs3)N2C1)c1cccc(Br)n1]

The title compound was prepared following the general procedure of Example 2. ESI MS m/z=683.94, 685.93 [M+H]⁺.

Example 367

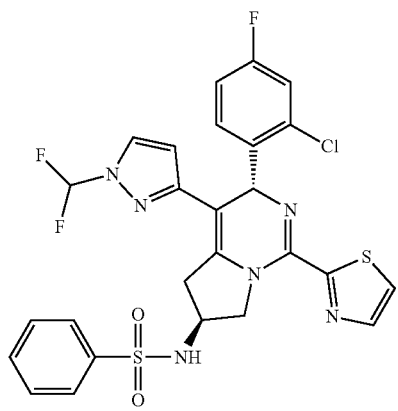 [SMILES: O=S(=O)(N[C@H]1CC2=C(c3ccn(C(F)F)n3)[C@H](c3ccc(F)cc3Cl)N=C(c3nccs3)N2C1)c1ccccc1]

The title compound was prepared following the general procedure of Example 2. ESI MS m/z=605.06, 609.96 [M+H]$^+$.

Example 369

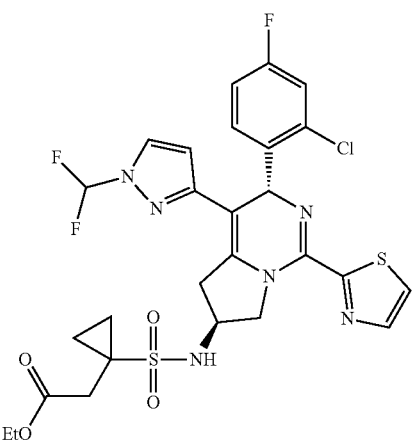

The title compound was prepared following the general procedure of Example 2. ESI MS m/z=655.13, 657.13 [M+H]$^+$.

Example 368

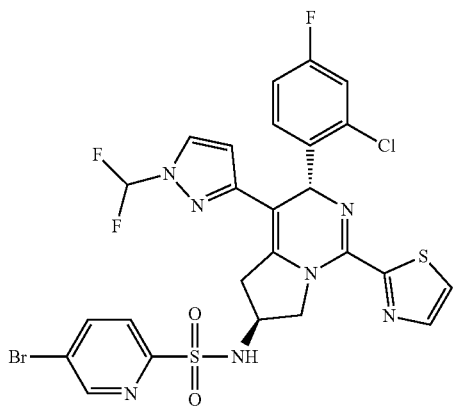 [SMILES: O=S(=O)(N[C@H]1CC2=C(c3ccn(C(F)F)n3)[C@H](c3ccc(F)cc3Cl)N=C(c3nccs3)N2C1)c1ccc(Br)cn1]

The title compound was prepared following the general procedure of Example 2. ESI MS m/z=683.96, 685.92 [M+H]$^+$.

Example 370

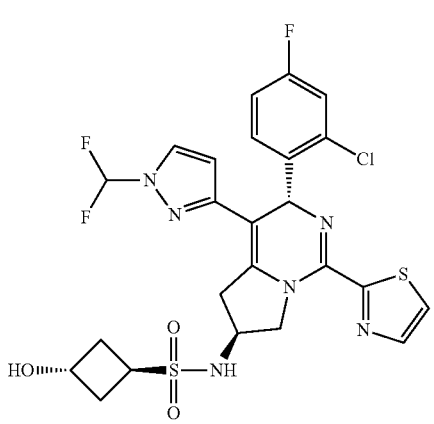 [SMILES: O=S(=O)(N[C@H]1CC2=C(c3ccn(C(F)F)n3)[C@H](c3ccc(F)cc3Cl)N=C(c3nccs3)N2C1)[C@H]1C[C@H](O)C1]

The title compound was prepared following the general procedure of Example 2. ESI MS m/z=599.04, 600.95 [M+H]$^+$.

Example 371

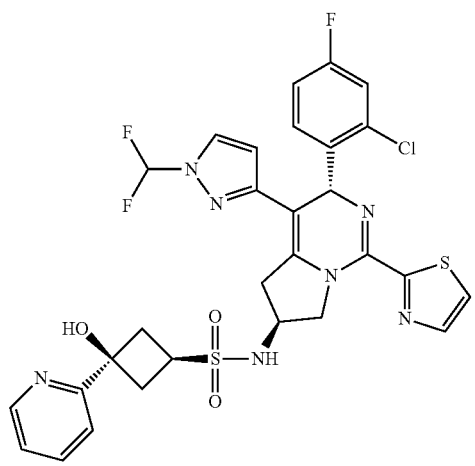 [SMILES: O=S(=O)(N[C@H]1CC2=C(c3ccn(C(F)F)n3)[C@H](c3ccc(F)cc3Cl)N=C(c3nccs3)N2C1)[C@H]1C[C@](O)(c2ccccn2)C1]

The title compound was prepared following the general procedure of Example 104. ESI MS m/z=676.12, 678.12 [M+H]+.

Example 372

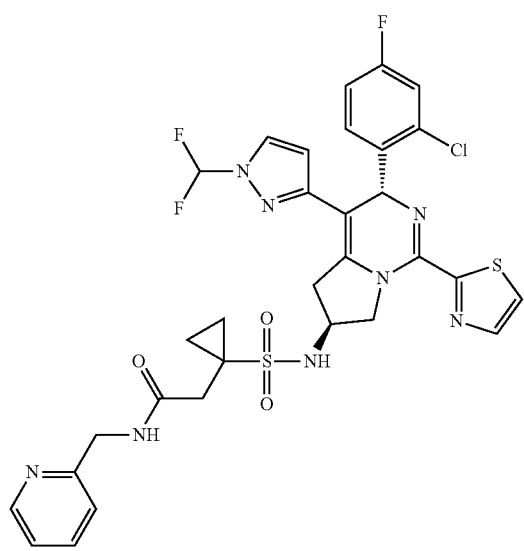 [SMILES: O=C(CC1(S(=O)(=O)N[C@H]2CC3=C(c4ccn(C(F)F)n4)[C@H](c4ccc(F)cc4Cl)N=C(c4nccs4)N3C2)CC1)NCc1ccccn1]

The title compound was prepared following the general procedure of Example 197. ESI MS m/z=717.14, 719.14 [M+H]+.

Example 373

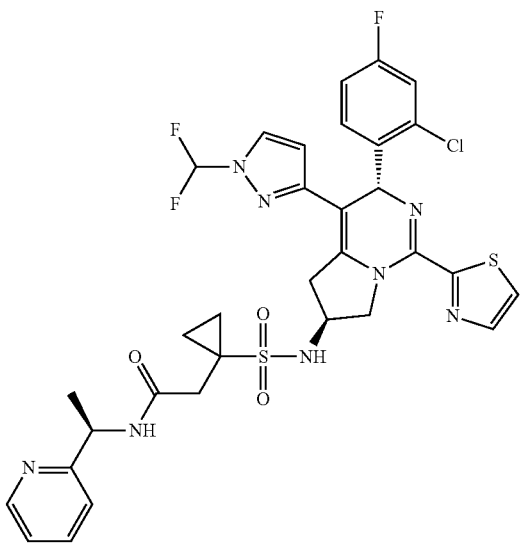 [SMILES: C[C@@H](NC(=O)CC1(S(=O)(=O)N[C@H]2CC3=C(c4ccn(C(F)F)n4)[C@H](c4ccc(F)cc4Cl)N=C(c4nccs4)N3C2)CC1)c1ccccn1]

The title compound was prepared following the general procedure of Example 197. ESI MS m/z=731.16, 733.16 [M+H]+.

Example 374

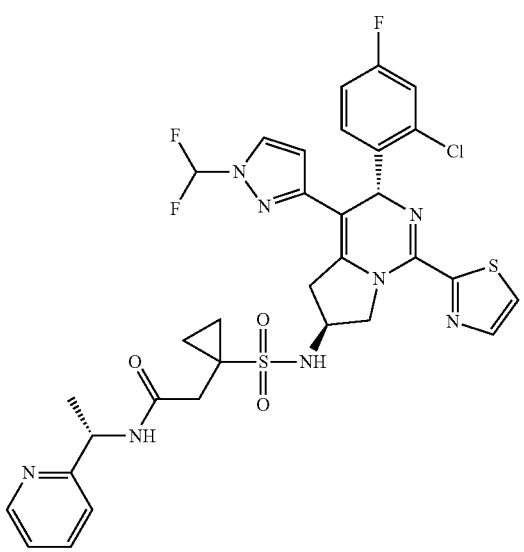 [SMILES: C[C@H](NC(=O)CC1(S(=O)(=O)N[C@H]2CC3=C(c4ccn(C(F)F)n4)[C@H](c4ccc(F)cc4Cl)N=C(c4nccs4)N3C2)CC1)c1ccccn1]

The title compound was prepared following the general procedure of Example 197. ESI MS m/z=731.16, 733.16 [M+H]+.

Example 375

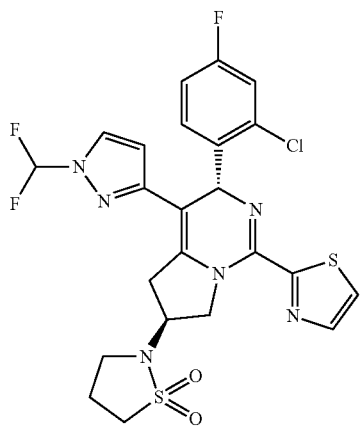 [SMILES: O=S1(=O)CCCN1[C@H]1CC2=C(c3ccn(C(F)F)n3)[C@H](c3ccc(F)cc3Cl)N=C(c3nccs3)N2C1]

The title compound was prepared following the general procedure of Example 2. ESI MS m/z=569.15, 571.15 [M+H]+.

Example 376

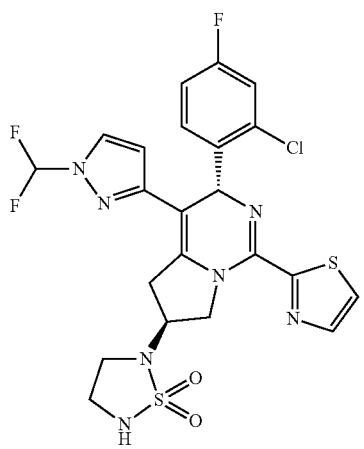 [SMILES: O=S1(=O)NCCN1[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=570.50, 572.50 [M+H]+.

Example 377

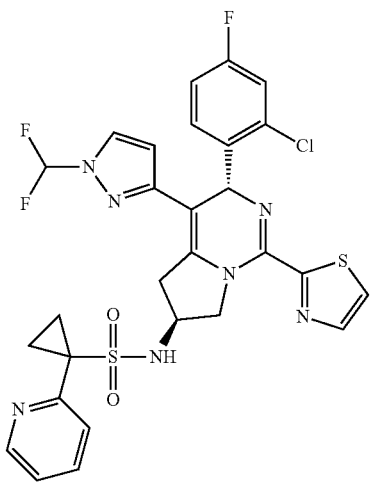 [SMILES: O=S(=O)(N[C@H]1CC2=C(c3ccn(C(F)F)n3)[C@H](c3ccc(F)cc3Cl)N=C(c3nccs3)N2C1)C1(c2ccccn2)CC1]

The title compound was prepared following the general procedure of Example 2. ESI MS m/z=646.15, 648.15 [M+H]+.

Example 378

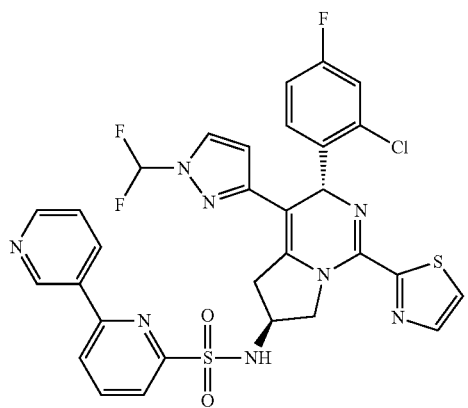 [SMILES: O=S(=O)(N[C@H]1CC2=C(c3ccn(C(F)F)n3)[C@H](c3ccc(F)cc3Cl)N=C(c3nccs3)N2C1)c1cccc(-c2cccnc2)n1]

The title compound was prepared following the general procedure of Example 2. ESI MS m/z=683.10, 685.00 [M+H]+.

Example 379

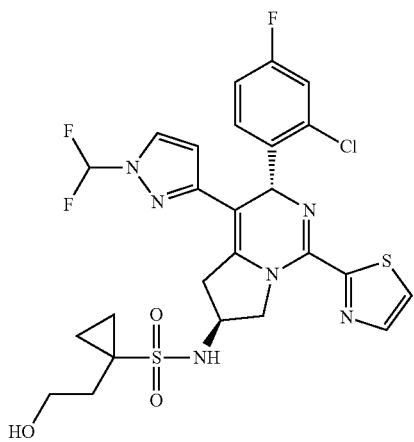 [SMILES: O=S(=O)(N[C@H]1CC2=C(c3ccn(C(F)F)n3)[C@H](c3ccc(F)cc3Cl)N=C(c3nccs3)N2C1)C1(CCO)CC1]

The title compound was prepared following the general procedure of Example 98. ESI MS m/z=613.11, 614.97 [M+H]+.

Example 381

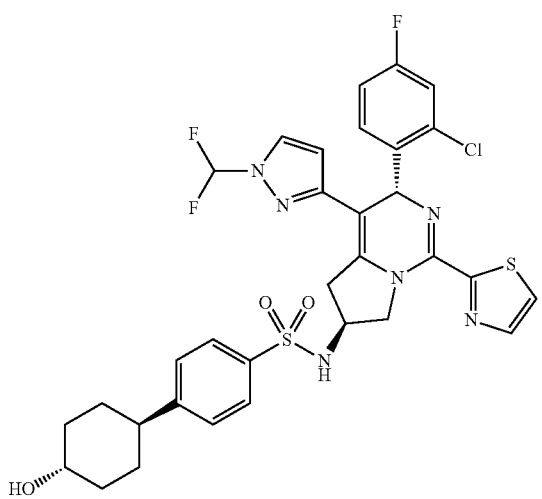

The title compound was prepared following the general procedure of Example 2. ESI MS m/z=703.15, 705.15 [M+H]+.

Example 380

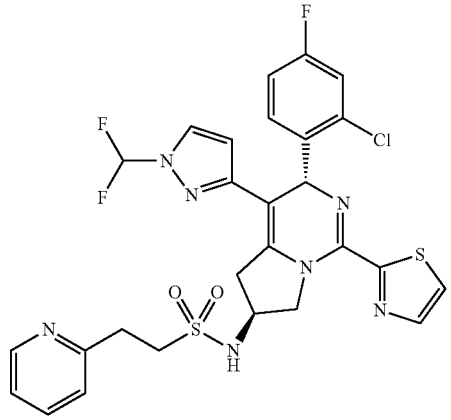 [SMILES: O=S(=O)(CCc1ccccn1)N[C@H]1CC2=C(c3ccn(C(F)F)n3)[C@H](c3ccc(F)cc3Cl)N=C(c3nccs3)N2C1]

The title compound was prepared following the general procedure of Example 2. ESI MS m/z=634.00, 636.00 [M+H]+.

Example 382

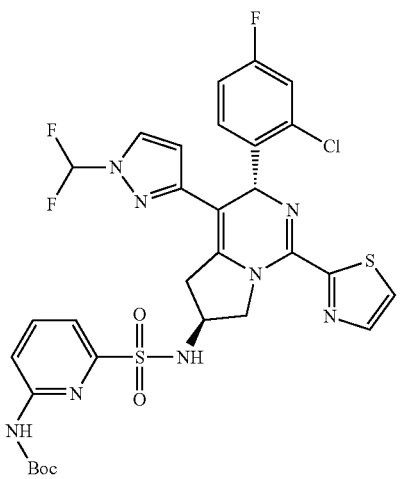 [SMILES: CC(C)(C)OC(=O)Nc1cccc(S(=O)(=O)N[C@H]2CC3=C(c4ccn(C(F)F)n4)[C@H](c4ccc(F)cc4Cl)N=C(c4nccs4)N3C2)n1]

The title compound was prepared following the general procedure of Example 2. ESI MS m/z=721.26, 723.07 [M+H]+.

Example 383

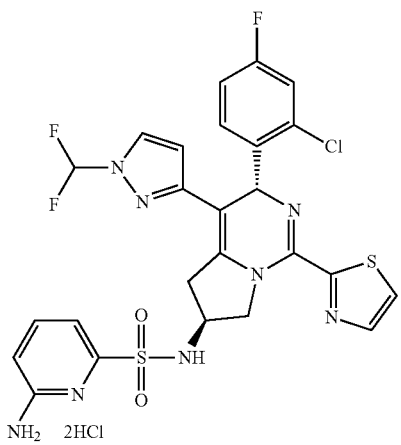 [SMILES: Nc1cccc(S(=O)(=O)N[C@H]2CC3=C(c4ccn(C(F)F)n4)[C@H](c4ccc(F)cc4Cl)N=C(c4nccs4)N3C2)n1 ; "2HCl"]

The title compound was prepared following the general procedure of step 1h. ESI MS m/z=621.14, 623.13 [M+H]+.

Example 384

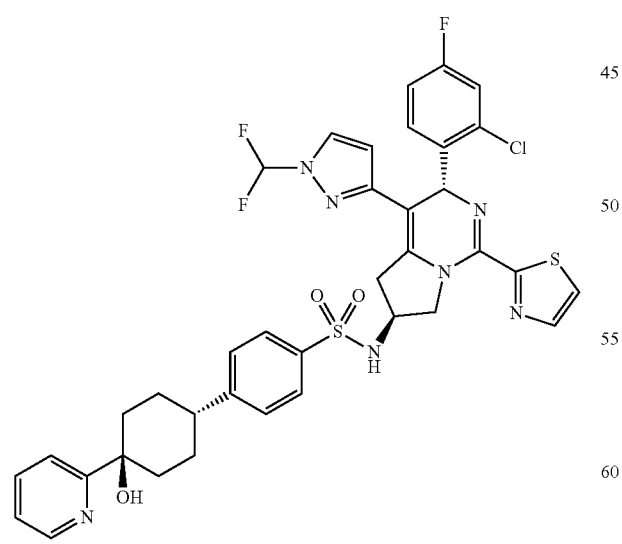

The title compound was prepared following the general procedure of Example 104. ESI MS m/z=780.25, 782.25 [M+H]+.

Example 385

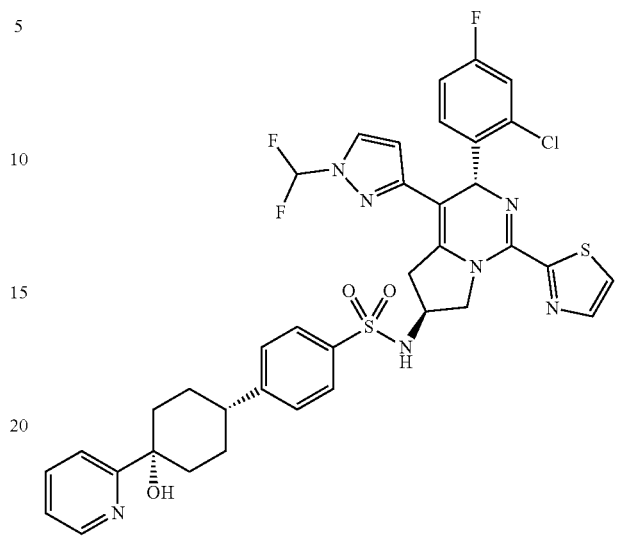

The title compound was isolated from Example 384. ESI MS m/z=780.25, 782.25 [M+H]+.

Example 386

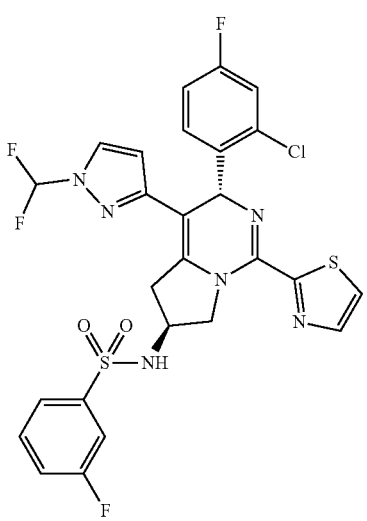 [SMILES: O=S(=O)(N[C@H]1CC2=C(c3ccn(C(F)F)n3)[C@H](c3ccc(F)cc3Cl)N=C(c3nccs3)N2C1)c1cccc(F)c1]

The title compound was prepared following the general procedure of Example 2. ESI MS m/z=623.10, 625.10 [M+H]+.

Example 387

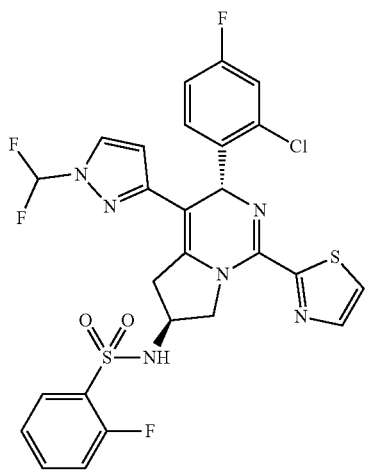 [SMILES: O=S(=O)(N[C@H]1CC2=C(c3ccn(C(F)F)n3)[C@H](c3ccc(F)cc3Cl)N=C(c3nccs3)N2C1)c1ccccc1F]

The title compound was prepared following the general procedure of Example 2. ESI MS m/z=623.10, 625.10 [M+H]+.

Example 388

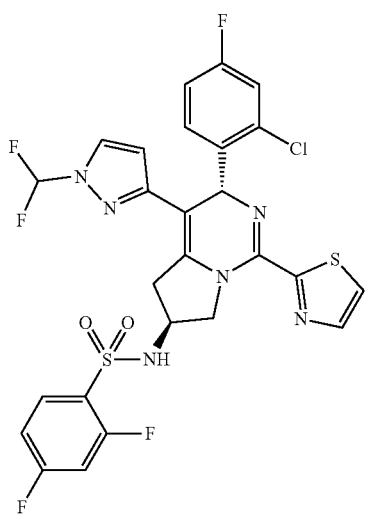 [SMILES: O=S(=O)(N[C@H]1CC2=C(c3ccn(C(F)F)n3)[C@H](c3ccc(F)cc3Cl)N=C(c3nccs3)N2C1)c1ccc(F)cc1F]

The title compound was prepared following the general procedure of Example 2. ESI MS m/z=641.05, 643.05 [M+H]+.

Example 389

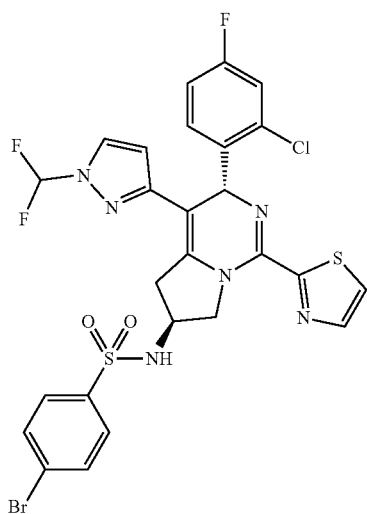 [SMILES: O=S(=O)(N[C@H]1CC2=C(c3ccn(C(F)F)n3)[C@H](c3ccc(F)cc3Cl)N=C(c3nccs3)N2C1)c1ccc(Br)cc1]

The title compound was prepared following the general procedure of Example 2. ESI MS m/z=685.00, 687.00 [M+H]+.

Example 390

The title compound was prepared following the general procedure of Example 2. ESI MS m/z=646.20, 648.20 [M+H]+.

Example 391

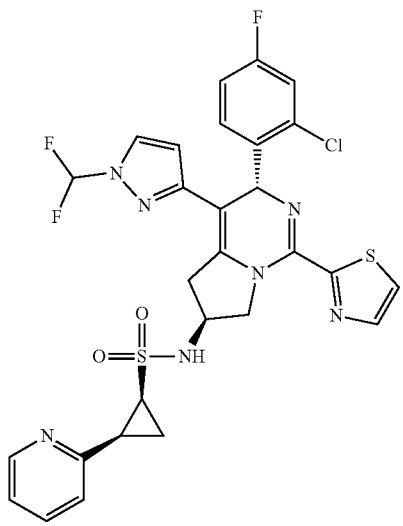 [SMILES: O=S(=O)(N[C@H]1CC2=C(c3ccn(C(F)F)n3)[C@H](c3ccc(F)cc3Cl)N=C(c3nccs3)N2C1)[C@H]1C[C@H]1c1ccccn1]

The title compound was prepared following the general procedure of Example 2. ESI MS m/z=646.20, 648.20 [M+H]$^+$.

Example 393

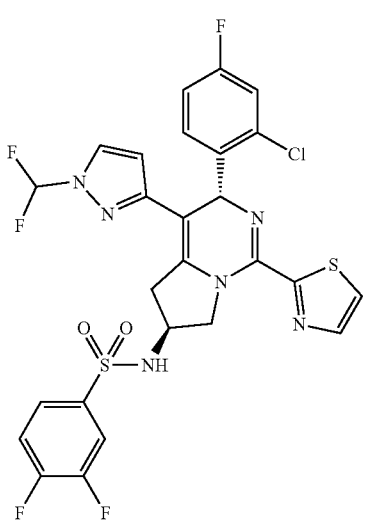

The title compound was prepared following the general procedure of Example 2. ESI MS m/z=641.10, 643.10 [M+H]$^+$.

Example 392

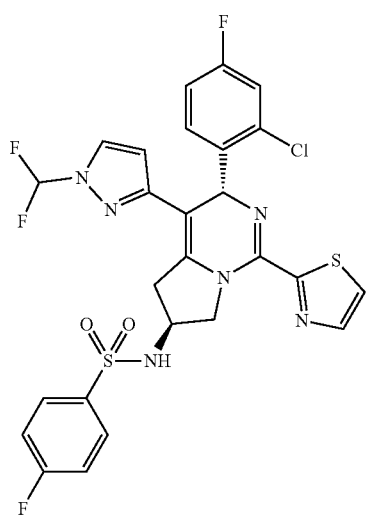 [SMILES: O=S(=O)(N[C@H]1CC2=C(c3ccn(C(F)F)n3)[C@H](c3ccc(F)cc3Cl)N=C(c3nccs3)N2C1)c1ccc(F)cc1]

The title compound was prepared following the general procedure of Example 2. ESI MS m/z=623.10, 625.10 [M+H]$^+$.

Example 394

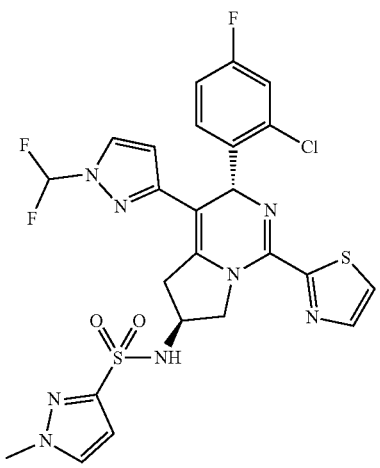 [SMILES: Cn1ccc(S(=O)(=O)N[C@H]2CC3=C(c4ccn(C(F)F)n4)[C@H](c4ccc(F)cc4Cl)N=C(c4nccs4)N3C2)n1]

The title compound was prepared following the general procedure of Example 2. ESI MS m/z=609.10, 611.10 [M+H]$^+$.

Example 395

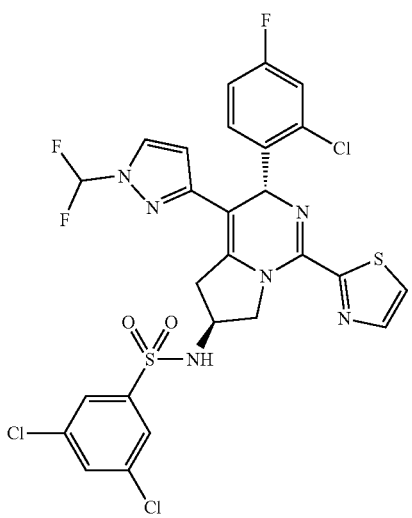 [SMILES: O=S(=O)(N[C@H]1CC2=C(c3ccn(C(F)F)n3)[C@H](c3ccc(F)cc3Cl)N=C(c3nccs3)N2C1)c1cc(Cl)cc(Cl)c1]

VI
The title compound was prepared following the general procedure of Example 2. ESI MS m/z=673.00, 675.00 [M+H]$^+$.

Example 396

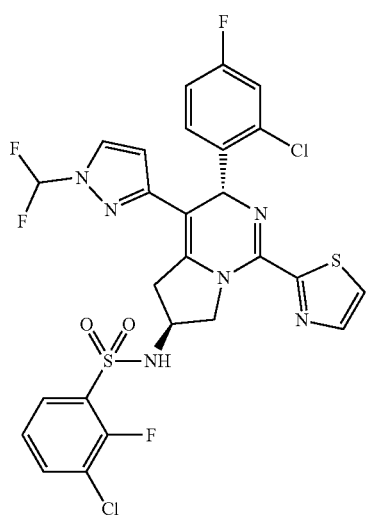 [SMILES: O=S(=O)(N[C@H]1CC2=C(c3ccn(C(F)F)n3)[C@H](c3ccc(F)cc3Cl)N=C(c3nccs3)N2C1)c1cccc(Cl)c1F]

The title compound was prepared following the general procedure of Example 2. ESI MS m/z=657.05, 659.05 [M+H]$^+$.

Example 397

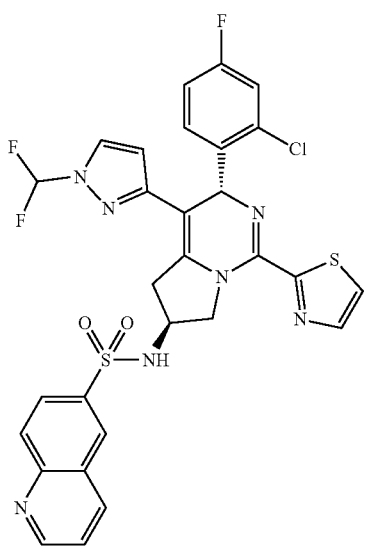 [SMILES: O=S(=O)(N[C@H]1CC2=C(c3ccn(C(F)F)n3)[C@H](c3ccc(F)cc3Cl)N=C(c3nccs3)N2C1)c1ccc2ncccc2c1]

The title compound was prepared following the general procedure of Example 2. ESI MS m/z=656.20, 658.20 [M+H]$^+$.

Example 398

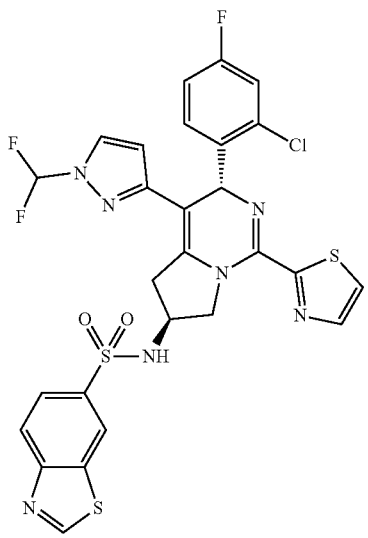 [SMILES: O=S(=O)(N[C@H]1CC2=C(c3ccn(C(F)F)n3)[C@H](c3ccc(F)cc3Cl)N=C(c3nccs3)N2C1)c1ccc2ncsc2c1]

The title compound was prepared following the general procedure of Example 2. ESI MS m/z=662.10, 664.10 [M+H]$^+$.

Example 399

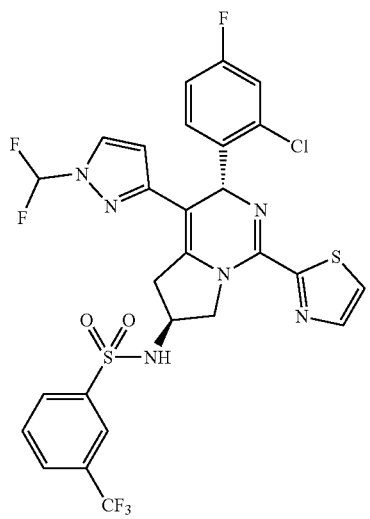 [SMILES: O=S(=O)(N[C@H]1CC2=C(c3ccn(C(F)F)n3)[C@H](c3ccc(F)cc3Cl)N=C(c3nccs3)N2C1)c1cccc(C(F)(F)F)c1]

The title compound was prepared following the general procedure of Example 2. ESI MS m/z=673.25, 675.25 [M+H]+.

Example 400

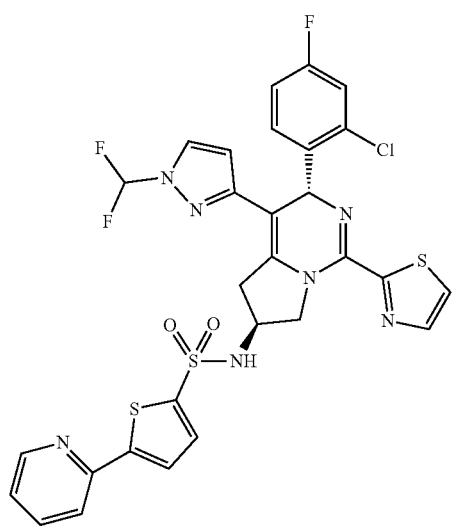 [SMILES: O=S(=O)(N[C@H]1CC2=C(c3ccn(C(F)F)n3)[C@H](c3ccc(F)cc3Cl)N=C(c3nccs3)N2C1)c1ccc(-c2ccccn2)s1]

The title compound was prepared following the general procedure of Example 2. ESI MS m/z=688.15, 690.15 [M+H]+.

Example 401

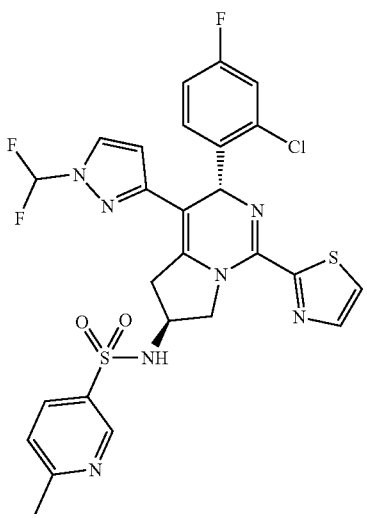 [SMILES: Cc1ccc(S(=O)(=O)N[C@H]2CC3=C(c4ccn(C(F)F)n4)[C@H](c4ccc(F)cc4Cl)N=C(c4nccs4)N3C2)cn1]

The title compound was prepared following the general procedure of Example 2. ESI MS m/z=620.15, 622.15 [M+H]+.

Example 402

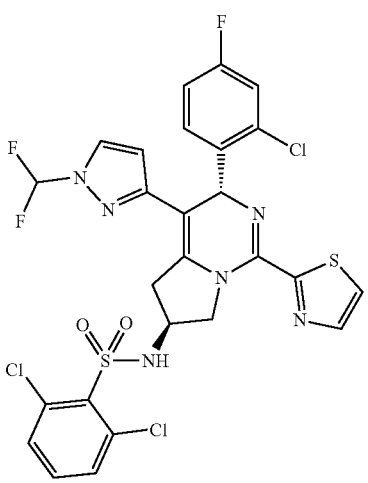 [SMILES: O=S(=O)(N[C@H]1CC2=C(c3ccn(C(F)F)n3)[C@H](c3ccc(F)cc3Cl)N=C(c3nccs3)N2C1)c1c(Cl)cccc1Cl]

The title compound was prepared following the general procedure of Example 2. ESI MS m/z=674.95, 676.95 [M+H]+.

Example 403

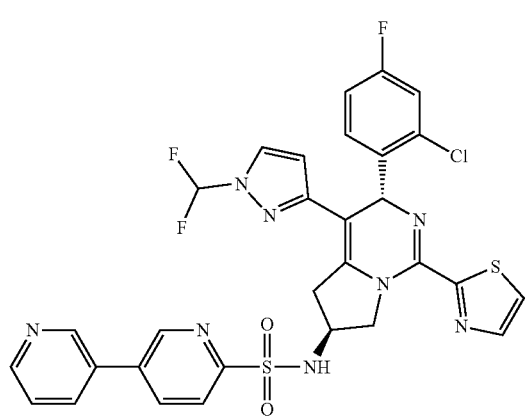 [SMILES: O=S(=O)(N[C@H]1CC2=C(c3ccn(C(F)F)n3)[C@H](c3ccc(F)cc3Cl)N=C(c3nccs3)N2C1)c1ccc(-c2cccnc2)cn1]

The title compound was prepared following the general procedure of Step 1d. ESI MS m/z=683.01, 684.92 [M+H]+.

Example 404

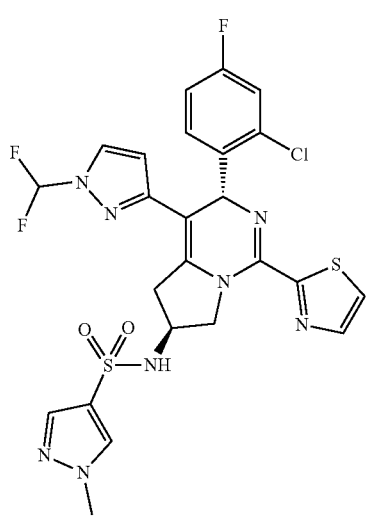 [SMILES: Cn1cc(S(=O)(=O)N[C@H]2CC3=C(c4ccn(C(F)F)n4)[C@H](c4ccc(F)cc4Cl)N=C(c4nccs4)N3C2)cn1]

The title compound was prepared following the general procedure of Example 2. ESI MS m/z=609.05 611.05 [M+H]+.

Example 405

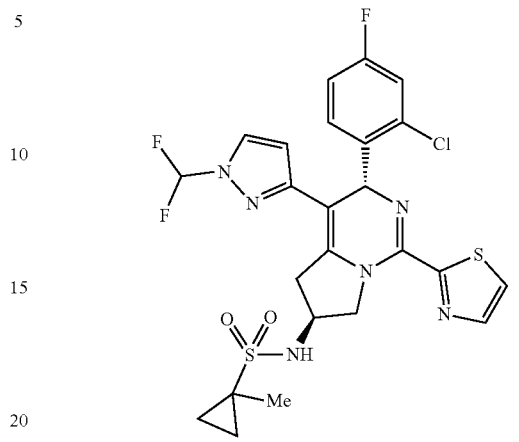

The title compound was prepared following the general procedure of Example 2. ESI MS m/z=583.15, 585.15 [M+H]+.

Example 406

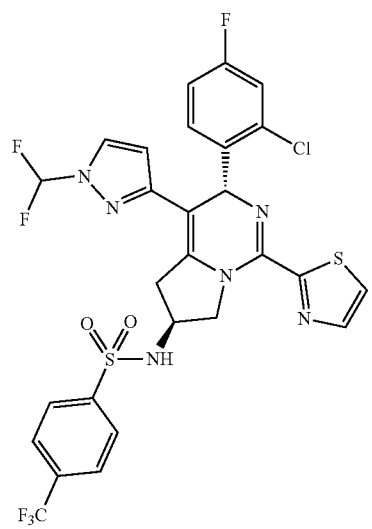 [SMILES: O=S(=O)(N[C@H]1CC2=C(c3ccn(C(F)F)n3)[C@H](c3ccc(F)cc3Cl)N=C(c3nccs3)N2C1)c1ccc(C(F)(F)F)cc1]

The title compound was prepared following the general procedure of Example 2. ESI MS m/z=673.00, 675.00 [M+H]+.

Example 407

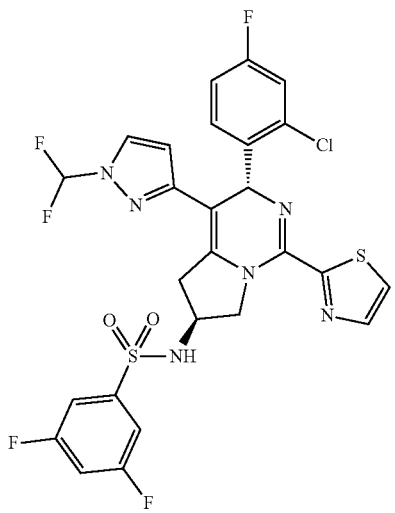 [SMILES: O=S(=O)(N[C@H]1CC2=C(c3ccn(C(F)F)n3)[C@H](c3ccc(F)cc3Cl)N=C(c3nccs3)N2C1)c1cc(F)cc(F)c1]

The title compound was prepared following the general procedure of Example 2. ESI MS m/z=641.00 643.00 [M+H]⁺.

Example 408

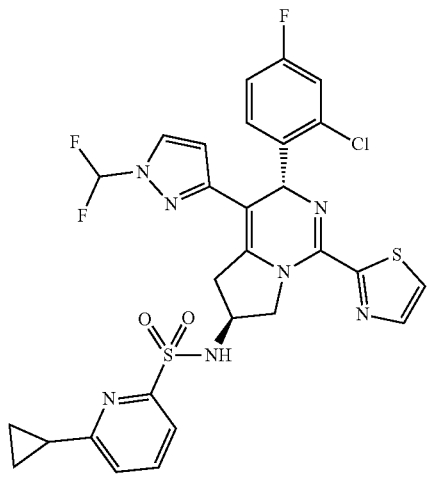 [SMILES: O=S(=O)(N[C@H]1CC2=C(c3ccn(C(F)F)n3)[C@H](c3ccc(F)cc3Cl)N=C(c3nccs3)N2C1)c1cccc(C2CC2)n1]

The title compound was prepared following the general procedure of Step 1d. ESI MS m/z=646.15, 648.15 [M+H]⁺.

Example 409

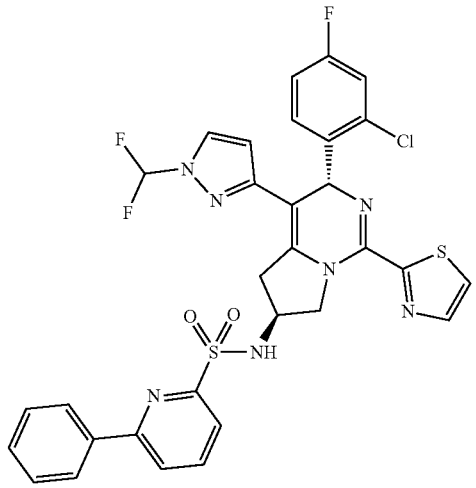 [SMILES: O=S(=O)(N[C@H]1CC2=C(c3ccn(C(F)F)n3)[C@H](c3ccc(F)cc3Cl)N=C(c3nccs3)N2C1)c1cccc(-c2ccccc2)n1]

The title compound was prepared following the general procedure of Step 1d. ESI MS m/z=682.15, 684.15 [M+H]⁺.

Example 410

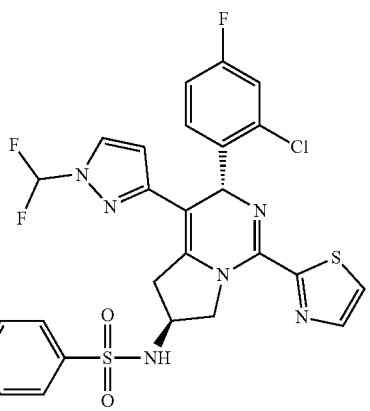

The title compound was prepared following the general procedure of Example 104. ESI MS m/z=717.45, 719.45 [M+H]⁺.

Example 411
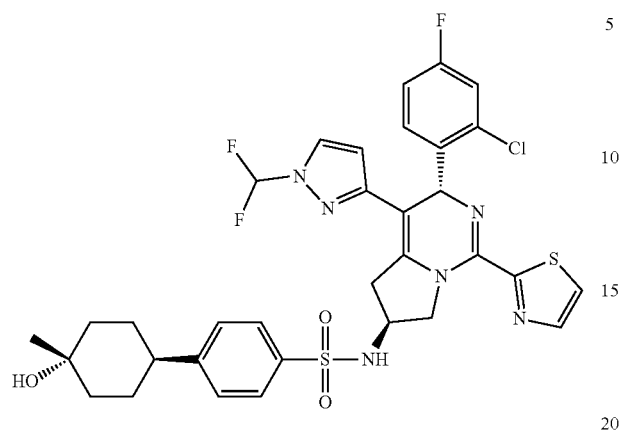
The title compound was isolated from Example 411. ESI MS m/z=717.25, 717.25 [M+H]+.
Example 413
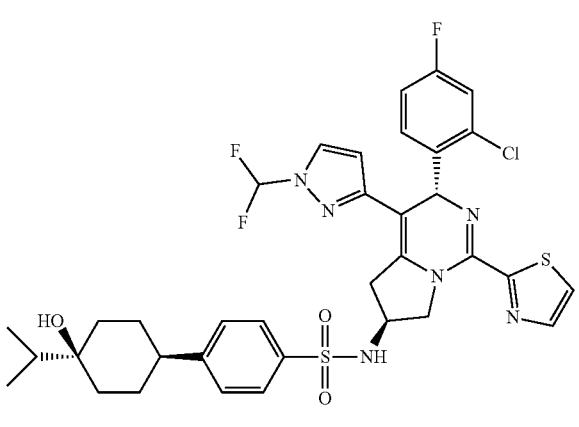
The title compound was prepared following the general procedure of Example 104. ESI MS m/z=745.35, 747.35 [M+H]+.
Example 412
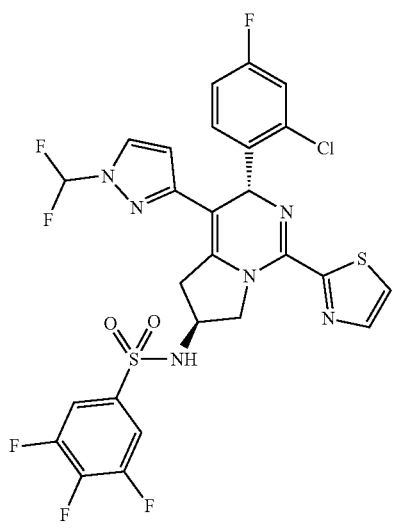 [SMILES: O=S(=O)(N[C@H]1CC2=C(c3ccn(C(F)F)n3)[C@H](c3ccc(F)cc3Cl)N=C(c3nccs3)N2C1)c1cc(F)c(F)c(F)c1]
The title compound was prepared following the general procedure of Example 2. ESI MS m/z=659.00, 661.00 [M+H]+.
Example 414
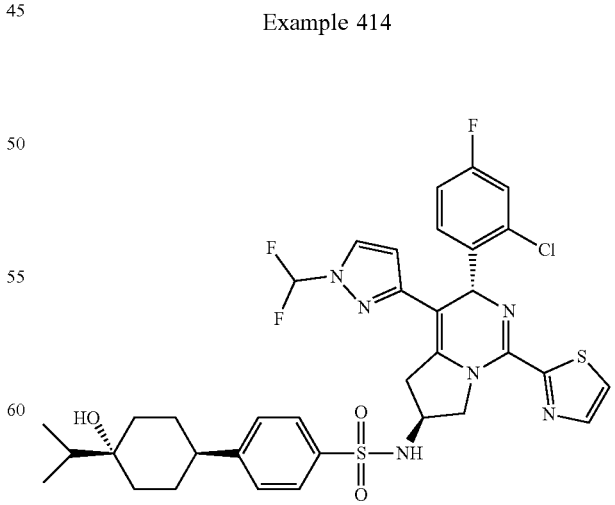
The title compound was isolated from Example 413. ESI MS m/z=745.10, 747.10 [M+H]+.

Example 415

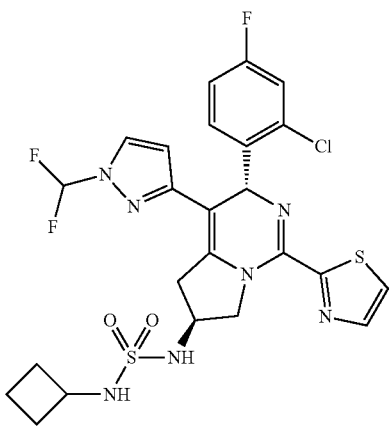 [SMILES: O=S(=O)(NC1CCC1)N[C@H]1CC2=C(c3ccn(C(F)F)n3)[C@H](c3ccc(F)cc3Cl)N=C(c3nccs3)N2C1]

The title compound was prepared following the general procedure of Example 73. ESI MS m/z=598.15, 600.15 [M+H]$^+$.

Example 417

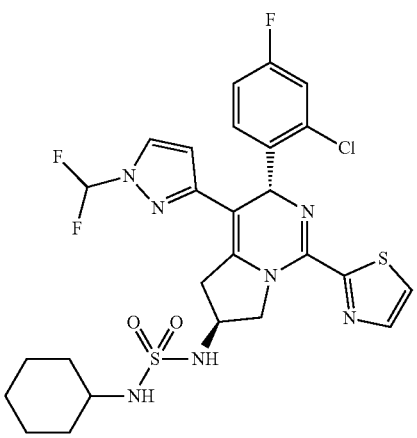

The title compound was prepared following the general procedure of Example 73. ESI MS m/z=626.20, 628.20 [M+H]$^+$.

Example 416

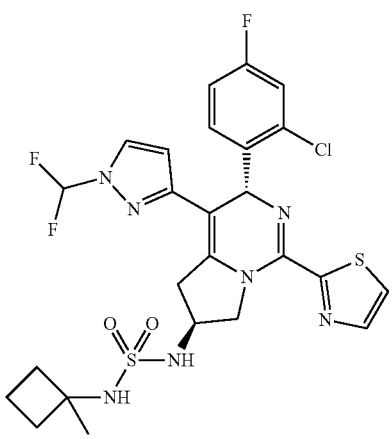 [SMILES: CC1(NS(=O)(=O)N[C@H]2CC3=C(c4ccn(C(F)F)n4)[C@H](c4ccc(F)cc4Cl)N=C(c4nccs4)N3C2)CCC1]

The title compound was prepared following the general procedure of Example 73. ESI MS m/z=612.15, 614.15 [M+H]$^+$.

Example 418

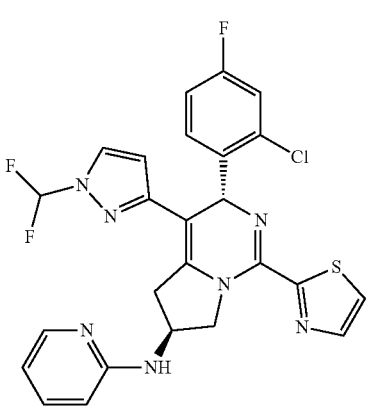 [SMILES: Fc1ccc([C@@H]2N=C(c3nccs3)N3C[C@@H](Nc4ccccn4)CC3=C2c2ccn(C(F)F)n2)c(Cl)c1]

The title compound was prepared following the general procedure of Example 197. ESI MS m/z=542.06, 543.94 [M+H]$^+$.

Example 419

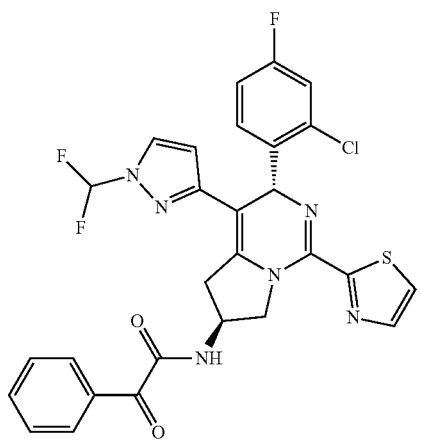 [SMILES: O=C(N[C@H]1CC2=C(c3ccn(C(F)F)n3)[C@H](c3ccc(F)cc3Cl)N=C(c3nccs3)N2C1)C(=O)c1ccccc1]

The title compound was prepared following the general procedure of Example 197. ESI MS m/z=597.29, 599.10 [M+H]$^+$.

Example 421

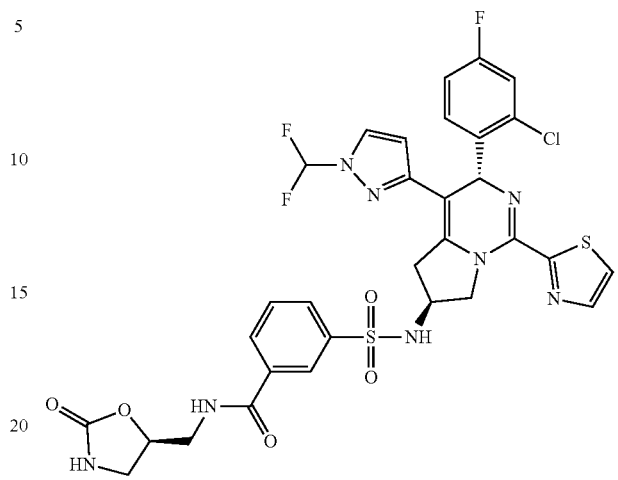

The title compound was prepared following the general procedure of Example 197. ESI MS m/z=747.12, 749.12 [M+H]$^+$.

Example 420

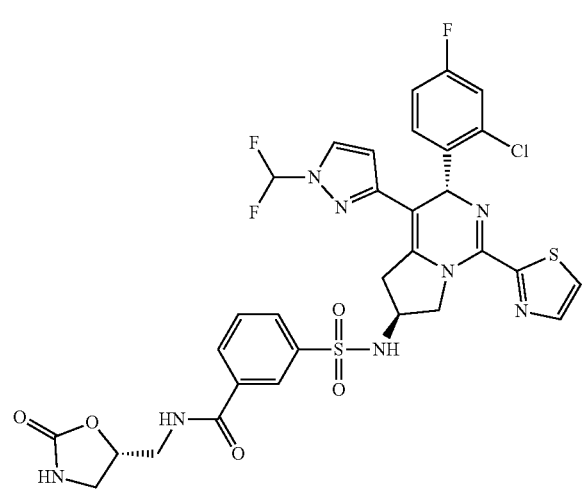 [SMILES: O=C1NC[C@@H](CNC(=O)c2cccc(S(=O)(=O)N[C@H]3CC4=C(c5ccn(C(F)F)n5)[C@H](c5ccc(F)cc5Cl)N=C(c5nccs5)N4C3)c2)O1]

The title compound was prepared following the general procedure of Example 197. ESI MS m/z=747.12, 749.12 [M+H]$^+$.

Example 422

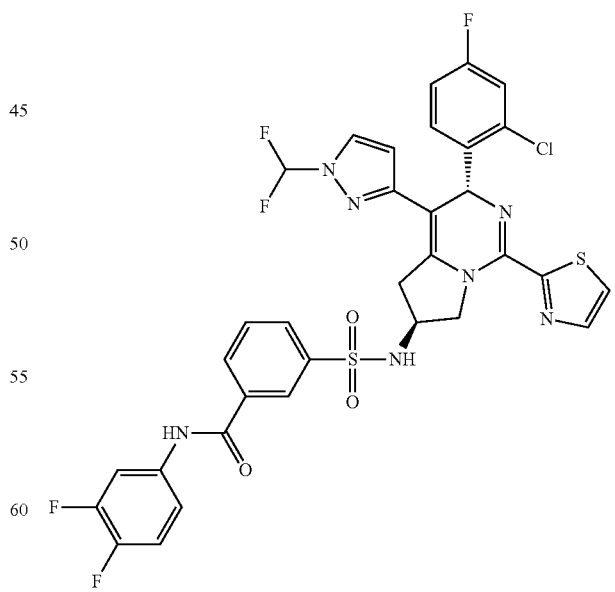

The title compound was prepared following the general procedure of Example 2. ESI MS m/z=760.10, 762.10 [M+H]$^+$.

Example 423

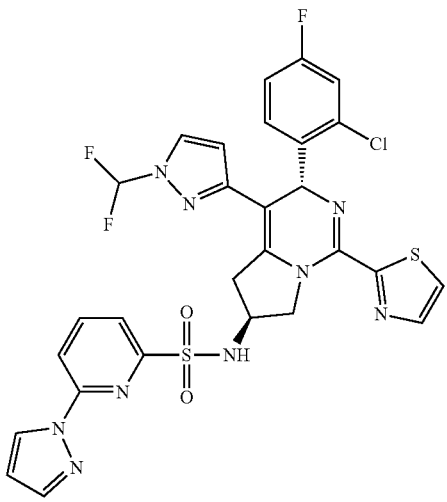 [SMILES: O=S(=O)(N[C@H]1CC2=C(c3ccn(C(F)F)n3)[C@H](c3ccc(F)cc3Cl)N=C(c3nccs3)N2C1)c1cccc(-n2cccn2)n1]

The title compound was prepared following the general procedure of Step 1d. ESI MS m/z=672.10, 674.10 [M+H]+.

Example 425

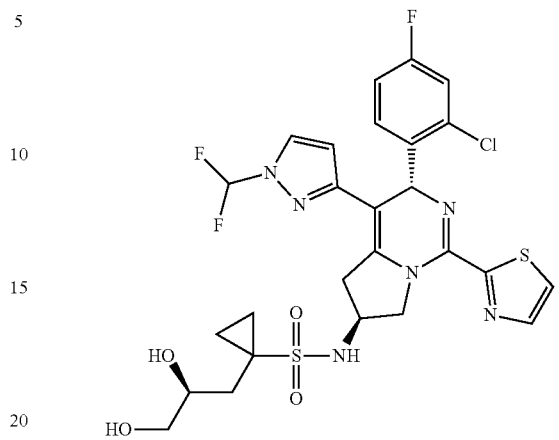

The title compound was prepared following the general procedure of Example 2. ESI MS m/z=643.12, 645.12 [M+H]+.

Example 424

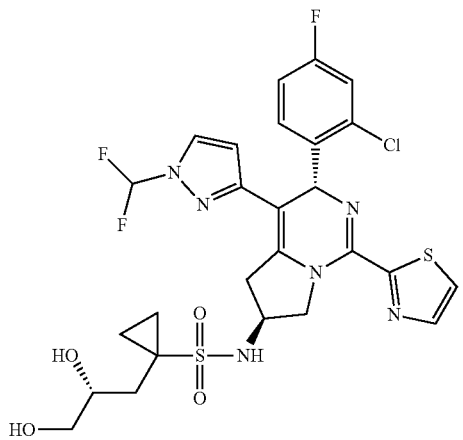 [SMILES: O=S(=O)(N[C@H]1CC2=C(c3ccn(C(F)F)n3)[C@H](c3ccc(F)cc3Cl)N=C(c3nccs3)N2C1)C1(C[C@@H](O)CO)CC1]

The title compound was prepared following the general procedure of Example 2. ESI MS m/z=643.12, 645.12 [M+H]+.

Example 426

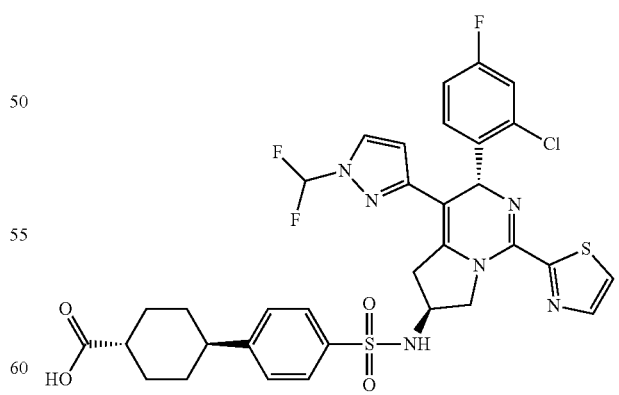

The title compound was prepared following the general procedure of Example 5. ESI MS m/z=731.35, 733.35 [M+H]+.

The following compounds are prepared following the general procedure described above:

| Example # | Structure |
|---|---|
| 1a | 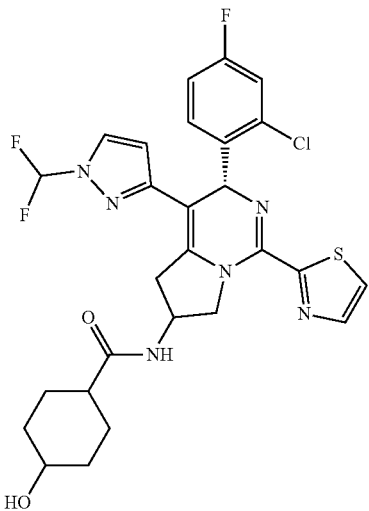 [SMILES: O=C(NC1CC2=C(c3ccn(C(F)F)n3)[C@H](c3ccc(F)cc3Cl)N=C(c3nccs3)N2C1)C1CCC(O)CC1] |
| 2a | 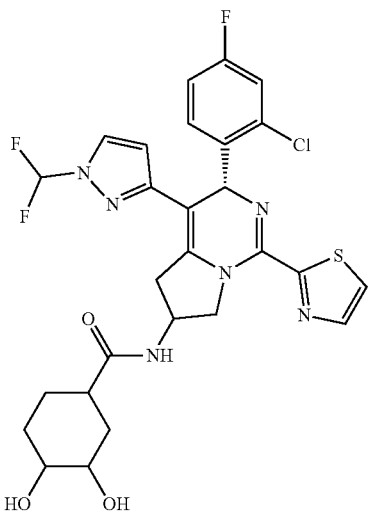 [SMILES: O=C(NC1CC2=C(c3ccn(C(F)F)n3)[C@H](c3ccc(F)cc3Cl)N=C(c3nccs3)N2C1)C1CCC(O)C(O)C1] |
| 3a | 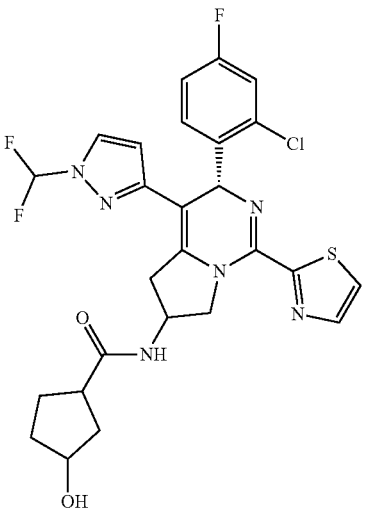 [SMILES: O=C(NC1CC2=C(c3ccn(C(F)F)n3)[C@H](c3ccc(F)cc3Cl)N=C(c3nccs3)N2C1)C1CCC(O)C1] |

| Example # | Structure |
|---|---|
| 4a | 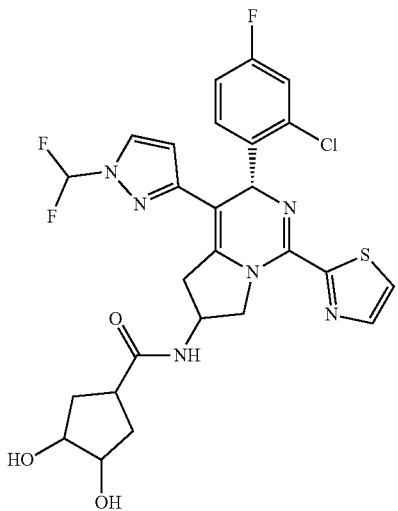 [SMILES: O=C(NC1CC2=C(c3ccn(C(F)F)n3)[C@H](c3ccc(F)cc3Cl)N=C(c3nccs3)N2C1)C1CC(O)C(O)C1] |
| 5a | 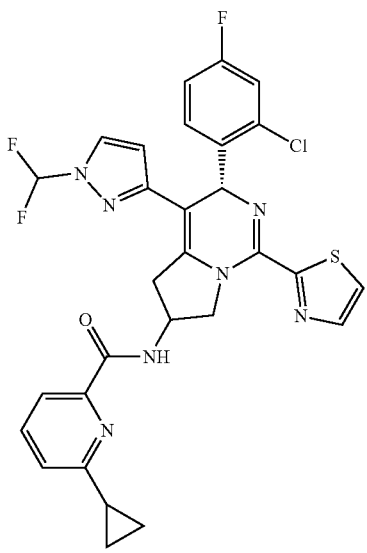 [SMILES: O=C(NC1CC2=C(c3ccn(C(F)F)n3)[C@H](c3ccc(F)cc3Cl)N=C(c3nccs3)N2C1)c1cccc(C2CC2)n1] |

-continued
| Example # | Structure |
|---|---|
| 6a | 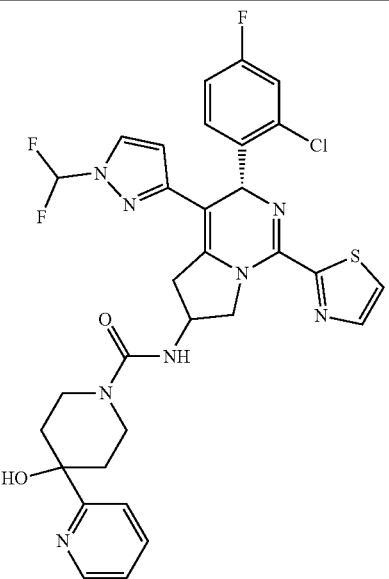 |
| 7a | 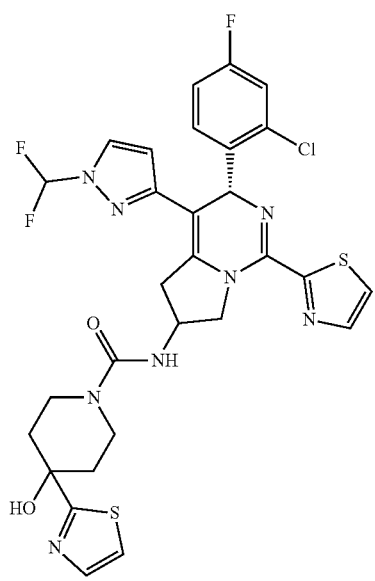 [SMILES: O=C(NC1CC2=C(c3ccn(C(F)F)n3)[C@H](c3ccc(F)cc3Cl)N=C(c3nccs3)N2C1)N1CCC(O)(c2nccs2)CC1] |
| 8a | 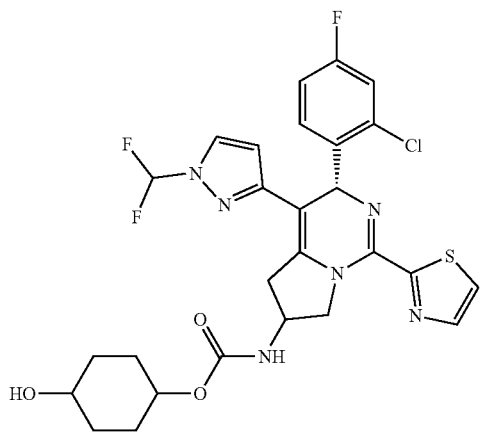 [SMILES: O=C(NC1CC2=C(c3ccn(C(F)F)n3)[C@H](c3ccc(F)cc3Cl)N=C(c3nccs3)N2C1)OC1CCC(O)CC1] |

| Example # | Structure |
|---|---|
| 9a | 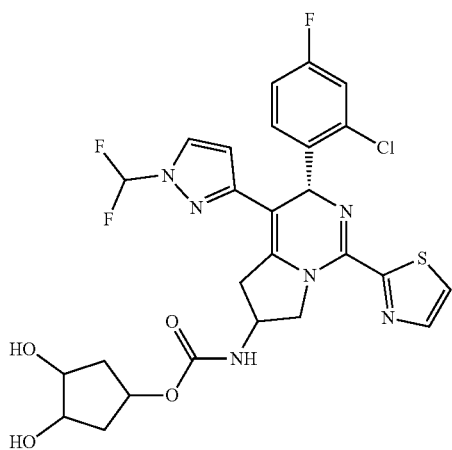 [SMILES: O=C(NC1CC2=C(c3ccn(C(F)F)n3)[C@H](c3ccc(F)cc3Cl)N=C(c3nccs3)N2C1)OC1CC(O)C(O)C1] |
| 10a | 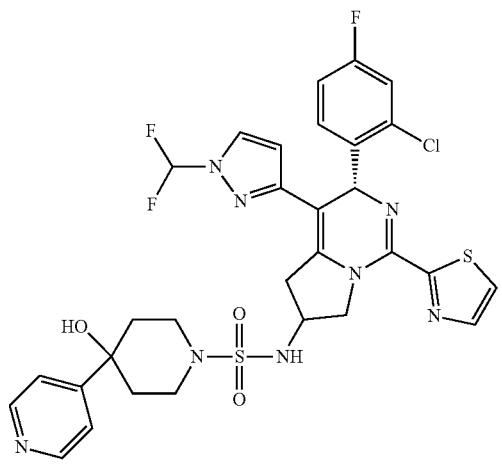 [SMILES: O=S(=O)(NC1CC2=C(c3ccn(C(F)F)n3)[C@H](c3ccc(F)cc3Cl)N=C(c3nccs3)N2C1)N1CCC(O)(c2ccncc2)CC1] |
| 11a | 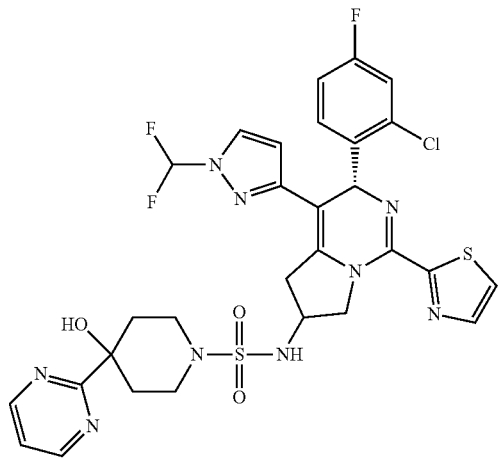 [SMILES: O=S(=O)(NC1CC2=C(c3ccn(C(F)F)n3)[C@H](c3ccc(F)cc3Cl)N=C(c3nccs3)N2C1)N1CCC(O)(c2ncccn2)CC1] |

| Example # | Structure |
|---|---|
| 12a | 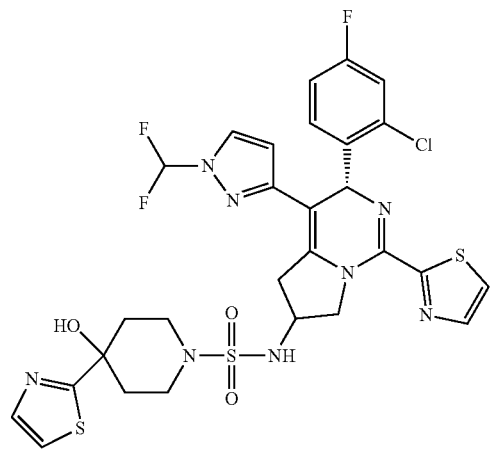 [SMILES: O=S(=O)(NC1CC2=C(c3ccn(C(F)F)n3)[C@H](c3ccc(F)cc3Cl)N=C(c3nccs3)N2C1)N1CCC(O)(c2nccs2)CC1] |
| 13a | 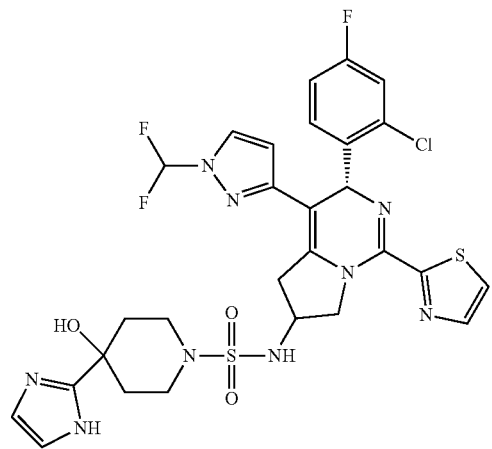 [SMILES: O=S(=O)(NC1CC2=C(c3ccn(C(F)F)n3)[C@H](c3ccc(F)cc3Cl)N=C(c3nccs3)N2C1)N1CCC(O)(c2ncc[nH]2)CC1] |
| 14a | 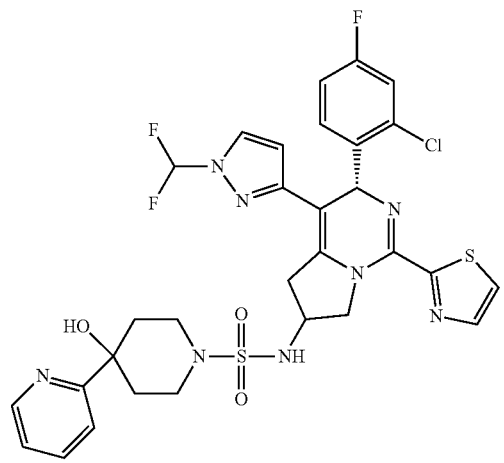 [SMILES: O=S(=O)(NC1CC2=C(c3ccn(C(F)F)n3)[C@H](c3ccc(F)cc3Cl)N=C(c3nccs3)N2C1)N1CCC(O)(c2ccccn2)CC1] |

| Example # | Structure |
|---|---|
| 15a | 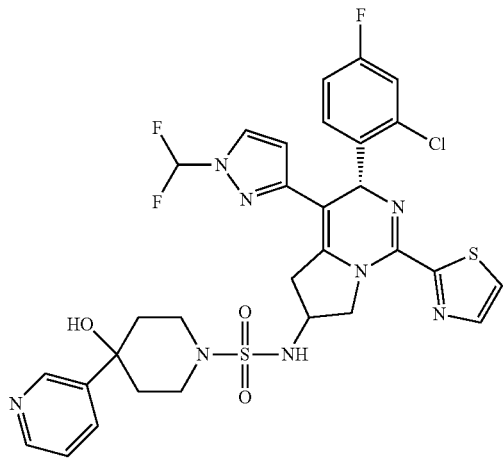 [SMILES: O=S(=O)(NC1CC2=C(c3ccn(C(F)F)n3)[C@H](c3ccc(F)cc3Cl)N=C(c3nccs3)N2C1)N1CCC(O)(c2cccnc2)CC1] |
| 16a | 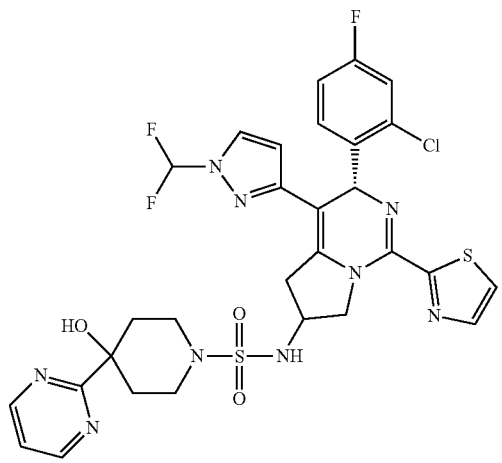 [SMILES: O=S(=O)(NC1CC2=C(c3ccn(C(F)F)n3)[C@H](c3ccc(F)cc3Cl)N=C(c3nccs3)N2C1)N1CCC(O)(c2ncccn2)CC1] |
| 17a | 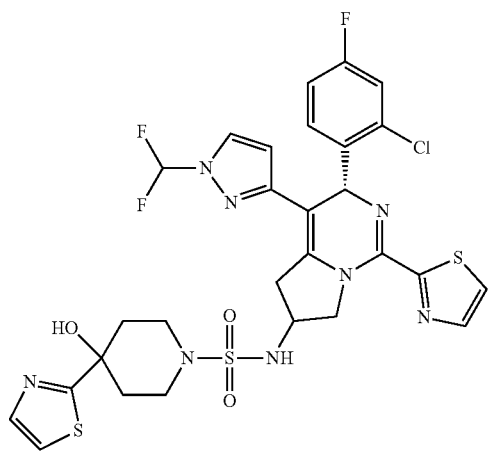 [SMILES: O=S(=O)(NC1CC2=C(c3ccn(C(F)F)n3)[C@H](c3ccc(F)cc3Cl)N=C(c3nccs3)N2C1)N1CCC(O)(c2nccs2)CC1] |

| Example # | Structure |
|---|---|
| 18a | 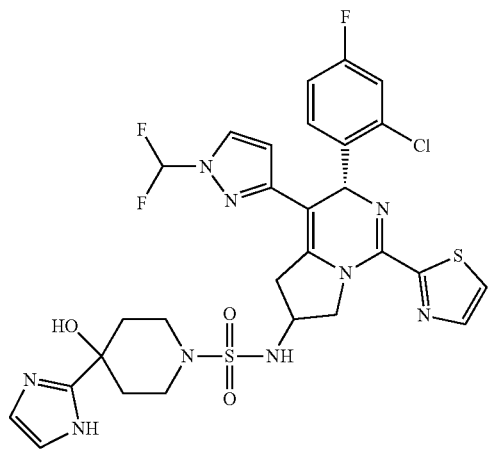 [SMILES: O=S(=O)(NC1CC2=C(c3ccn(C(F)F)n3)[C@H](c3ccc(F)cc3Cl)N=C(c3nccs3)N2C1)N1CCC(O)(c2ncc[nH]2)CC1] |
| 19a | 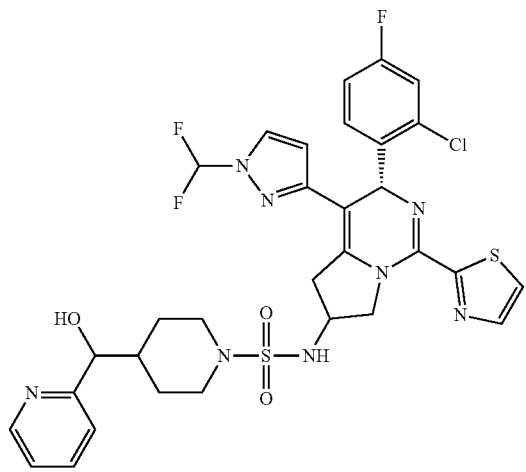 [SMILES: O=S(=O)(NC1CC2=C(c3ccn(C(F)F)n3)[C@H](c3ccc(F)cc3Cl)N=C(c3nccs3)N2C1)N1CCC(C(O)c2ccccn2)CC1] |
| 20a | 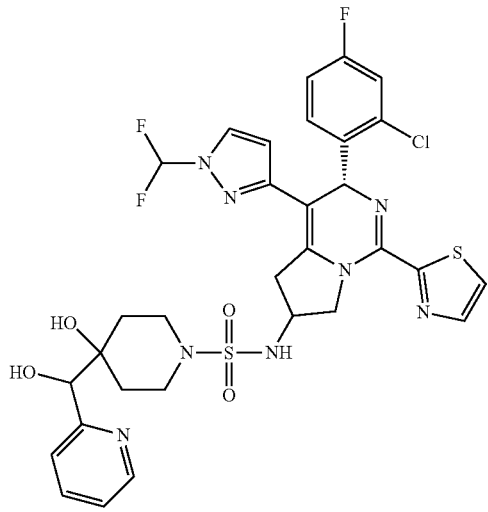 [SMILES: O=S(=O)(NC1CC2=C(c3ccn(C(F)F)n3)[C@H](c3ccc(F)cc3Cl)N=C(c3nccs3)N2C1)N1CCC(O)(C(O)c2ccccn2)CC1] |

-continued
| Example # | Structure |
|---|---|
| 21a | 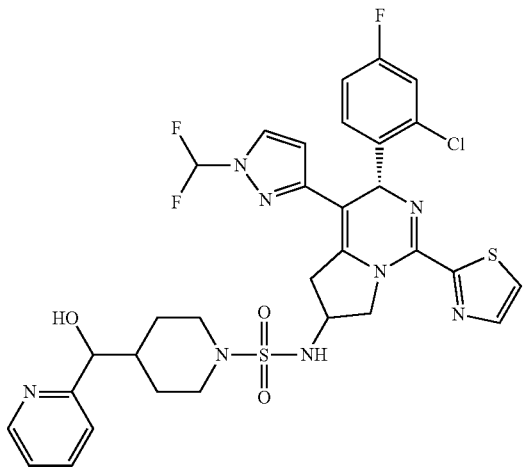 [SMILES: O=S(=O)(NC1CC2=C(c3ccn(C(F)F)n3)[C@H](c3ccc(F)cc3Cl)N=C(c3nccs3)N2C1)N1CCC(C(O)c2ccccn2)CC1] |
| 22a | 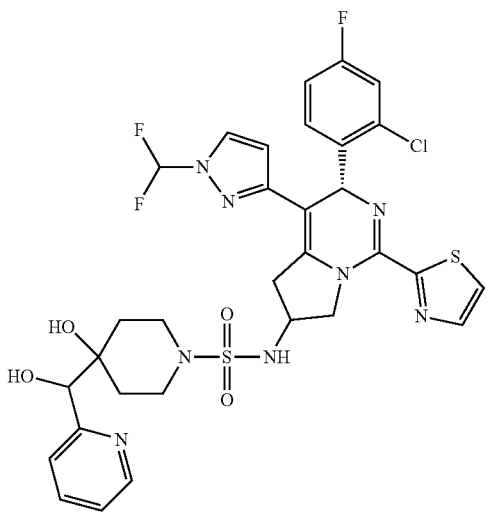 [SMILES: O=S(=O)(NC1CC2=C(c3ccn(C(F)F)n3)[C@H](c3ccc(F)cc3Cl)N=C(c3nccs3)N2C1)N1CCC(O)(C(O)c2ccccn2)CC1] |
| 23a | 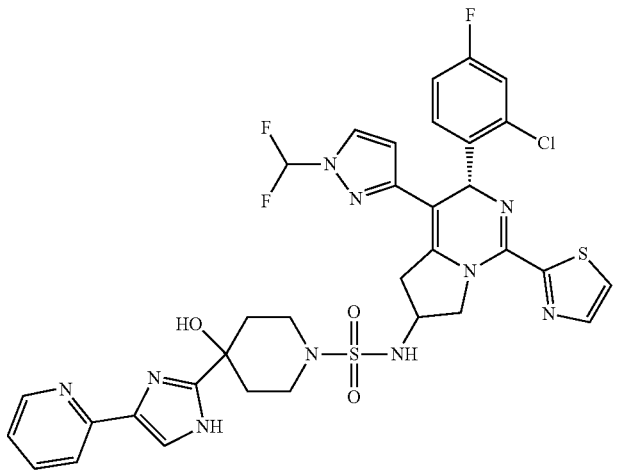 [SMILES: O=S(=O)(NC1CC2=C(c3ccn(C(F)F)n3)[C@H](c3ccc(F)cc3Cl)N=C(c3nccs3)N2C1)N1CCC(O)(c2nc(-c3ccccn3)c[nH]2)CC1] |

| Example # | Structure |
|---|---|
| 24a | 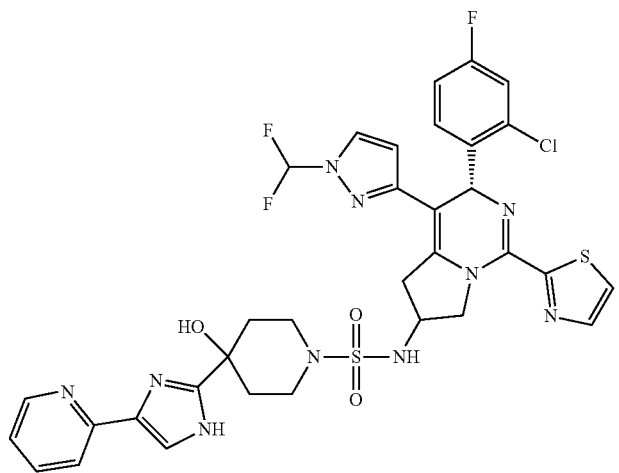 [SMILES: O=S(=O)(NC1CC2=C(c3ccn(C(F)F)n3)[C@H](c3ccc(F)cc3Cl)N=C(c3nccs3)N2C1)N1CCC(O)(c2nc(-c3ccccn3)c[nH]2)CC1] |
| 25a | 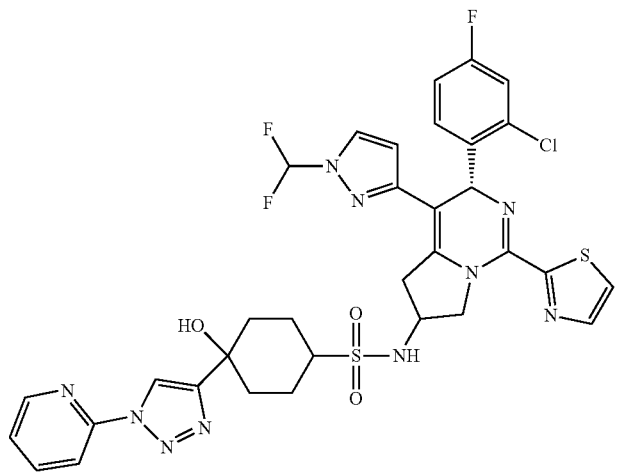 |
| 26a | 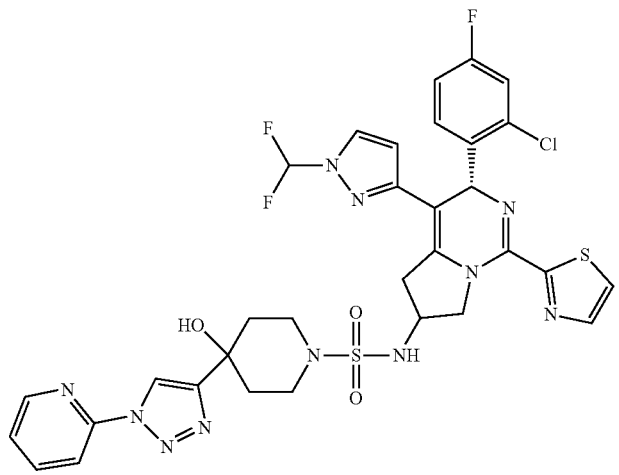 [SMILES: O=S(=O)(NC1CC2=C(c3ccn(C(F)F)n3)[C@H](c3ccc(F)cc3Cl)N=C(c3nccs3)N2C1)C1CCC(O)(c2cn(-c3ccccn3)nn2)CC1] |

| Example # | Structure |
|---|---|
| 27a | 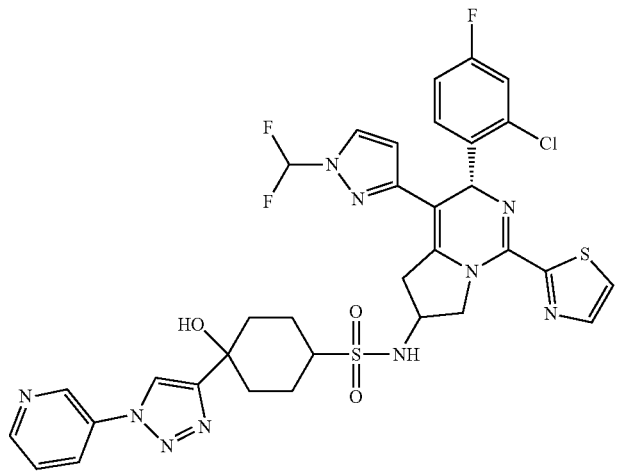 |
| 28a | 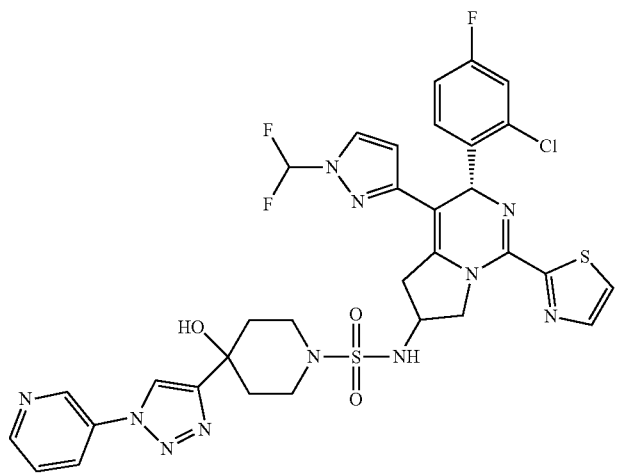 [SMILES: O=S(=O)(NC1CC2=C(c3ccn(C(F)F)n3)[C@H](c3ccc(F)cc3Cl)N=C(c3nccs3)N2C1)C1CCC(O)(c2cn(-c3cccnc3)nn2)CC1] |
| 29a | 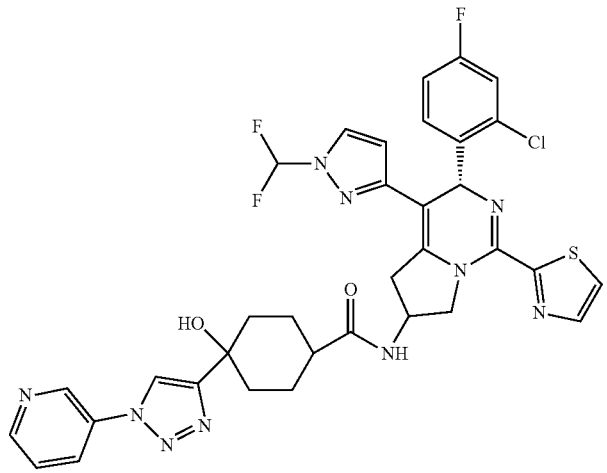 [SMILES: O=C(NC1CC2=C(c3ccn(C(F)F)n3)[C@H](c3ccc(F)cc3Cl)N=C(c3nccs3)N2C1)C1CCC(O)(c2cn(-c3cccnc3)nn2)CC1] |

| Example # | Structure |
|---|---|
| 30a | (structure shown) |

BIOLOGICAL ACTIVITY

Methods: HepAD38 cells are maintained as previously reported (Ladner et al, *Antimicrob. Agents Chemother.* 1997, 4, 1715). Briefly, cells are passaged upon attaining confluency in DMEM/F12 media in the presence of 10% FBS, Penn/Strep, 250 µg/mL G418, and 1 µg/ml tetracycline. Novel compounds are screened by first washing cells three times with PBS to remove tetracycline, and plating in 96 well plates at 35,000 cells/well. Compounds dissolved in DMSO are then diluted 1:200 into wells containing cells. Five days after compound addition, material is harvested for analysis. For an extended 8 day analysis, cells are plated and treated as described above, but media and compound are refreshed on d2 and d5 post initial treatment.

On harvest day, virion DNA is obtained by lysing with Sidestep Lysis and Stabilization Buffer and then quantified via quantitative real time PCR. Commercially available ELISA kits are used to quantitate the viral proteins HBsAg (Alpco) or HbeAg (US Biological) by following the manufacturer's recommended protocol after diluting samples to match the linear range of their respective assays. Irrespective of readout, compound concentrations that reduce viral product accumulation in the cell lysates or supernatants by 50% relative to no drug controls ($EC_{50}$) are reported; $EC_{50}$ ranges are as follows: A<0.1 µM; B 0.1-0.4 µM; C>0.4 µM.

Compound toxicity is evaluated by seeding cells at 15,000 cells/well and treating with compound as described above. Three days after compound addition, cells are treated with ATPLite reagent and compound concentrations that reduce total ATP levels in wells by 50% relative to no drug controls ($CC_{50}$) are reported; $CC_{50}$ ranges are as follows: A>25 µM; B 10-25 µM; C<10 µM.

TABLE 1

Summary of Activities

| Compd. Number | HepAD38 $EC_{50}$ (µM) | HepG2 $CC_{50}$ (µM) | Compd. Number | HepAD38 $EC_{50}$ (µM) | HepG2 $CC_{50}$ (µM) |
|---|---|---|---|---|---|
| 2 | A | | 4 | B | |
| 5 | A | | 6 | A | |

TABLE 1-continued

Summary of Activities

| Compd. Number | HepAD38 $EC_{50}$ (µM) | HepG2 $CC_{50}$ (µM) | Compd. Number | HepAD38 $EC_{50}$ (µM) | HepG2 $CC_{50}$ (µM) |
|---|---|---|---|---|---|
| 7 | C | | 8 | B | |
| 9 | A | | 10 | C | |
| 11 | A | | 12 | B | |
| 13 | B | | 14 | B | |
| 15 | B | | 16 | C | |
| 17 | B | | 18 | C | |
| 19 | B | | 20 | A | A |
| 21 | A | B | 22 | B | |
| 23 | B | | 24 | B | |
| 25 | B | | 26 | C | |
| 27 | B | | 28 | B | |
| 29 | C | | 30 | B | |
| 31 | A | | 32 | B | |
| 33 | B | | 34 | A | |
| 35 | A | | 36 | A | |
| 37 | C | | 38 | C | |
| 39 | C | | 40 | B | |
| 41 | B | | 42 | C | |
| 43 | C | | 44 | C | |
| 45 | C | | 46 | C | |
| 47 | C | | 48 | C | |
| 49 | C | | 50 | B | |
| 51 | C | | 52 | A | |
| 53 | A | | 54 | B | |
| 55 | B | | 56 | B | |
| 57 | A | | 58 | B | |
| 59 | B | | 60 | C | |
| 61 | A | | 62 | A | |
| 63 | C | | 64 | C | |
| 65 | C | | 66 | C | |
| 67 | C | | 68 | C | |
| 69 | C | | 70 | A | A |
| 71 | B | | 72 | A | A |
| 73 | A | B | 74 | A | A |
| 75 | A | A | 76 | A | |
| 77 | A | | 78 | A | A |
| 79 | A | A | 80 | A | A |
| 81 | A | A | 82 | B | |
| 83 | B | | 87 | A | |
| 88 | A | A | 89 | A | A |
| 90 | A | | 91 | A | A |
| 92 | A | A | 93 | A | A |
| 94 | A | A | 95 | A | A |
| 96 | A | A | 97 | A | A |

TABLE 1-continued

Summary of Activities

| Compd. Number | HepAD38 EC$_{50}$ (µM) | HepG2 CC$_{50}$ (µM) |
|---|---|---|
| 98 | A | A |
| 99 | A | A |
| 100 | A | A |
| 101 | A | |
| 102 | A | |
| 103 | A | |
| 104 | A | |
| 105 | A | |
| 106 | C | |
| 107 | C | |
| 108 | B | |
| 109 | B | |
| 110 | B | |
| 111 | C | |
| 112 | C | |
| 113 | C | |
| 114 | C | |
| 115 | C | |
| 116 | C | |
| 117 | C | |
| 118 | C | |
| 119 | C | |
| 120 | C | |
| 121 | C | |
| 122 | C | |
| 123 | C | |
| 124 | A | |
| 125 | A | |
| 126 | C | |
| 127 | C | |
| 128 | C | |
| 129 | C | |
| 130 | B | |
| 131 | B | |
| 132 | C | |
| 133 | C | |
| 134 | B | |
| 135 | A | A |
| 136 | B | |
| 137 | C | |
| 138 | C | |
| 139 | B | |
| 140 | A | A |
| 141 | C | |
| 142 | C | |
| 143 | B | |
| 144 | B | |
| 145 | C | |
| 146 | C | |
| 147 | C | |
| 148 | C | |
| 149 | C | |
| 150 | A | A |
| 151 | A | A |
| 152 | A | A |
| 153 | A | A |
| 154 | A | A |
| 155 | A | A |
| 156 | A | A |
| 157 | A | A |
| 158 | B | |
| 159 | C | |
| 160 | A | |
| 161 | B | |
| 162 | A | |
| 163 | A | |
| 164 | C | |
| 165 | B | |
| 166 | B | |
| 167 | C | |
| 168 | A | |
| 169 | B | |
| 170 | B | |
| 171 | B | |
| 172 | B | |
| 173 | A | |
| 174 | B | |
| 175 | B | |
| 176 | A | |
| 177 | A | C |
| 178 | A | |
| 179 | C | |
| 180 | C | |
| 181 | B | |
| 182 | B | |
| 183 | B | |
| 184 | C | |
| 185 | B | |
| 186 | B | |
| 187 | C | |
| 188 | C | |
| 189 | C | |
| 190 | C | |
| 191 | C | |
| 192 | C | |
| 193 | C | |
| 194 | B | |
| 195 | A | |
| 196 | B | |
| 197 | B | |
| 198 | A | |
| 199 | B | |
| 200 | C | |
| 201 | A | |
| 202 | A | |
| 203 | A | |
| 204 | A | |
| 205 | A | |
| 206 | B | |
| 207 | A | |
| 208 | A | |
| 209 | A | |
| 210 | A | |
| 211 | B | |
| 212 | B | |
| 213 | A | B |
| 214 | A | B |
| 216 | B | |
| 217 | C | |
| 218 | C | |
| 219 | B | |
| 220 | C | |
| 221 | B | |
| 222 | B | |
| 223 | B | |
| 224 | A | |
| 225 | A | |
| 226 | B | |
| 227 | A | |
| 228 | C | |
| 229 | B | |
| 230 | B | |
| 231 | A | |
| 232 | A | |
| 233 | A | |
| 234 | A | |
| 235 | A | A |
| 236 | A | |
| 237 | B | |
| 238 | B | |
| 239 | B | |
| 240 | A | |
| 241 | B | |
| 242 | B | |
| 243 | B | |
| 244 | B | |
| 245 | B | |
| 246 | B | |
| 247 | C | |
| 248 | C | |
| 249 | B | |
| 250 | B | |
| 251 | A | |
| 252 | C | |
| 253 | A | |
| 254 | A | |
| 255 | B | |
| 256 | A | A |
| 257 | A | B |
| 258 | A | |
| 259 | A | A |
| 260 | A | A |
| 261 | A | A |
| 262 | A | |
| 263 | B | |
| 264 | A | A |
| 265 | A | |
| 266 | A | A |
| 267 | A | A |
| 268 | A | |
| 269 | A | A |
| 270 | A | C |
| 271 | A | B |
| 272 | A | |
| 273 | A | C |
| 274 | A | C |
| 275 | A | B |
| 276 | A | C |
| 277 | A | |
| 278 | A | |
| 279 | A | |
| 280 | A | A |
| 281 | A | |
| 282 | A | A |
| 283 | B | |
| 284 | A | |
| 285 | A | A |
| 286 | A | |
| 287 | A | B |
| 288 | A | |
| 289 | A | A |
| 290 | A | A |
| 291 | A | |
| 292 | A | |
| 293 | A | A |
| 294 | A | A |
| 295 | A | |
| 296 | A | |
| 297 | B | |
| 298 | B | |
| 299 | A | |
| 300 | A | |
| 301 | A | A |
| 302 | A | A |
| 303 | A | A |
| 304 | A | A |
| 305 | B | |
| 306 | B | |
| 307 | A | |
| 308 | A | |
| 309 | A | A |
| 310 | A | |
| 311 | A | |
| 312 | B | |
| 313 | A | |
| 314 | B | |
| 315 | B | |
| 316 | B | |
| 317 | A | |
| 318 | A | |
| 319 | A | |
| 320 | B | |
| 321 | A | |
| 322 | B | |
| 323 | A | B |
| 324 | A | B |
| 325 | B | |
| 326 | B | |
| 327 | A | |
| 328 | A | |
| 329 | A | |
| 330 | B | |
| 331 | B | |
| 332 | A | A |
| 333 | A | |
| 334 | A | C |
| 335 | A | A |
| 336 | A | A |
| 337 | A | A |
| 338 | A | |
| 339 | A | A |
| 340 | A | A |
| 341 | B | |
| 342 | A | A |
| 343 | A | |
| 344 | B | |
| 345 | A | |
| 346 | A | |
| 347 | B | |
| 348 | A | |
| 349 | A | |
| 350 | B | |
| 351 | A | |
| 352 | B | |
| 353 | A | A |
| 354 | B | |
| 355 | B | |
| 356 | B | |
| 357 | A | A |
| 358 | A | A |
| 359 | A | A |
| 360 | B | |
| 361 | A | A |
| 362 | A | A |
| 363 | A | B |
| 364 | A | A |
| 365 | A | A |
| 366 | A | |
| 367 | A | A |
| 368 | A | A |
| 369 | A | A |
| 370 | A | A |
| 371 | A | B |
| 372 | A | |
| 373 | A | |
| 374 | A | |
| 375 | B | |
| 376 | A | A |
| 377 | A | A |
| 378 | A | A |
| 379 | A | B |
| 380 | B | |
| 381 | A | B |
| 382 | B | |
| 383 | A | A |
| 384 | A | |
| 385 | A | A |
| 386 | A | B |
| 387 | A | A |
| 388 | A | A |
| 389 | A | A |
| 390 | B | |
| 391 | B | |
| 392 | B | |
| 393 | B | |
| 394 | A | A |
| 395 | B | |
| 396 | B | |
| 397 | A | |
| 398 | A | |

TABLE 1-continued

Summary of Activities

| Compd. Number | HepAD38 EC$_{50}$ (μM) | HepG2 CC$_{50}$ (μM) | Compd. Number | HepAD38 EC$_{50}$ (μM) | HepG2 CC$_{50}$ (μM) |
|---|---|---|---|---|---|
| 399 | B | | 400 | A | |
| 401 | A | A | 402 | B | |
| 403 | A | A | 404 | A | |
| 405 | A | | 406 | A | |
| 407 | B | | 408 | A | |
| 409 | A | | 410 | A | A |
| 411 | A | B | 412 | A | |
| 413 | A | | 414 | A | |
| 415 | A | | 416 | A | |
| 417 | A | | 418 | B | |
| 419 | B | | 420 | A | A |
| 421 | A | A | 422 | B | |
| 423 | B | | 424 | A | A |
| 425 | A | | 426 | A | A |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound selected from the group consisting of:

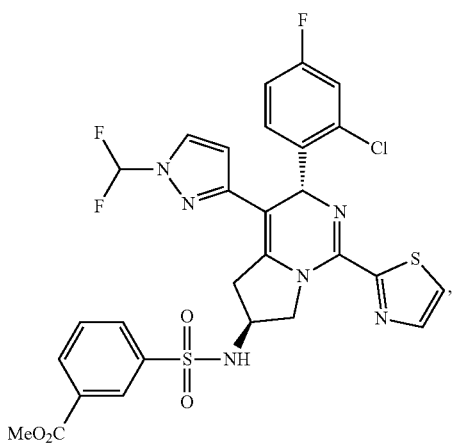

2

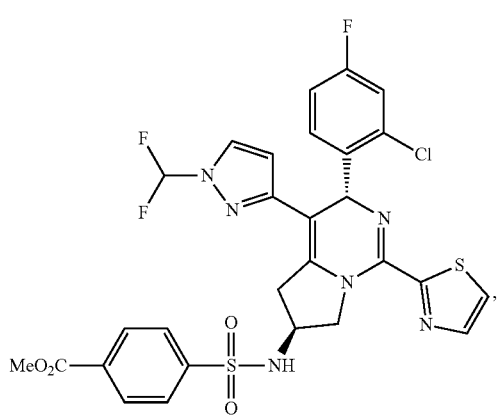

3

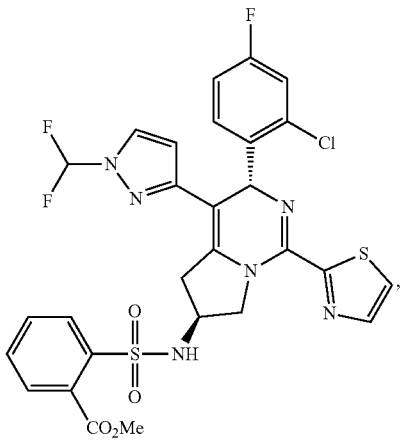

4

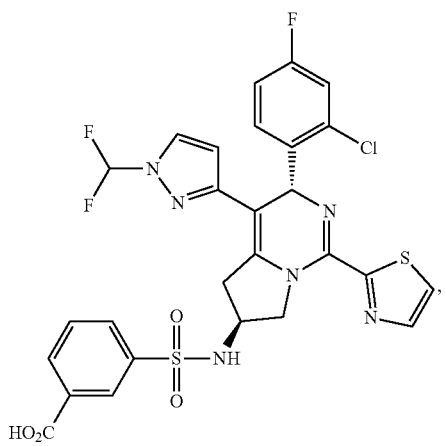

5

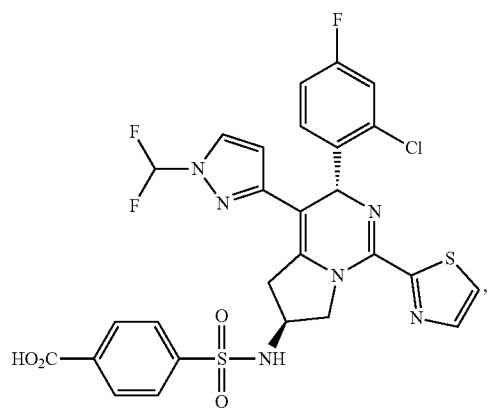

6

295
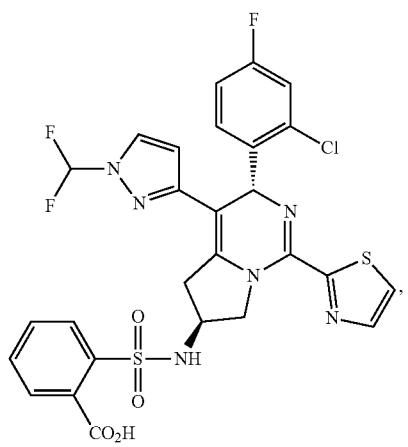
7
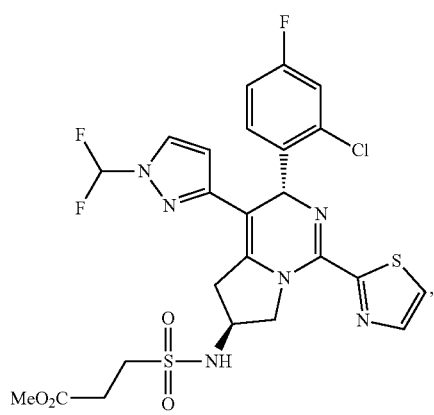
8
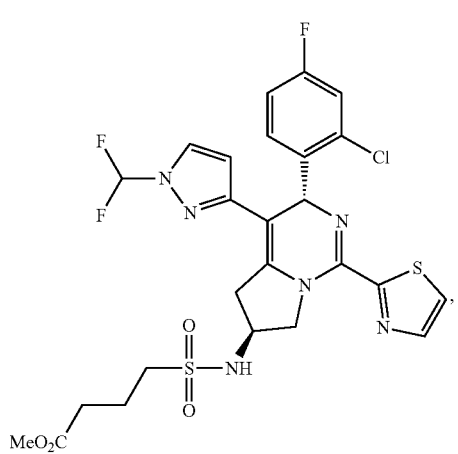
9
296
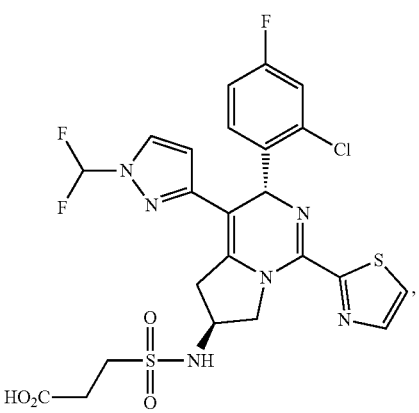
10
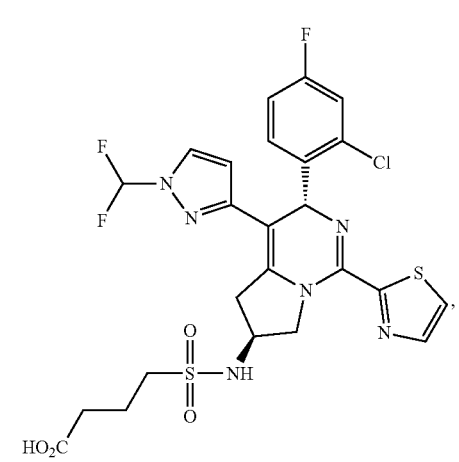
11
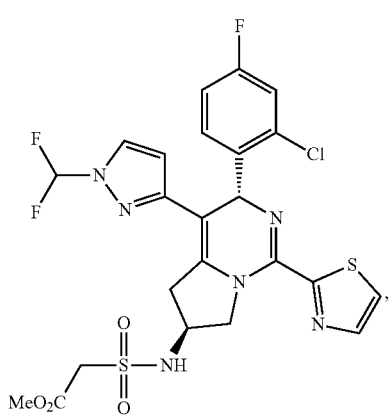
12

297
-continued
13
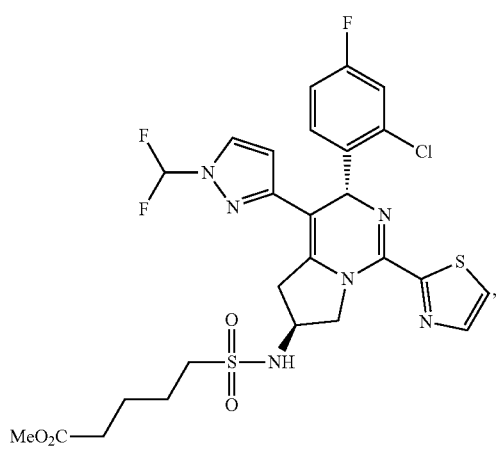
18
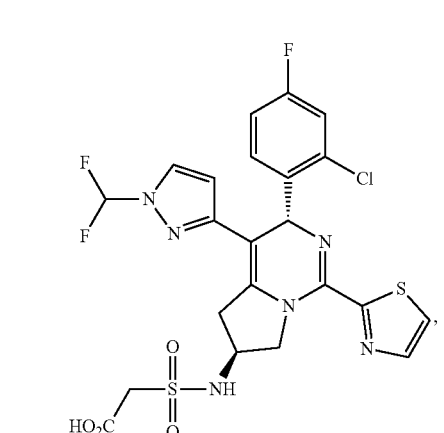
19
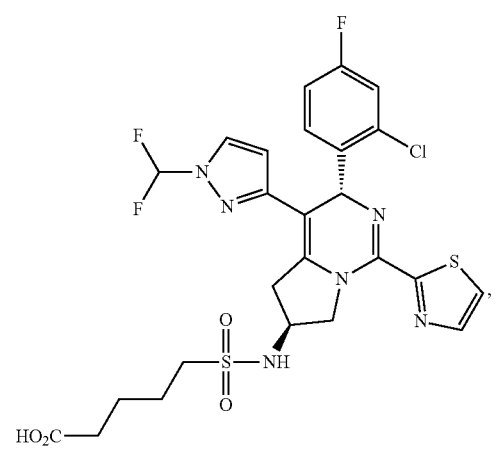
298
-continued
22
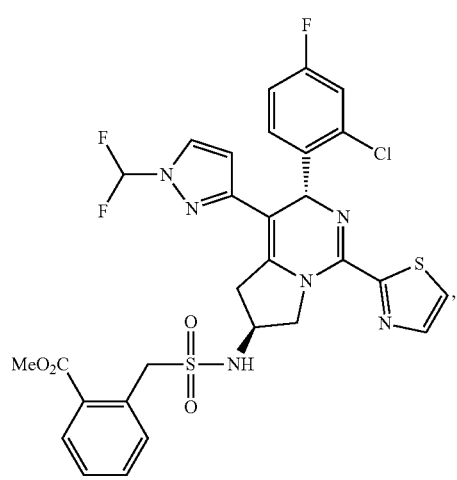
23
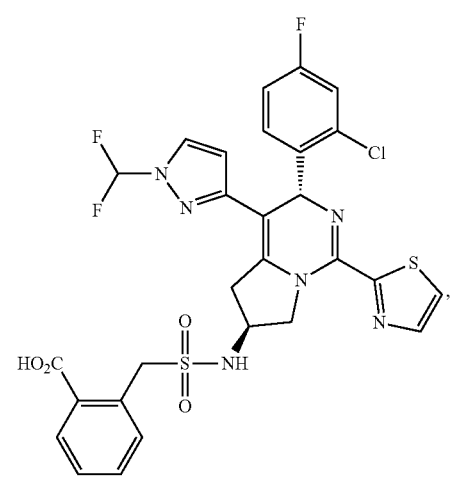
24
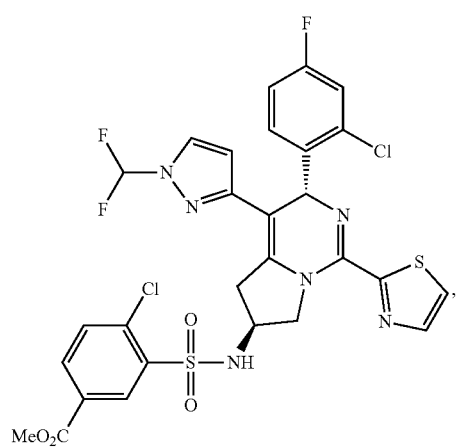

299
-continued
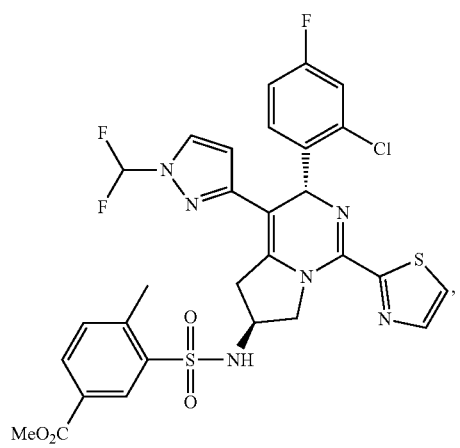
25
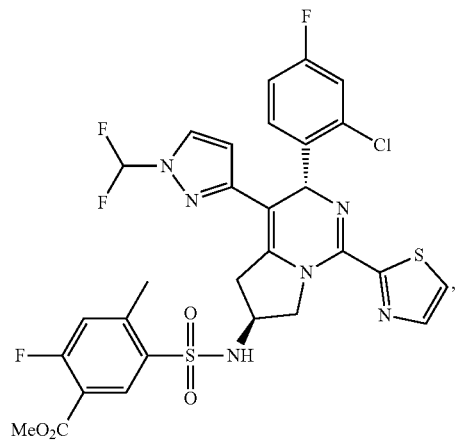
26
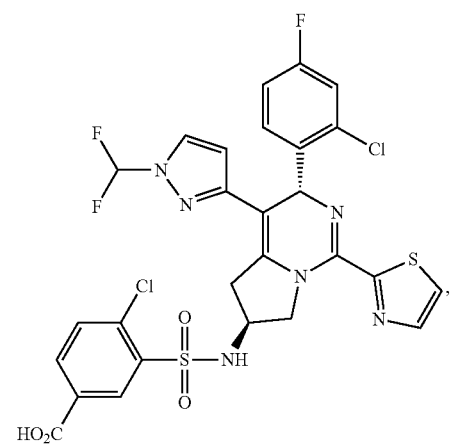
27
300
-continued
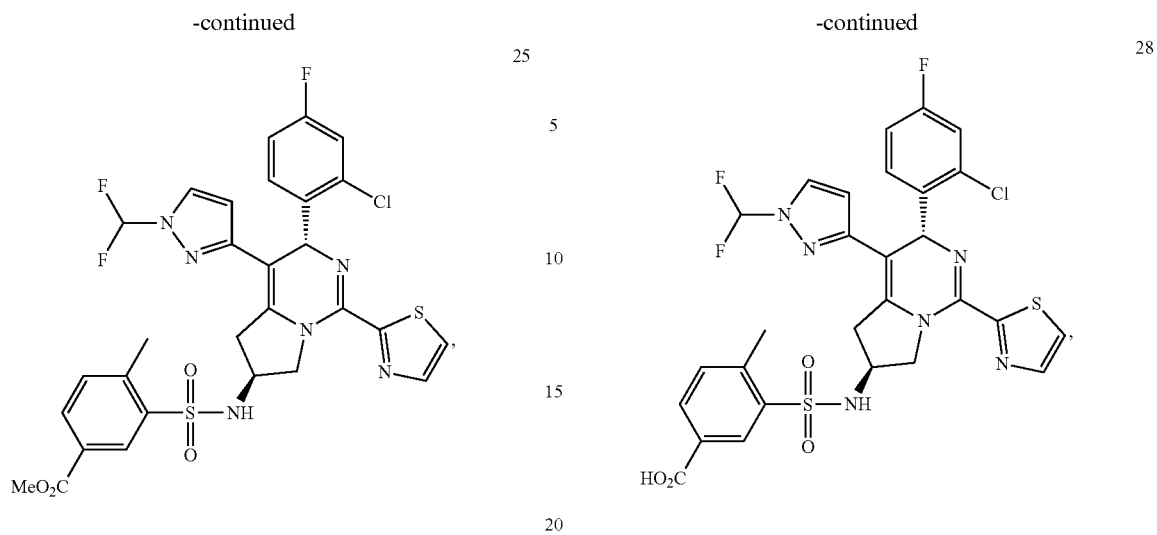
28
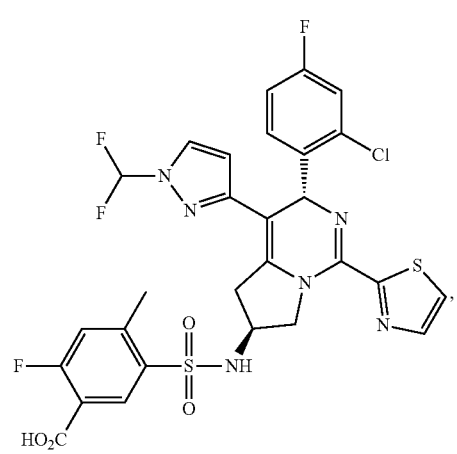
29
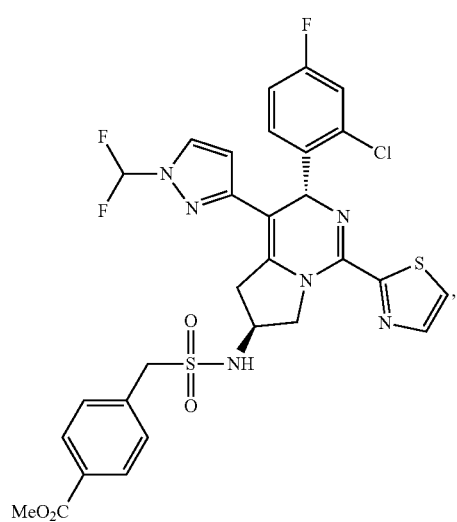
34

-continued
36
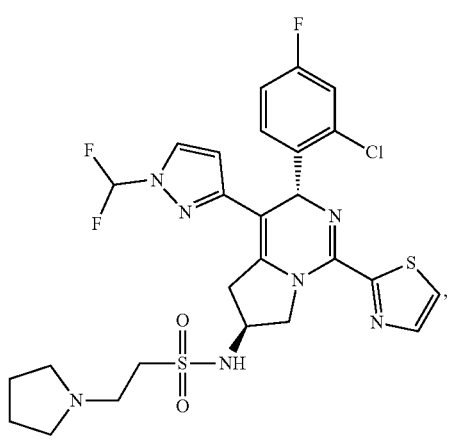
52
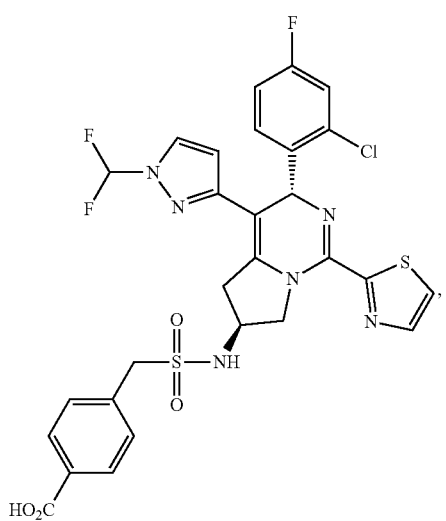
53
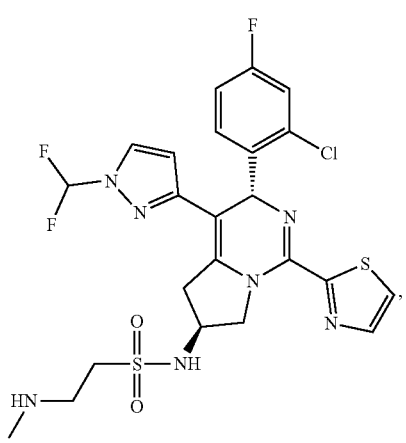
-continued
54
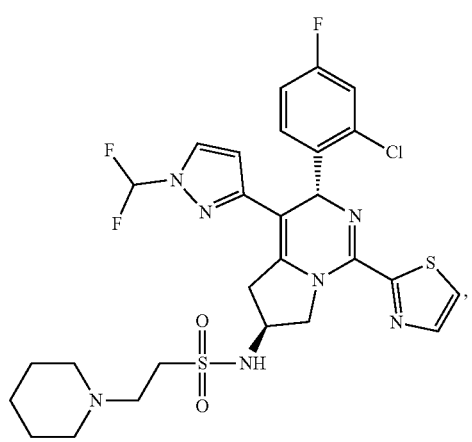
55
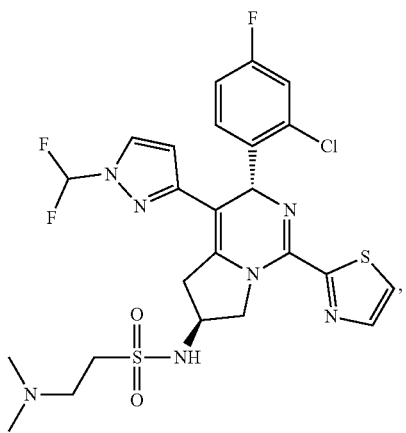
56
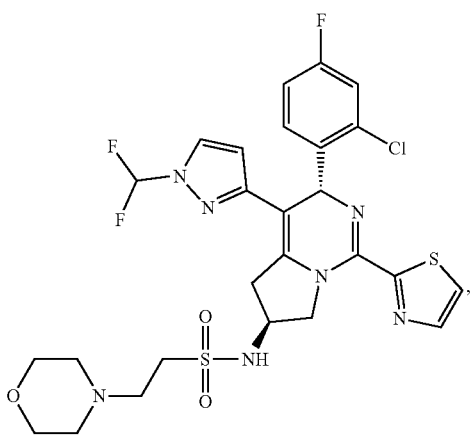

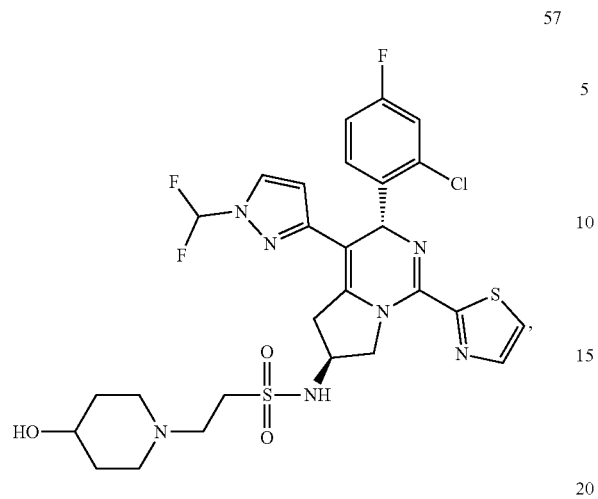
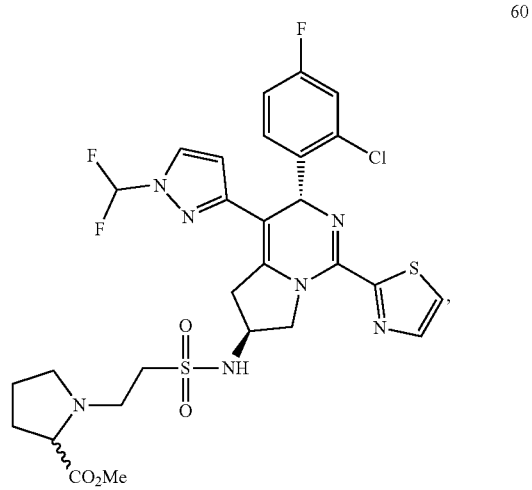
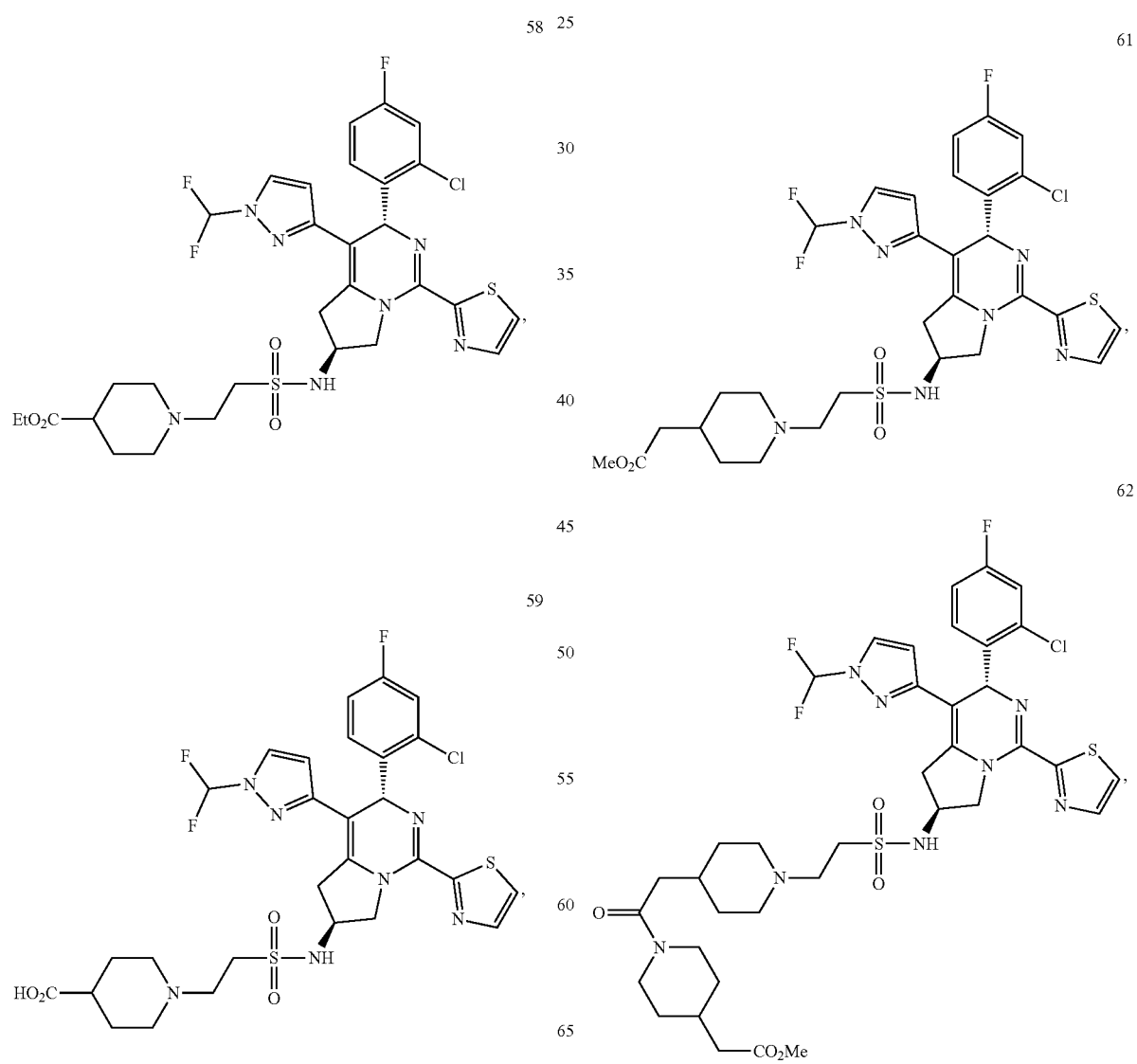

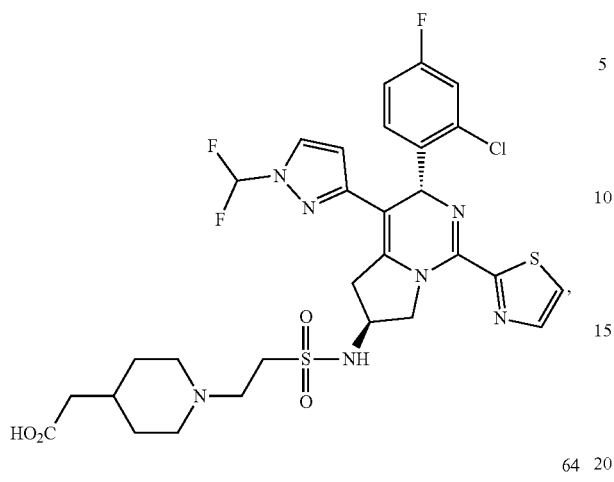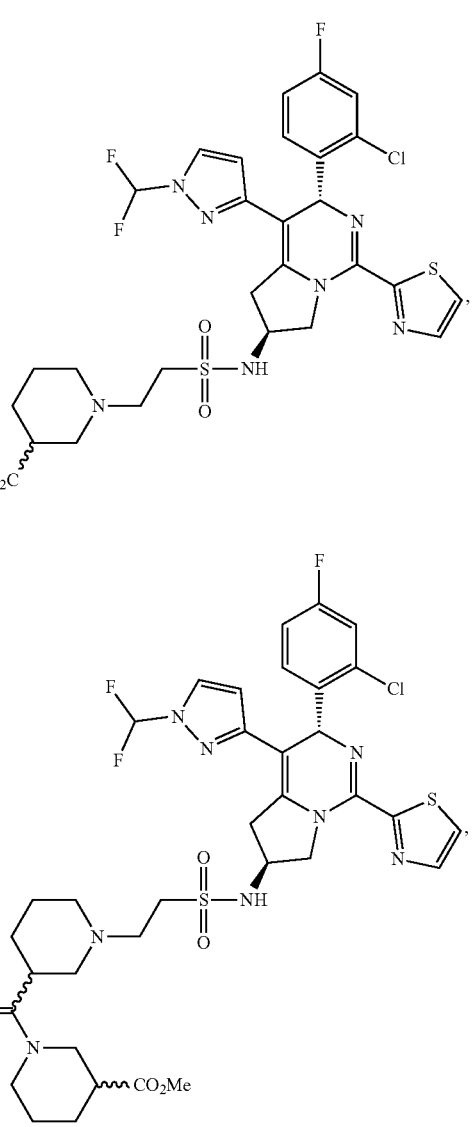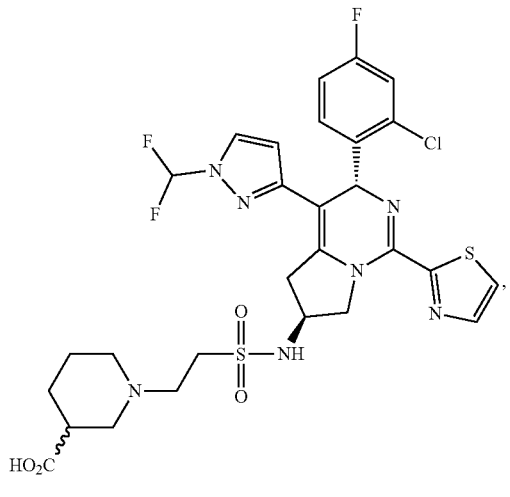

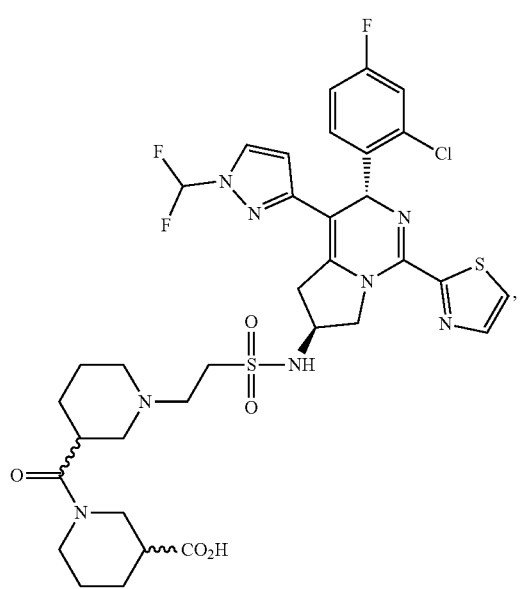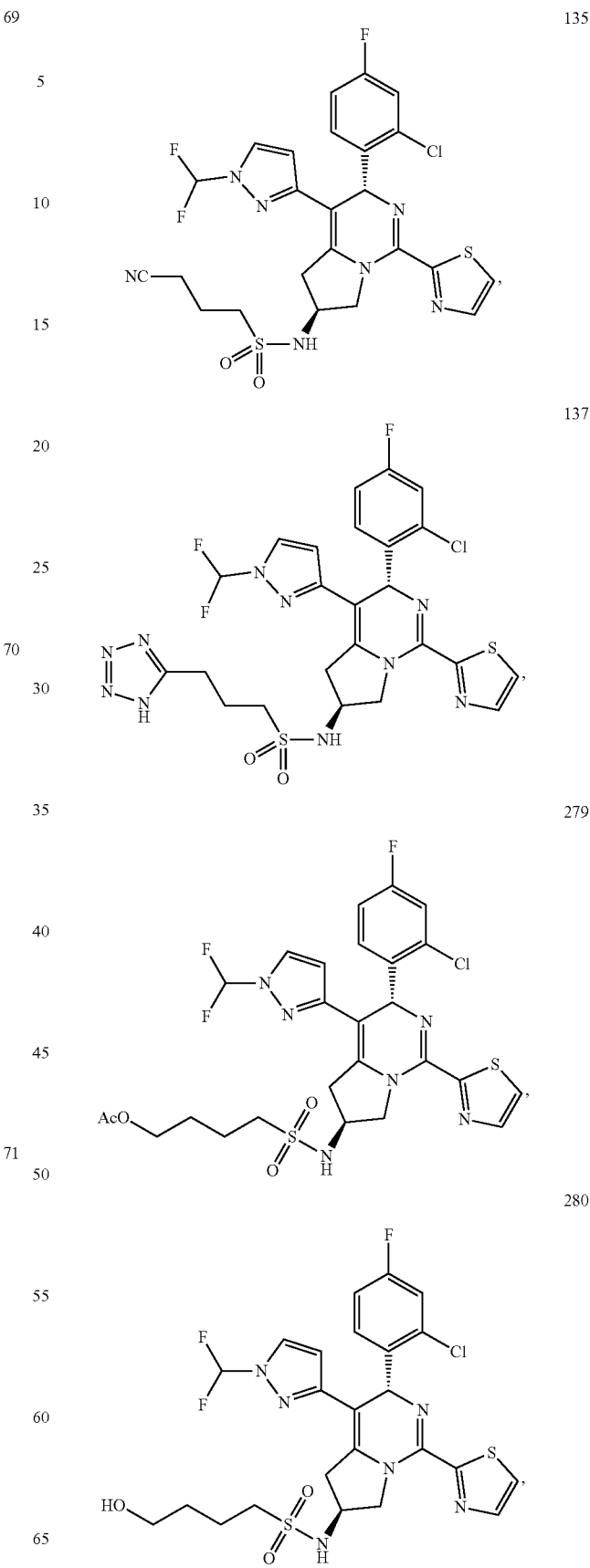

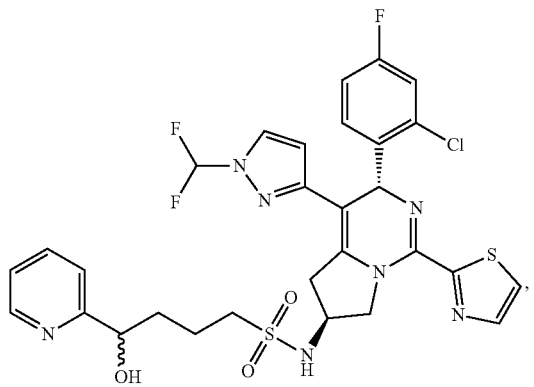
297
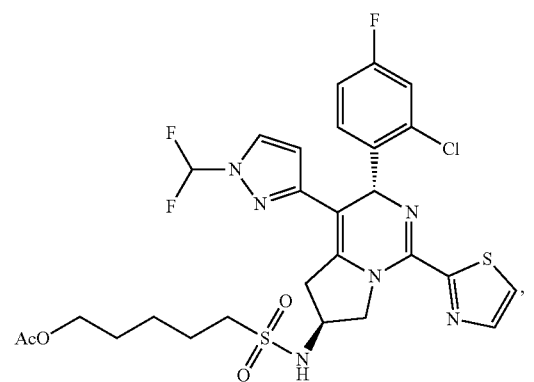
310
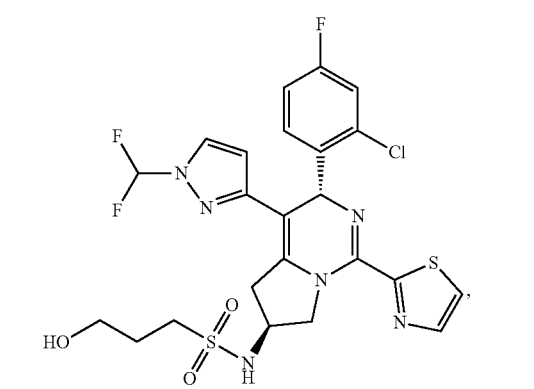
313
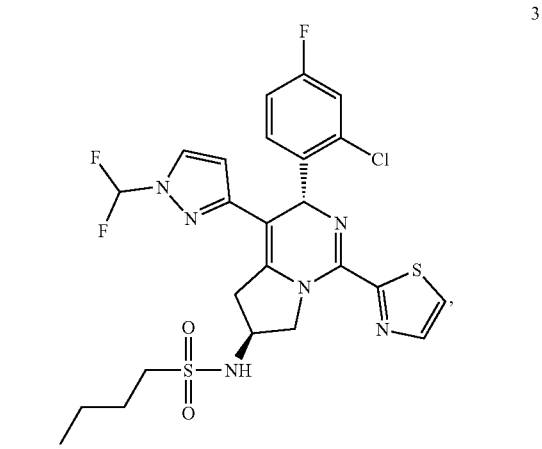
319
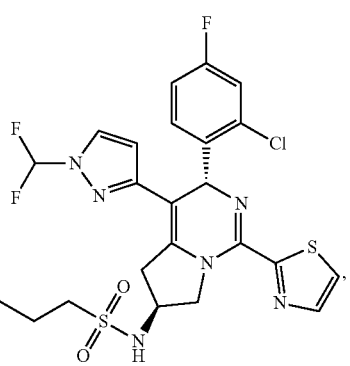
327
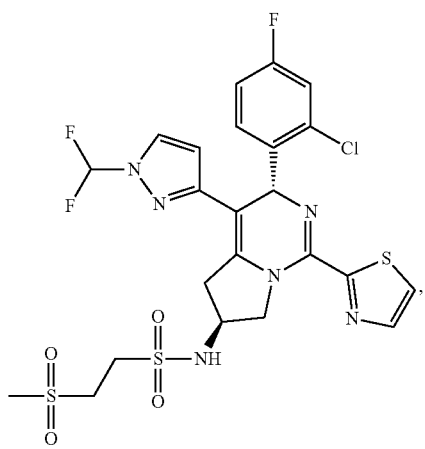
328
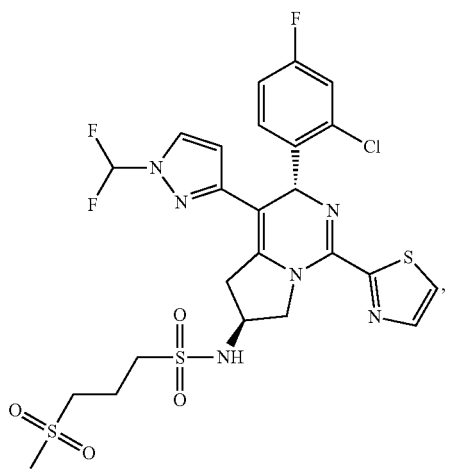
329

311
-continued

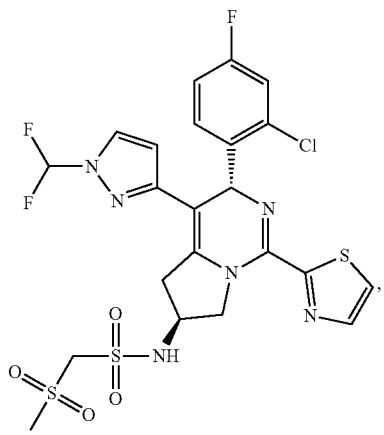
335

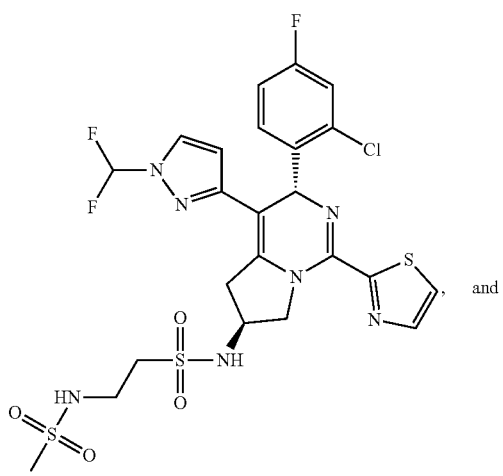
344

312
-continued

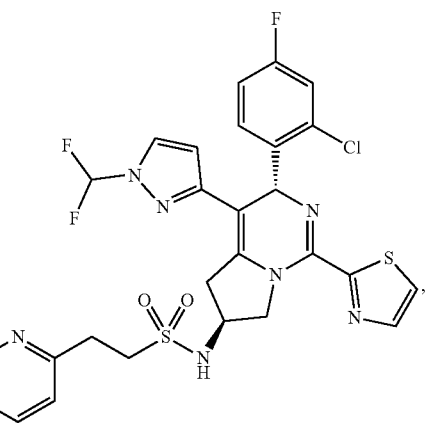
380 or a pharmaceutically acceptable salt thereof.

2. A pharmaceutical composition comprising a pharmaceutically acceptable carrier or excipient in combination with a compound of claim 1, or a pharmaceutically acceptable salt thereof.

3. A method for treating a hepatitis B virus infection in a subject in need thereof, wherein the method comprises administering to the subject a therapeutically effective amount of at least one compound according to claim 1, or a pharmaceutically acceptable salt thereof.

4. The method according to claim 3, wherein the method further comprises administering to the subject at least one additional therapeutic agent selected from the group consisting of a hepatitis B virus polymerase inhibitor, an inducer of cellular viral ribonucleic acid sensor, interferon, a literature-described capsid assembly modulator, a reverse transcriptase inhibitor, a therapeutic vaccine, a toll-like receptor agonist, a viral entry inhibitor, and a viral maturation inhibitor.

5. The method of claim 4, wherein the compound, or a pharmaceutically acceptable salt thereof, and the at least one additional therapeutic agent are co-administered.

6. The method of claim 4, wherein the compound, or a pharmaceutically acceptable salt thereof, and the at least one additional therapeutic agent are co-formulated.

* * * * *

UNITED STATES PATENT AND TRADEMARK OFFICE
CERTIFICATE OF CORRECTION

PATENT NO. : 11,472,808 B2  
APPLICATION NO. : 16/892464  
DATED : October 18, 2022  
INVENTOR(S) : Yao-Ling Qiu et al.

Page 1 of 1

It is certified that error appears in the above-identified patent and that said Letters Patent is hereby corrected as shown below:

In the Claims

At Column 309

In Claim 1, Lines 20-35 delete " 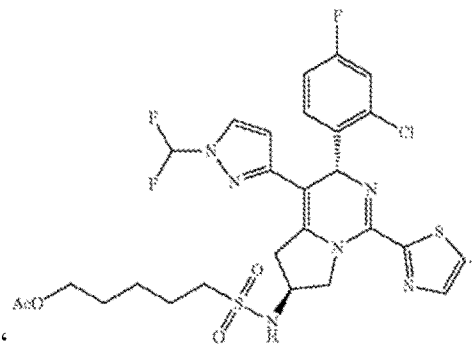 " and insert 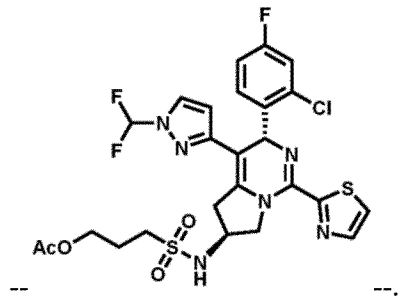 --.

Signed and Sealed this  
Twenty-eighth Day of February, 2023

Katherine Kelly Vidal  
*Director of the United States Patent and Trademark Office*